US006974684B2

(12) United States Patent
Anderson et al.

(10) Patent No.: US 6,974,684 B2
(45) Date of Patent: Dec. 13, 2005

(54) THERAPEUTIC POLYPEPTIDES, NUCLEIC ACIDS ENCODING SAME, AND METHODS OF USE

(75) Inventors: David W. Anderson, Branford, CT (US); John P. Alsobrook II, Madison, CT (US); Ferenc L. Boldog, North Haven, CT (US); Catherine E. Burgess, Wethersfield, CT (US); Stacie J. Casman, North Haven, CT (US); Shlomit R. Edinger, New Haven, CT (US); Esha A. Gangolli, Madison, CT (US); Linda Gorman, Branford, CT (US); Xiaojia Sasha Guo, Branford, CT (US); Nikolai Khramtsov, Branford, CT (US); Denise M. Lepley, Branford, CT (US); John R. MacDougall, Hamden, CT (US); Carol E. A. Pena, New Haven, CT (US); John A. Peyman, New Haven, CT (US); Meera Patturajan, Branford, CT (US); Daniel K. Rieger, Branford, CT (US); Richard A. Shimkets, Guilford, CT (US); Glennda Smithson, Guilford, CT (US); Kimberly A. Spytek, New Haven, CT (US); Corine A. M. Vernet, Branford, CT (US); Edward Z. Voss, Wallingford, CT (US); Mei Zhong, Branford, CT (US)

(73) Assignee: CuraGen Corporation, New Havem, CT (US)

( * ) Notice: Subject to any disclaimer, the term of this patent is extended or adjusted under 35 U.S.C. 154(b) by 328 days.

(21) Appl. No.: 10/211,689

(22) Filed: Aug. 1, 2002

(65) Prior Publication Data

US 2003/0232347 A1 Dec. 18, 2003

Related U.S. Application Data

(60) Provisional application No. 60/311,751, filed on Aug. 10, 2001, provisional application No. 60/310,802, filed on Aug. 8, 2001, provisional application No. 60/310,795, filed on Aug. 8, 2001, provisional application No. 60/311,292, filed on Aug. 9, 2001, provisional application No. 60/361,159, filed on Feb. 28, 2002, provisional application No. 60/373,050, filed on Apr. 16, 2002, provisional application No. 60/380,970, filed on May 15, 2002, provisional application No. 60/311,979, filed on Aug. 13, 2001, provisional application No. 60/381,030, filed on May 16, 2002, provisional application No. 60/323,944, filed on Sep. 21, 2001, provisional application No. 60/311,571, filed on Aug. 10, 2001, provisional application No. 60/311,594, filed on Aug. 10, 2001, provisional application No. 60/313,201, filed on Aug. 17, 2001, provisional application No. 60/359,294, filed on Feb. 21, 2002, provisional application No. 60/372,998, filed on Apr. 16, 2002, provisional application No. 60/380,971, filed on May 15, 2002, provisional application No. 60/312,892, filed on Aug. 16, 2001, provisional application No. 60/322,716, filed on Sep. 17, 2001, provisional application No. 60/360,890, filed on Feb. 28, 2002, provisional application No. 60/314,031, filed on Aug. 21, 2001, and provisional application No. 60/315,853, filed on Aug. 29, 2001.

(51) Int. Cl.$^7$ .......................... C12Q 1/68; C07H 21/02
(52) U.S. Cl. ...................... 435/69.1; 536/23.1
(58) Field of Search .................. 530/350; 435/7.1, 435/6, 320.1, 325, 69.1, 7; 514/2; 536/23.1

(56) References Cited

U.S. PATENT DOCUMENTS

| | | | |
|---|---|---|---|
| 3,773,919 A | 11/1973 | Boswell et al. | 424/19 |
| 4,485,045 A | 11/1984 | Regen | 260/403 |
| 4,522,811 A | 6/1985 | Eppstein et al. | 514/2 |
| 4,544,545 A | 10/1985 | Ryan et al. | 424/1.1 |
| 4,676,980 A | 6/1987 | Segal et al. | 424/85 |
| 4,683,195 A | 7/1987 | Mullis et al. | 435/6 |
| 4,683,202 A | 7/1987 | Mullis | 435/91 |
| 4,736,866 A | 4/1988 | Leder et al. | 800/1 |
| 4,816,567 A | 3/1989 | Cabilly et al. | 530/387 |
| 4,870,009 A | 9/1989 | Evans et al. | 435/70 |
| 4,873,191 A | 10/1989 | Wagner et al. | 435/172.3 |
| 4,873,316 A | 10/1989 | Meade et al. | 530/412 |
| 4,946,778 A | 8/1990 | Ladner et al. | 435/69.6 |
| 4,987,071 A | 1/1991 | Cech et al. | 435/91 |
| 5,013,556 A | 5/1991 | Woodle et al. | 424/450 |
| 5,116,742 A | 5/1992 | Cech et al. | 435/91 |
| 5,223,409 A | 6/1993 | Ladner et al. | 435/69.7 |
| 5,225,539 A | 7/1993 | Winter | 530/387.3 |
| 5,233,409 A | 8/1993 | Schwab | 356/402 |
| 5,272,057 A | 12/1993 | Smulson et al. | 435/6 |
| 5,283,317 A | 2/1994 | Saifer et al. | 528/405 |
| 5,328,470 A | 7/1994 | Nabel et al. | 604/101 |
| 5,459,039 A | 10/1995 | Modrich et al. | 435/6 |
| 5,493,531 A | 2/1996 | Pascucci et al. | 365/200 |

(Continued)

OTHER PUBLICATIONS

International Search Report for PCT/US02/24492, mailed on Aug. 27, 2004.
Lin, S. C. and M. Morrison–Bogorad (1991). "Cloning and characterization of a testis–specific thymosin beta 10 cDNA. Expression in post–meiotic male germ cells." J Biol Chem 266(34): 23347–53.
Torsher, L. C., C. Shub, et al. (1998). "Risk of patients with severe aortic stenosis undergoing noncardiac surgery." Am J Cardiol 81(4): 448–52.

(Continued)

Primary Examiner—Jon Weber
Assistant Examiner—Robert B. Mondesi
(74) Attorney, Agent, or Firm—Mei L. Benni; George M. Yahwak; CuraGen Corporation

(57) ABSTRACT

Disclosed herein are nucleic acid sequences that encode G-coupled protein-receptor related polypeptides. Also disclosed are polypeptides encoded by these nucleic acid sequences, and antibodies, which immunospecifically-bind to the polypeptide, as well as derivatives, variants, mutants, or fragments of the aforementioned polypeptide, polynucleotide, or antibody. The invention further discloses therapeutic, diagnostic and research methods for diagnosis, treatment, and prevention of disorders involving any one of these novel human nucleic acids and proteins.

17 Claims, No Drawings

U.S. PATENT DOCUMENTS

| | | | |
|---|---|---|---|
| 5,545,806 A | 8/1996 | Lonberg et al. ................. | 800/2 |
| 5,545,807 A | 8/1996 | Surani et al. ................... | 800/2 |
| 5,569,825 A | 10/1996 | Lonberg et al. ................. | 800/2 |
| 5,625,126 A | 4/1997 | Lonberg et al. ................. | 800/2 |
| 5,633,425 A | 5/1997 | Lonberg et al. ................. | 800/2 |
| 5,661,016 A | 8/1997 | Lonberg et al. ........... | 435/172.3 |
| 5,916,771 A | 6/1999 | Hori et al. ................... | 435/69.6 |
| 5,939,598 A | 8/1999 | Kucherlapati et al. ......... | 800/25 |
| 6,057,101 A | 5/2000 | Nandabalan et al. ............ | 435/6 |
| 6,083,693 A | 7/2000 | Nandabalan et al. ............ | 435/6 |
| 2002/0001825 A1 | 1/2002 | Itoh ........................... | 435/69.4 |

OTHER PUBLICATIONS

Genbank Accession No.: A31358 (Mar. 17, 1999).
Genbank Accession No.: AAA63238 (Mar. 7, 1995).
Genbank Accession No.: AAB26122 (Jun. 28, 1993).
Genbank Accession No.: AAB31182 (Sep. 23, 1994).
Genbank Accession No.: AAB35016 (Oct. 30, 1995).
Genbank Accession No.: AAB35017 (Oct. 30, 1995).
Genbank Accession No.: AAB47288 (Feb. 13, 1997).
Genbank Accession No.: AAB49593 (Mar. 13, 1997).
Genbank Accession No.: AAB49599 (Mar. 13, 1997).
Genbank Accession No.: AAB65815 (Aug. 6, 1997).
Genbank Accession No.: AAB65816 (Aug. 6, 1997).
Genbank Accession No.: AAB65888 (Aug. 23, 2003).
Genbank Accession No.: AAB67858 (Aug. 28, 1997).
Genbank Accession No.: AAB80998 (Nov. 21, 2002).
Genbank Accession No.: AAB90549 (Mar. 17, 2003).
Genbank Accession No.: AAB90583 (Mar. 17, 2003).
Genbank Accession No.: AAB91223 (Mar. 17, 2003).
Genbank Accession No.: AAE03780 (Sep. 29, 1999).
Genbank Accession No.: AAE04406 (Sep. 29, 1999).
Genbank Accession No.: AAE09439 (Sep. 29, 1999).
Genbank Accession No.: AAE09707 (Sep. 29, 1999).
Genbank Accession No.: AAE13293 (Sep. 29, 1999).
Genbank Accession No.: AAE13296 (Sep. 29, 1999).
Genbank Accession No.: AAE13298 (Sep. 29, 1999).
Genbank Accession No.: AAE13538 (Sep. 29, 1999).
Genbank Accession No.: AAE15158 (Sep. 29, 1999).
Genbank Accession No.: AAE15341 (Sep. 29, 1999).
Genbank Accession No.: AAE15348 (Sep. 29, 1999).
Genbank Accession No.: AAE18819 (Sep. 29, 1999).
Genbank Accession No.: AAH29485 (Oct. 7, 2003).
Genbank Accession No.: AAK30146 (Apr. 8, 2001).
Genbank Accession No.: AAM03072 (Oct. 7, 2003).
Genbank Accession No.: AAM15317 (Mar. 11, 2002).
Genbank Accession No.: AAM27792 (Jun. 13, 2002).
Genbank Accession No.: AAM34215 (May 22, 2002).
Genbank Accession No.: AAM38687 (May 29, 2002).
Genbank Accession No.: AAM38889 (May 29, 2002).
Genbank Accession No.: AAM40473 (May 23, 2002).
Genbank Accession No.: AAM40675 (May 23, 2002).
Genbank Accession No.: AAM46865 (Jun. 3, 2002).
Genbank Accession No.: AAM67501 (Sep. 18, 2002).
Genbank Accession No.: AAR64190 (Dec. 18, 2003).
Genbank Accession No.: AAR77097 (Dec. 18, 2003).
Genbank Accession No.: AAR96932 (Jan. 20, 2004).
Genbank Accession No.: AAR96935 (Jan. 20, 2004).
Genbank Accession No.: BAB84561 (Apr. 5, 2002).
Genbank Accession No.: C33356 (Dec. 2, 1994).
Genbank Accession No.: CAA03641 (Mar. 9, 1998).
Genbank Accession No.: CAC38717 (May 11, 2001).
Genbank Accession No.: CAC41224 (Jun. 8, 2001).
Genbank Accession No.: JC2451 (May 3, 1996).
Genbank Accession No.: JC5697 (Mar. 17, 1999).
Genbank Accession No.: P01588 (Mar. 15, 2004).
Genbank Accession No.: P02649 (Mar. 15, 2004).
Genbank Accession No.: P07865 (Oct. 16, 2001).
Genbank Accession No.: P10082 (Sep. 15, 2003).
Genbank Accession No.: P13472 (Mar. 15, 2004).
Genbank Accession No.: P19879 (Jun. 15, 2002).
Genbank Accession No.: P20774 (Sep. 15, 2003).
Genbank Accession No.: P21752 (Mar. 15, 2004).
Genbank Accession No.: P21753 (Jun. 15, 2002).
Genbank Accession No.: P22724 (Mar. 15, 2004).
Genbank Accession No.: P29676 (Oct. 16, 2001).
Genbank Accession No.: P41273 (Jun. 15, 2002).
Genbank Accession No.: P41274 (Jun. 15, 2002).
Genbank Accession No.: P42514 (Oct. 16, 2001).
Genbank Accession No.: P49337 (Mar. 15, 2004).
Genbank Accession No.: P56705 (Jun. 15, 2004).
Genbank Accession No.: P70379 (Sep. 15, 2003).
Genbank Accession No.: Q28513 (Oct. 16, 2001).
SWALL (SPTR) Accession No.: Q62000 (Feb. 28, 2003).
SWALL (SPTR) Accession No.: Q8R002 (Jun. 1, 2002).
SWALL (SPTR) Accession No.: Q8R4X0 (Jun. 1, 2002).
SWALL (SPTR) Accession No.: Q8R5L7 (Jun. 15, 2004).
SWALL (SPTR) Accession No.: Q91XD0 (Oct. 16, 2001).
SWALL (SPTR) Accession No.: Q92915 (Nov. 1, 1997).
SWALL (SPTR) Accession No.: Q93QG0 (Dec. 1, 2001).
SWALL (SPTR) Accession No.: Q99988 (Oct. 16, 2001).
SWALL (SPTR) Accession No.: Q9BWA0 (Jun. 1, 2001).
SWALL (SPTR) Accession No.: Q9BXJ0 (Feb. 28, 2003).
SWALL (SPTR) Accession No.: Q9GJU3 (Mar. 29, 2004).
SWALL (SPTR) Accession No.: Q9GLM7 (Mar. 1, 2001).
SWALL (SPTR) Accession No.: Q9GLM8 (Mar. 1, 2001).
SWALL (SPTR) Accession No.: Q9IAI6 (Oct. 1, 2000).
SWALL (SPTR) Accession No.: Q9PEB0 (Oct. 10, 2003).
SWALL (SPTR) Accession No.: Q9QXQ5 (Oct. 16, 2001).
SWALL (SPTR) Accession No.: Q9Z0J6 (Oct. 16, 2001).
SWALL (SPTR) Accession No.: Q9Z0J7 (Oct. 16, 2001).
Genbank Accession No.: S15073 (Jul. 16, 1999).
Genbank Accession No.: S34568 (May 9, 1997).
Genbank Accession No.: S34569 (May 9, 1997).
Genbank Accession No.: T14782 (Sep. 2, 2000).
Genbank Accession No.: TNRTA (Jun. 16, 2000).
Cedazo–Minguez, A. and R. F. Cowburn (2001). "Apolipoprotein E: a major piece in the Alzheimer's disease puzzle." J Cell Mol Med 5(3): 254–66.
Yamauchi, T., J. Kamon, et al. (2001). "The fat–derived hormone adiponectin reverses insulin resistance associated with both lipoatrophy and obesity." Nat Med 7(8): 941–6.

SEQUENCE LISTING

<160> NUMBER OF SEQ ID NOS: 132

<210> SEQ ID NO 1
<211> LENGTH: 975
<212> TYPE: DNA
<213> ORGANISM: Homo sapiens
<220> FEATURE:
<221> NAME/KEY: CDS
<222> LOCATION: (49)..(942)

<400> SEQUENCE: 1

```
agcaggccac tagtttatta acttccagcc accttgattt ttgctaaa atg aag act         57
                                                     Met Lys Thr
                                                       1 ctg cag tct aca ctt ctc cta tta ctg ctt gtg cct ctg ata aag cca        105
Leu Gln Ser Thr Leu Leu Leu Leu Leu Val Pro Leu Ile Lys Pro
      5                  10                  15 gca cca cca acc cag cag gac tca cgc att atc tat gat tat gga aca        153
Ala Pro Pro Thr Gln Gln Asp Ser Arg Ile Ile Tyr Asp Tyr Gly Thr
 20                  25                  30                  35 gat aat ttt gaa gaa tcc ata ttt agc caa gat tat gag gat aaa tac        201
Asp Asn Phe Glu Glu Ser Ile Phe Ser Gln Asp Tyr Glu Asp Lys Tyr
                 40                  45                  50 ctg gat gga aaa aat att aag gaa aaa gaa act gtg ata ata ccc aat        249
Leu Asp Gly Lys Asn Ile Lys Glu Lys Glu Thr Val Ile Ile Pro Asn
             55                  60                  65 gag aaa agt ctt caa tta caa aaa gat gag gca ata aca cca tta cct        297
Glu Lys Ser Leu Gln Leu Gln Lys Asp Glu Ala Ile Thr Pro Leu Pro
         70                  75                  80 ccc aag aaa gaa aat gat gaa atg ccc acg tgt ctg ctg tgt gtt tgt        345
Pro Lys Lys Glu Asn Asp Glu Met Pro Thr Cys Leu Leu Cys Val Cys
     85                  90                  95 tta agt ggc tct gta tac tgt gaa gaa gtt gac att gat gct gta cca        393
Leu Ser Gly Ser Val Tyr Cys Glu Glu Val Asp Ile Asp Ala Val Pro
100                 105                 110                 115 ccc tta cca aag gaa tca gcc tat ctt tac gca cga ttc aac aaa att        441
Pro Leu Pro Lys Glu Ser Ala Tyr Leu Tyr Ala Arg Phe Asn Lys Ile
                120                 125                 130 aaa aag ctg act gcc aaa gat ttt gca gac ata cct aac tta aga aga        489
Lys Lys Leu Thr Ala Lys Asp Phe Ala Asp Ile Pro Asn Leu Arg Arg
            135                 140                 145 ctc gat ttt aca gga aat ttg ata gaa gat ata gaa gat ggt act ttt        537
Leu Asp Phe Thr Gly Asn Leu Ile Glu Asp Ile Glu Asp Gly Thr Phe
        150                 155                 160 tca aaa ctt tct ctg tta gaa gaa ctt tca ctt gct gaa aat caa cta        585
Ser Lys Leu Ser Leu Leu Glu Glu Leu Ser Leu Ala Glu Asn Gln Leu
    165                 170                 175 cta aaa ctt cca gtt ctt cct ccc aag ctc act tta ttt aat gca aaa        633
Leu Lys Leu Pro Val Leu Pro Pro Lys Leu Thr Leu Phe Asn Ala Lys
180                 185                 190                 195 tac aac aaa atc aag agt agg gga atc aaa gca aat gca ttc aaa aaa        681
Tyr Asn Lys Ile Lys Ser Arg Gly Ile Lys Ala Asn Ala Phe Lys Lys
                200                 205                 210 ctg aat aac ctc acc ttc ctc tgc ttg gac cat aat gcc ctg gaa tcc        729
Leu Asn Asn Leu Thr Phe Leu Cys Leu Asp His Asn Ala Leu Glu Ser
            215                 220                 225 gtg cct ctt aat tta cca gaa agt cta cgt gta att cat ctt cag ttc        777
Val Pro Leu Asn Leu Pro Glu Ser Leu Arg Val Ile His Leu Gln Phe
        230                 235                 240
```

```
aac aac ata gct tca att aca gat gac aca ttc tgc aag gct aat gac    825
Asn Asn Ile Ala Ser Ile Thr Asp Asp Thr Phe Cys Lys Ala Asn Asp
    245                 250                 255 acc agt tac atc cgg gac cgc att gaa gag ata cgc ctg gag ggc aat    873
Thr Ser Tyr Ile Arg Asp Arg Ile Glu Glu Ile Arg Leu Glu Gly Asn
260                 265                 270                 275 cca atc gtc ctg gga aag cat cca aac agt ttt att tgc tta aaa aga    921
Pro Ile Val Leu Gly Lys His Pro Asn Ser Phe Ile Cys Leu Lys Arg
                280                 285                 290 tta ccg ata ggg tca tac ttt taacctctat tggtacaaca tataaatgaa agt   975
Leu Pro Ile Gly Ser Tyr Phe
                295

<210> SEQ ID NO 2
<211> LENGTH: 298
<212> TYPE: PRT
<213> ORGANISM: Homo sapiens

<400> SEQUENCE: 2

Met Lys Thr Leu Gln Ser Thr Leu Leu Leu Leu Leu Val Pro Leu
 1               5                  10                  15

Ile Lys Pro Ala Pro Pro Thr Gln Gln Asp Ser Arg Ile Ile Tyr Asp
            20                  25                  30

Tyr Gly Thr Asp Asn Phe Glu Glu Ser Ile Phe Ser Gln Asp Tyr Glu
        35                  40                  45

Asp Lys Tyr Leu Asp Gly Lys Asn Ile Lys Glu Lys Glu Thr Val Ile
    50                  55                  60

Ile Pro Asn Glu Lys Ser Leu Gln Leu Gln Lys Asp Glu Ala Ile Thr
65                  70                  75                  80

Pro Leu Pro Pro Lys Lys Glu Asn Asp Glu Met Pro Thr Cys Leu Leu
                85                  90                  95

Cys Val Cys Leu Ser Gly Ser Val Tyr Cys Glu Glu Val Asp Ile Asp
            100                 105                 110

Ala Val Pro Pro Leu Pro Lys Glu Ser Ala Tyr Leu Tyr Ala Arg Phe
        115                 120                 125

Asn Lys Ile Lys Lys Leu Thr Ala Lys Asp Phe Ala Asp Ile Pro Asn
    130                 135                 140

Leu Arg Arg Leu Asp Phe Thr Gly Asn Leu Ile Glu Asp Ile Glu Asp
145                 150                 155                 160

Gly Thr Phe Ser Lys Leu Ser Leu Leu Glu Glu Leu Ser Leu Ala Glu
                165                 170                 175

Asn Gln Leu Leu Lys Leu Pro Val Leu Pro Pro Lys Leu Thr Leu Phe
            180                 185                 190

Asn Ala Lys Tyr Asn Lys Ile Lys Ser Arg Gly Ile Lys Ala Asn Ala
        195                 200                 205

Phe Lys Lys Leu Asn Asn Leu Thr Phe Leu Cys Leu Asp His Asn Ala
    210                 215                 220

Leu Glu Ser Val Pro Leu Asn Leu Pro Glu Ser Leu Arg Val Ile His
225                 230                 235                 240

Leu Gln Phe Asn Asn Ile Ala Ser Ile Thr Asp Asp Thr Phe Cys Lys
                245                 250                 255

Ala Asn Asp Thr Ser Tyr Ile Arg Asp Arg Ile Glu Glu Ile Arg Leu
            260                 265                 270

Glu Gly Asn Pro Ile Val Leu Gly Lys His Pro Asn Ser Phe Ile Cys
        275                 280                 285
```

```
          Leu Lys Arg Leu Pro Ile Gly Ser Tyr Phe
              290                 295

<210> SEQ ID NO 3
<211> LENGTH: 849
<212> TYPE: DNA
<213> ORGANISM: Homo sapiens
<220> FEATURE:
<221> NAME/KEY: CDS
<222> LOCATION: (1)..(849)

<400> SEQUENCE: 3 gga tcc gca cca cca acc cag cag gac tca cgc att atc tat gat tat       48
Gly Ser Ala Pro Pro Thr Gln Gln Asp Ser Arg Ile Ile Tyr Asp Tyr
  1               5                  10                  15 gga aca gat aat ttt gaa gaa tcc ata ttt agc caa gat tat gag gat       96
Gly Thr Asp Asn Phe Glu Glu Ser Ile Phe Ser Gln Asp Tyr Glu Asp
             20                  25                  30 aaa tac ctg gat gga aaa aat att aag gaa aaa gaa act gtg ata ata      144
Lys Tyr Leu Asp Gly Lys Asn Ile Lys Glu Lys Glu Thr Val Ile Ile
         35                  40                  45 ccc aat gag aaa agt ctt caa tta caa aaa gat gag gca ata aca cca      192
Pro Asn Glu Lys Ser Leu Gln Leu Gln Lys Asp Glu Ala Ile Thr Pro
     50                  55                  60 tta cct ccc aag aaa gaa aat gat gaa atg ccc acg tgt ctg ctg tgt      240
Leu Pro Pro Lys Lys Glu Asn Asp Glu Met Pro Thr Cys Leu Leu Cys
 65                  70                  75                  80 gtt tgt tta agt ggc tct gta tac tgt gaa gaa gtt gac att gat gct      288
Val Cys Leu Ser Gly Ser Val Tyr Cys Glu Glu Val Asp Ile Asp Ala
                 85                  90                  95 gta cca ccc tta cca aag gaa tca gcc tat ctt tac gca cga ttc aac      336
Val Pro Pro Leu Pro Lys Glu Ser Ala Tyr Leu Tyr Ala Arg Phe Asn
            100                 105                 110 aaa att aaa aag ctg act gcc aaa gat ttt gca gac ata cct aac tta      384
Lys Ile Lys Lys Leu Thr Ala Lys Asp Phe Ala Asp Ile Pro Asn Leu
        115                 120                 125 aga aga ctc gat ttt aca gga aat ttg ata gaa gat ata gaa gat ggt      432
Arg Arg Leu Asp Phe Thr Gly Asn Leu Ile Glu Asp Ile Glu Asp Gly
    130                 135                 140 act ttt tca aaa ctt tct ctg tta gaa gaa ctt tca ctt gct gaa aat      480
Thr Phe Ser Lys Leu Ser Leu Leu Glu Glu Leu Ser Leu Ala Glu Asn
145                 150                 155                 160 caa cta cta aaa ctt cca gtt ctt cct ccc aag ctc act tta ttt aat      528
Gln Leu Leu Lys Leu Pro Val Leu Pro Pro Lys Leu Thr Leu Phe Asn
                165                 170                 175 gca aaa tac aac aaa atc aag agt agg gga atc aaa gca aat gca ttc      576
Ala Lys Tyr Asn Lys Ile Lys Ser Arg Gly Ile Lys Ala Asn Ala Phe
            180                 185                 190 aaa aaa ctg aat aac ctc acc ttc ctc tgc ttg gac cat aat gcc ctg      624
Lys Lys Leu Asn Asn Leu Thr Phe Leu Cys Leu Asp His Asn Ala Leu
        195                 200                 205 gaa tcc gtg cct ctt aat tta cca gaa agt cta cgt gta att cat ctt      672
Glu Ser Val Pro Leu Asn Leu Pro Glu Ser Leu Arg Val Ile His Leu
    210                 215                 220 cag ttc aac aac ata gct tca att aca gat gac aca ttc tgc aag gct      720
Gln Phe Asn Asn Ile Ala Ser Ile Thr Asp Asp Thr Phe Cys Lys Ala
225                 230                 235                 240 aac gac acc agt tac atc cgg gac cgc att gaa gag ata cgc ctg gag      768
Asn Asp Thr Ser Tyr Ile Arg Asp Arg Ile Glu Glu Ile Arg Leu Glu
                245                 250                 255
```

```
ggc aat cca atc gtc ctg gga aag cat cca aac agt ttt att tgc tta      816
Gly Asn Pro Ile Val Leu Gly Lys His Pro Asn Ser Phe Ile Cys Leu
        260                 265                 270 aaa aga tta ccg ata ggg tca tac ttt ctc gag                          849
Lys Arg Leu Pro Ile Gly Ser Tyr Phe Leu Glu
        275                 280
```

<210> SEQ ID NO 4
<211> LENGTH: 283
<212> TYPE: PRT
<213> ORGANISM: Homo sapiens

<400> SEQUENCE: 4

```
Gly Ser Ala Pro Pro Thr Gln Gln Asp Ser Arg Ile Ile Tyr Asp Tyr
 1               5                  10                  15

Gly Thr Asp Asn Phe Glu Glu Ser Ile Phe Ser Gln Asp Tyr Glu Asp
                20                  25                  30

Lys Tyr Leu Asp Gly Lys Asn Ile Lys Glu Lys Glu Thr Val Ile Ile
            35                  40                  45

Pro Asn Glu Lys Ser Leu Gln Leu Gln Lys Asp Glu Ala Ile Thr Pro
         50                  55                  60

Leu Pro Pro Lys Lys Glu Asn Asp Glu Met Pro Thr Cys Leu Leu Cys
65                  70                  75                  80

Val Cys Leu Ser Gly Ser Val Tyr Cys Glu Glu Val Asp Ile Asp Ala
                85                  90                  95

Val Pro Pro Leu Pro Lys Glu Ser Ala Tyr Leu Tyr Ala Arg Phe Asn
            100                 105                 110

Lys Ile Lys Lys Leu Thr Ala Lys Asp Phe Ala Asp Ile Pro Asn Leu
        115                 120                 125

Arg Arg Leu Asp Phe Thr Gly Asn Leu Ile Glu Asp Ile Glu Asp Gly
    130                 135                 140

Thr Phe Ser Lys Leu Ser Leu Leu Glu Glu Leu Ser Leu Ala Glu Asn
145                 150                 155                 160

Gln Leu Leu Lys Leu Pro Val Leu Pro Pro Lys Leu Thr Leu Phe Asn
                165                 170                 175

Ala Lys Tyr Asn Lys Ile Lys Ser Arg Gly Ile Lys Ala Asn Ala Phe
            180                 185                 190

Lys Lys Leu Asn Asn Leu Thr Phe Leu Cys Leu Asp His Asn Ala Leu
        195                 200                 205

Glu Ser Val Pro Leu Asn Leu Pro Glu Ser Leu Arg Val Ile His Leu
    210                 215                 220

Gln Phe Asn Asn Ile Ala Ser Ile Thr Asp Asp Thr Phe Cys Lys Ala
225                 230                 235                 240

Asn Asp Thr Ser Tyr Ile Arg Asp Arg Ile Glu Glu Ile Arg Leu Glu
                245                 250                 255

Gly Asn Pro Ile Val Leu Gly Lys His Pro Asn Ser Phe Ile Cys Leu
            260                 265                 270

Lys Arg Leu Pro Ile Gly Ser Tyr Phe Leu Glu
        275                 280
```

<210> SEQ ID NO 5
<211> LENGTH: 126
<212> TYPE: DNA
<213> ORGANISM: Homo sapiens
<220> FEATURE:
<221> NAME/KEY: CDS
<222> LOCATION: (1)..(126)

-continued

```
<400> SEQUENCE: 5 gca gac aaa cca gac gtg ggg gga atc gcc agc ttc aat agg gcc aag       48
Ala Asp Lys Pro Asp Val Gly Gly Ile Ala Ser Phe Asn Arg Ala Lys
 1               5                  10                  15 ctg aag aaa acg gag acg cag gag aag aac acc ctg ccg acc aaa gag       96
Leu Lys Lys Thr Glu Thr Gln Glu Lys Asn Thr Leu Pro Thr Lys Glu
                20                  25                  30 acc act ggg cag aag cgg agt gaa att tcc                              126
Thr Thr Gly Gln Lys Arg Ser Glu Ile Ser
            35                  40

<210> SEQ ID NO 6
<211> LENGTH: 42
<212> TYPE: PRT
<213> ORGANISM: Homo sapiens

<400> SEQUENCE: 6

Ala Asp Lys Pro Asp Val Gly Gly Ile Ala Ser Phe Asn Arg Ala Lys
 1               5                  10                  15

Leu Lys Lys Thr Glu Thr Gln Glu Lys Asn Thr Leu Pro Thr Lys Glu
                20                  25                  30

Thr Thr Gly Gln Lys Arg Ser Glu Ile Ser
            35                  40

<210> SEQ ID NO 7
<211> LENGTH: 84
<212> TYPE: DNA
<213> ORGANISM: Homo sapiens
<220> FEATURE:
<221> NAME/KEY: CDS
<222> LOCATION: (1)..(84)

<400> SEQUENCE: 7 tca gat gca gct gta gac acc agc tct gaa atc att gcc aag gac tta       48
Ser Asp Ala Ala Val Asp Thr Ser Ser Glu Ile Ile Ala Lys Asp Leu
 1               5                  10                  15 aag gag aag aag gaa gtt gtg aaa gag gcg gaa aat                       84
Lys Glu Lys Lys Glu Val Val Lys Glu Ala Glu Asn
                20                  25

<210> SEQ ID NO 8
<211> LENGTH: 28
<212> TYPE: PRT
<213> ORGANISM: Homo sapiens

<400> SEQUENCE: 8

Ser Asp Ala Ala Val Asp Thr Ser Ser Glu Ile Ile Ala Lys Asp Leu
 1               5                  10                  15

Lys Glu Lys Lys Glu Val Val Lys Glu Ala Glu Asn
                20                  25

<210> SEQ ID NO 9
<211> LENGTH: 657
<212> TYPE: DNA
<213> ORGANISM: Homo sapiens
<220> FEATURE:
<221> NAME/KEY: CDS
<222> LOCATION: (15)..(635)

<400> SEQUENCE: 9
ccggtgccag cgct atg agg cca ctc ctc gtc ctg ctg ctc ctg ggc ctg       50
              Met Arg Pro Leu Leu Val Leu Leu Leu Leu Gly Leu
               1               5                  10
```

```
gcg gcc ggc tcg ccc cca ctg gac gac aac aag atc ccc agc ctc tgc      98
Ala Ala Gly Ser Pro Pro Leu Asp Asp Asn Lys Ile Pro Ser Leu Cys
            15                  20                  25 ccg ggg cac ccc ggc ctt cca gga ctg ccg gga cct cga ggg gac ccc     146
Pro Gly His Pro Gly Leu Pro Gly Leu Pro Gly Pro Arg Gly Asp Pro
        30                  35                  40 ggg ccg cga gga gag gcg gga ccc gcg ggg ccc acc ggg cct gcc ggg     194
Gly Pro Arg Gly Glu Ala Gly Pro Ala Gly Pro Thr Gly Pro Ala Gly
45                  50                  55                  60 gag tgc tcg gtg cct ccg cga tcc gcc ttc agc gcc aag cgc tcc gag     242
Glu Cys Ser Val Pro Pro Arg Ser Ala Phe Ser Ala Lys Arg Ser Glu
                    65                  70                  75 agc cgg gtg cct ccg ccg tct gac gca ccc ttg ccc ttc gac cgc gtg     290
Ser Arg Val Pro Pro Pro Ser Asp Ala Pro Leu Pro Phe Asp Arg Val
                80                  85                  90 ctg gtg aac gag cag gga cat tac gac gcc gtc acc ggc aag ttc acc     338
Leu Val Asn Glu Gln Gly His Tyr Asp Ala Val Thr Gly Lys Phe Thr
            95                  100                 105 tgc cag gtg cct ggg gtc tac tac ttc gcc gtc cat gcc acc gtc tac     386
Cys Gln Val Pro Gly Val Tyr Tyr Phe Ala Val His Ala Thr Val Tyr
        110                 115                 120 cgg gcc agc ctg cag ttt gat ctg gtg aag aat ggc gaa tcc att gcc     434
Arg Ala Ser Leu Gln Phe Asp Leu Val Lys Asn Gly Glu Ser Ile Ala
125                 130                 135                 140 tct ttc ttc cag ttt ttc ggg ggg tgg ccc aag cca gcc tcg ctc tcg     482
Ser Phe Phe Gln Phe Phe Gly Gly Trp Pro Lys Pro Ala Ser Leu Ser
                    145                 150                 155 ggg ggg gcc atg gtg agg ctg gag cct gag gac caa gtg tgg gtg cag     530
Gly Gly Ala Met Val Arg Leu Glu Pro Glu Asp Gln Val Trp Val Gln
                160                 165                 170 gtg ggt gtg ggt gac tac att ggc atc tat gcc agc atc aag aca gac     578
Val Gly Val Gly Asp Tyr Ile Gly Ile Tyr Ala Ser Ile Lys Thr Asp
            175                 180                 185 agc acc ttc tcc gga ttt ctg gtg tac tcc gac tgg cgc agc tcc cca     626
Ser Thr Phe Ser Gly Phe Leu Val Tyr Ser Asp Trp Arg Ser Ser Pro
        190                 195                 200 gtc ttt gct tagtgcccac tgcaaagtga gc                                657
Val Phe Ala
205
```

<210> SEQ ID NO 10
<211> LENGTH: 207
<212> TYPE: PRT
<213> ORGANISM: Homo sapiens

<400> SEQUENCE: 10

```
Met Arg Pro Leu Leu Val Leu Leu Leu Gly Leu Ala Ala Gly Ser
 1               5                  10                  15

Pro Pro Leu Asp Asp Asn Lys Ile Pro Ser Leu Cys Pro Gly His Pro
                20                  25                  30

Gly Leu Pro Gly Leu Pro Gly Pro Arg Gly Asp Pro Gly Pro Arg Gly
            35                  40                  45

Glu Ala Gly Pro Ala Gly Pro Thr Gly Pro Ala Gly Glu Cys Ser Val
        50                  55                  60

Pro Pro Arg Ser Ala Phe Ser Ala Lys Arg Ser Glu Ser Arg Val Pro
65                  70                  75                  80

Pro Pro Ser Asp Ala Pro Leu Pro Phe Asp Arg Val Leu Val Asn Glu
                85                  90                  95

Gln Gly His Tyr Asp Ala Val Thr Gly Lys Phe Thr Cys Gln Val Pro
```

```
                      100                 105                 110
Gly Val Tyr Tyr Phe Ala Val His Ala Thr Val Tyr Arg Ala Ser Leu
            115                 120                 125

Gln Phe Asp Leu Val Lys Asn Gly Glu Ser Ile Ala Ser Phe Phe Gln
130                 135                 140

Phe Phe Gly Gly Trp Pro Lys Pro Ala Ser Leu Ser Gly Gly Ala Met
145                 150                 155                 160

Val Arg Leu Glu Pro Glu Asp Gln Val Trp Val Gln Val Gly Val Gly
                165                 170                 175

Asp Tyr Ile Gly Ile Tyr Ala Ser Ile Lys Thr Asp Ser Thr Phe Ser
            180                 185                 190

Gly Phe Leu Val Tyr Ser Asp Trp Arg Ser Ser Pro Val Phe Ala
            195                 200                 205

<210> SEQ ID NO 11
<211> LENGTH: 643
<212> TYPE: DNA
<213> ORGANISM: Homo sapiens
<220> FEATURE:
<221> NAME/KEY: CDS
<222> LOCATION: (14)..(634)

<400> SEQUENCE: 11
caccggatcc acc atg agg cca ctc ctc gtc ctg ctg ctc ctg ggc ctg         49
               Met Arg Pro Leu Leu Val Leu Leu Leu Leu Gly Leu
                 1               5                  10 gcg gcc ggc tcg ccc cca ctg gac gac aac aag atc ccc agc ctc tgc        97
Ala Ala Gly Ser Pro Pro Leu Asp Asp Asn Lys Ile Pro Ser Leu Cys
         15                  20                  25 ccg ggg cac ccc ggc ctt cca gga ctg ccg gga cct cga ggg gac ccc       145
Pro Gly His Pro Gly Leu Pro Gly Leu Pro Gly Pro Arg Gly Asp Pro
     30                  35                  40 ggg ccg cga gga gag gcg gga ccc gcg ggg ccc acc ggg cct gcc ggg       193
Gly Pro Arg Gly Glu Ala Gly Pro Ala Gly Pro Thr Gly Pro Ala Gly
 45                  50                  55                  60 gag tgc tcg gtg cct ccg cga tcc gcc ttc agc gcc aag cgc tcc gag       241
Glu Cys Ser Val Pro Pro Arg Ser Ala Phe Ser Ala Lys Arg Ser Glu
                 65                  70                  75 agc cgg gtg cct ccg ccg tct gac gca ccc ttg ccc ttc gac cgc gtg       289
Ser Arg Val Pro Pro Pro Ser Asp Ala Pro Leu Pro Phe Asp Arg Val
             80                  85                  90 ctg gtg aac gag cag gga cat tac gac gcc gtc acc ggc aag ttc acc       337
Leu Val Asn Glu Gln Gly His Tyr Asp Ala Val Thr Gly Lys Phe Thr
         95                 100                 105 tgc cag gtg cct ggg gtc tac tac ttc gcc gtc cat gcc acc gtc tac       385
Cys Gln Val Pro Gly Val Tyr Tyr Phe Ala Val His Ala Thr Val Tyr
    110                 115                 120 cgg gcc agc ctg cag ttt gat ctg gtg aag aat ggc gaa tcc att gcc       433
Arg Ala Ser Leu Gln Phe Asp Leu Val Lys Asn Gly Glu Ser Ile Ala
125                 130                 135                 140 tct ttc ttc cag ttt ttc ggg ggg tgg ccc aag cca gcc tcg ctc tcg       481
Ser Phe Phe Gln Phe Phe Gly Gly Trp Pro Lys Pro Ala Ser Leu Ser
                145                 150                 155 ggg ggg gcc atg gtg agg ctg gag cct gag gac caa gtg tgg gtg cag       529
Gly Gly Ala Met Val Arg Leu Glu Pro Glu Asp Gln Val Trp Val Gln
            160                 165                 170 gtg ggt gtg ggt gac tac att ggc atc tat gcc agc atc aag aca gac       577
Val Gly Val Gly Asp Tyr Ile Gly Ile Tyr Ala Ser Ile Lys Thr Asp
        175                 180                 185
```

-continued

```
agc acc ttc tcc gga ttt ctg gtg tac tcc gac tgg cgc agc tcc cca       625
Ser Thr Phe Ser Gly Phe Leu Val Tyr Ser Asp Trp Arg Ser Ser Pro
    190                 195                 200 gtc ttt gct gtcgacggc                                                  643
Val Phe Ala
205
```

<210> SEQ ID NO 12
<211> LENGTH: 207
<212> TYPE: PRT
<213> ORGANISM: Homo sapiens

<400> SEQUENCE: 12

```
Met Arg Pro Leu Leu Val Leu Leu Leu Gly Leu Ala Ala Gly Ser
 1               5                  10                  15

Pro Pro Leu Asp Asp Asn Lys Ile Pro Ser Leu Cys Pro Gly His Pro
                20                  25                  30

Gly Leu Pro Gly Leu Pro Gly Pro Arg Gly Asp Pro Gly Pro Arg Gly
            35                  40                  45

Glu Ala Gly Pro Ala Gly Pro Thr Gly Pro Ala Gly Glu Cys Ser Val
    50                  55                  60

Pro Pro Arg Ser Ala Phe Ser Ala Lys Arg Ser Glu Ser Arg Val Pro
65                  70                  75                  80

Pro Pro Ser Asp Ala Pro Leu Pro Phe Asp Arg Val Leu Val Asn Glu
                85                  90                  95

Gln Gly His Tyr Asp Ala Val Thr Gly Lys Phe Thr Cys Gln Val Pro
            100                 105                 110

Gly Val Tyr Tyr Phe Ala Val His Ala Thr Val Tyr Arg Ala Ser Leu
        115                 120                 125

Gln Phe Asp Leu Val Lys Asn Gly Glu Ser Ile Ala Ser Phe Phe Gln
    130                 135                 140

Phe Phe Gly Gly Trp Pro Lys Pro Ala Ser Leu Ser Gly Gly Ala Met
145                 150                 155                 160

Val Arg Leu Glu Pro Glu Asp Gln Val Trp Val Gln Val Gly Val Gly
                165                 170                 175

Asp Tyr Ile Gly Ile Tyr Ala Ser Ile Lys Thr Asp Ser Thr Phe Ser
            180                 185                 190

Gly Phe Leu Val Tyr Ser Asp Trp Arg Ser Ser Pro Val Phe Ala
        195                 200                 205
```

<210> SEQ ID NO 13
<211> LENGTH: 643
<212> TYPE: DNA
<213> ORGANISM: Homo sapiens
<220> FEATURE:
<221> NAME/KEY: CDS
<222> LOCATION: (2)..(643)

<400> SEQUENCE: 13

```
c acc gga tcc acc atg agg cca ctc ctc gtc ctg ctg ctc ctg ggc ctg      49
  Thr Gly Ser Thr Met Arg Pro Leu Leu Val Leu Leu Leu Leu Gly Leu
             1               5                  10                  15 gcg gcc ggc tcg ccc cca ctg gac gac aac aag atc ccc agc ctc tgc        97
Ala Ala Gly Ser Pro Pro Leu Asp Asp Asn Lys Ile Pro Ser Leu Cys
                20                  25                  30 ccg ggg cac ccc ggc ctt cca gga ctg ccg gga cct cga ggg gac ccc       145
Pro Gly His Pro Gly Leu Pro Gly Leu Pro Gly Pro Arg Gly Asp Pro
            35                  40                  45 ggg ccg cga gga gag gcg gga ccc gcg ggg ccc acc ggg cct gcc ggg       193
```

|  |  |  |  |  |  |  |  |  |  |  |  |  |  |  |  |
|---|---|---|---|---|---|---|---|---|---|---|---|---|---|---|---|
| Gly | Pro | Arg | Gly | Glu | Ala | Gly | Pro | Ala | Gly | Pro | Thr | Gly | Pro | Ala | Gly |
|  | 50 |  |  |  | 55 |  |  |  | 60 |  |  |  |  |  |  |

```
gag tgc tcg gtg cct ccg cga tcc gcc ttc agc gcc aag cgc tcc gag    241
Glu Cys Ser Val Pro Pro Arg Ser Ala Phe Ser Ala Lys Arg Ser Glu
 65              70                  75                  80 agc cgg gtg cct ccg ccg tct gac gca ccc ttg ccc ttc gac cgc gtg    289
Ser Arg Val Pro Pro Pro Ser Asp Ala Pro Leu Pro Phe Asp Arg Val
                 85                  90                  95 ctg gtg aac gag cag gga cat tac gac gcc gtc acc ggc aag ttc acc    337
Leu Val Asn Glu Gln Gly His Tyr Asp Ala Val Thr Gly Lys Phe Thr
            100                 105                 110 tgc cag gtg cct ggg gtc tac tac ttc gcc gtc cat gcc acc gtc tac    385
Cys Gln Val Pro Gly Val Tyr Tyr Phe Ala Val His Ala Thr Val Tyr
        115                 120                 125 cgg gcc agc ctg cag ttt gat ctg gtg aag aat ggc gaa tcc att gcc    433
Arg Ala Ser Leu Gln Phe Asp Leu Val Lys Asn Gly Glu Ser Ile Ala
    130                 135                 140 tct ttc ttc cag ttt ttc ggg ggg tgg ccc aag cca gcc tcg ctc tcg    481
Ser Phe Phe Gln Phe Phe Gly Gly Trp Pro Lys Pro Ala Ser Leu Ser
145                 150                 155                 160 ggg ggg gcc atg gtg agg ctg gag cct gag gac caa gtg tgg gtg cag    529
Gly Gly Ala Met Val Arg Leu Glu Pro Glu Asp Gln Val Trp Val Gln
                165                 170                 175 gtg ggt gtg ggt gac tac att ggc atc tat gcc agc atc aag aca gac    577
Val Gly Val Gly Asp Tyr Ile Gly Ile Tyr Ala Ser Ile Lys Thr Asp
            180                 185                 190 agc acc ttc tcc gga ttt ctg gtg tac tcc gac tgg cgc agc tcc cca    625
Ser Thr Phe Ser Gly Phe Leu Val Tyr Ser Asp Trp Arg Ser Ser Pro
        195                 200                 205 gtc ttt gct gtc gac ggc                                            643
Val Phe Ala Val Asp Gly
    210

<210> SEQ ID NO 14
<211> LENGTH: 214
<212> TYPE: PRT
<213> ORGANISM: Homo sapiens

<400> SEQUENCE: 14

Thr Gly Ser Thr Met Arg Pro Leu Leu Val Leu Leu Leu Gly Leu
  1               5                  10                  15

Ala Ala Gly Ser Pro Pro Leu Asp Asp Asn Lys Ile Pro Ser Leu Cys
                 20                  25                  30

Pro Gly His Pro Gly Leu Pro Gly Leu Pro Gly Pro Arg Gly Asp Pro
            35                  40                  45

Gly Pro Arg Gly Glu Ala Gly Pro Ala Gly Pro Thr Gly Pro Ala Gly
        50                  55                  60

Glu Cys Ser Val Pro Pro Arg Ser Ala Phe Ser Ala Lys Arg Ser Glu
 65                  70                  75                  80

Ser Arg Val Pro Pro Pro Ser Asp Ala Pro Leu Pro Phe Asp Arg Val
                 85                  90                  95

Leu Val Asn Glu Gln Gly His Tyr Asp Ala Val Thr Gly Lys Phe Thr
            100                 105                 110

Cys Gln Val Pro Gly Val Tyr Tyr Phe Ala Val His Ala Thr Val Tyr
        115                 120                 125

Arg Ala Ser Leu Gln Phe Asp Leu Val Lys Asn Gly Glu Ser Ile Ala
    130                 135                 140

Ser Phe Phe Gln Phe Phe Gly Gly Trp Pro Lys Pro Ala Ser Leu Ser
```

```
                  145                 150                 155                 160
Gly Gly Ala Met Val Arg Leu Glu Pro Glu Asp Gln Val Trp Val Gln
                    165                 170                 175

Val Gly Val Gly Asp Tyr Ile Gly Ile Tyr Ala Ser Ile Lys Thr Asp
                180                 185                 190

Ser Thr Phe Ser Gly Phe Leu Val Tyr Ser Asp Trp Arg Ser Ser Pro
            195                 200                 205

Val Phe Ala Val Asp Gly
        210

<210> SEQ ID NO 15
<211> LENGTH: 595
<212> TYPE: DNA
<213> ORGANISM: Homo sapiens
<220> FEATURE:
<221> NAME/KEY: CDS
<222> LOCATION: (2)..(595)

<400> SEQUENCE: 15 c acc gga tcc tcg ccc cca ctg gac gac aac aag atc ccc agc ctc tgc        49
  Thr Gly Ser Ser Pro Pro Leu Asp Asp Asn Lys Ile Pro Ser Leu Cys
  1               5                  10                  15 ccg ggg cac ccc ggc ctt cca gga ctg ccg gga cct cga ggg gac ccc          97
Pro Gly His Pro Gly Leu Pro Gly Leu Pro Gly Pro Arg Gly Asp Pro
             20                  25                  30 ggg ccg cga gga gag gcg gga ccc gcg ggg ccc acc ggg cct gcc ggg         145
Gly Pro Arg Gly Glu Ala Gly Pro Ala Gly Pro Thr Gly Pro Ala Gly
         35                  40                  45 gag tgc tcg gtg cct ccg cga tcc gcc ttc agc gcc aag cgc tcc gag         193
Glu Cys Ser Val Pro Pro Arg Ser Ala Phe Ser Ala Lys Arg Ser Glu
 50                  55                  60 agc cgg gtg cct ccg ccg tct gac gca ccc ttg ccc ttc gac cgc gtg         241
Ser Arg Val Pro Pro Pro Ser Asp Ala Pro Leu Pro Phe Asp Arg Val
 65                  70                  75                  80 ctg gtg aac gag cag gga cat tac gac gcc gtc acc ggc aag ttc acc         289
Leu Val Asn Glu Gln Gly His Tyr Asp Ala Val Thr Gly Lys Phe Thr
                 85                  90                  95 tgc cag gtg cct ggg gtc tac tac ttc gcc gtc cat gcc acc gtc tac         337
Cys Gln Val Pro Gly Val Tyr Tyr Phe Ala Val His Ala Thr Val Tyr
            100                 105                 110 cgg gcc agc ctg cag ttt gat ctg gtg aag aat ggc gaa tcc att gcc         385
Arg Ala Ser Leu Gln Phe Asp Leu Val Lys Asn Gly Glu Ser Ile Ala
        115                 120                 125 tct ttc ttc cag ttt ttc ggg ggg tgg ccc aag cca gcc tcg ctc tcg         433
Ser Phe Phe Gln Phe Phe Gly Gly Trp Pro Lys Pro Ala Ser Leu Ser
    130                 135                 140 ggg ggg gcc atg gtg agg ctg gag cct gag gac caa gtg tgg gtg cag         481
Gly Gly Ala Met Val Arg Leu Glu Pro Glu Asp Gln Val Trp Val Gln
145                 150                 155                 160 gtg ggt gtg ggt gac tac att ggc atc tat gcc agc atc aag aca gac         529
Val Gly Val Gly Asp Tyr Ile Gly Ile Tyr Ala Ser Ile Lys Thr Asp
                165                 170                 175 agc acc ttc tcc gga ttt ctg gtg tac tcc gac tgg cgc agc tcc cca         577
Ser Thr Phe Ser Gly Phe Leu Val Tyr Ser Asp Trp Arg Ser Ser Pro
            180                 185                 190 gtc ttt gct gtc gac ggc                                                  595
Val Phe Ala Val Asp Gly
        195

<210> SEQ ID NO 16
```

-continued

```
<211> LENGTH: 198
<212> TYPE: PRT
<213> ORGANISM: Homo sapiens

<400> SEQUENCE: 16

Thr Gly Ser Ser Pro Pro Leu Asp Asp Asn Lys Ile Pro Ser Leu Cys
 1               5                  10                  15

Pro Gly His Pro Gly Leu Pro Gly Leu Pro Gly Pro Arg Gly Asp Pro
                20                  25                  30

Gly Pro Arg Gly Glu Ala Gly Pro Ala Gly Pro Thr Gly Pro Ala Gly
            35                  40                  45

Glu Cys Ser Val Pro Pro Arg Ser Ala Phe Ser Ala Lys Arg Ser Glu
    50                  55                  60

Ser Arg Val Pro Pro Ser Asp Ala Pro Leu Pro Phe Asp Arg Val
 65                  70                  75                  80

Leu Val Asn Glu Gln Gly His Tyr Asp Ala Val Thr Gly Lys Phe Thr
                85                  90                  95

Cys Gln Val Pro Gly Val Tyr Tyr Phe Ala Val His Ala Thr Val Tyr
                100                 105                 110

Arg Ala Ser Leu Gln Phe Asp Leu Val Lys Asn Gly Glu Ser Ile Ala
            115                 120                 125

Ser Phe Phe Gln Phe Gly Gly Trp Pro Lys Pro Ala Ser Leu Ser
    130                 135                 140

Gly Gly Ala Met Val Arg Leu Glu Pro Glu Asp Gln Val Trp Val Gln
145                 150                 155                 160

Val Gly Val Gly Asp Tyr Ile Gly Ile Tyr Ala Ser Ile Lys Thr Asp
                165                 170                 175

Ser Thr Phe Ser Gly Phe Leu Val Tyr Ser Asp Trp Arg Ser Ser Pro
            180                 185                 190

Val Phe Ala Val Asp Gly
        195

<210> SEQ ID NO 17
<211> LENGTH: 500
<212> TYPE: DNA
<213> ORGANISM: Homo sapiens
<220> FEATURE:
<221> NAME/KEY: CDS
<222> LOCATION: (182)..(493)

<400> SEQUENCE: 17
cccggagccg accggggcc accgcgcccg ctctgctccg acaccgcgcc ccctggacag        60
ccgccctctc ctccaggccc gtggggctgg ccctgcaccg ccgagcttcc cgggatgagg      120
gcccccggtg tggtcacccg gcgcgcccca ggtcgctgag ggaccccggc caggcgcgga      180 g atg ggg gtg cac gaa tgt cct gcc tgg ctg tgg ctt ctc ctg tcc ctg      229
  Met Gly Val His Glu Cys Pro Ala Trp Leu Trp Leu Leu Leu Ser Leu
   1               5                  10                  15 ctg tcg ctc cct ctg ggc ctc cca gtc ctg ggc gcc cca cca cgc ctc        277
Leu Ser Leu Pro Leu Gly Leu Pro Val Leu Gly Ala Pro Pro Arg Leu
                20                  25                  30 atc tgt gac agc cga gtc ctg gag agg tac ctc ttg gag gcc aag gag        325
Ile Cys Asp Ser Arg Val Leu Glu Arg Tyr Leu Leu Glu Ala Lys Glu
            35                  40                  45 gcc gag aat atc acg aag gaa gcc atc tcc cct cca gat gcg gcc tca        373
Ala Glu Asn Ile Thr Lys Glu Ala Ile Ser Pro Pro Asp Ala Ala Ser
    50                  55                  60 gct gct cca ctc cga aca atc act gct gac act ttc cgc aaa ctc ttc        421
Ala Ala Pro Leu Arg Thr Ile Thr Ala Asp Thr Phe Arg Lys Leu Phe
```

-continued

```
Ala Ala Pro Leu Arg Thr Ile Thr Ala Asp Thr Phe Arg Lys Leu Phe
 65                  70                  75                  80 cga gtc tac tcc aat ttc ctc cgg gga aag ctg aag ctg tac aca ggg    469
Arg Val Tyr Ser Asn Phe Leu Arg Gly Lys Leu Lys Leu Tyr Thr Gly
             85                  90                  95 gag gcc tgc agg aca ggg gac aga tgaccag                            500
Glu Ala Cys Arg Thr Gly Asp Arg
            100
```

<210> SEQ ID NO 18
<211> LENGTH: 104
<212> TYPE: PRT
<213> ORGANISM: Homo sapiens

<400> SEQUENCE: 18

```
Met Gly Val His Glu Cys Pro Ala Trp Leu Trp Leu Leu Leu Ser Leu
 1               5                  10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Lys Glu Ala Ile Ser Pro Pro Asp Ala Ala Ser
    50                  55                  60

Ala Ala Pro Leu Arg Thr Ile Thr Ala Asp Thr Phe Arg Lys Leu Phe
 65                  70                  75                  80

Arg Val Tyr Ser Asn Phe Leu Arg Gly Lys Leu Lys Leu Tyr Thr Gly
             85                  90                  95

Glu Ala Cys Arg Thr Gly Asp Arg
            100
```

<210> SEQ ID NO 19
<211> LENGTH: 324
<212> TYPE: DNA
<213> ORGANISM: Homo sapiens
<220> FEATURE:
<221> NAME/KEY: CDS
<222> LOCATION: (3)..(317)

<400> SEQUENCE: 19

```
cc tgg cta tct gtt cta gaa tgt cct gcc tgg ctg tgg ctt ctc ctg    47
   Trp Leu Ser Val Leu Glu Cys Pro Ala Trp Leu Trp Leu Leu Leu
    1               5                  10                  15 tcc ctg ctg tcg ctc cct ctg ggc ctc cca gtc ctg ggc gcc cca        95
Ser Leu Leu Ser Leu Pro Leu Gly Leu Pro Val Leu Gly Ala Pro Pro
            20                  25                  30 cgc ctc atc tgt gac agc cga gtc ctg gag agg tac ctc ttg gag gcc   143
Arg Leu Ile Cys Asp Ser Arg Val Leu Glu Arg Tyr Leu Leu Glu Ala
        35                  40                  45 aag gag gcc gag aat atc acg aag gaa gcc atc tcc cct cca gat gcg   191
Lys Glu Ala Glu Asn Ile Thr Lys Glu Ala Ile Ser Pro Pro Asp Ala
    50                  55                  60 gcc tca gct gct cca ctc cga aca atc act gct gac act ttc cgc aaa   239
Ala Ser Ala Ala Pro Leu Arg Thr Ile Thr Ala Asp Thr Phe Arg Lys
 65                  70                  75 ctc ttc cga gtc tac tcc aat ttc ctc cgg gga aag ctg aag ctg tac   287
Leu Phe Arg Val Tyr Ser Asn Phe Leu Arg Gly Lys Leu Lys Leu Tyr
 80                  85                  90                  95 aca ggg gag gcc tgc agg aca ggg gac aga tgaccag                   324
Thr Gly Glu Ala Cys Arg Thr Gly Asp Arg
               100                 105
```

<210> SEQ ID NO 20
<211> LENGTH: 105
<212> TYPE: PRT
<213> ORGANISM: Homo sapiens

<400> SEQUENCE: 20

```
Trp Leu Ser Val Leu Glu Cys Pro Ala Trp Leu Trp Leu Leu Leu Ser
  1               5                  10                  15

Leu Leu Ser Leu Pro Leu Gly Leu Pro Val Leu Gly Ala Pro Pro Arg
             20                  25                  30

Leu Ile Cys Asp Ser Arg Val Leu Glu Arg Tyr Leu Leu Glu Ala Lys
         35                  40                  45

Glu Ala Glu Asn Ile Thr Lys Glu Ala Ile Ser Pro Pro Asp Ala Ala
     50                  55                  60

Ser Ala Ala Pro Leu Arg Thr Ile Thr Ala Asp Thr Phe Arg Lys Leu
 65                  70                  75                  80

Phe Arg Val Tyr Ser Asn Phe Leu Arg Gly Lys Leu Lys Leu Tyr Thr
                 85                  90                  95

Gly Glu Ala Cys Arg Thr Gly Asp Arg
            100                 105
```

<210> SEQ ID NO 21
<211> LENGTH: 282
<212> TYPE: DNA
<213> ORGANISM: Homo sapiens
<220> FEATURE:
<221> NAME/KEY: CDS
<222> LOCATION: (1)..(282)

<400> SEQUENCE: 21

```
gga tcc tgg ctt ctc ctg tcc ctg ctg tcg ctc cct ctg ggc ctc cca        48
Gly Ser Trp Leu Leu Leu Ser Leu Leu Ser Leu Pro Leu Gly Leu Pro
  1               5                  10                  15 gtc ctg ggc gcc cca cca cgc ctc atc tgt gac agc cga gtc ctg gag        96
Val Leu Gly Ala Pro Pro Arg Leu Ile Cys Asp Ser Arg Val Leu Glu
             20                  25                  30 agg tac ctc ttg gag gcc aag gag gcc gag aat atc acg aag gaa gcc       144
Arg Tyr Leu Leu Glu Ala Lys Glu Ala Glu Asn Ile Thr Lys Glu Ala
         35                  40                  45 atc tcc cct cca gat gcg gcc tca gct gct cca ctc cga aca atc act       192
Ile Ser Pro Pro Asp Ala Ala Ser Ala Ala Pro Leu Arg Thr Ile Thr
     50                  55                  60 gct gac act ttc cgc aaa ctc ttc cga gtc tac tcc aat ttc ctc cgg       240
Ala Asp Thr Phe Arg Lys Leu Phe Arg Val Tyr Ser Asn Phe Leu Arg
 65                  70                  75                  80 gga aag ctg aag ctg tac aca ggg gag gcc tgc agg ctc gag               282
Gly Lys Leu Lys Leu Tyr Thr Gly Glu Ala Cys Arg Leu Glu
                 85                  90
```

<210> SEQ ID NO 22
<211> LENGTH: 94
<212> TYPE: PRT
<213> ORGANISM: Homo sapiens

<400> SEQUENCE: 22

```
Gly Ser Trp Leu Leu Leu Ser Leu Leu Ser Leu Pro Leu Gly Leu Pro
  1               5                  10                  15

Val Leu Gly Ala Pro Pro Arg Leu Ile Cys Asp Ser Arg Val Leu Glu
             20                  25                  30

Arg Tyr Leu Leu Glu Ala Lys Glu Ala Glu Asn Ile Thr Lys Glu Ala
```

```
                      35                  40                  45
Ile Ser Pro Pro Asp Ala Ala Ser Ala Ala Pro Leu Arg Thr Ile Thr
 50                  55                  60

Ala Asp Thr Phe Arg Lys Leu Phe Arg Val Tyr Ser Asn Phe Leu Arg
 65                  70                  75                  80

Gly Lys Leu Lys Leu Tyr Thr Gly Glu Ala Cys Arg Leu Glu
                 85                  90

<210> SEQ ID NO 23
<211> LENGTH: 333
<212> TYPE: DNA
<213> ORGANISM: Homo sapiens
<220> FEATURE:
<221> NAME/KEY: CDS
<222> LOCATION: (1)..(321)

<400> SEQUENCE: 23 cgc gga tcc atg ggg gtg cac gaa tgt cct gcc tgg ctg tgg ctt ctc       48
Arg Gly Ser Met Gly Val His Glu Cys Pro Ala Trp Leu Trp Leu Leu
 1               5                  10                  15 ctg tcc ctg ctg tcg ctc cct ctg ggc ctc cca gtc ctg ggc gcc cca       96
Leu Ser Leu Leu Ser Leu Pro Leu Gly Leu Pro Val Leu Gly Ala Pro
                 20                  25                  30 cca cgc ctc atc tgt gac agc cga gtc ctg gag agg tac ctc ttg gag      144
Pro Arg Leu Ile Cys Asp Ser Arg Val Leu Glu Arg Tyr Leu Leu Glu
             35                  40                  45 gcc aag gag gcc gag aat atc acg aag gaa gcc atc tcc cct cca gat      192
Ala Lys Glu Ala Glu Asn Ile Thr Lys Glu Ala Ile Ser Pro Pro Asp
 50                  55                  60 gcg gcc tca gct gct cca ctc cga aca atc act gct gac act ttc cgc      240
Ala Ala Ser Ala Ala Pro Leu Arg Thr Ile Thr Ala Asp Thr Phe Arg
 65                  70                  75                  80 aaa ctc ttc cga gtc tac tcc aat ttc ctc cgg gga aag ctg aag ctg      288
Lys Leu Phe Arg Val Tyr Ser Asn Phe Leu Arg Gly Lys Leu Lys Leu
                 85                  90                  95 tac aca ggg gag gcc tgc agg aca ggg gac aga tgactcgagc gg            333
Tyr Thr Gly Glu Ala Cys Arg Thr Gly Asp Arg
                100                 105

<210> SEQ ID NO 24
<211> LENGTH: 107
<212> TYPE: PRT
<213> ORGANISM: Homo sapiens

<400> SEQUENCE: 24

Arg Gly Ser Met Gly Val His Glu Cys Pro Ala Trp Leu Trp Leu Leu
 1               5                  10                  15

Leu Ser Leu Leu Ser Leu Pro Leu Gly Leu Pro Val Leu Gly Ala Pro
                 20                  25                  30

Pro Arg Leu Ile Cys Asp Ser Arg Val Leu Glu Arg Tyr Leu Leu Glu
             35                  40                  45

Ala Lys Glu Ala Glu Asn Ile Thr Lys Glu Ala Ile Ser Pro Pro Asp
 50                  55                  60

Ala Ala Ser Ala Ala Pro Leu Arg Thr Ile Thr Ala Asp Thr Phe Arg
 65                  70                  75                  80

Lys Leu Phe Arg Val Tyr Ser Asn Phe Leu Arg Gly Lys Leu Lys Leu
                 85                  90                  95

Tyr Thr Gly Glu Ala Cys Arg Thr Gly Asp Arg
                100                 105
```

<210> SEQ ID NO 25
<211> LENGTH: 330
<212> TYPE: DNA
<213> ORGANISM: Homo sapiens
<220> FEATURE:
<221> NAME/KEY: CDS
<222> LOCATION: (1)..(330)

<400> SEQUENCE: 25

| cgc | gga | tcc | atg | ggg | gtg | cac | gaa | tgt | cct | gcc | tgg | ctg | tgg | ctt | ctc | 48 |
| Arg | Gly | Ser | Met | Gly | Val | His | Glu | Cys | Pro | Ala | Trp | Leu | Trp | Leu | Leu | |
| 1 | | | | 5 | | | | | 10 | | | | | 15 | | |

| ctg | tcc | ctg | ctg | tcg | ctc | cct | ctg | ggc | ctc | cca | gtc | ctg | ggc | gcc | cca | 96 |
| Leu | Ser | Leu | Leu | Ser | Leu | Pro | Leu | Gly | Leu | Pro | Val | Leu | Gly | Ala | Pro | |
| | | | | 20 | | | | | 25 | | | | | 30 | | |

| cca | cgc | ctc | atc | tgt | gac | agc | cga | gtc | ctg | gag | agg | tac | ctc | ttg | gag | 144 |
| Pro | Arg | Leu | Ile | Cys | Asp | Ser | Arg | Val | Leu | Glu | Arg | Tyr | Leu | Leu | Glu | |
| | | | 35 | | | | | 40 | | | | | 45 | | | |

| gcc | aag | gag | gcc | gag | aat | atc | acg | aag | gaa | gcc | atc | tcc | cct | cca | gat | 192 |
| Ala | Lys | Glu | Ala | Glu | Asn | Ile | Thr | Lys | Glu | Ala | Ile | Ser | Pro | Pro | Asp | |
| | 50 | | | | | 55 | | | | | 60 | | | | | |

| gcg | gcc | tca | gct | gct | cca | ctc | cga | aca | atc | act | gct | gac | act | ttc | cgc | 240 |
| Ala | Ala | Ser | Ala | Ala | Pro | Leu | Arg | Thr | Ile | Thr | Ala | Asp | Thr | Phe | Arg | |
| 65 | | | | | 70 | | | | | 75 | | | | | 80 | |

| aaa | ctc | ttc | cga | gtc | tac | tcc | aat | ttc | ctc | cgg | gga | aag | ctg | aag | ctg | 288 |
| Lys | Leu | Phe | Arg | Val | Tyr | Ser | Asn | Phe | Leu | Arg | Gly | Lys | Leu | Lys | Leu | |
| | | | | 85 | | | | | 90 | | | | | 95 | | |

| tac | aca | ggg | gag | gcc | tgc | agg | aca | ggg | gac | aga | ctc | gag | cgg | | | 330 |
| Tyr | Thr | Gly | Glu | Ala | Cys | Arg | Thr | Gly | Asp | Arg | Leu | Glu | Arg | | | |
| | | | 100 | | | | | 105 | | | | | 110 | | | |

<210> SEQ ID NO 26
<211> LENGTH: 110
<212> TYPE: PRT
<213> ORGANISM: Homo sapiens

<400> SEQUENCE: 26

Arg Gly Ser Met Gly Val His Glu Cys Pro Ala Trp Leu Trp Leu Leu
1               5                   10                  15

Leu Ser Leu Leu Ser Leu Pro Leu Gly Leu Pro Val Leu Gly Ala Pro
            20                  25                  30

Pro Arg Leu Ile Cys Asp Ser Arg Val Leu Glu Arg Tyr Leu Leu Glu
        35                  40                  45

Ala Lys Glu Ala Glu Asn Ile Thr Lys Glu Ala Ile Ser Pro Pro Asp
    50                  55                  60

Ala Ala Ser Ala Ala Pro Leu Arg Thr Ile Thr Ala Asp Thr Phe Arg
65                  70                  75                  80

Lys Leu Phe Arg Val Tyr Ser Asn Phe Leu Arg Gly Lys Leu Lys Leu
                85                  90                  95

Tyr Thr Gly Glu Ala Cys Arg Thr Gly Asp Arg Leu Glu Arg
            100                 105                 110

<210> SEQ ID NO 27
<211> LENGTH: 333
<212> TYPE: DNA
<213> ORGANISM: Homo sapiens
<220> FEATURE:
<221> NAME/KEY: CDS
<222> LOCATION: (1)..(321)

<400> SEQUENCE: 27

```
cgc gga tcc atg ggg gtg cac gaa tgt cct gcc tgg ctg tgg ctt ctc     48
Arg Gly Ser Met Gly Val His Glu Cys Pro Ala Trp Leu Trp Leu Leu
 1               5                  10                  15 ctg tcc ctg ctg tcg ctc cct ctg ggc ctc cca gtc ctg ggc gcc cca     96
Leu Ser Leu Leu Ser Leu Pro Leu Gly Leu Pro Val Leu Gly Ala Pro
             20                  25                  30 cca cgc ctc atc tgt gac agc cga gtc ctg gag agg tac ctc ttg gag    144
Pro Arg Leu Ile Cys Asp Ser Arg Val Leu Glu Arg Tyr Leu Leu Glu
         35                  40                  45 gcc aag gag gcc gag aat atc acg aag gaa gcc atc tcc cct cca gat    192
Ala Lys Glu Ala Glu Asn Ile Thr Lys Glu Ala Ile Ser Pro Pro Asp
 50                  55                  60 gcg gcc tca gct gct cca ctc cga aca atc act gct gac act ttc cgc    240
Ala Ala Ser Ala Ala Pro Leu Arg Thr Ile Thr Ala Asp Thr Phe Arg
 65                  70                  75                  80 aaa ctc ttc cga gtc tac tcc aat ttc ctc cgg gga aag ctg aag ctg    288
Lys Leu Phe Arg Val Tyr Ser Asn Phe Leu Arg Gly Lys Leu Lys Leu
                 85                  90                  95 tac aca ggg gag gcc tgc agg aca ggg gac aga tgactcgagc gg          333
Tyr Thr Gly Glu Ala Cys Arg Thr Gly Asp Arg
             100                 105

<210> SEQ ID NO 28
<211> LENGTH: 107
<212> TYPE: PRT
<213> ORGANISM: Homo sapiens

<400> SEQUENCE: 28

Arg Gly Ser Met Gly Val His Glu Cys Pro Ala Trp Leu Trp Leu Leu
 1               5                  10                  15

Leu Ser Leu Leu Ser Leu Pro Leu Gly Leu Pro Val Leu Gly Ala Pro
             20                  25                  30

Pro Arg Leu Ile Cys Asp Ser Arg Val Leu Glu Arg Tyr Leu Leu Glu
         35                  40                  45

Ala Lys Glu Ala Glu Asn Ile Thr Lys Glu Ala Ile Ser Pro Pro Asp
 50                  55                  60

Ala Ala Ser Ala Ala Pro Leu Arg Thr Ile Thr Ala Asp Thr Phe Arg
 65                  70                  75                  80

Lys Leu Phe Arg Val Tyr Ser Asn Phe Leu Arg Gly Lys Leu Lys Leu
                 85                  90                  95

Tyr Thr Gly Glu Ala Cys Arg Thr Gly Asp Arg
             100                 105

<210> SEQ ID NO 29
<211> LENGTH: 684
<212> TYPE: DNA
<213> ORGANISM: Homo sapiens
<220> FEATURE:
<221> NAME/KEY: CDS
<222> LOCATION: (18)..(599)

<400> SEQUENCE: 29
caatcacagg caggaag atg aag gtt ctg tgg gct gcg ttg ctg gtc aca      50
                  Met Lys Val Leu Trp Ala Ala Leu Leu Val Thr
                   1               5                  10 ttc ctg gca gga tgc cag gcc aag gtg gag caa gcg gtg gag aca gag     98
Phe Leu Ala Gly Cys Gln Ala Lys Val Glu Gln Ala Val Glu Thr Glu
             15                  20                  25 ccg gag ccc gag ctg cgc cag cag acc gag tgg cag agc ggc cag cgc    146
Pro Glu Pro Glu Leu Arg Gln Gln Thr Glu Trp Gln Ser Gly Gln Arg
         30                  35                  40
```

```
tgg gaa ctg gca ctg ggt cgc ttt tgg gat tac ctg cgc tgg gtg cag      194
Trp Glu Leu Ala Leu Gly Arg Phe Trp Asp Tyr Leu Arg Trp Val Gln
             45                  50                  55 aca ctg tct gag cag gtg cag gag gag ctg ctc agc tcc cag gtc acc      242
Thr Leu Ser Glu Gln Val Gln Glu Glu Leu Leu Ser Ser Gln Val Thr
 60                  65                  70                  75 cag gaa ctg agg gcg ctg atg gac gag acc atg aag gag ttg aag gcc      290
Gln Glu Leu Arg Ala Leu Met Asp Glu Thr Met Lys Glu Leu Lys Ala
                 80                  85                  90 tac aaa tcg gaa ctg gag gaa caa ctg acc ccg gtg gcg gag gag acg      338
Tyr Lys Ser Glu Leu Glu Glu Gln Leu Thr Pro Val Ala Glu Glu Thr
                     95                 100                 105 cgg gca cgg ctg tcc aag gag ctg cag gcg gcg cag gcc cgg ctg ggc      386
Arg Ala Arg Leu Ser Lys Glu Leu Gln Ala Ala Gln Ala Arg Leu Gly
            110                 115                 120 gcg gac gag gtg aag ggg cag gtg gcg gag gtg cgc gcc aag ctg gag      434
Ala Asp Glu Val Lys Gly Gln Val Ala Glu Val Arg Ala Lys Leu Glu
        125                 130                 135 gag cag gcc cag cag ata cgc ctg cag gcc gag gcc ttc cag gcc cgc      482
Glu Gln Ala Gln Gln Ile Arg Leu Gln Ala Glu Ala Phe Gln Ala Arg
140                 145                 150                 155 ctc aag agc tgg ttc gag ccc ctg gtg gaa gac atg cag cgc cag tgg      530
Leu Lys Ser Trp Phe Glu Pro Leu Val Glu Asp Met Gln Arg Gln Trp
                    160                 165                 170 gcc ggg ctg gtg gag aag gtg cag gct gcc gtg ggc acc agc gcc gcc      578
Ala Gly Leu Val Glu Lys Val Gln Ala Ala Val Gly Thr Ser Ala Ala
                175                 180                 185 cct gtg ccc agc gac aat cac tgaacgccga agcctgcagc catgcgaccc         629
Pro Val Pro Ser Asp Asn His
            190 cacgccaccc cgtgcctcct gcctccgcgc agcctgcagc gggagaccct gtccc         684

<210> SEQ ID NO 30
<211> LENGTH: 194
<212> TYPE: PRT
<213> ORGANISM: Homo sapiens

<400> SEQUENCE: 30

Met Lys Val Leu Trp Ala Ala Leu Leu Val Thr Phe Leu Ala Gly Cys
  1               5                  10                  15

Gln Ala Lys Val Glu Gln Ala Val Glu Thr Glu Pro Glu Pro Glu Leu
                 20                  25                  30

Arg Gln Gln Thr Glu Trp Gln Ser Gly Gln Arg Trp Glu Leu Ala Leu
             35                  40                  45

Gly Arg Phe Trp Asp Tyr Leu Arg Trp Val Gln Thr Leu Ser Glu Gln
         50                  55                  60

Val Gln Glu Glu Leu Leu Ser Ser Gln Val Thr Gln Glu Leu Arg Ala
 65                  70                  75                  80

Leu Met Asp Glu Thr Met Lys Glu Leu Lys Ala Tyr Lys Ser Glu Leu
                 85                  90                  95

Glu Glu Gln Leu Thr Pro Val Ala Glu Thr Arg Ala Arg Leu Ser
            100                 105                 110

Lys Glu Leu Gln Ala Ala Gln Ala Arg Leu Gly Ala Asp Glu Val Lys
        115                 120                 125

Gly Gln Val Ala Glu Val Arg Ala Lys Leu Glu Glu Gln Ala Gln Gln
    130                 135                 140

Ile Arg Leu Gln Ala Glu Ala Phe Gln Ala Arg Leu Lys Ser Trp Phe
```

```
                145                 150                 155                 160
Glu Pro Leu Val Glu Asp Met Gln Arg Gln Trp Ala Gly Leu Val Glu
                    165                 170                 175

Lys Val Gln Ala Ala Val Gly Thr Ser Ala Ala Pro Val Pro Ser Asp
                180                 185                 190

Asn His

<210> SEQ ID NO 31
<211> LENGTH: 802
<212> TYPE: DNA
<213> ORGANISM: Homo sapiens
<220> FEATURE:
<221> NAME/KEY: CDS
<222> LOCATION: (18)..(716)

<400> SEQUENCE: 31
caatcacagg caggaag atg aag gtt ctg tgg gct gcg ttg ctg gtc aca         50
                   Met Lys Val Leu Trp Ala Ala Leu Leu Val Thr
                     1               5                  10 ttc ctg gca gga tgc cag gcc aag gtg gag caa gcg gtg gag aca gag       98
Phe Leu Ala Gly Cys Gln Ala Lys Val Glu Gln Ala Val Glu Thr Glu
             15                  20                  25 ccg gag ccc gag ctg cgc cag cag acc gag tgg cag agc ggc cag cgc      146
Pro Glu Pro Glu Leu Arg Gln Gln Thr Glu Trp Gln Ser Gly Gln Arg
         30                  35                  40 tgg gaa ctg gca ctg ggt cgc ttt tgg gat tac ctg cgc tgg gtg cag      194
Trp Glu Leu Ala Leu Gly Arg Phe Trp Asp Tyr Leu Arg Trp Val Gln
     45                  50                  55 aca ctg tct gag cag gtg cag gag gag ctg ctc agc tcc cag gtc acc      242
Thr Leu Ser Glu Gln Val Gln Glu Glu Leu Leu Ser Ser Gln Val Thr
 60                  65                  70                  75 cag gaa ctg agg gcg ctg atg gac gag acc atg aag gag ttg aag gcc      290
Gln Glu Leu Arg Ala Leu Met Asp Glu Thr Met Lys Glu Leu Lys Ala
                 80                  85                  90 tac aaa tcg gaa ctg gag gaa caa ctg acc ccg gtg gcg gag gag acg      338
Tyr Lys Ser Glu Leu Glu Glu Gln Leu Thr Pro Val Ala Glu Glu Thr
             95                 100                 105 cgg gca cgg ctg tcc aag gag ctg ggg ccc ctg gtg gaa cag ggc cgc      386
Arg Ala Arg Leu Ser Lys Glu Leu Gly Pro Leu Val Glu Gln Gly Arg
         110                 115                 120 gtg cgg gcc gcc act gtg ggc ttc ctg gcc ggc cag ccg cta cag gag      434
Val Arg Ala Ala Thr Val Gly Phe Leu Ala Gly Gln Pro Leu Gln Glu
     125                 130                 135 cgg gcc cag gcc tgg ggc gag cgg ctg cgc gcg cgg atg gag gag atg      482
Arg Ala Gln Ala Trp Gly Glu Arg Leu Arg Ala Arg Met Glu Glu Met
140                 145                 150                 155 ggc agc cgg acc cgc gac cgc ctg gac gag gtg aag gag cag gtg gcg      530
Gly Ser Arg Thr Arg Asp Arg Leu Asp Glu Val Lys Glu Gln Val Ala
                 160                 165                 170 gag gtg cgc gcc aag ctg gag gag cag gcc cag cag ata cgc ctg cag      578
Glu Val Arg Ala Lys Leu Glu Glu Gln Ala Gln Gln Ile Arg Leu Gln
             175                 180                 185 gcc gag gcc ttc cag gcc cgc ctc aag agc tgg ttc gag ccc ctg gtg      626
Ala Glu Ala Phe Gln Ala Arg Leu Lys Ser Trp Phe Glu Pro Leu Val
         190                 195                 200 gaa gac atg cag cgc cag tgg gcc ggg ctg gtg gag aag gtg cag gct      674
Glu Asp Met Gln Arg Gln Trp Ala Gly Leu Val Glu Lys Val Gln Ala
 205                 210                 215 gcc gtg ggc acc agc gcc gcc cct gtg ccc agc gac aat cac                716
Ala Val Gly Thr Ser Ala Ala Pro Val Pro Ser Asp Asn His
```

```
                220                225                230 tgaacgccga agcctgcagc catgcgaccc cacgccaccc cgtgcctcct gcctccgcgc        776
agcctgcagc gggagaccct gtccct                                             802

<210> SEQ ID NO 32
<211> LENGTH: 233
<212> TYPE: PRT
<213> ORGANISM: Homo sapiens

<400> SEQUENCE: 32

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gly Pro Leu Val Glu Gln Gly Arg Val Arg Ala Ala Thr
        115                 120                 125

Val Gly Phe Leu Ala Gly Gln Pro Leu Gln Glu Arg Ala Gln Ala Trp
    130                 135                 140

Gly Glu Arg Leu Arg Ala Arg Met Glu Glu Met Gly Ser Arg Thr Arg
145                 150                 155                 160

Asp Arg Leu Asp Glu Val Lys Glu Gln Val Ala Glu Val Arg Ala Lys
                165                 170                 175

Leu Glu Glu Gln Ala Gln Gln Ile Arg Leu Gln Ala Glu Ala Phe Gln
            180                 185                 190

Ala Arg Leu Lys Ser Trp Phe Glu Pro Leu Val Glu Asp Met Gln Arg
        195                 200                 205

Gln Trp Ala Gly Leu Val Glu Lys Val Gln Ala Ala Val Gly Thr Ser
    210                 215                 220

Ala Ala Pro Val Pro Ser Asp Asn His
225                 230

<210> SEQ ID NO 33
<211> LENGTH: 788
<212> TYPE: DNA
<213> ORGANISM: Homo sapiens
<220> FEATURE:
<221> NAME/KEY: CDS
<222> LOCATION: (18)..(704)

<400> SEQUENCE: 33
caatcacagg caggaag atg aag gtt ctg tgg gct gcg ttg ctg gtc aca          50
                   Met Lys Val Leu Trp Ala Ala Leu Leu Val Thr
                   1               5                   10 ttc ctg gca gga tgc cag gcc aag gtg gag caa gcg gtg gag aca gag        98
Phe Leu Ala Gly Cys Gln Ala Lys Val Glu Gln Ala Val Glu Thr Glu
            15                  20                  25 ccg gag ccc gag ctg cgc cag cag acc gag tgg cag agc ggc cag cgc       146
```

```
Pro Glu Pro Glu Leu Arg Gln Gln Thr Glu Trp Gln Ser Gly Gln Arg
            30                  35                  40 tgg gaa ctg gca ctg ggt cgc ttt tgg gat tac ctg cgc tgg gtg cag       194
Trp Glu Leu Ala Leu Gly Arg Phe Trp Asp Tyr Leu Arg Trp Val Gln
        45                  50                  55 aca ctg tct gag cag gtg cag gag gag ctg ctc agc tcc cag gtc acc       242
Thr Leu Ser Glu Gln Val Gln Glu Glu Leu Leu Ser Ser Gln Val Thr
60                  65                  70                  75 cag gaa ctg agg gcg ctg atg gac gag acc atg aag gag ttg aag gcc       290
Gln Glu Leu Arg Ala Leu Met Asp Glu Thr Met Lys Glu Leu Lys Ala
                80                  85                  90 tac aaa tcg gaa ctg gag gaa caa ctg acc ccg gtg gcg gag gag acg       338
Tyr Lys Ser Glu Leu Glu Glu Gln Leu Thr Pro Val Ala Glu Glu Thr
            95                  100                 105 cgg gca cgg ctg tcc aag gag ctg cag gcg gcg cag gcc cgg ctg ggc       386
Arg Ala Arg Leu Ser Lys Glu Leu Gln Ala Ala Gln Ala Arg Leu Gly
        110                 115                 120 gcg gac atg gag gac gtg cgc ggc cgc ctg gtg cag tac cgc ggc gag       434
Ala Asp Met Glu Asp Val Arg Gly Arg Leu Val Gln Tyr Arg Gly Glu
125                 130                 135 gtg cag gcc atg ctc ggc cag agc acc gag gag ctg cgg gtg cgc ctc       482
Val Gln Ala Met Leu Gly Gln Ser Thr Glu Glu Leu Arg Val Arg Leu
140                 145                 150                 155 gcc tcc cac ctg cgc aag ctg cgt aag cgg ctc ctc cgc gat gcc gat       530
Ala Ser His Leu Arg Lys Leu Arg Lys Arg Leu Leu Arg Asp Ala Asp
                160                 165                 170 gac ctg gag gag cag gcc cag cag ata cgc ctg cag gcc gag gcc ttc       578
Asp Leu Glu Glu Gln Ala Gln Gln Ile Arg Leu Gln Ala Glu Ala Phe
                175                 180                 185 cag gcc cgc ctc aag agc tgg ttc gag ccc ctg gtg gaa gac atg cag       626
Gln Ala Arg Leu Lys Ser Trp Phe Glu Pro Leu Val Glu Asp Met Gln
            190                 195                 200 cgc cag tgg gcc ggg ctg gtg gag aag gtg cag gct gcc gtg ggc acc       674
Arg Gln Trp Ala Gly Leu Val Glu Lys Val Gln Ala Ala Val Gly Thr
        205                 210                 215 agc gcc gcc cct gtg ccc agc gac aat cac tgaacgccga agcctgcagc         724
Ser Ala Ala Pro Val Pro Ser Asp Asn His
220                 225 catgcgaccc cacgccaccc cgtgcctcct gcctccgcgc agcctgcagc gggagaccct     784
gtcc                                                                  788

<210> SEQ ID NO 34
<211> LENGTH: 229
<212> TYPE: PRT
<213> ORGANISM: Homo sapiens

<400> SEQUENCE: 34

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
```

-continued

```
                     85                  90                  95
Glu Glu Gln Leu Thr Pro Val Ala Glu Thr Arg Ala Arg Leu Ser
            100                 105                 110
Lys Glu Leu Gln Ala Ala Gln Ala Arg Leu Gly Ala Asp Met Glu Asp
            115                 120                 125
Val Arg Gly Arg Leu Val Gln Tyr Arg Gly Glu Val Gln Ala Met Leu
    130                 135                 140
Gly Gln Ser Thr Glu Glu Leu Arg Val Arg Leu Ala Ser His Leu Arg
145                 150                 155                 160
Lys Leu Arg Lys Arg Leu Leu Arg Asp Ala Asp Asp Leu Glu Glu Gln
                165                 170                 175
Ala Gln Gln Ile Arg Leu Gln Ala Glu Ala Phe Gln Ala Arg Leu Lys
            180                 185                 190
Ser Trp Phe Glu Pro Leu Val Glu Asp Met Gln Arg Gln Trp Ala Gly
            195                 200                 205
Leu Val Glu Lys Val Gln Ala Ala Val Gly Thr Ser Ala Ala Pro Val
    210                 215                 220
Pro Ser Asp Asn His
225

<210> SEQ ID NO 35
<211> LENGTH: 718
<212> TYPE: DNA
<213> ORGANISM: Homo sapiens
<220> FEATURE:
<221> NAME/KEY: CDS
<222> LOCATION: (2)..(718)

<400> SEQUENCE: 35 c acc gga tcc atg aag gtt ctg tgg gct gcg ttg ctg gtc aca ttc ctg      49
  Thr Gly Ser Met Lys Val Leu Trp Ala Ala Leu Leu Val Thr Phe Leu
    1               5                  10                  15 gca gga tgc cag gcc aag gtg gag caa gcg gtg gag aca gag ccg gag        97
Ala Gly Cys Gln Ala Lys Val Glu Gln Ala Val Glu Thr Glu Pro Glu
                20                  25                  30 ccc gag ctg cgc cag cag acc gag tgg cag agc ggc cag cgc tgg gaa        145
Pro Glu Leu Arg Gln Gln Thr Glu Trp Gln Ser Gly Gln Arg Trp Glu
            35                  40                  45 ctg gca ctg ggt cgc ttt tgg gat tac ctg cgc tgg gtg cag aca ctg        193
Leu Ala Leu Gly Arg Phe Trp Asp Tyr Leu Arg Trp Val Gln Thr Leu
        50                  55                  60 tct gag cag gtg cag gag gag ctc ctc agc tcc cag gtc acc cag gaa        241
Ser Glu Gln Val Gln Glu Glu Leu Leu Ser Ser Gln Val Thr Gln Glu
65                  70                  75                  80 ctg agg gcg ctg atg gac gag acc atg aag gag ttg aag gcc tac aaa        289
Leu Arg Ala Leu Met Asp Glu Thr Met Lys Glu Leu Lys Ala Tyr Lys
                85                  90                  95 tcg gaa ctg gag gaa caa ctg acc ccg gtg gcg gag gag acg cgg gca        337
Ser Glu Leu Glu Glu Gln Leu Thr Pro Val Ala Glu Glu Thr Arg Ala
            100                 105                 110 cgg ctg tcc aag gag ctg ggg ccc ctg gtg gaa cag ggc cgc gtg cgg        385
Arg Leu Ser Lys Glu Leu Gly Pro Leu Val Glu Gln Gly Arg Val Arg
        115                 120                 125 gcc gcc act gtg ggc ttc ctg gcc ggc cag ccg cta cag gag cgg gcc        433
Ala Ala Thr Val Gly Phe Leu Ala Gly Gln Pro Leu Gln Glu Arg Ala
    130                 135                 140 cag gcc tgg ggc gag cgg ctg cgc gcg cgg atg gag gag atg ggc agc        481
Gln Ala Trp Gly Glu Arg Leu Arg Ala Arg Met Glu Glu Met Gly Ser
145                 150                 155                 160
```

```
cgg acc cgc gac cgc ctg gac gag gtg aag gag cag gtg gcg gag gtg      529
Arg Thr Arg Asp Arg Leu Asp Glu Val Lys Glu Gln Val Ala Glu Val
            165                 170                 175 cgc gcc aag ctg gag gag cag gcc cag cag ata cgc ctg cag gcc gag      577
Arg Ala Lys Leu Glu Glu Gln Ala Gln Gln Ile Arg Leu Gln Ala Glu
        180                 185                 190 gcc ttc cag gcc cgc ctc aag agc tgg ttc gag ccc ctg gtg gaa gac      625
Ala Phe Gln Ala Arg Leu Lys Ser Trp Phe Glu Pro Leu Val Glu Asp
    195                 200                 205 atg cag cgc cag tgg gcc ggg ctg gtg gag aag gtg cag gct gcc gtg      673
Met Gln Arg Gln Trp Ala Gly Leu Val Glu Lys Val Gln Ala Ala Val
210                 215                 220 ggc acc agc gcc gcc cct gtg ccc agc gac aat cac ctc gag ggc          718
Gly Thr Ser Ala Ala Pro Val Pro Ser Asp Asn His Leu Glu Gly
225                 230                 235
```

<210> SEQ ID NO 36
<211> LENGTH: 239
<212> TYPE: PRT
<213> ORGANISM: Homo sapiens

<400> SEQUENCE: 36

```
Thr Gly Ser Met Lys Val Leu Trp Ala Ala Leu Leu Val Thr Phe Leu
 1               5                  10                  15

Ala Gly Cys Gln Ala Lys Val Glu Gln Ala Val Glu Thr Glu Pro Glu
            20                  25                  30

Pro Glu Leu Arg Gln Gln Thr Glu Trp Gln Ser Gly Gln Arg Trp Glu
        35                  40                  45

Leu Ala Leu Gly Arg Phe Trp Asp Tyr Leu Arg Trp Val Gln Thr Leu
    50                  55                  60

Ser Glu Gln Val Gln Glu Glu Leu Leu Ser Ser Gln Val Thr Gln Glu
65                  70                  75                  80

Leu Arg Ala Leu Met Asp Glu Thr Met Lys Glu Leu Lys Ala Tyr Lys
                85                  90                  95

Ser Glu Leu Glu Glu Gln Leu Thr Pro Val Ala Glu Glu Thr Arg Ala
            100                 105                 110

Arg Leu Ser Lys Glu Leu Gly Pro Leu Val Glu Gln Gly Arg Val Arg
        115                 120                 125

Ala Ala Thr Val Gly Phe Leu Ala Gly Gln Pro Leu Gln Glu Arg Ala
130                 135                 140

Gln Ala Trp Gly Glu Arg Leu Arg Ala Arg Met Glu Glu Met Gly Ser
145                 150                 155                 160

Arg Thr Arg Asp Arg Leu Asp Glu Val Lys Glu Gln Val Ala Glu Val
                165                 170                 175

Arg Ala Lys Leu Glu Glu Gln Ala Gln Gln Ile Arg Leu Gln Ala Glu
            180                 185                 190

Ala Phe Gln Ala Arg Leu Lys Ser Trp Phe Glu Pro Leu Val Glu Asp
        195                 200                 205

Met Gln Arg Gln Trp Ala Gly Leu Val Glu Lys Val Gln Ala Ala Val
    210                 215                 220

Gly Thr Ser Ala Ala Pro Val Pro Ser Asp Asn His Leu Glu Gly
225                 230                 235
```

<210> SEQ ID NO 37
<211> LENGTH: 664
<212> TYPE: DNA
<213> ORGANISM: Homo sapiens

```
<220> FEATURE:
<221> NAME/KEY: CDS
<222> LOCATION: (2)..(664)

<400> SEQUENCE: 37 c acc gga tcc aag gtg gag caa gcg gtg gag aca gag ccg gag ccc gag         49
  Thr Gly Ser Lys Val Glu Gln Ala Val Glu Thr Glu Pro Glu Pro Glu
    1               5                  10                  15 ctg cgc cag cag acc gag tgg cag agc ggc cag cgc tgg gaa ctg gca           97
Leu Arg Gln Gln Thr Glu Trp Gln Ser Gly Gln Arg Trp Glu Leu Ala
                 20                  25                  30 ctg ggt cgc ttt tgg gat tac ctg cgc tgg gtg cag aca ctg tct gag          145
Leu Gly Arg Phe Trp Asp Tyr Leu Arg Trp Val Gln Thr Leu Ser Glu
             35                  40                  45 cag gtg cag gag gag ctg ctc agc tcc cag gtc acc cag gaa ctg agg          193
Gln Val Gln Glu Glu Leu Leu Ser Ser Gln Val Thr Gln Glu Leu Arg
         50                  55                  60 gcg ctg atg gac gag acc atg aag gag ttg aag gcc tac aaa tcg gaa          241
Ala Leu Met Asp Glu Thr Met Lys Glu Leu Lys Ala Tyr Lys Ser Glu
 65                  70                  75                  80 ctg gag gaa caa ctg acc ccg gtg gcg gag gag acg cgg gca cgg ctg          289
Leu Glu Glu Gln Leu Thr Pro Val Ala Glu Glu Thr Arg Ala Arg Leu
                 85                  90                  95 tcc aag gag ctg ggg ccc ctg gtg gaa cag ggc cgc gtg cgg gcc gcc          337
Ser Lys Glu Leu Gly Pro Leu Val Glu Gln Gly Arg Val Arg Ala Ala
            100                 105                 110 act gtg ggc ttc ctg gcc ggc cag ccg cta cag gag cgg gcc cag gcc          385
Thr Val Gly Phe Leu Ala Gly Gln Pro Leu Gln Glu Arg Ala Gln Ala
        115                 120                 125 tgg ggc gag cgg ctg cgc gcg cgg atg gag gag atg ggc agc cgg acc          433
Trp Gly Glu Arg Leu Arg Ala Arg Met Glu Glu Met Gly Ser Arg Thr
    130                 135                 140 cgc gac cgc ctg gac gag gtg aag gag cag gtg gcg gag gtg cgc gcc          481
Arg Asp Arg Leu Asp Glu Val Lys Glu Gln Val Ala Glu Val Arg Ala
145                 150                 155                 160 aag ctg gag gag cag gcc cag cag ata cgc ctg cag gcc gag gcc ttc          529
Lys Leu Glu Glu Gln Ala Gln Gln Ile Arg Leu Gln Ala Glu Ala Phe
                165                 170                 175 cag gcc cgc ctc aag agc tgg ttc gag ccc ctg gtg gaa gac atg cag          577
Gln Ala Arg Leu Lys Ser Trp Phe Glu Pro Leu Val Glu Asp Met Gln
            180                 185                 190 cgc cag tgg gcc ggg ctg gtg gag aag gtg cag gct gcc gtg ggc acc          625
Arg Gln Trp Ala Gly Leu Val Glu Lys Val Gln Ala Ala Val Gly Thr
        195                 200                 205 agc gcc gcc cct gtg ccc agc gac aat cac ctc gag ggc                      664
Ser Ala Ala Pro Val Pro Ser Asp Asn His Leu Glu Gly
    210                 215                 220

<210> SEQ ID NO 38
<211> LENGTH: 221
<212> TYPE: PRT
<213> ORGANISM: Homo sapiens

<400> SEQUENCE: 38

Thr Gly Ser Lys Val Glu Gln Ala Val Glu Thr Glu Pro Glu Pro Glu
  1               5                  10                  15

Leu Arg Gln Gln Thr Glu Trp Gln Ser Gly Gln Arg Trp Glu Leu Ala
                 20                  25                  30

Leu Gly Arg Phe Trp Asp Tyr Leu Arg Trp Val Gln Thr Leu Ser Glu
             35                  40                  45
```

-continued

```
Gln Val Gln Glu Glu Leu Leu Ser Ser Gln Val Thr Gln Glu Leu Arg
 50                  55                  60

Ala Leu Met Asp Glu Thr Met Lys Glu Leu Lys Ala Tyr Lys Ser Glu
 65                  70                  75                  80

Leu Glu Glu Gln Leu Thr Pro Val Ala Glu Glu Thr Arg Ala Arg Leu
                 85                  90                  95

Ser Lys Glu Leu Gly Pro Leu Val Glu Gln Gly Arg Val Arg Ala Ala
             100                 105                 110

Thr Val Gly Phe Leu Ala Gly Gln Pro Leu Gln Glu Arg Ala Gln Ala
             115                 120                 125

Trp Gly Glu Arg Leu Arg Ala Arg Met Glu Glu Met Gly Ser Arg Thr
130                 135                 140

Arg Asp Arg Leu Asp Glu Val Lys Glu Gln Val Ala Glu Val Arg Ala
145                 150                 155                 160

Lys Leu Glu Glu Gln Ala Gln Gln Ile Arg Leu Gln Ala Glu Ala Phe
                165                 170                 175

Gln Ala Arg Leu Lys Ser Trp Phe Glu Pro Leu Val Glu Asp Met Gln
            180                 185                 190

Arg Gln Trp Ala Gly Leu Val Glu Lys Val Gln Ala Ala Val Gly Thr
        195                 200                 205

Ser Ala Ala Pro Val Pro Ser Asp Asn His Leu Glu Gly
    210                 215                 220

<210> SEQ ID NO 39
<211> LENGTH: 616
<212> TYPE: DNA
<213> ORGANISM: Homo sapiens
<220> FEATURE:
<221> NAME/KEY: CDS
<222> LOCATION: (2)..(616)

<400> SEQUENCE: 39 c acc gga tcc aag gtt ctg tgg gct gcg ttg ctg gtc aca ttc ctg gca     49
  Thr Gly Ser Lys Val Leu Trp Ala Ala Leu Leu Val Thr Phe Leu Ala
    1               5                  10                  15 gga tgc cag gcc aag gtg gag caa gcg gtg gag aca gag ccg gag ccc      97
Gly Cys Gln Ala Lys Val Glu Gln Ala Val Glu Thr Glu Pro Glu Pro
             20                  25                  30 gag ctg cgc cag cag acc gag tgg cag agc ggc cag cgc tgg gaa ctg     145
Glu Leu Arg Gln Gln Thr Glu Trp Gln Ser Gly Gln Arg Trp Glu Leu
         35                  40                  45 gca ctg ggt cgc ttt tgg gat tac ctg cgc tgg gtg cag aca ctg tct     193
Ala Leu Gly Arg Phe Trp Asp Tyr Leu Arg Trp Val Gln Thr Leu Ser
     50                  55                  60 gag cag gtg cag gag gag ctg ctc agc tcc cag gtc acc cag gaa ctg     241
Glu Gln Val Gln Glu Glu Leu Leu Ser Ser Gln Val Thr Gln Glu Leu
 65                  70                  75                  80 agg gcg ctg atg gac gag acc atg aag gag ttg aag gcc tac aaa tcg     289
Arg Ala Leu Met Asp Glu Thr Met Lys Glu Leu Lys Ala Tyr Lys Ser
                 85                  90                  95 gaa ctg gag gaa caa ctg acc ccg gtg gcg gag gag acg cgg gca cgg     337
Glu Leu Glu Glu Gln Leu Thr Pro Val Ala Glu Glu Thr Arg Ala Arg
             100                 105                 110 ctg tcc aag gag ctg ggg ccc ctg gtg gaa cag ggc cgc gtg cgg gcc     385
Leu Ser Lys Glu Leu Gly Pro Leu Val Glu Gln Gly Arg Val Arg Ala
             115                 120                 125 gcc act gtg ggc ttc ctg gcc ggc cag ccg cta cag gag cgg gcc cag     433
Ala Thr Val Gly Phe Leu Ala Gly Gln Pro Leu Gln Glu Arg Ala Gln
130                 135                 140
```

```
gcc tgg ggc gag cgg ctg cgc gcg cgg atg gag gag atg ggc agc cgg      481
Ala Trp Gly Glu Arg Leu Arg Ala Arg Met Glu Glu Met Gly Ser Arg
145                 150                 155                 160 acc cgc gac cgc ctg gac gag gtg aag gag cag gtg gcg gag gtg cgc      529
Thr Arg Asp Arg Leu Asp Glu Val Lys Glu Gln Val Ala Glu Val Arg
                165                 170                 175 gcc aag ctg gag gag cag gcc cag cag ata cgc ctg cag gcc gag gcc      577
Ala Lys Leu Glu Glu Gln Ala Gln Gln Ile Arg Leu Gln Ala Glu Ala
            180                 185                 190 ttc cag gcc cgc ctc aag agc tgg ttc gag ctc gag ggc                  616
Phe Gln Ala Arg Leu Lys Ser Trp Phe Glu Leu Glu Gly
        195                 200                 205

<210> SEQ ID NO 40
<211> LENGTH: 205
<212> TYPE: PRT
<213> ORGANISM: Homo sapiens

<400> SEQUENCE: 40

Thr Gly Ser Lys Val Leu Trp Ala Ala Leu Leu Val Thr Phe Leu Ala
 1               5                  10                  15

Gly Cys Gln Ala Lys Val Glu Gln Ala Val Glu Thr Glu Pro Glu Pro
                20                  25                  30

Glu Leu Arg Gln Gln Thr Glu Trp Gln Ser Gly Gln Arg Trp Glu Leu
            35                  40                  45

Ala Leu Gly Arg Phe Trp Asp Tyr Leu Arg Trp Val Gln Thr Leu Ser
        50                  55                  60

Glu Gln Val Gln Glu Glu Leu Leu Ser Ser Gln Val Thr Gln Glu Leu
65                  70                  75                  80

Arg Ala Leu Met Asp Glu Thr Met Lys Glu Leu Lys Ala Tyr Lys Ser
                85                  90                  95

Glu Leu Glu Glu Gln Leu Thr Pro Val Ala Glu Glu Thr Arg Ala Arg
            100                 105                 110

Leu Ser Lys Glu Leu Gly Pro Leu Val Glu Gln Gly Arg Val Arg Ala
        115                 120                 125

Ala Thr Val Gly Phe Leu Ala Gly Gln Pro Leu Gln Glu Arg Ala Gln
    130                 135                 140

Ala Trp Gly Glu Arg Leu Arg Ala Arg Met Glu Glu Met Gly Ser Arg
145                 150                 155                 160

Thr Arg Asp Arg Leu Asp Glu Val Lys Glu Gln Val Ala Glu Val Arg
                165                 170                 175

Ala Lys Leu Glu Glu Gln Ala Gln Gln Ile Arg Leu Gln Ala Glu Ala
            180                 185                 190

Phe Gln Ala Arg Leu Lys Ser Trp Phe Glu Leu Glu Gly
        195                 200                 205

<210> SEQ ID NO 41
<211> LENGTH: 709
<212> TYPE: DNA
<213> ORGANISM: Homo sapiens
<220> FEATURE:
<221> NAME/KEY: CDS
<222> LOCATION: (2)..(709)

<400> SEQUENCE: 41 c acc gga tcc acc atg aag gtt ctg tgg gct gcg ttg ctg gtc aca ttc   49
  Thr Gly Ser Thr Met Lys Val Leu Trp Ala Ala Leu Leu Val Thr Phe
   1               5                  10                  15
```

| | | |
|---|---|---|
| ctg gca gga tgc cag gcc aag gtg gag caa gcg gtg gag aca gag ccg<br>Leu Ala Gly Cys Gln Ala Lys Val Glu Gln Ala Val Glu Thr Glu Pro<br>20                       25                    30 | | 97 |
| gag ccc gag ctg cgc cag cag acc gag tgg cag agc ggc cag cgc tgg<br>Glu Pro Glu Leu Arg Gln Gln Thr Glu Trp Gln Ser Gly Gln Arg Trp<br>35                       40                    45 | | 145 |
| gaa ctg gca ctg ggt cgc ttt tgg gat tac ctg cgc tgg gtg cag aca<br>Glu Leu Ala Leu Gly Arg Phe Trp Asp Tyr Leu Arg Trp Val Gln Thr<br>50                       55                    60 | | 193 |
| ctg tct gag cag gtg cag gag gag ctc agc tcc cag gtc acc cag<br>Leu Ser Glu Gln Val Gln Glu Glu Leu Leu Ser Ser Gln Val Thr Gln<br>65                       70                    75                    80 | | 241 |
| gaa ctg agg gcg ctg atg gac gag acc atg aag gag ttg aag gcc tac<br>Glu Leu Arg Ala Leu Met Asp Glu Thr Met Lys Glu Leu Lys Ala Tyr<br>                          85                    90                    95 | | 289 |
| aaa tcg gaa ctg gag gaa caa ctg acc ccg gtg gcg gag gag acg cgg<br>Lys Ser Glu Leu Glu Glu Gln Leu Thr Pro Val Ala Glu Glu Thr Arg<br>                    100                 105                110 | | 337 |
| gca cgg ctg tcc aag gag ctg cag gcg gcg cag gcc cgg ctg ggc gcg<br>Ala Arg Leu Ser Lys Glu Leu Gln Ala Ala Gln Ala Arg Leu Gly Ala<br>                115                 120                125 | | 385 |
| gac atg gag gac gtg cgc ggc cgc ctg gtg cag tac cgc ggc gag gtg<br>Asp Met Glu Asp Val Arg Gly Arg Leu Val Gln Tyr Arg Gly Glu Val<br>130                       135                 140 | | 433 |
| cag gcc atg ctc ggc cag agc acc gag gag ctg cgg gtg cgc ctc gcc<br>Gln Ala Met Leu Gly Gln Ser Thr Glu Glu Leu Arg Val Arg Leu Ala<br>145                      150                 155                160 | | 481 |
| tcc cac ctg cgc aag ctg cgt aag cgg ctc ctc cgc gat gcc gat gac<br>Ser His Leu Arg Lys Leu Arg Lys Arg Leu Leu Arg Asp Ala Asp Asp<br>                165                 170                175 | | 529 |
| ctg gag gag cag gcc cag cag ata cgc ctg cag gcc gag gcc ttc cag<br>Leu Glu Glu Gln Ala Gln Gln Ile Arg Leu Gln Ala Glu Ala Phe Gln<br>                    180                 185                190 | | 577 |
| gcc cgc ctc aag agc tgg ttc gag ccc ctg gtg gaa gac atg cag cgc<br>Ala Arg Leu Lys Ser Trp Phe Glu Pro Leu Val Glu Asp Met Gln Arg<br>                195                 200                205 | | 625 |
| cag tgg gcc ggg ctg gtg gag aag gtg cag gct gcc gtg ggc acc agc<br>Gln Trp Ala Gly Leu Val Glu Lys Val Gln Ala Ala Val Gly Thr Ser<br>210                       215                 220 | | 673 |
| gcc gcc cct gtg ccc agc gac aat cac ctc gag ggc<br>Ala Ala Pro Val Pro Ser Asp Asn His Leu Glu Gly<br>225                       230                 235 | | 709 |

<210> SEQ ID NO 42
<211> LENGTH: 236
<212> TYPE: PRT
<213> ORGANISM: Homo sapiens

<400> SEQUENCE: 42

Thr Gly Ser Thr Met Lys Val Leu Trp Ala Ala Leu Leu Val Thr Phe
1               5                   10                  15

Leu Ala Gly Cys Gln Ala Lys Val Glu Gln Ala Val Glu Thr Glu Pro
                20                  25                  30

Glu Pro Glu Leu Arg Gln Gln Thr Glu Trp Gln Ser Gly Gln Arg Trp
            35                  40                  45

Glu Leu Ala Leu Gly Arg Phe Trp Asp Tyr Leu Arg Trp Val Gln Thr
        50                  55                  60

Leu Ser Glu Gln Val Gln Glu Glu Leu Leu Ser Ser Gln Val Thr Gln
65                  70                  75                  80

-continued

```
Glu Leu Arg Ala Leu Met Asp Glu Thr Met Lys Glu Leu Lys Ala Tyr
             85                  90                  95

Lys Ser Glu Leu Glu Glu Gln Leu Thr Pro Val Ala Glu Glu Thr Arg
            100                 105                 110

Ala Arg Leu Ser Lys Glu Leu Gln Ala Ala Gln Ala Arg Leu Gly Ala
        115                 120                 125

Asp Met Glu Asp Val Arg Gly Arg Leu Val Gln Tyr Arg Gly Glu Val
    130                 135                 140

Gln Ala Met Leu Gly Gln Ser Thr Glu Glu Leu Arg Val Arg Leu Ala
145                 150                 155                 160

Ser His Leu Arg Lys Leu Arg Lys Arg Leu Leu Arg Asp Ala Asp Asp
                165                 170                 175

Leu Glu Glu Gln Ala Gln Gln Ile Arg Leu Gln Ala Glu Ala Phe Gln
            180                 185                 190

Ala Arg Leu Lys Ser Trp Phe Glu Pro Leu Val Glu Asp Met Gln Arg
        195                 200                 205

Gln Trp Ala Gly Leu Val Glu Lys Val Gln Ala Ala Val Gly Thr Ser
    210                 215                 220

Ala Ala Pro Val Pro Ser Asp Asn His Leu Glu Gly
225                 230                 235

<210> SEQ ID NO 43
<211> LENGTH: 652
<212> TYPE: DNA
<213> ORGANISM: Homo sapiens
<220> FEATURE:
<221> NAME/KEY: CDS
<222> LOCATION: (2)..(652)

<400> SEQUENCE: 43 c acc gga tcc aag gtg gag caa gcg gtg gag aca gag ccg gag ccc gag      49
  Thr Gly Ser Lys Val Glu Gln Ala Val Glu Thr Glu Pro Glu Pro Glu
    1               5                  10                  15 ctg cgc cag cag acc gag tgg cag agc ggc cag cgc tgg gaa ctg gca      97
Leu Arg Gln Gln Thr Glu Trp Gln Ser Gly Gln Arg Trp Glu Leu Ala
             20                  25                  30 ctg ggt cgc ttt tgg gat tac ctg cgc tgg gtg cag aca ctg tct gag     145
Leu Gly Arg Phe Trp Asp Tyr Leu Arg Trp Val Gln Thr Leu Ser Glu
        35                  40                  45 cag gtg cag gag gag ctg ctc agc tcc cag gtc acc cag gaa ctg agg     193
Gln Val Gln Glu Glu Leu Leu Ser Ser Gln Val Thr Gln Glu Leu Arg
    50                  55                  60 gcg ctg atg gac gag acc atg aag gag ttg aag gcc tac aaa tcg gaa     241
Ala Leu Met Asp Glu Thr Met Lys Glu Leu Lys Ala Tyr Lys Ser Glu
65                  70                  75                  80 ctg gag gaa caa ctg acc ccg gtg gcg gag gag acg cgg gca cgg ctg     289
Leu Glu Glu Gln Leu Thr Pro Val Ala Glu Glu Thr Arg Ala Arg Leu
                85                  90                  95 tcc aag gag ctg cag gcg gcg cag gcc cgg ctg ggc gcg gac atg gag     337
Ser Lys Glu Leu Gln Ala Ala Gln Ala Arg Leu Gly Ala Asp Met Glu
            100                 105                 110 gac gtg cgc ggc cgc ctg gtg cag tac cgc ggc gag gtg cag gcc atg     385
Asp Val Arg Gly Arg Leu Val Gln Tyr Arg Gly Glu Val Gln Ala Met
        115                 120                 125 ctc ggc cag agc acc gag gag ctg cgg gtg cgc ctc gcc tcc cac ctg     433
Leu Gly Gln Ser Thr Glu Glu Leu Arg Val Arg Leu Ala Ser His Leu
    130                 135                 140 cgc aag ctg cgt aag cgg ctc ctc cgc gat gcc gat gac ctg gag gag     481
Arg Lys Leu Arg Lys Arg Leu Leu Arg Asp Ala Asp Asp Leu Glu Glu
```

```
                    145                 150                 155                 160
cag gcc cag cag ata cgc ctg cag gcc gag gcc ttc cag gcc cgc ctc          529
Gln Ala Gln Gln Ile Arg Leu Gln Ala Glu Ala Phe Gln Ala Arg Leu
                    165                 170                 175 aag agc tgg ttc gag ccc ctg gtg gaa gac atg cag cgc cag tgg gcc          577
Lys Ser Trp Phe Glu Pro Leu Val Glu Asp Met Gln Arg Gln Trp Ala
                180                 185                 190 ggg ctg gtg gag aag gtg cag gct gcc gtg ggc acc agc gcc gcc cct          625
Gly Leu Val Glu Lys Val Gln Ala Ala Val Gly Thr Ser Ala Ala Pro
            195                 200                 205 gtg ccc agc gac aat cac ctc gag ggc                                      652
Val Pro Ser Asp Asn His Leu Glu Gly
        210                 215
```

<210> SEQ ID NO 44
<211> LENGTH: 217
<212> TYPE: PRT
<213> ORGANISM: Homo sapiens

<400> SEQUENCE: 44

```
Thr Gly Ser Lys Val Glu Gln Ala Val Glu Thr Glu Pro Pro Glu
 1               5                  10                  15

Leu Arg Gln Gln Thr Glu Trp Gln Ser Gly Gln Arg Trp Glu Leu Ala
                20                  25                  30

Leu Gly Arg Phe Trp Asp Tyr Leu Arg Trp Val Gln Thr Leu Ser Glu
            35                  40                  45

Gln Val Gln Glu Glu Leu Leu Ser Ser Gln Val Thr Gln Glu Leu Arg
        50                  55                  60

Ala Leu Met Asp Glu Thr Met Lys Glu Leu Lys Ala Tyr Lys Ser Glu
 65                 70                  75                  80

Leu Glu Glu Gln Leu Thr Pro Val Ala Glu Thr Arg Ala Arg Leu
                85                  90                  95

Ser Lys Glu Leu Gln Ala Ala Gln Ala Arg Leu Gly Ala Asp Met Glu
            100                 105                 110

Asp Val Arg Gly Arg Leu Val Gln Tyr Arg Gly Glu Val Gln Ala Met
        115                 120                 125

Leu Gly Gln Ser Thr Glu Glu Leu Arg Val Arg Leu Ala Ser His Leu
    130                 135                 140

Arg Lys Leu Arg Lys Arg Leu Leu Arg Asp Ala Asp Asp Leu Glu Glu
145                 150                 155                 160

Gln Ala Gln Gln Ile Arg Leu Gln Ala Glu Ala Phe Gln Ala Arg Leu
                165                 170                 175

Lys Ser Trp Phe Glu Pro Leu Val Glu Asp Met Gln Arg Gln Trp Ala
            180                 185                 190

Gly Leu Val Glu Lys Val Gln Ala Ala Val Gly Thr Ser Ala Ala Pro
        195                 200                 205

Val Pro Ser Asp Asn His Leu Glu Gly
    210                 215
```

<210> SEQ ID NO 45
<211> LENGTH: 691
<212> TYPE: DNA
<213> ORGANISM: Homo sapiens
<220> FEATURE:
<221> NAME/KEY: CDS
<222> LOCATION: (2)..(691)

<400> SEQUENCE: 45

```
c acc gga tcc aag gtt ctg tgg gct gcg ttg ctg gtc aca ttc ctg gca    49
  Thr Gly Ser Lys Val Leu Trp Ala Ala Leu Leu Val Thr Phe Leu Ala
    1               5                  10                  15 gga tgc cag gcc aag gtg gag caa gcg gtg gag aca gag ccg gag ccc     97
Gly Cys Gln Ala Lys Val Glu Gln Ala Val Glu Thr Glu Pro Glu Pro
              20                  25                  30 gag ctg cgc cag cag acc gag tgg cag agc ggc cag cgc tgg gaa ctg    145
Glu Leu Arg Gln Gln Thr Glu Trp Gln Ser Gly Gln Arg Trp Glu Leu
         35                  40                  45 gca ctg ggt cgc ttt tgg gat tac ctg cgc tgg gtg cag aca ctg tct    193
Ala Leu Gly Arg Phe Trp Asp Tyr Leu Arg Trp Val Gln Thr Leu Ser
     50                  55                  60 gag cag gtg cag gag gag ctc ctc agc tcc cag gtc acc cag gaa ctg    241
Glu Gln Val Gln Glu Glu Leu Leu Ser Ser Gln Val Thr Gln Glu Leu
 65                  70                  75                  80 agg gcg ctg atg gac gag acc atg aag gag ttg aag gcc tac aaa tcg    289
Arg Ala Leu Met Asp Glu Thr Met Lys Glu Leu Lys Ala Tyr Lys Ser
                 85                  90                  95 gaa ctg gag gaa caa ctg acc ccg gtg gcg gag gag acg cgg gca cgg    337
Glu Leu Glu Glu Gln Leu Thr Pro Val Ala Glu Glu Thr Arg Ala Arg
            100                 105                 110 ctg tcc aag gag ctg cag gcg gcg cag gcc cgg ctg ggc gcg gac atg    385
Leu Ser Lys Glu Leu Gln Ala Ala Gln Ala Arg Leu Gly Ala Asp Met
        115                 120                 125 gag gac gtg cgc ggc cgc ctg gtg cag tac cgc ggc gag gtg cag gcc    433
Glu Asp Val Arg Gly Arg Leu Val Gln Tyr Arg Gly Glu Val Gln Ala
    130                 135                 140 atg ctc ggc cag agc acc gag gag ctg cgg gtg cgc ctc gcc tcc cac    481
Met Leu Gly Gln Ser Thr Glu Glu Leu Arg Val Arg Leu Ala Ser His
145                 150                 155                 160 ctg cgc aag ctg cgt aag cgg ctc ctc cgc gat gcc gat gac ctg gag    529
Leu Arg Lys Leu Arg Lys Arg Leu Leu Arg Asp Ala Asp Asp Leu Glu
                165                 170                 175 gag cag gcc cag cag ata cgc ctg cag gcc gag gcc ttc cag gcc cgc    577
Glu Gln Ala Gln Gln Ile Arg Leu Gln Ala Glu Ala Phe Gln Ala Arg
            180                 185                 190 ctc aag agc tgg ttc gag ccc ctg gtg gaa gac atg cag cgc cag tgg    625
Leu Lys Ser Trp Phe Glu Pro Leu Val Glu Asp Met Gln Arg Gln Trp
        195                 200                 205 gcc ggg ctg gtg gag aag gtg cag gct gcc gtg ggc acc agc gcc gcc    673
Ala Gly Leu Val Glu Lys Val Gln Ala Ala Val Gly Thr Ser Ala Ala
    210                 215                 220 cct gtg ccc ctc gag ggc                                            691
Pro Val Pro Leu Glu Gly
225                 230
```

<210> SEQ ID NO 46
<211> LENGTH: 230
<212> TYPE: PRT
<213> ORGANISM: Homo sapiens

<400> SEQUENCE: 46

```
Thr Gly Ser Lys Val Leu Trp Ala Ala Leu Leu Val Thr Phe Leu Ala
  1               5                  10                  15

Gly Cys Gln Ala Lys Val Glu Gln Ala Val Glu Thr Glu Pro Glu Pro
             20                  25                  30

Glu Leu Arg Gln Gln Thr Glu Trp Gln Ser Gly Gln Arg Trp Glu Leu
         35                  40                  45

Ala Leu Gly Arg Phe Trp Asp Tyr Leu Arg Trp Val Gln Thr Leu Ser
     50                  55                  60
```

```
Glu Gln Val Gln Glu Leu Leu Ser Ser Gln Val Thr Gln Glu Leu
 65                  70                  75                  80

Arg Ala Leu Met Asp Glu Thr Met Lys Glu Leu Lys Ala Tyr Lys Ser
                 85                  90                  95

Glu Leu Glu Glu Gln Leu Thr Pro Val Ala Glu Thr Arg Ala Arg
            100                 105                 110

Leu Ser Lys Glu Leu Gln Ala Ala Gln Ala Arg Leu Gly Ala Asp Met
            115                 120                 125

Glu Asp Val Arg Gly Arg Leu Val Gln Tyr Arg Gly Glu Val Gln Ala
130                 135                 140

Met Leu Gly Gln Ser Thr Glu Glu Leu Arg Val Arg Leu Ala Ser His
145                 150                 155                 160

Leu Arg Lys Leu Arg Lys Arg Leu Leu Arg Asp Ala Asp Asp Leu Glu
                165                 170                 175

Glu Gln Ala Gln Gln Ile Arg Leu Gln Ala Glu Ala Phe Gln Ala Arg
            180                 185                 190

Leu Lys Ser Trp Phe Glu Pro Leu Val Glu Asp Met Gln Arg Gln Trp
            195                 200                 205

Ala Gly Leu Val Glu Lys Val Gln Ala Ala Val Gly Thr Ser Ala Ala
210                 215                 220

Pro Val Pro Leu Glu Gly
225                 230

<210> SEQ ID NO 47
<211> LENGTH: 747
<212> TYPE: DNA
<213> ORGANISM: Homo sapiens
<220> FEATURE:
<221> NAME/KEY: CDS
<222> LOCATION: (2)..(646)

<400> SEQUENCE: 47 c atg gaa tac gcc tct gac gct tca ctg gac ccc gaa gcc ccg tgg cct      49
  Met Glu Tyr Ala Ser Asp Ala Ser Leu Asp Pro Glu Ala Pro Trp Pro
   1               5                  10                  15 ccc gcg ccc cgc gct cgc gcc tgc cgc gta ctg cct tgg gcc ctg gtc      97
Pro Ala Pro Arg Ala Arg Ala Cys Arg Val Leu Pro Trp Ala Leu Val
             20                  25                  30 gcg ggg ctg ctg ctg ctg ctg ctc act gcc gcc tgc gcc gtc ttc         145
Ala Gly Leu Leu Leu Leu Leu Leu Thr Ala Ala Cys Ala Val Phe
         35                  40                  45 ctc gcc tgc ccc tgg gcc gtg tcc ggg gct cgc gcc tcg ccc ggc tcc      193
Leu Ala Cys Pro Trp Ala Val Ser Gly Ala Arg Ala Ser Pro Gly Ser
 50                  55                  60 gcg gcc agc ccg aga ctc cgc gag ggt ccc gag ctt tcg ccc gac gat      241
Ala Ala Ser Pro Arg Leu Arg Glu Gly Pro Glu Leu Ser Pro Asp Asp
             70                  75                  80 ccc gcc ggc ctc ttg gac ctc cgg cag ggc atg ttt gcg cag ctg gtg      289
Pro Ala Gly Leu Leu Asp Leu Arg Gln Gly Met Phe Ala Gln Leu Val
         85                  90                  95 gcc aag gct gga gtc tac tat gtc ttc ttt caa cta gag ctg cgg cgc      337
Ala Lys Ala Gly Val Tyr Tyr Val Phe Phe Gln Leu Glu Leu Arg Arg
            100                 105                 110 gtg gtg gcc ggc gag ggc tca ggc tcc gtt tca ctt gcg ctg cac ctg      385
Val Val Ala Gly Glu Gly Ser Gly Ser Val Ser Leu Ala Leu His Leu
        115                 120                 125 cag cca ctg cgc tct gct gct ggg gcc gcc gcc ctg gct ttg acc gtg      433
Gln Pro Leu Arg Ser Ala Ala Gly Ala Ala Ala Leu Ala Leu Thr Val
```

-continued

```
         130                 135                 140
gac ctg cca ccc gcc tcc tcc gag gct cgg aac tcg gcc ttc ggt ttc    481
Asp Leu Pro Pro Ala Ser Ser Glu Ala Arg Asn Ser Ala Phe Gly Phe
145                 150                 155                 160 cag ggc cgc ttg ctg cac ctg agt gcc ggc cag cgc ctg ggc gtc cat    529
Gln Gly Arg Leu Leu His Leu Ser Ala Gly Gln Arg Leu Gly Val His
                165                 170                 175 ctt cac act gag gcc agg gca cgc cat gcc tgg cag ctt acc cag ggc    577
Leu His Thr Glu Ala Arg Ala Arg His Ala Trp Gln Leu Thr Gln Gly
            180                 185                 190 gcc aca gtc ttg gga ctc ttc cgg gtg acc ccc gaa atc cca gcc gga    625
Ala Thr Val Leu Gly Leu Phe Arg Val Thr Pro Glu Ile Pro Ala Gly
        195                 200                 205 ctc cct tca ccg agg tcg gaa taacgcccag cctgggtgcg gcccacctgg       676
Leu Pro Ser Pro Arg Ser Glu
    210                 215 acagagtccg aatcctactc catccttcat ggagacccct ggtgctgggt ccctgctgct    736
ttctctacct c                                                         747
```

<210> SEQ ID NO 48
<211> LENGTH: 215
<212> TYPE: PRT
<213> ORGANISM: Homo sapiens

<400> SEQUENCE: 48

```
Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
                20                  25                  30

Ala Gly Leu Leu Leu Leu Leu Leu Thr Ala Ala Cys Ala Val Phe
            35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Lys Ala Gly Val Tyr Tyr Val Phe Phe Gln Leu Glu Leu Arg Arg
                100                 105                 110

Val Val Ala Gly Glu Gly Ser Gly Ser Val Ser Leu Ala Leu His Leu
            115                 120                 125

Gln Pro Leu Arg Ser Ala Ala Gly Ala Ala Leu Ala Leu Thr Val
    130                 135                 140

Asp Leu Pro Pro Ala Ser Ser Glu Ala Arg Asn Ser Ala Phe Gly Phe
145                 150                 155                 160

Gln Gly Arg Leu Leu His Leu Ser Ala Gly Gln Arg Leu Gly Val His
                165                 170                 175

Leu His Thr Glu Ala Arg Ala Arg His Ala Trp Gln Leu Thr Gln Gly
            180                 185                 190

Ala Thr Val Leu Gly Leu Phe Arg Val Thr Pro Glu Ile Pro Ala Gly
        195                 200                 205

Leu Pro Ser Pro Arg Ser Glu
    210                 215
```

<210> SEQ ID NO 49
<211> LENGTH: 442

-continued

```
<212> TYPE: DNA
<213> ORGANISM: Homo sapiens
<220> FEATURE:
<221> NAME/KEY: CDS
<222> LOCATION: (75)..(341)

<400> SEQUENCE: 49
gtcatggaat acgcctctga cgctgtcagg aatacgcctc tgacgctgtc atggaatacg      60
cctctgacgc tgtc atg gaa tac gcc tct gac gct tca ctg gac ccc gaa      110
                Met Glu Tyr Ala Ser Asp Ala Ser Leu Asp Pro Glu
                 1               5                  10 gcc ccg tgg cct ccc gcg ccc cgc gct cgc gcc tgc cgc gta ctg cct      158
Ala Pro Trp Pro Pro Ala Pro Arg Ala Arg Ala Cys Arg Val Leu Pro
        15                  20                  25 tgg gcc ctg gtc gcg ggg ctg ctg ctg ctg ctg ctc gct gcc ggc          206
Trp Ala Leu Val Ala Gly Leu Leu Leu Leu Leu Leu Ala Ala Gly
 30                  35                  40 cag cgc ctg ggc gtc cat ctt cac act gag gcc agg gca cgc cat gcc      254
Gln Arg Leu Gly Val His Leu His Thr Glu Ala Arg Ala Arg His Ala
 45                  50                  55                  60 tgg cag ctt acc cag ggc gcc aca gtc ttg gga ctc ttc cgg gtg acc      302
Trp Gln Leu Thr Gln Gly Ala Thr Val Leu Gly Leu Phe Arg Val Thr
                 65                  70                  75 ccc gaa atc cca gcc gga ctc cct tca ccg agg tcg gaa taacgcccag       351
Pro Glu Ile Pro Ala Gly Leu Pro Ser Pro Arg Ser Glu
                 80                  85 cctgggtgca gcccacctgg acagagtccg aatcctactc catccttcat ggagacccct    411
ggtgccgggt ccctgctgct ttctctacct c                                    442

<210> SEQ ID NO 50
<211> LENGTH: 89
<212> TYPE: PRT
<213> ORGANISM: Homo sapiens

<400> SEQUENCE: 50

Met Glu Tyr Ala Ser Asp Ala Ser Leu Asp Pro Glu Ala Pro Trp Pro
 1               5                  10                  15

Pro Ala Pro Arg Ala Arg Ala Cys Arg Val Leu Pro Trp Ala Leu Val
                 20                  25                  30

Ala Gly Leu Leu Leu Leu Leu Leu Ala Ala Gly Gln Arg Leu Gly
         35                  40                  45

Val His Leu His Thr Glu Ala Arg Ala Arg His Ala Trp Gln Leu Thr
     50                  55                  60

Gln Gly Ala Thr Val Leu Gly Leu Phe Arg Val Thr Pro Glu Ile Pro
 65                  70                  75                  80

Ala Gly Leu Pro Ser Pro Arg Ser Glu
                 85

<210> SEQ ID NO 51
<211> LENGTH: 289
<212> TYPE: DNA
<213> ORGANISM: Homo sapiens
<220> FEATURE:
<221> NAME/KEY: CDS
<222> LOCATION: (2)..(289)

<400> SEQUENCE: 51 c acc gga tcc acc atg gaa tac gcc tct gac gct tca ctg gac ccc gaa   49
  Thr Gly Ser Thr Met Glu Tyr Ala Ser Asp Ala Ser Leu Asp Pro Glu
   1               5                  10                  15
```

```
gcc ccg tgg cct ccc gcg ccc cgc gct cgc gcc tgc cgc gta ctg cct      97
Ala Pro Trp Pro Pro Ala Pro Arg Ala Arg Ala Cys Arg Val Leu Pro
         20                  25                  30 tgg gcc ctg gtc gcg ggg ctg ctg ctg ctg ctg ctc gct gcc ggc          145
Trp Ala Leu Val Ala Gly Leu Leu Leu Leu Leu Leu Ala Ala Gly
     35                  40                  45 cag cgc ctg ggc gtc cat ctt cac act gag gcc agg gca cgc cat gcc     193
Gln Arg Leu Gly Val His Leu His Thr Glu Ala Arg Ala Arg His Ala
 50                  55                  60 tgg cag ctt acc cag ggc gcc aca gtc ttg gga ctc ttc cgg gtg acc     241
Trp Gln Leu Thr Gln Gly Ala Thr Val Leu Gly Leu Phe Arg Val Thr
 65                  70                  75                  80 ccc gaa atc cca gcc gga ctc cct tca ccg agg tcg gaa ctc gag ggc     289
Pro Glu Ile Pro Ala Gly Leu Pro Ser Pro Arg Ser Glu Leu Glu Gly
             85                  90                  95
```

<210> SEQ ID NO 52
<211> LENGTH: 96
<212> TYPE: PRT
<213> ORGANISM: Homo sapiens

<400> SEQUENCE: 52

```
Thr Gly Ser Thr Met Glu Tyr Ala Ser Asp Ala Ser Leu Asp Pro Glu
 1               5                  10                  15

Ala Pro Trp Pro Pro Ala Pro Arg Ala Arg Ala Cys Arg Val Leu Pro
             20                  25                  30

Trp Ala Leu Val Ala Gly Leu Leu Leu Leu Leu Leu Ala Ala Gly
         35                  40                  45

Gln Arg Leu Gly Val His Leu His Thr Glu Ala Arg Ala Arg His Ala
 50                  55                  60

Trp Gln Leu Thr Gln Gly Ala Thr Val Leu Gly Leu Phe Arg Val Thr
 65                  70                  75                  80

Pro Glu Ile Pro Ala Gly Leu Pro Ser Pro Arg Ser Glu Leu Glu Gly
             85                  90                  95
```

<210> SEQ ID NO 53
<211> LENGTH: 178
<212> TYPE: DNA
<213> ORGANISM: Homo sapiens
<220> FEATURE:
<221> NAME/KEY: CDS
<222> LOCATION: (2)..(178)

<400> SEQUENCE: 53

```
c acc gga tcc gcc tgc cgc gta ctg cct tgg gcc ctg gtc gcg ggg ctg    49
  Thr Gly Ser Ala Cys Arg Val Leu Pro Trp Ala Leu Val Ala Gly Leu
   1               5                  10                  15 ctg ctg ctg ctg ctc gct gcc ggc cag cgc ctg ggc gtc cat ctt          97
Leu Leu Leu Leu Leu Ala Ala Gly Gln Arg Leu Gly Val His Leu
             20                  25                  30 cac act gag gcc agg gca cgc cat gcc tgg cag ctt acc cag ggc gcc    145
His Thr Glu Ala Arg Ala Arg His Ala Trp Gln Leu Thr Gln Gly Ala
     35                  40                  45 aca gtc ttg gga ctc ttc cgg gtg ctc gag ggc                         178
Thr Val Leu Gly Leu Phe Arg Val Leu Glu Gly
 50                  55
```

<210> SEQ ID NO 54
<211> LENGTH: 59
<212> TYPE: PRT
<213> ORGANISM: Homo sapiens -continued

```
<400> SEQUENCE: 54

Thr Gly Ser Ala Cys Arg Val Leu Pro Trp Ala Leu Val Ala Gly Leu
  1               5                  10                  15

Leu Leu Leu Leu Leu Leu Ala Ala Gly Gln Arg Leu Gly Val His Leu
             20                  25                  30

His Thr Glu Ala Arg Ala Arg His Ala Trp Gln Leu Thr Gln Gly Ala
         35                  40                  45

Thr Val Leu Gly Leu Phe Arg Val Leu Glu Gly
     50                  55

<210> SEQ ID NO 55
<211> LENGTH: 598
<212> TYPE: DNA
<213> ORGANISM: Homo sapiens
<220> FEATURE:
<221> NAME/KEY: CDS
<222> LOCATION: (45)..(569)

<400> SEQUENCE: 55
gcggccgcag ccgctgcccc gggccgggcg cccgcggcgg cacc atg agt ccc cgc       56
                                                Met Ser Pro Arg
                                                  1 tcg tgc ctg cgt tcg ctg cgc ctc ctc gtc ttc gcc gtc ttc tca gcc      104
Ser Cys Leu Arg Ser Leu Arg Leu Leu Val Phe Ala Val Phe Ser Ala
  5                  10                  15                  20 gcc gcg agc aac tgg ctg tac ctg gcc aag ctg tcg tcg gtg ggg agc      152
Ala Ala Ser Asn Trp Leu Tyr Leu Ala Lys Leu Ser Ser Val Gly Ser
                 25                  30                  35 atc tca gag gag gag acg tgc gag aaa ctc aag ggc ctg atc cag agg      200
Ile Ser Glu Glu Glu Thr Cys Glu Lys Leu Lys Gly Leu Ile Gln Arg
         40                  45                  50 cag gtg cag atg tgc aag cgg aac ctg gaa gtc atg gac tcg gtg cgc      248
Gln Val Gln Met Cys Lys Arg Asn Leu Glu Val Met Asp Ser Val Arg
     55                  60                  65 cgc ggt gcc cag ctg gcc att gag gag tgc cag tac cag ttc cgg aac      296
Arg Gly Ala Gln Leu Ala Ile Glu Glu Cys Gln Tyr Gln Phe Arg Asn
 70                  75                  80 cgg cgc tgg aac tgc tcc aca ctc gac tcc ttg ccc gtc ttc ggc aag      344
Arg Arg Trp Asn Cys Ser Thr Leu Asp Ser Leu Pro Val Phe Gly Lys
 85                  90                  95                 100 gtg gtg acg caa ggt ggc aaa gcc tgg cat gga gga gac agt gga tgt      392
Val Val Thr Gln Gly Gly Lys Ala Trp His Gly Gly Asp Ser Gly Cys
                105                 110                 115 cat cta ctg aca gaa agc agg tca ggg gag agg act caa agg cgc aag      440
His Leu Leu Thr Glu Ser Arg Ser Gly Glu Arg Thr Gln Arg Arg Lys
                120                 125                 130 gaa gga ggt agc ctg ggg caa tgc tgg cct gaa gcc atc gtg ggt act      488
Glu Gly Gly Ser Leu Gly Gln Cys Trp Pro Glu Ala Ile Val Gly Thr
            135                 140                 145 cag gac ccc atg aga agc ccc cct tac ctt tgg ggg agg aac caa ggg      536
Gln Asp Pro Met Arg Ser Pro Pro Tyr Leu Trp Gly Arg Asn Gln Gly
    150                 155                 160 ggc acc cac acc ggc tca gca tct gag gga cac tgagattcct actaggcctg   589
Gly Thr His Thr Gly Ser Ala Ser Glu Gly His
165                 170                 175 ggtggtacc                                                            598

<210> SEQ ID NO 56
<211> LENGTH: 175
<212> TYPE: PRT
```

-continued

```
<213> ORGANISM: Homo sapiens

<400> SEQUENCE: 56

Met Ser Pro Arg Ser Cys Leu Arg Ser Leu Arg Leu Leu Val Phe Ala
 1               5                  10                  15

Val Phe Ser Ala Ala Ser Asn Trp Leu Tyr Leu Ala Lys Leu Ser
                20                  25                  30

Ser Val Gly Ser Ile Ser Glu Glu Thr Cys Glu Lys Leu Lys Gly
            35                  40                  45

Leu Ile Gln Arg Gln Val Gln Met Cys Lys Arg Asn Leu Glu Val Met
         50                  55                  60

Asp Ser Val Arg Arg Gly Ala Gln Leu Ala Ile Glu Glu Cys Gln Tyr
 65                  70                  75                  80

Gln Phe Arg Asn Arg Arg Trp Asn Cys Ser Thr Leu Asp Ser Leu Pro
                 85                  90                  95

Val Phe Gly Lys Val Val Thr Gln Gly Gly Lys Ala Trp His Gly Gly
                100                 105                 110

Asp Ser Gly Cys His Leu Leu Thr Glu Ser Arg Ser Gly Glu Arg Thr
            115                 120                 125

Gln Arg Arg Lys Glu Gly Gly Ser Leu Gly Gln Cys Trp Pro Glu Ala
        130                 135                 140

Ile Val Gly Thr Gln Asp Pro Met Arg Ser Pro Tyr Leu Trp Gly
145                 150                 155                 160

Arg Asn Gln Gly Gly Thr His Thr Gly Ser Ala Ser Glu Gly His
                165                 170                 175

<210> SEQ ID NO 57
<211> LENGTH: 1047
<212> TYPE: DNA
<213> ORGANISM: Homo sapiens
<220> FEATURE:
<221> NAME/KEY: CDS
<222> LOCATION: (1)..(906)

<400> SEQUENCE: 57 atg gcc gcg gcc atc gct agc ggc ttg atc cgc cag aag cgg cag gcg     48
Met Ala Ala Ala Ile Ala Ser Gly Leu Ile Arg Gln Lys Arg Gln Ala
 1               5                  10                  15 cgg gag cag cac tgg gac cgg ccg tct gcc agc agg agg cgg agc agc     96
Arg Glu Gln His Trp Asp Arg Pro Ser Ala Ser Arg Arg Arg Ser Ser
                20                  25                  30 ccc agc aag aac cgc ggg ctc tgc aac ggc aac ctg gtg gat atc ttc    144
Pro Ser Lys Asn Arg Gly Leu Cys Asn Gly Asn Leu Val Asp Ile Phe
            35                  40                  45 tcc aaa gtg cgc atc ttc ggc ctc aag aag cgc agg ttg cgg cgc caa    192
Ser Lys Val Arg Ile Phe Gly Leu Lys Lys Arg Arg Leu Arg Arg Gln
         50                  55                  60 gat ccc cag ctc aag ggt ata gtg acc agg tta tat tgc agg caa ggc    240
Asp Pro Gln Leu Lys Gly Ile Val Thr Arg Leu Tyr Cys Arg Gln Gly
 65                  70                  75                  80 tac tac ttg caa atg cac ccc gat gga gct ctc gat gga acc aag gat    288
Tyr Tyr Leu Gln Met His Pro Asp Gly Ala Leu Asp Gly Thr Lys Asp
                 85                  90                  95 gac agc act aat tct aca ctc ttc aac ctc ata cca gtg gga cta cgt    336
Asp Ser Thr Asn Ser Thr Leu Phe Asn Leu Ile Pro Val Gly Leu Arg
                100                 105                 110 gtt gtt gcc atc cag gga gtg aaa aca ggg ttg tat ata gcc atg aat    384
Val Val Ala Ile Gln Gly Val Lys Thr Gly Leu Tyr Ile Ala Met Asn
            115                 120                 125
```

|  |  |  |  |  |  |  |  |  |  |  |  |  |  |  |  | |
|---|---|---|---|---|---|---|---|---|---|---|---|---|---|---|---|---|
| gga | gaa | ggt | tac | ctc | tac | cca | tca | gaa | ctt | ttt | acc | cct | gaa | tgc | aag | 432 |
| Gly | Glu | Gly | Tyr | Leu | Tyr | Pro | Ser | Glu | Leu | Phe | Thr | Pro | Glu | Cys | Lys | |
|  |  | 130 |  |  |  | 135 |  |  |  |  | 140 |  |  |  |  | |
| ttt | aaa | gaa | tct | gtt | ttt | gaa | aat | tat | tat | gta | atc | tac | tca | tcc | atg | 480 |
| Phe | Lys | Glu | Ser | Val | Phe | Glu | Asn | Tyr | Tyr | Val | Ile | Tyr | Ser | Ser | Met | |
| 145 |  |  |  |  | 150 |  |  |  |  | 155 |  |  |  |  | 160 | |
| ttg | tac | aga | caa | cag | gaa | tct | ggt | aga | gcc | tgg | ttt | ttg | gga | tta | aat | 528 |
| Leu | Tyr | Arg | Gln | Gln | Glu | Ser | Gly | Arg | Ala | Trp | Phe | Leu | Gly | Leu | Asn | |
|  |  |  |  | 165 |  |  |  |  | 170 |  |  |  |  | 175 |  | |
| aag | gaa | ggg | caa | gct | atg | aaa | ggg | aac | aga | gta | aag | aaa | acc | aaa | cca | 576 |
| Lys | Glu | Gly | Gln | Ala | Met | Lys | Gly | Asn | Arg | Val | Lys | Lys | Thr | Lys | Pro | |
|  |  |  | 180 |  |  |  |  | 185 |  |  |  |  | 190 |  |  | |
| gca | gct | cat | ttt | cta | ccc | aag | cca | ttg | gaa | gtt | gcc | atg | tac | cga | gaa | 624 |
| Ala | Ala | His | Phe | Leu | Pro | Lys | Pro | Leu | Glu | Val | Ala | Met | Tyr | Arg | Glu | |
|  |  | 195 |  |  |  |  | 200 |  |  |  |  | 205 |  |  |  | |
| cca | tct | ttg | cat | gat | gtt | ggg | gaa | acg | gtc | ccg | aag | cct | ggg | gtg | acg | 672 |
| Pro | Ser | Leu | His | Asp | Val | Gly | Glu | Thr | Val | Pro | Lys | Pro | Gly | Val | Thr | |
|  | 210 |  |  |  |  | 215 |  |  |  |  | 220 |  |  |  |  | |
| cca | agt | aaa | agc | aca | agt | gcg | tct | aaa | tcc | att | tca | gat | ata | ctc | cgt | 720 |
| Pro | Ser | Lys | Ser | Thr | Ser | Ala | Ser | Lys | Ser | Ile | Ser | Asp | Ile | Leu | Arg | |
| 225 |  |  |  |  | 230 |  |  |  |  | 235 |  |  |  |  | 240 | |
| cct | gtt | ttt | aat | gaa | cca | aac | tta | acg | cca | tcc | ccg | ttt | ctg | gct | gcg | 768 |
| Pro | Val | Phe | Asn | Glu | Pro | Asn | Leu | Thr | Pro | Ser | Pro | Phe | Leu | Ala | Ala | |
|  |  |  |  | 245 |  |  |  |  | 250 |  |  |  |  | 255 |  | |
| ttc | ccc | tca | tac | tca | gca | gag | cat | ggg | caa | gac | ggc | tgt | tgt | gtt | ctt | 816 |
| Phe | Pro | Ser | Tyr | Ser | Ala | Glu | His | Gly | Gln | Asp | Gly | Cys | Cys | Val | Leu | |
|  |  |  | 260 |  |  |  |  | 265 |  |  |  |  | 270 |  |  | |
| tcg | tgg | tcc | gta | aag | ttt | aac | ttt | ctg | atc | ctt | aat | agg | agg | ata | agc | 864 |
| Ser | Trp | Ser | Val | Lys | Phe | Asn | Phe | Leu | Ile | Leu | Asn | Arg | Arg | Ile | Ser | |
|  |  | 275 |  |  |  |  | 280 |  |  |  |  | 285 |  |  |  | |
| gcc | gtg | ata | gag | aaa | tcc | aaa | ggt | cat | ttg | tat | tac | gat | ggc |  |  | 906 |
| Ala | Val | Ile | Glu | Lys | Ser | Lys | Gly | His | Leu | Tyr | Tyr | Asp | Gly |  |  | |
|  | 290 |  |  |  |  | 295 |  |  |  |  | 300 |  |  |  |  | | tagataatgt aatgaattcc aatgtctgtg catcagcgaa tacgtcatca aaattgctac    966 aaaacaataa taataggttg ttcacagctt aaaatgttta ggtagtgaag aggaaagaat    1026 ataacctaca ttatttattg a    1047

<210> SEQ ID NO 58
<211> LENGTH: 302
<212> TYPE: PRT
<213> ORGANISM: Homo sapiens

<400> SEQUENCE: 58

Met Ala Ala Ala Ile Ala Ser Gly Leu Ile Arg Gln Lys Arg Gln Ala
1               5                   10                  15

Arg Glu Gln His Trp Asp Arg Pro Ser Ala Ser Arg Arg Ser Ser
            20                  25                  30

Pro Ser Lys Asn Arg Gly Leu Cys Asn Gly Asn Leu Val Asp Ile Phe
        35                  40                  45

Ser Lys Val Arg Ile Phe Gly Leu Lys Lys Arg Leu Arg Arg Gln
    50                  55                  60

Asp Pro Gln Leu Lys Gly Ile Val Thr Arg Leu Tyr Cys Arg Gln Gly
65                  70                  75                  80

Tyr Tyr Leu Gln Met His Pro Asp Gly Ala Leu Asp Gly Thr Lys Asp
                85                  90                  95

Asp Ser Thr Asn Ser Thr Leu Phe Asn Leu Ile Pro Val Gly Leu Arg
            100                 105                 110

-continued

Val Val Ala Ile Gln Gly Val Lys Thr Gly Leu Tyr Ile Ala Met Asn
         115                 120                 125

Gly Glu Gly Tyr Leu Tyr Pro Ser Glu Leu Phe Thr Pro Glu Cys Lys
     130                 135                 140

Phe Lys Glu Ser Val Phe Glu Asn Tyr Tyr Val Ile Tyr Ser Ser Met
145                 150                 155                 160

Leu Tyr Arg Gln Gln Glu Ser Gly Arg Ala Trp Phe Leu Gly Leu Asn
                165                 170                 175

Lys Glu Gly Gln Ala Met Lys Gly Asn Arg Val Lys Lys Thr Lys Pro
            180                 185                 190

Ala Ala His Phe Leu Pro Lys Pro Leu Glu Val Ala Met Tyr Arg Glu
        195                 200                 205

Pro Ser Leu His Asp Val Gly Glu Thr Val Pro Lys Pro Gly Val Thr
    210                 215                 220

Pro Ser Lys Ser Thr Ser Ala Ser Lys Ser Ile Ser Asp Ile Leu Arg
225                 230                 235                 240

Pro Val Phe Asn Glu Pro Asn Leu Thr Pro Ser Pro Phe Leu Ala Ala
                245                 250                 255

Phe Pro Ser Tyr Ser Ala Glu His Gly Gln Asp Gly Cys Cys Val Leu
            260                 265                 270

Ser Trp Ser Val Lys Phe Asn Phe Leu Ile Leu Asn Arg Arg Ile Ser
        275                 280                 285

Ala Val Ile Glu Lys Ser Lys Gly His Leu Tyr Tyr Asp Gly
    290                 295                 300

<210> SEQ ID NO 59
<211> LENGTH: 30
<212> TYPE: DNA
<213> ORGANISM: Homo sapiens
<220> FEATURE:
<221> NAME/KEY: CDS
<222> LOCATION: (1)..(30)

<400> SEQUENCE: 59 ggc aag ctc tgg gcc atc ggt cac ttc atg                              30
Gly Lys Leu Trp Ala Ile Gly His Phe Met
1               5                   10

<210> SEQ ID NO 60
<211> LENGTH: 10
<212> TYPE: PRT
<213> ORGANISM: Homo sapiens

<400> SEQUENCE: 60

Gly Lys Leu Trp Ala Ile Gly His Phe Met
1               5                   10

<210> SEQ ID NO 61
<211> LENGTH: 126
<212> TYPE: DNA
<213> ORGANISM: Homo sapiens
<220> FEATURE:
<221> NAME/KEY: CDS
<222> LOCATION: (1)..(126)

<400> SEQUENCE: 61 gca cac aaa cta gac ctg gaa gaa att gcc agc ttg gat aag gcc aag    48
Ala His Lys Leu Asp Leu Glu Glu Ile Ala Ser Leu Asp Lys Ala Lys
1               5                   10                  15 ctg aag gcc aca gag atg cag aag aac act ctg atg acc aaa gag acc    96

```
Leu Lys Ala Thr Glu Met Gln Lys Asn Thr Leu Met Thr Lys Glu Thr
            20                  25                  30 aca gag cag gag aag tgg agt gaa att tcc                          126
Thr Glu Gln Glu Lys Trp Ser Glu Ile Ser
        35                  40
```

<210> SEQ ID NO 62
<211> LENGTH: 42
<212> TYPE: PRT
<213> ORGANISM: Homo sapiens

<400> SEQUENCE: 62

```
Ala His Lys Leu Asp Leu Glu Glu Ile Ala Ser Leu Asp Lys Ala Lys
  1               5                  10                  15

Leu Lys Ala Thr Glu Met Gln Lys Asn Thr Leu Met Thr Lys Glu Thr
            20                  25                  30

Thr Glu Gln Glu Lys Trp Ser Glu Ile Ser
        35                  40
```

<210> SEQ ID NO 63
<211> LENGTH: 108
<212> TYPE: DNA
<213> ORGANISM: Homo sapiens
<220> FEATURE:
<221> NAME/KEY: CDS
<222> LOCATION: (1)..(108)

<400> SEQUENCE: 63

```
tgc ccc atc aaa ccc gag gct cct ggc gaa gac gag tcc ctg gag gag   48
Cys Pro Ile Lys Pro Glu Ala Pro Gly Glu Asp Glu Ser Leu Glu Glu
  1               5                  10                  15 ctg agc cac tat tat gct tcc ctg tgc cac tac ctc aac gtg gtc acc   96
Leu Ser His Tyr Tyr Ala Ser Leu Cys His Tyr Leu Asn Val Val Thr
            20                  25                  30 aga cag tta att                                                  108
Arg Gln Leu Ile
        35
```

<210> SEQ ID NO 64
<211> LENGTH: 36
<212> TYPE: PRT
<213> ORGANISM: Homo sapiens

<400> SEQUENCE: 64

```
Cys Pro Ile Lys Pro Glu Ala Pro Gly Glu Asp Glu Ser Leu Glu Glu
  1               5                  10                  15

Leu Ser His Tyr Tyr Ala Ser Leu Cys His Tyr Leu Asn Val Val Thr
            20                  25                  30

Arg Gln Leu Ile
        35
```

<210> SEQ ID NO 65
<211> LENGTH: 45
<212> TYPE: DNA
<213> ORGANISM: Homo sapiens
<220> FEATURE:
<221> NAME/KEY: CDS
<222> LOCATION: (1)..(45)

<400> SEQUENCE: 65

```
gct tcc ctg tgc cac tac ctc aac gtg gtc acc aga cag tta att       45
Ala Ser Leu Cys His Tyr Leu Asn Val Val Thr Arg Gln Leu Ile
  1               5                  10                  15
```

```
<210> SEQ ID NO 66
<211> LENGTH: 15
<212> TYPE: PRT
<213> ORGANISM: Homo sapiens

<400> SEQUENCE: 66

Ala Ser Leu Cys His Tyr Leu Asn Val Val Thr Arg Gln Leu Ile
 1               5                  10                  15

<210> SEQ ID NO 67
<211> LENGTH: 69
<212> TYPE: DNA
<213> ORGANISM: Homo sapiens
<220> FEATURE:
<221> NAME/KEY: CDS
<222> LOCATION: (1)..(69)

<400> SEQUENCE: 67 ctg gag gag ctg agc cac tat tat gct tcc ctg tgc cac tac ctc aac      48
Leu Glu Glu Leu Ser His Tyr Tyr Ala Ser Leu Cys His Tyr Leu Asn
 1               5                  10                  15 gtg gtc acc aga cag tta att                                          69
Val Val Thr Arg Gln Leu Ile
            20

<210> SEQ ID NO 68
<211> LENGTH: 23
<212> TYPE: PRT
<213> ORGANISM: Homo sapiens

<400> SEQUENCE: 68

Leu Glu Glu Leu Ser His Tyr Tyr Ala Ser Leu Cys His Tyr Leu Asn
 1               5                  10                  15

Val Val Thr Arg Gln Leu Ile
            20

<210> SEQ ID NO 69
<211> LENGTH: 72
<212> TYPE: DNA
<213> ORGANISM: Homo sapiens
<220> FEATURE:
<221> NAME/KEY: CDS
<222> LOCATION: (1)..(72)

<400> SEQUENCE: 69 cgg agc aca ccg aac atc agg ccc gcg cac aga ctg aca aga gtg aac      48
Arg Ser Thr Pro Asn Ile Arg Pro Ala His Arg Leu Thr Arg Val Asn
 1               5                  10                  15 ctg ccc atg ccg cgc cgc tac tac                                      72
Leu Pro Met Pro Arg Arg Tyr Tyr
            20

<210> SEQ ID NO 70
<211> LENGTH: 24
<212> TYPE: PRT
<213> ORGANISM: Homo sapiens

<400> SEQUENCE: 70

Arg Ser Thr Pro Asn Ile Arg Pro Ala His Arg Leu Thr Arg Val Asn
 1               5                  10                  15

Leu Pro Met Pro Arg Arg Tyr Tyr
            20

<210> SEQ ID NO 71
```

```
<211> LENGTH: 934
<212> TYPE: DNA
<213> ORGANISM: Homo sapiens
<220> FEATURE:
<221> NAME/KEY: CDS
<222> LOCATION: (2)..(925)

<400> SEQUENCE: 71 c atg ccc ggg caa gaa ctc agg acg ctg aat ggc tct cag atg ctc ctg        49
  Met Pro Gly Gln Glu Leu Arg Thr Leu Asn Gly Ser Gln Met Leu Leu
  1               5                  10                  15 gtg ttg ctg gtg ctc tcg tgg ctg ccg cat ggg ggc gcc ctg tct ctg          97
Val Leu Leu Val Leu Ser Trp Leu Pro His Gly Gly Ala Leu Ser Leu
             20                  25                  30 gcc gag gcg agc cgc gca agt ttc ccg gga ccc tca gag ttg cac acc         145
Ala Glu Ala Ser Arg Ala Ser Phe Pro Gly Pro Ser Glu Leu His Thr
         35                  40                  45 gaa gac tcc aga ttc cga gag ttg cgg aaa cgc tac gag gac ctg cta         193
Glu Asp Ser Arg Phe Arg Glu Leu Arg Lys Arg Tyr Glu Asp Leu Leu
     50                  55                  60 acc agg ctg cgg gcc aac cag agc tgg gaa gat tcg aac acc gac ctc         241
Thr Arg Leu Arg Ala Asn Gln Ser Trp Glu Asp Ser Asn Thr Asp Leu
 65                  70                  75                  80 gtc ccg gcc cct gca gtc cgg ata ctc acg cca gaa gtg cgg ctg gga         289
Val Pro Ala Pro Ala Val Arg Ile Leu Thr Pro Glu Val Arg Leu Gly
                 85                  90                  95 tcc ggc ggc cac ctg cac ctg cgt atc tct cgg gcc gcc ctt ccc gag         337
Ser Gly Gly His Leu His Leu Arg Ile Ser Arg Ala Ala Leu Pro Glu
            100                 105                 110 ggg ctc ccc gag gcc tcc cgc ctt cac cgg gct ctg ttc cgg ctg tcc         385
Gly Leu Pro Glu Ala Ser Arg Leu His Arg Ala Leu Phe Arg Leu Ser
        115                 120                 125 ccg acg gcg tca agg tcg tgg gac gtg aca cga cct ctg cgg cgt cag         433
Pro Thr Ala Ser Arg Ser Trp Asp Val Thr Arg Pro Leu Arg Arg Gln
    130                 135                 140 ctc agc ctt gca aga ccc cag gcg ccc gcg ctg cac ctg cga ctg tcg         481
Leu Ser Leu Ala Arg Pro Gln Ala Pro Ala Leu His Leu Arg Leu Ser
145                 150                 155                 160 ccg ccg ccg tcg cag tcg gac caa ctg ctg gca gaa tct tcg tcc gca         529
Pro Pro Pro Ser Gln Ser Asp Gln Leu Leu Ala Glu Ser Ser Ser Ala
                165                 170                 175 cgg ccc cag ctg gag ttg cac ttg cgg ccg caa gcc gcc agg ggg cgc         577
Arg Pro Gln Leu Glu Leu His Leu Arg Pro Gln Ala Ala Arg Gly Arg
            180                 185                 190 cgc aga gcg cgt gcg cgc aac ggg gac cac tgt ccg ctc ggg ccc ggg         625
Arg Arg Ala Arg Ala Arg Asn Gly Asp His Cys Pro Leu Gly Pro Gly
        195                 200                 205 cgt tgc tgc cgt ctg cac acg gtc cgc gcg tcg ctg gaa gac ctg ggc         673
Arg Cys Cys Arg Leu His Thr Val Arg Ala Ser Leu Glu Asp Leu Gly
    210                 215                 220 tgg gcc gat tgg gtg ttg tcg cca cgg gag gtg caa gtg acc atg tgc         721
Trp Ala Asp Trp Val Leu Ser Pro Arg Glu Val Gln Val Thr Met Cys
225                 230                 235                 240 atc ggc gcg tgc ccg agc cag ttc cgg gcg gca aac atg cac gcg cag         769
Ile Gly Ala Cys Pro Ser Gln Phe Arg Ala Ala Asn Met His Ala Gln
                245                 250                 255 atc aag acg agc ctg cac cgc ctg aag ccc gac acg gtg cca gcg tcc         817
Ile Lys Thr Ser Leu His Arg Leu Lys Pro Asp Thr Val Pro Ala Ser
            260                 265                 270 tgc tgc gtg ccc gcc agc tac aat ccc atg gtg ctc att caa aag acc         865
Cys Cys Val Pro Ala Ser Tyr Asn Pro Met Val Leu Ile Gln Lys Thr
```

```
                275                 280                 285
gac acc ggg gtg tcg ctc cag acc tat gat gac ttg tta gcc aaa gac     913
Asp Thr Gly Val Ser Leu Gln Thr Tyr Asp Asp Leu Leu Ala Lys Asp
290                 295                 300 tgc cac tgc ata tgaactagt                                           934
Cys His Cys Ile
305
```

<210> SEQ ID NO 72
<211> LENGTH: 308
<212> TYPE: PRT
<213> ORGANISM: Homo sapiens

<400> SEQUENCE: 72

```
Met Pro Gly Gln Glu Leu Arg Thr Leu Asn Gly Ser Gln Met Leu Leu
 1               5                  10                  15

Val Leu Leu Val Leu Ser Trp Leu Pro His Gly Gly Ala Leu Ser Leu
             20                  25                  30

Ala Glu Ala Ser Arg Ala Ser Phe Pro Gly Pro Ser Glu Leu His Thr
         35                  40                  45

Glu Asp Ser Arg Phe Arg Glu Leu Arg Lys Arg Tyr Glu Asp Leu Leu
     50                  55                  60

Thr Arg Leu Arg Ala Asn Gln Ser Trp Glu Asp Ser Asn Thr Asp Leu
 65                  70                  75                  80

Val Pro Ala Pro Ala Val Arg Ile Leu Thr Pro Glu Val Arg Leu Gly
                 85                  90                  95

Ser Gly Gly His Leu His Leu Arg Ile Ser Arg Ala Ala Leu Pro Glu
             100                 105                 110

Gly Leu Pro Glu Ala Ser Arg Leu His Arg Ala Leu Phe Arg Leu Ser
         115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
        195                 200                 205

Arg Cys Cys Arg Leu His Thr Val Arg Ala Ser Leu Glu Asp Leu Gly
    210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Ser
            260                 265                 270

Cys Cys Val Pro Ala Ser Tyr Asn Pro Met Val Leu Ile Gln Lys Thr
        275                 280                 285

Asp Thr Gly Val Ser Leu Gln Thr Tyr Asp Asp Leu Leu Ala Lys Asp
    290                 295                 300

Cys His Cys Ile
305
```

```
<210> SEQ ID NO 73
<211> LENGTH: 306
<212> TYPE: DNA
<213> ORGANISM: Homo sapiens
<220> FEATURE:
<221> NAME/KEY: CDS
<222> LOCATION: (1)..(306)

<400> SEQUENCE: 73 aga tct tgc cgt ctg cac acg gtc cgc gcg tcg ctg gaa gac ctg ggc      48
Arg Ser Cys Arg Leu His Thr Val Arg Ala Ser Leu Glu Asp Leu Gly
  1               5                  10                  15 tgg gcc gat tgg gtg ctg tcg cca cgg gag gtg caa gtg acc atg tgc      96
Trp Ala Asp Trp Val Leu Ser Pro Arg Glu Val Gln Val Thr Met Cys
             20                  25                  30 atc ggc gcg tgc ccg agc cag ttc cgg gcg gca aac atg cac gcg cag     144
Ile Gly Ala Cys Pro Ser Gln Phe Arg Ala Ala Asn Met His Ala Gln
         35                  40                  45 atc aag acg agc ctg cac cgc ctg aag ccc gac acg gtg cca gcg ccc     192
Ile Lys Thr Ser Leu His Arg Leu Lys Pro Asp Thr Val Pro Ala Pro
     50                  55                  60 tgc tgc gtg ccc gcc agc tac aat ccc atg gtg ctc att caa aag acc     240
Cys Cys Val Pro Ala Ser Tyr Asn Pro Met Val Leu Ile Gln Lys Thr
 65                  70                  75                  80 gac acc ggg gtg tcg ctc cag acc tat gat gac ttg tta gcc aaa gac     288
Asp Thr Gly Val Ser Leu Gln Thr Tyr Asp Asp Leu Leu Ala Lys Asp
                 85                  90                  95 tgc cac tgc ata ctc gag                                             306
Cys His Cys Ile Leu Glu
            100

<210> SEQ ID NO 74
<211> LENGTH: 102
<212> TYPE: PRT
<213> ORGANISM: Homo sapiens

<400> SEQUENCE: 74

Arg Ser Cys Arg Leu His Thr Val Arg Ala Ser Leu Glu Asp Leu Gly
  1               5                  10                  15

Trp Ala Asp Trp Val Leu Ser Pro Arg Glu Val Gln Val Thr Met Cys
             20                  25                  30

Ile Gly Ala Cys Pro Ser Gln Phe Arg Ala Ala Asn Met His Ala Gln
         35                  40                  45

Ile Lys Thr Ser Leu His Arg Leu Lys Pro Asp Thr Val Pro Ala Pro
     50                  55                  60

Cys Cys Val Pro Ala Ser Tyr Asn Pro Met Val Leu Ile Gln Lys Thr
 65                  70                  75                  80

Asp Thr Gly Val Ser Leu Gln Thr Tyr Asp Asp Leu Leu Ala Lys Asp
                 85                  90                  95

Cys His Cys Ile Leu Glu
            100

<210> SEQ ID NO 75
<211> LENGTH: 849
<212> TYPE: DNA
<213> ORGANISM: Homo sapiens
<220> FEATURE:
<221> NAME/KEY: CDS
<222> LOCATION: (1)..(849)

<400> SEQUENCE: 75 aga tct ctg tct ctg gcc gag gcg agc cgc gca agt ttc ccg gga ccc      48
```

```
Arg Ser Leu Ser Leu Ala Glu Ala Ser Arg Ala Ser Phe Pro Gly Pro
 1               5                  10                  15 tca gag ttg cac tcc gaa gac tcc aga ttc cga gag ttg cgg aaa cgc        96
Ser Glu Leu His Ser Glu Asp Ser Arg Phe Arg Glu Leu Arg Lys Arg
                 20                  25                  30 tac gag gac ctg cta acc agg ctg cgg gcc aac cag agc tgg gaa gat       144
Tyr Glu Asp Leu Leu Thr Arg Leu Arg Ala Asn Gln Ser Trp Glu Asp
             35                  40                  45 tcg aac acc gac ctc gtc ccg gcc cct gca gtc cgg ata ctc acg cca       192
Ser Asn Thr Asp Leu Val Pro Ala Pro Ala Val Arg Ile Leu Thr Pro
 50                  55                  60 gaa gtg cgg ctg gga tcc ggc ggc cac ctg cac ctg cgt atc tct cgg       240
Glu Val Arg Leu Gly Ser Gly Gly His Leu His Leu Arg Ile Ser Arg
 65                  70                  75                  80 gcc gcc ctt ccc gag ggg ctc ccc gag gcc tcc cgc ctt cac cgg gct       288
Ala Ala Leu Pro Glu Gly Leu Pro Glu Ala Ser Arg Leu His Arg Ala
                 85                  90                  95 ctg ttc cgg ctg tcc ccg acg gcg tca agg tcg tgg gac gtg aca cga       336
Leu Phe Arg Leu Ser Pro Thr Ala Ser Arg Ser Trp Asp Val Thr Arg
             100                 105                 110 ccg ctg cgg cgt cag ctc agc ctt gca aga ccc cag gcg ccc gcg ctg       384
Pro Leu Arg Arg Gln Leu Ser Leu Ala Arg Pro Gln Ala Pro Ala Leu
         115                 120                 125 cac ctg cga ctg tcg ccg ccg ccg tcg cag tcg gac caa ctg ctg gca       432
His Leu Arg Leu Ser Pro Pro Pro Ser Gln Ser Asp Gln Leu Leu Ala
     130                 135                 140 gaa tct tcg tcc gca cgg ccc cag ctg gag ttg cac ttg cgg ccg caa       480
Glu Ser Ser Ser Ala Arg Pro Gln Leu Glu Leu His Leu Arg Pro Gln
145                 150                 155                 160 gcc gcc agg ggg cgc cgc aga gcg cgt gcg cgc aac ggg gac cac tgt       528
Ala Ala Arg Gly Arg Arg Arg Ala Arg Ala Arg Asn Gly Asp His Cys
                 165                 170                 175 ccg ctc ggg ccc ggg cgt tgc tgc cgt ctg cac acg gtc cgc gcg tcg       576
Pro Leu Gly Pro Gly Arg Cys Cys Arg Leu His Thr Val Arg Ala Ser
             180                 185                 190 ctg gaa gac ctg ggc tgg gcc gat tgg gtg ctg tcg cca cgg gag gtg       624
Leu Glu Asp Leu Gly Trp Ala Asp Trp Val Leu Ser Pro Arg Glu Val
         195                 200                 205 caa gtg acc atg tgc atc ggc gcg tgc ccg agc cag ttc cgg gcg gca       672
Gln Val Thr Met Cys Ile Gly Ala Cys Pro Ser Gln Phe Arg Ala Ala
     210                 215                 220 aac atg cac gcg cag atc aag acg agc ctg cac cgc ctg aag ccc gac       720
Asn Met His Ala Gln Ile Lys Thr Ser Leu His Arg Leu Lys Pro Asp
225                 230                 235                 240 acg gtg cca gcg ccc tgc tgc gtg ccc gcc agc tac aat ccc atg gtg       768
Thr Val Pro Ala Pro Cys Cys Val Pro Ala Ser Tyr Asn Pro Met Val
                 245                 250                 255 ctc att caa aag acc gac acc ggg gtg tcg ctc cag acc tat gat gac       816
Leu Ile Gln Lys Thr Asp Thr Gly Val Ser Leu Gln Thr Tyr Asp Asp
             260                 265                 270 ttg tta gcc aaa gac tgc cac tgc ata ctc gag                           849
Leu Leu Ala Lys Asp Cys His Cys Ile Leu Glu
         275                 280

<210> SEQ ID NO 76
<211> LENGTH: 283
<212> TYPE: PRT
<213> ORGANISM: Homo sapiens

<400> SEQUENCE: 76
```

```
Arg Ser Leu Ser Leu Ala Glu Ala Ser Arg Ala Ser Phe Pro Gly Pro
 1               5                  10                  15

Ser Glu Leu His Ser Glu Asp Ser Arg Phe Arg Glu Leu Arg Lys Arg
                 20                  25                  30

Tyr Glu Asp Leu Leu Thr Arg Leu Arg Ala Asn Gln Ser Trp Glu Asp
             35                  40                  45

Ser Asn Thr Asp Leu Val Pro Ala Pro Ala Val Arg Ile Leu Thr Pro
 50                  55                  60

Glu Val Arg Leu Gly Ser Gly His Leu His Leu Arg Ile Ser Arg
 65                  70                  75                  80

Ala Ala Leu Pro Glu Gly Leu Pro Glu Ala Ser Arg Leu His Arg Ala
                 85                  90                  95

Leu Phe Arg Leu Ser Pro Thr Ala Ser Arg Ser Trp Asp Val Thr Arg
                100                 105                 110

Pro Leu Arg Arg Gln Leu Ser Leu Ala Arg Pro Gln Ala Pro Ala Leu
            115                 120                 125

His Leu Arg Leu Ser Pro Pro Ser Gln Ser Asp Gln Leu Leu Ala
            130                 135                 140

Glu Ser Ser Ala Arg Pro Gln Leu Glu Leu His Leu Arg Pro Gln
145                 150                 155                 160

Ala Ala Arg Gly Arg Arg Ala Arg Ala Arg Asn Gly Asp His Cys
                165                 170                 175

Pro Leu Gly Pro Gly Arg Cys Cys Arg Leu His Thr Val Arg Ala Ser
            180                 185                 190

Leu Glu Asp Leu Gly Trp Ala Asp Trp Val Leu Ser Pro Arg Glu Val
            195                 200                 205

Gln Val Thr Met Cys Ile Gly Ala Cys Pro Ser Gln Phe Arg Ala Ala
210                 215                 220

Asn Met His Ala Gln Ile Lys Thr Ser Leu His Arg Leu Lys Pro Asp
225                 230                 235                 240

Thr Val Pro Ala Pro Cys Cys Val Pro Ala Ser Tyr Asn Pro Met Val
                245                 250                 255

Leu Ile Gln Lys Thr Asp Thr Gly Val Ser Leu Gln Thr Tyr Asp Asp
            260                 265                 270

Leu Leu Ala Lys Asp Cys His Cys Ile Leu Glu
            275                 280

<210> SEQ ID NO 77
<211> LENGTH: 27
<212> TYPE: DNA
<213> ORGANISM: Homo sapiens
<220> FEATURE:
<221> NAME/KEY: CDS
<222> LOCATION: (1)..(27)

<400> SEQUENCE: 77 tgc tac ttc cag aac tgc ccg agg ggc                                   27
Cys Tyr Phe Gln Asn Cys Pro Arg Gly
 1               5

<210> SEQ ID NO 78
<211> LENGTH: 9
<212> TYPE: PRT
<213> ORGANISM: Homo sapiens

<400> SEQUENCE: 78

Cys Tyr Phe Gln Asn Cys Pro Arg Gly
 1               5
```

<210> SEQ ID NO 79
<211> LENGTH: 21
<212> TYPE: DNA
<213> ORGANISM: Artificial Sequence
<220> FEATURE:
<223> OTHER INFORMATION: Description of Artifical Sequence: Primer/
      Probe

<400> SEQUENCE: 79
gtgaacgagc agggacatta c                                         21

<210> SEQ ID NO 80
<211> LENGTH: 23
<212> TYPE: DNA
<213> ORGANISM: Artificial Sequence
<220> FEATURE:
<223> OTHER INFORMATION: Description of Artifical Sequence: Primer/
      Probe

<400> SEQUENCE: 80
caagttcacc tgccaggtgc ctg                                       23

<210> SEQ ID NO 81
<211> LENGTH: 21
<212> TYPE: DNA
<213> ORGANISM: Artificial Sequence
<220> FEATURE:
<223> OTHER INFORMATION: Description of Artifical Sequence: Primer/
      Probe

<400> SEQUENCE: 81
atggacggcg aagtagtaga c                                         21

<210> SEQ ID NO 82
<211> LENGTH: 17
<212> TYPE: DNA
<213> ORGANISM: Artificial Sequence
<220> FEATURE:
<223> OTHER INFORMATION: Description of Artifical Sequence: Primer/
      Probe

<400> SEQUENCE: 82
ctcgtcctgc tgctcct                                              17

<210> SEQ ID NO 83
<211> LENGTH: 23
<212> TYPE: DNA
<213> ORGANISM: Artificial Sequence
<220> FEATURE:
<223> OTHER INFORMATION: Description of Artifical Sequence: Primer/
      Probe

<400> SEQUENCE: 83
acaacaagat ccccagcctc tgc                                       23

<210> SEQ ID NO 84
<211> LENGTH: 16
<212> TYPE: DNA
<213> ORGANISM: Artificial Sequence
<220> FEATURE:
<223> OTHER INFORMATION: Description of Artifical Sequence: Primer/
      Probe

<400> SEQUENCE: 84
ccggcagtcc tggaag                                               16

```
<210> SEQ ID NO 85
<211> LENGTH: 15
<212> TYPE: DNA
<213> ORGANISM: Artificial Sequence
<220> FEATURE:
<223> OTHER INFORMATION: Description of Artifical Sequence: Primer/
      Probe

<400> SEQUENCE: 85
ttccaggact gccgg                                                         15

<210> SEQ ID NO 86
<211> LENGTH: 18
<212> TYPE: DNA
<213> ORGANISM: Artificial Sequence
<220> FEATURE:
<223> OTHER INFORMATION: Description of Artifical Sequence: Primer/
      Probe

<400> SEQUENCE: 86
ctcggtgcct ccgcgatc                                                      18

<210> SEQ ID NO 87
<211> LENGTH: 15
<212> TYPE: DNA
<213> ORGANISM: Artificial Sequence
<220> FEATURE:
<223> OTHER INFORMATION: Description of Artifical Sequence: Primer/
      Probe

<400> SEQUENCE: 87
cgcttggcgc tgaag                                                         15

<210> SEQ ID NO 88
<211> LENGTH: 20
<212> TYPE: DNA
<213> ORGANISM: Artificial Sequence
<220> FEATURE:
<223> OTHER INFORMATION: Description of Artifical Sequence: Primer/
      Probe

<400> SEQUENCE: 88
gaatatcacg aaggaagcca                                                    20

<210> SEQ ID NO 89
<211> LENGTH: 23
<212> TYPE: DNA
<213> ORGANISM: Artificial Sequence
<220> FEATURE:
<223> OTHER INFORMATION: Description of Artifical Sequence: Primer/
      Probe

<400> SEQUENCE: 89
cctcagctgc tccactccga aca                                                23

<210> SEQ ID NO 90
<211> LENGTH: 20
<212> TYPE: DNA
<213> ORGANISM: Artificial Sequence
<220> FEATURE:
<223> OTHER INFORMATION: Description of Artifical Sequence: Primer/
      Probe

<400> SEQUENCE: 90
cggaaagtgt cagcagtgat                                                    20
```

```
<210> SEQ ID NO 91
<211> LENGTH: 22
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 91
acaatcactg ctgacacttt cc                                               22

<210> SEQ ID NO 92
<211> LENGTH: 26
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 92
ttccgagtct actccaattt cctccg                                           26

<210> SEQ ID NO 93
<211> LENGTH: 22
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 93
cctgtgtaca gcttcagctt tc                                               22

<210> SEQ ID NO 94
<211> LENGTH: 15
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 94
cgcggacgag gtgaa                                                       15

<210> SEQ ID NO 95
<211> LENGTH: 18
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 95
cgcgcacctc cgccacct                                                    18

<210> SEQ ID NO 96
<211> LENGTH: 18
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 96
gtatctgctg ggcctgct                                                    18

<210> SEQ ID NO 97
```

```
<211> LENGTH: 18
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 97
cctggacgag gtgaagga                                                   18

<210> SEQ ID NO 98
<211> LENGTH: 19
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 98
cagcttggcg cgcacctcc                                                  19

<210> SEQ ID NO 99
<211> LENGTH: 18
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 99
cctgcaggcg tatctgct                                                   18

<210> SEQ ID NO 100
<211> LENGTH: 17
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 100
gccgatgacc tggagga                                                    17

<210> SEQ ID NO 101
<211> LENGTH: 22
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 101
cccagcagat acgcctgcag gc                                              22

<210> SEQ ID NO 102
<211> LENGTH: 15
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 102
aggcgggcct ggaag                                                      15

<210> SEQ ID NO 103
<211> LENGTH: 22
```

```
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 103
gccaaggctg gagtctacta tg                                            22

<210> SEQ ID NO 104
<211> LENGTH: 20
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 104
tcacttgcgc tgcacctgca                                               20

<210> SEQ ID NO 105
<211> LENGTH: 20
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 105
cctggcctca gtgtgaagat                                               20

<210> SEQ ID NO 106
<211> LENGTH: 20
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 106
gaagcgtcag aggcgtattc                                               20

<210> SEQ ID NO 107
<211> LENGTH: 26
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 107
atggaatacg cctctgacgc tgtcat                                        26

<210> SEQ ID NO 108
<211> LENGTH: 20
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 108
ctgacgctgt caggaatacg                                               20

<210> SEQ ID NO 109
<211> LENGTH: 14
<212> TYPE: DNA
```

```
<213> ORGANISM: Artificial Sequence
<220> FEATURE:
<223> OTHER INFORMATION: Description of Artifical Sequence:  Primer/
      Probe

<400> SEQUENCE: 109
gccggcagcg agca                                                    14

<210> SEQ ID NO 110
<211> LENGTH: 24
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 110
agcagcagcc ccgcgaccag ggcc                                         24

<210> SEQ ID NO 111
<211> LENGTH: 16
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 111
tcgcgcctgc cgcgta                                                  16

<210> SEQ ID NO 112
<211> LENGTH: 19
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 112
gctggaactg ctccacact                                               19

<210> SEQ ID NO 113
<211> LENGTH: 23
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 113
actccttgcc cgtcttcggc aag                                          23

<210> SEQ ID NO 114
<211> LENGTH: 21
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 114
gacatccact gtctcctcca t                                            21

<210> SEQ ID NO 115
<211> LENGTH: 21
<212> TYPE: DNA
<213> ORGANISM: Artificial Sequence
```

```
<220> FEATURE:
<223> OTHER INFORMATION: Description of Artifical Sequence:  Primer/
      Probe

<400> SEQUENCE: 115
gacgccaagt aaaagcacaa g                                            21

<210> SEQ ID NO 116
<211> LENGTH: 30
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 116
tgcgtctaaa tccatttcag atatactccg                                   30

<210> SEQ ID NO 117
<211> LENGTH: 22
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 117
tggcgttaag tttggttcat ta                                           22

<210> SEQ ID NO 118
<211> LENGTH: 24
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 118
atttcagata tactccgtcc tgtt                                         24

<210> SEQ ID NO 119
<211> LENGTH: 26
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 119
aatgaaccaa acttaacgcc atcccc                                       26

<210> SEQ ID NO 120
<211> LENGTH: 15
<212> TYPE: DNA
<213> ORGANISM: Artificial Sequence
<220> FEATURE:
<223> OTHER INFORMATION: Description of Artifical Sequence:  Primer/
      Probe

<400> SEQUENCE: 120
gggaacgcag ccaga                                                   15

<210> SEQ ID NO 121
<211> LENGTH: 173
<212> TYPE: DNA
<213> ORGANISM: Homo sapiens
```

-continued

<400> SEQUENCE: 121

```
aaatcctccg ggctcttagg aaatttcact ccgcttctgc ccagtggtct ctttggtcgg    60
cagggtgttc ttctcctgcg tctccgtttt cttcagcttg ccctattga agctggcgat   120
tcccccacg tctggtttgt ctgccatttt cttaaaacaa tcggtaccat ccg          173
```

<210> SEQ ID NO 122
<211> LENGTH: 43
<212> TYPE: PRT
<213> ORGANISM: Homo sapiens

<400> SEQUENCE: 122

```
Met Ala Asp Lys Pro Asp Val Gly Gly Ile Ala Ser Phe Asn Arg Ala
 1               5                  10                  15

Lys Leu Lys Lys Thr Glu Thr Gln Glu Lys Asn Thr Leu Pro Thr Lys
            20                  25                  30

Glu Thr Thr Gly Gln Lys Arg Ser Glu Ile Ser
        35                  40
```

<210> SEQ ID NO 123
<211> LENGTH: 330
<212> TYPE: DNA
<213> ORGANISM: Homo sapiens
<220> FEATURE:
<221> NAME/KEY: CDS
<222> LOCATION: (1)..(327)

<400> SEQUENCE: 123

```
atg tca gat gca gct gta gac acc agc tct gaa atc att gcc aag gac     48
Met Ser Asp Ala Ala Val Asp Thr Ser Ser Glu Ile Ile Ala Lys Asp
 1               5                  10                  15 tta aag gag aag aag gaa gtt gtg aaa gag gcg gaa aat gga aga gac     96
Leu Lys Glu Lys Lys Glu Val Val Lys Glu Ala Glu Asn Gly Arg Asp
            20                  25                  30 gcc cct gct aac ggg aat gct aat gag gaa aat ggg gag cag gag gct    144
Ala Pro Ala Asn Gly Asn Ala Asn Glu Glu Asn Gly Glu Gln Glu Ala
        35                  40                  45 gac aag gag gta gat gaa gaa ggg gaa gaa agt ggg gag gaa gag gag    192
Asp Lys Glu Val Asp Glu Glu Gly Glu Glu Ser Gly Glu Glu Glu Glu
    50                  55                  60 gag gaa aaa gaa ggt gat ggt gag gaa gag gat gga gat gaa gag gaa    240
Glu Glu Lys Glu Gly Asp Gly Glu Glu Glu Asp Gly Asp Glu Glu Glu
65                  70                  75                  80 gct gag tct gct aca ggc aag cgg gca gct gaa gat gat gag gat gat    288
Ala Glu Ser Ala Thr Gly Lys Arg Ala Ala Glu Asp Asp Glu Asp Asp
                85                  90                  95 gat gtc gat acc aag aag cag aag acc gac aag gat gac taa            330
Asp Val Asp Thr Lys Lys Gln Lys Thr Asp Lys Asp Asp
            100                 105
```

<210> SEQ ID NO 124
<211> LENGTH: 109
<212> TYPE: PRT
<213> ORGANISM: Homo sapiens

<400> SEQUENCE: 124

```
Met Ser Asp Ala Ala Val Asp Thr Ser Ser Glu Ile Ile Ala Lys Asp
 1               5                  10                  15

Leu Lys Glu Lys Lys Glu Val Val Lys Glu Ala Glu Asn Gly Arg Asp
            20                  25                  30

Ala Pro Ala Asn Gly Asn Ala Asn Glu Glu Asn Gly Glu Gln Glu Ala
```

```
                35                  40                  45
Asp Lys Glu Val Asp Glu Gly Glu Ser Gly Glu Glu Glu
 50                  55                  60

Glu Glu Lys Glu Gly Asp Gly Glu Glu Asp Gly Asp Glu Glu
 65                  70                  75                  80

Ala Glu Ser Ala Thr Gly Lys Arg Ala Ala Glu Asp Glu Asp
                 85                  90                  95

Asp Val Asp Thr Lys Lys Gln Lys Thr Asp Lys Asp
            100                 105

<210> SEQ ID NO 125
<211> LENGTH: 646
<212> TYPE: DNA
<213> ORGANISM: Homo sapiens
<220> FEATURE:
<221> NAME/KEY: CDS
<222> LOCATION: (62)..(397)

<400> SEQUENCE: 125
agcgcgcccg aacgaagccg cggcccgggc acagcatggc ccgcggcggg agggcgctcg    60 g atg ttc ggc agc ctc ctg cac ttc gcc ctg ctc gct gcc ggc gtc gtc   109
  Met Phe Gly Ser Leu Leu His Phe Ala Leu Leu Ala Ala Gly Val Val
   1               5                  10                  15 ccg ctc agc tgg gat ctc ccg gag ccc cgc agc cga gcc agc aag atc      157
Pro Leu Ser Trp Asp Leu Pro Glu Pro Arg Ser Arg Ala Ser Lys Ile
             20                  25                  30 cga gtg cac tcg cga ggc aag ctc tgg gcc atc ggt cac ttc atg ggc      205
Arg Val His Ser Arg Gly Lys Leu Trp Ala Ile Gly His Phe Met Gly
         35                  40                  45 aag aag agt ctg gag cct tcc agc cca tcc cca ttg ggg aca gct ccc      253
Lys Lys Ser Leu Glu Pro Ser Ser Pro Ser Pro Leu Gly Thr Ala Pro
     50                  55                  60 cac acc tcc ctg agg gac cag cga ctg cag ctg agt cat gat ctg ctc      301
His Thr Ser Leu Arg Asp Gln Arg Leu Gln Leu Ser His Asp Leu Leu
 65                  70                  75                  80 gga atc ctc ctg cta aag aag gct ctg ggc gtg agc ctc agc cgc ccc      349
Gly Ile Leu Leu Leu Lys Lys Ala Leu Gly Val Ser Leu Ser Arg Pro
                 85                  90                  95 gca ccc caa atc cag tac agg agg ctg ctg gta caa ata ctg cag aaa      397
Ala Pro Gln Ile Gln Tyr Arg Arg Leu Leu Val Gln Ile Leu Gln Lys
            100                 105                 110 tgacaccaat aatggggcag acacaacagc gtggcttaga ttgtgcccac ccagggaagg    457
tgctgaatgg gaccctgttg atggccccat ctggatgtaa atcctgagct caaatctctg    517
ttactccatt actgtgattt ctggctgggt caccagaaat atcgctgatg cagacacaga    577
ttatgttcct gctgtatttc ctgcttccct gttgaattgg tgaataaaac cttgctctat    637
acatacaaa                                                            646

<210> SEQ ID NO 126
<211> LENGTH: 112
<212> TYPE: PRT
<213> ORGANISM: Homo sapiens

<400> SEQUENCE: 126

Met Phe Gly Ser Leu Leu His Phe Ala Leu Leu Ala Ala Gly Val Val
 1               5                  10                  15

Pro Leu Ser Trp Asp Leu Pro Glu Pro Arg Ser Arg Ala Ser Lys Ile
             20                  25                  30
```

-continued

```
Arg Val His Ser Arg Gly Lys Leu Trp Ala Ile Gly His Phe Met Gly
         35                  40                  45

Lys Lys Ser Leu Glu Pro Ser Ser Pro Ser Pro Leu Gly Thr Ala Pro
 50                  55                  60

His Thr Ser Leu Arg Asp Gln Arg Leu Gln Leu Ser His Asp Leu Leu
 65                  70                  75                  80

Gly Ile Leu Leu Lys Lys Ala Leu Gly Val Ser Leu Ser Arg Pro
                 85                  90                  95

Ala Pro Gln Ile Gln Tyr Arg Arg Leu Leu Val Gln Ile Leu Gln Lys
            100                 105                 110

<210> SEQ ID NO 127
<211> LENGTH: 147
<212> TYPE: DNA
<213> ORGANISM: Homo sapiens
<220> FEATURE:
<221> NAME/KEY: CDS
<222> LOCATION: (6)..(134)

<400> SEQUENCE: 127 agaaa atg gca cac aaa cta gac ctg gaa gaa att gcc agc ttg gat aag      50
      Met Ala His Lys Leu Asp Leu Glu Glu Ile Ala Ser Leu Asp Lys
       1               5                  10                  15 gcc aag ctg aag gcc aca gag atg cag aag aac act ctg atg acc aaa       98
Ala Lys Leu Lys Ala Thr Glu Met Gln Lys Asn Thr Leu Met Thr Lys
             20                  25                  30 gag acc aca gag cag gag aag tgg agt gaa att tcc tgagagcctc gag       147
Glu Thr Thr Glu Gln Glu Lys Trp Ser Glu Ile Ser
         35                  40

<210> SEQ ID NO 128
<211> LENGTH: 43
<212> TYPE: PRT
<213> ORGANISM: Homo sapiens

<400> SEQUENCE: 128

Met Ala His Lys Leu Asp Leu Glu Glu Ile Ala Ser Leu Asp Lys Ala
 1               5                  10                  15

Lys Leu Lys Ala Thr Glu Met Gln Lys Asn Thr Leu Met Thr Lys Glu
            20                  25                  30

Thr Thr Glu Gln Glu Lys Trp Ser Glu Ile Ser
         35                  40

<210> SEQ ID NO 129
<211> LENGTH: 348
<212> TYPE: DNA
<213> ORGANISM: Homo sapiens
<220> FEATURE:
<221> NAME/KEY: CDS
<222> LOCATION: (9)..(320)

<400> SEQUENCE: 129 ctatccct atg gtg tcg gtg tgc agg ccg tgg cct gct gtg gcc ata gca      50
        Met Val Ser Val Cys Arg Pro Trp Pro Ala Val Ala Ile Ala
         1               5                  10 ctt ctg gct ctg ctg gtc tgc ctg ggg gcg ctg gtc gac acc tgc ccc       98
Leu Leu Ala Leu Leu Val Cys Leu Gly Ala Leu Val Asp Thr Cys Pro
 15                  20                  25                  30 atc aaa ccc gag gct cct ggc gaa gac gag tcc ctg gag gag ctg agc      146
Ile Lys Pro Glu Ala Pro Gly Glu Asp Glu Ser Leu Glu Glu Leu Ser
             35                  40                  45 cac tat tat gct tcc ctg tgc cac tac ctc aac gtg gtc acc aga cag      194
```

```
                                                                                  -continued His Tyr Tyr Ala Ser Leu Cys His Tyr Leu Asn Val Val Thr Arg Gln
                50                  55                  60 tta att tca gag aga aac cta cca gac acc att gtg tcc aag gaa gta           242
Leu Ile Ser Glu Arg Asn Leu Pro Asp Thr Ile Val Ser Lys Glu Val
        65                  70                  75 ttt ttc aca agc aca aag gaa aga cct gtg agg aca cag aag gaa ggt           290
Phe Phe Thr Ser Thr Lys Glu Arg Pro Val Arg Thr Gln Lys Glu Gly
 80                  85                  90 tgc cat ctg caa gcc aag gag aga agc ctc tgaaaaaacc aaacctgctg             340
Cys His Leu Gln Ala Lys Glu Arg Ser Leu
 95              100 gcaccttg                                                                  348

<210> SEQ ID NO 130
<211> LENGTH: 104
<212> TYPE: PRT
<213> ORGANISM: Homo sapiens

<400> SEQUENCE: 130

Met Val Ser Val Cys Arg Pro Trp Pro Ala Val Ala Ile Ala Leu Leu
 1               5                  10                  15

Ala Leu Leu Val Cys Leu Gly Ala Leu Val Asp Thr Cys Pro Ile Lys
                20                  25                  30

Pro Glu Ala Pro Gly Glu Asp Glu Ser Leu Glu Glu Leu Ser His Tyr
            35                  40                  45

Tyr Ala Ser Leu Cys His Tyr Leu Asn Val Val Thr Arg Gln Leu Ile
        50                  55                  60

Ser Glu Arg Asn Leu Pro Asp Thr Ile Val Ser Lys Glu Val Phe Phe
 65                  70                  75                  80

Thr Ser Thr Lys Glu Arg Pro Val Arg Thr Gln Lys Glu Gly Cys His
                85                  90                  95

Leu Gln Ala Lys Glu Arg Ser Leu
            100

<210> SEQ ID NO 131
<211> LENGTH: 515
<212> TYPE: DNA
<213> ORGANISM: Homo sapiens
<220> FEATURE:
<221> NAME/KEY: CDS
<222> LOCATION: (11)..(490)

<400> SEQUENCE: 131
gcctgacacc atg ctg ccc gcc tgc ttc ctc ggc cta ctg gcc ttc tcc          49
           Met Leu Pro Ala Cys Phe Leu Gly Leu Leu Ala Phe Ser
            1               5                  10 tcc gcg tgc tac ttc cag aac tgc ccg agg ggc ggc aag agg gcc atg         97
Ser Ala Cys Tyr Phe Gln Asn Cys Pro Arg Gly Gly Lys Arg Ala Met
         15                  20                  25 tcc gac ctg gag ctg aga cag tgc ctc ccc tgc ggc ccc ggg ggc aaa        145
Ser Asp Leu Glu Leu Arg Gln Cys Leu Pro Cys Gly Pro Gly Gly Lys
 30                  35                  40                  45 ggc cgc tgc ttc ggg ccc agc att tgc tgc gcg gac gag ctg ggc tgc        193
Gly Arg Cys Phe Gly Pro Ser Ile Cys Cys Ala Asp Glu Leu Gly Cys
                 50                  55                  60 ttc gtg ggc acg gct gag gcg ctg cgc tgc cag gag gag aac tac ctg        241
Phe Val Gly Thr Ala Glu Ala Leu Arg Cys Gln Glu Glu Asn Tyr Leu
             65                  70                  75 ccg tcg ccc tgc cag tcc ggc cag aag gcg tgc ggg agc ggg ggc cgc        289
Pro Ser Pro Cys Gln Ser Gly Gln Lys Ala Cys Gly Ser Gly Gly Arg
```

-continued

```
                       80                      85                      90
tgc gcc gcc ttc ggc gtt tgc tgc aac gac gag agc tgc gtg acc gag       337
Cys Ala Ala Phe Gly Val Cys Cys Asn Asp Glu Ser Cys Val Thr Glu
     95                     100                     105 tcc gag tgc cgc gag ggc ttt cac cgc cgc gcc cgc gcc agc gac cgg       385
Ser Glu Cys Arg Glu Gly Phe His Arg Arg Ala Arg Ala Ser Asp Arg
110                     115                     120                 125 agc aac gcc acg caa ctg gac agg ccg gcc ggg gcc ttg ctg ctg cgg       433
Ser Asn Ala Thr Gln Leu Asp Arg Pro Ala Gly Ala Leu Leu Leu Arg
                    130                     135                 140 ctg gtg cag ctg gcc ggg gcg ccc gag ccc ttt gag ccc gcc cag ccc       481
Leu Val Gln Leu Ala Gly Ala Pro Glu Pro Phe Glu Pro Ala Gln Pro
                145                     150                 155 gac gcc tac tgagccccgc gctcgcccca ccggc                               515
Asp Ala Tyr
        160

<210> SEQ ID NO 132
<211> LENGTH: 160
<212> TYPE: PRT
<213> ORGANISM: Homo sapiens

<400> SEQUENCE: 132

Met Leu Pro Ala Cys Phe Leu Gly Leu Leu Ala Phe Ser Ser Ala Cys
 1               5                  10                  15

Tyr Phe Gln Asn Cys Pro Arg Gly Gly Lys Arg Ala Met Ser Asp Leu
                20                  25                  30

Glu Leu Arg Gln Cys Leu Pro Cys Gly Pro Gly Gly Lys Gly Arg Cys
            35                  40                  45

Phe Gly Pro Ser Ile Cys Cys Ala Asp Glu Leu Gly Cys Phe Val Gly
        50                  55                  60

Thr Ala Glu Ala Leu Arg Cys Gln Glu Glu Asn Tyr Leu Pro Ser Pro
65                  70                  75                  80

Cys Gln Ser Gly Gln Lys Ala Cys Gly Ser Gly Gly Arg Cys Ala Ala
                85                  90                  95

Phe Gly Val Cys Cys Asn Asp Glu Ser Cys Val Thr Glu Ser Glu Cys
                100                 105                 110

Arg Glu Gly Phe His Arg Arg Ala Arg Ala Ser Asp Arg Ser Asn Ala
            115                 120                 125

Thr Gln Leu Asp Arg Pro Ala Gly Ala Leu Leu Leu Arg Leu Val Gln
        130                 135                 140

Leu Ala Gly Ala Pro Glu Pro Phe Glu Pro Ala Gln Pro Asp Ala Tyr
145                 150                 155                 160
```

US 6,974,684 B2

THERAPEUTIC POLYPEPTIDES, NUCLEIC ACIDS ENCODING SAME, AND METHODS OF USE

RELATED APPLICATIONS

This application claims priority to U.S. Ser. No. 60/311,751, filed on Aug. 10, 2001; U.S. Ser. No. 60/310,802, filed on Aug. 8, 2001; U.S. Ser. No. 60/310,795, filed on Aug. 8, 2001; U.S. Ser. No. 60/311,292, filed on Aug. 9, 2001; U.S. Ser. No. 60/361,159, filed on Feb. 28, 2002; U.S. Ser. No. 60/373,050, filed on Apr. 16, 2002; U.S. Ser. No. 60/380,970, filed on May 15, 2002; U.S. Ser. No. 60/311,979, filed on Aug. 13, 2001; U.S. Ser. No. 60/381,030, filed on May 16, 2002; U.S. Ser. No. 60/323,944, filed on Sep. 21, 2001; U.S. Ser. No. 60/311,571, filed on Aug. 10, 2001; U.S. Ser. No. 60/311,594, filed on Aug. 10, 2001; U.S. Ser. No. 60/313,201, filed on Aug. 17, 2001; U.S. Ser. No. 60/359,294, filed on Feb. 21, 2002; U.S. Ser. No. 60/372,998, filed on Apr. 16, 2002; U.S. Ser. No. 60/380,971, filed on May 15, 2002; U.S. Ser. No. 60/312,892, filed on Aug. 16, 2001; U.S. Ser. No. 60/322,716, filed on Sep. 17, 2001; U.S. Ser. No. 60/360,890, filed on Feb. 28, 2002; U.S. Ser. No. 60/314,031, filed on Aug. 21, 2001; U.S. Ser. No. 60/315,853, filed on Aug. 29, 2001; each of which is incorporated by reference in its entirety.

FIELD OF THE INVENTION

The present invention relates to novel polypeptides, and the nucleic acids encoding them, having properties related to stimulation of biochemical or physiological responses in a cell, a tissue, an organ or an organism. More particularly, the novel polypeptides are gene products of novel genes, or are specified biologically active fragments or derivatives thereof. Methods of use encompass diagnostic and prognostic assay procedures as well as methods of treating diverse pathological conditions.

BACKGROUND OF THE INVENTION

Eukaryotic cells are characterized by biochemical and physiological processes, which under normal conditions are exquisitely balanced to achieve the preservation and propagation of the cells. When such cells are components of multicellular organisms such as vertebrates or, more particularly, organisms such as mammals, the regulation of the biochemical and physiological processes involves intricate signaling pathways. Frequently, such signaling pathways include constituted of extracellular signaling proteins, cellular receptors that bind the signaling proteins and signal transducing components located within the cells.

Signaling proteins may be classified as endocrine effectors, paracrine effectors or autocrine effectors. Endocrine effectors are signaling molecules secreted by a given organ into the circulatory system, which are then transported to a distant target organ or tissue. The target cells include the receptors for the endocrine effector, and when the endocrine effector binds, a signaling cascade is induced. Paracrine effectors involve secreting cells and receptor cells in close proximity to each other, such as two different classes of cells in the same tissue or organ. One class of cells secretes the paracrine effector, which then reaches the second class of cells, for example by diffusion through the extracellular fluid. The second class of cells contains the receptors for the paracrine effector; binding of the effector results in induction of the signaling cascade that elicits the corresponding biochemical or physiological effect. Autocrine effectors are highly analogous to paracrine effectors, except that the same cell type that secretes the autocrine effector also contains the receptor. Thus the autocrine effector binds to receptors on the same cell, or on identical neighboring cells. The binding process then elicits the characteristic biochemical or physiological effect.

Signaling processes may elicit a variety of effects on cells and tissues including, by way of nonlimiting example, induction of cell or tissue proliferation, suppression of growth or proliferation, induction of differentiation or maturation of a cell or tissue, and suppression of differentiation or maturation of a cell or tissue.

Many pathological conditions involve dysregulation of expression of important effector proteins. In certain classes of pathologies the dysregulation is manifested as diminished or suppressed level of synthesis and secretion of protein effectors. In other classes of pathologies the dysregulation is manifested as increased or up-regulated level of synthesis and secretion of protein effectors. In a clinical setting a subject may be suspected of suffering from a condition brought on by altered or mis-regulated levels of a protein effector of interest. Therefore there is a need to assay for the level of the protein effector of interest in a biological sample from such a subject, and to compare the level with that characteristic of a nonpathological condition. There also is a need to provide the protein effector as a product of manufacture. Administration of the effector to a subject in need thereof is useful in treatment of the pathological condition. Accordingly, there is a need for a method of treatment of a pathological condition brought on by a diminished or suppressed levels of the protein effector of interest. In addition, there is a need for a method of treatment of a pathological condition brought on by a increased or up-regulated levels of the protein effector of interest.

SUMMARY OF THE INVENTION

The invention is based in part upon the discovery of isolated polypeptides including amino acid sequences selected from mature forms of the amino acid sequences selected from the group consisting of SEQ ID NOs:122, 124, 126, 128, 130, 132, and SEQ ID NO:2n, wherein n is an integer between 1 and 39. The invention also is based in part upon variants of a mature form of the amino acid sequence selected from the group consisting of SEQ ID NOs:122, 124, 126, 128, 130, 132, and SEQ ID NO:2n, wherein n is an integer between 1 and 39, wherein any amino acid in the mature form is changed to a different amino acid, provided that no more than 15% of the amino acid residues in the sequence of the mature form are so changed. In another embodiment, the invention includes the amino acid sequences selected from the group consisting of SEQ ID NOs:122, 124, 126, 128, 130, 132, and SEQ ID NO:2n, wherein n is an integer between 1 and 39. In another embodiment, the invention also comprises variants of the amino acid sequence selected from the group consisting of SEQ ID NOs:122, 124, 126, 128, 130, 132, and SEQ ID NO:2n, wherein n is an integer between 1 and 39 wherein any amino acid specified in the chosen sequence is changed to a different amino acid, provided that no more than 15% of the amino acid residues in the sequence are so changed. The invention also involves fragments of any of the mature forms of the amino acid sequences selected from the group consisting of SEQ ID NOs:122, 124, 126, 128, 130, 132, and SEQ ID NO:2n, wherein n is an integer between 1 and 39, or any other amino acid sequence selected from this group. The invention also comprises fragments from these groups in which up to 15% of the residues are changed.

In another embodiment, the invention encompasses polypeptides that are naturally occurring allelic variants of the sequence selected from the group consisting of SEQ ID NOs:122, 124, 126, 128, 130, 132, and SEQ ID NO:2n, wherein n is an integer between 1 and 39. These allelic variants include amino acid sequences that are the translations of nucleic acid sequences differing by a single nucleotide from nucleic acid sequences selected from the group consisting of SEQ ID NOS: 121, 123, 125, 127, 129, 131, and 2n−1, wherein n is an integer between 1 and 39. The variant polypeptide where any amino acid changed in the chosen sequence is changed to provide a conservative substitution.

In another embodiment, the invention comprises a pharmaceutical composition involving a polypeptide with an amino acid sequence selected from the group consisting of SEQ ID NOs:122, 124, 126, 128, 130, 132, and SEQ ID NO:2n, wherein n is an integer between 1 and 39 and a pharmaceutically acceptable carrier. In another embodiment, the invention involves a kit, including, in one or more containers, this pharmaceutical composition.

In another embodiment, the invention includes the use of a therapeutic in the manufacture of a medicament for treating a syndrome associated with a human disease, the disease being selected from a pathology associated with a polypeptide with an amino acid sequence selected from the group consisting of SEQ ID NOs:122, 124, 126, 128, 130, 132, and SEQ ID NO:2n, wherein n is an integer between 1 and 39 wherein said therapeutic is the polypeptide selected from this group.

In another embodiment, the invention comprises a method for determining the presence or amount of a polypeptide with an amino acid sequence selected from the group consisting of SEQ ID NOs:122, 124, 126, 128, 130, 132, and SEQ ID NO:2n, wherein n is an integer between 1 and 39 in a sample, the method involving providing the sample; introducing the sample to an antibody that binds immunospecifically to the polypeptide; and determining the presence or amount of antibody bound to the polypeptide, thereby determining the presence or amount of polypeptide in the sample.

In another embodiment, the invention includes a method for determining the presence of or predisposition to a disease associated with altered levels of a polypeptide with an amino acid sequence selected from the group consisting of SEQ ID NOs:122, 124, 126, 128, 130, 132, and SEQ ID NO:2n, wherein n is an integer between 1 and 39 in a first mammalian subject, the method involving measuring the level of expression of the polypeptide in a sample from the first mammalian subject; and comparing the amount of the polypeptide in this sample to the amount of the polypeptide present in a control sample from a second mammalian subject known not to have, or not to be predisposed to, the disease, wherein an alteration in the expression level of the polypeptide in the first subject as compared to the control sample indicates the presence of or predisposition to the disease.

In another embodiment, the invention involves a method of identifying an agent that binds to a polypeptide with an amino acid sequence selected from the group consisting of SEQ ID NOs:122, 124, 126, 128, 130, 132, and SEQ ID NO:2n, wherein n is an integer between 1 and 39, the method including introducing the polypeptide to the agent; and determining whether the agent binds to the polypeptide. The agent could be a cellular receptor or a downstream effector.

In another embodiment, the invention involves a method for identifying a potential therapeutic agent for use in treatment of a pathology, wherein the pathology is related to aberrant expression or aberrant physiological interactions of a polypeptide with an amino acid sequence selected from the group consisting of SEQ ID NOs:122, 124, 126, 128, 130, 132, and SEQ ID NO:2n, wherein n is an integer between 1 and 39, the method including providing a cell expressing the polypeptide of the invention and having a property or function ascribable to the polypeptide; contacting the cell with a composition comprising a candidate substance; and determining whether the substance alters the property or function ascribable to the polypeptide; whereby, if an alteration observed in the presence of the substance is not observed when the cell is contacted with a composition devoid of the substance, the substance is identified as a potential therapeutic agent.

In another embodiment, the invention involves a method for screening for a modulator of activity or of latency or predisposition to a pathology associated with a polypeptide having an amino acid sequence selected from the group consisting of SEQ ID NOs:122, 124, 126, 128, 130, 132, and SEQ ID NO:2n, wherein n is an integer between 1 and 39, the method including administering a test compound to a test animal at increased risk for a pathology associated with the polypeptide of the invention, wherein the test animal recombinantly expresses the polypeptide of the invention; measuring the activity of the polypeptide in the test animal after administering the test compound; and comparing the activity of the protein in the test animal with the activity of the polypeptide in a control animal not administered the polypeptide, wherein a change in the activity of the polypeptide in the test animal relative to the control animal indicates the test compound is a modulator of latency of, or predisposition to, a pathology associated with the polypeptide of the invention. The recombinant test animal could express a test protein transgene or express the transgene under the control of a promoter at an increased level relative to a wild-type test animal The promoter may or may not b the native gene promoter of the transgene.

In another embodiment, the invention involves a method for modulating the activity of a polypeptide with an amino acid sequence selected from the group consisting of SEQ ID NOs:122, 124, 126, 128, 130, 132, and SEQ ID NO:2n, wherein n is an integer between 1 and 39, the method including introducing a cell sample expressing the polypeptide with a compound that binds to the polypeptide in an amount sufficient to modulate the activity of the polypeptide.

In another embodiment, the invention involves a method of treating or preventing a pathology associated with a polypeptide with an amino acid sequence selected from the group consisting of SEQ ID NOs:122, 124, 126, 128, 130, 132, and SEQ ID NO:2n, wherein n is an integer between 1 and 39, the method including administering the polypeptide to a subject in which such treatment or prevention is desired in an amount sufficient to treat or prevent the pathology in the subject. The subject could be human.

In another embodiment, the invention involves a method of treating a pathological state in a mammal, the method including administering to the mammal a polypeptide in an amount that is sufficient to alleviate the pathological state, wherein the polypeptide is a polypeptide having an amino acid sequence at least 95% identical to a polypeptide having the amino acid sequence selected from the group consisting of SEQ ID NOs:122, 124, 126, 128, 130, 132, and SEQ ID NO:2n, wherein n is an integer between 1 and 39 or a biologically active fragment thereof.

In another embodiment, the invention involves an isolated nucleic acid molecule comprising a nucleic acid sequence encoding a polypeptide having an amino acid sequence selected from the group consisting of a mature form of the amino acid sequence given SEQ ID NOs:122, 124, 126, 128, 130, 132, and SEQ ID NO:2n, wherein n is an integer between 1 and 39; a variant of a mature form of the amino acid sequence selected from the group consisting of SEQ ID NOs:122, 124, 126, 128, 130, 132, and SEQ ID NO:2n, wherein n is an integer between 1 and 39 wherein any amino acid in the mature form of the chosen sequence is changed to a different amino acid, provided that no more than 15% of the amino acid residues in the sequence of the mature form are so changed; the amino acid sequence selected from the group consisting of SEQ ID NOs:122, 124, 126, 128, 130, 132, and SEQ ID NO:2n, wherein n is an integer between 1 and 39; a variant of the amino acid sequence selected from the group consisting of SEQ ID NOs:122, 124, 126, 128, 130, 132, and SEQ ID NO:2n, wherein n is an integer between 1 and 39, in which any amino acid specified in the chosen sequence is changed to a different amino acid, provided that no more than 15% of the amino acid residues in the sequence are so changed; a nucleic acid fragment encoding at least a portion of a polypeptide comprising the amino acid sequence selected from the group consisting of SEQ ID NOs:122, 124, 126, 128, 130, 132, and SEQ ID NO:2n, wherein n is an integer between 1 and 39 or any variant of the polypeptide wherein any amino acid of the chosen sequence is changed to a different amino acid, provided that no more than 10% of the amino acid residues in the sequence are so changed; and the complement of any of the nucleic acid molecules.

In another embodiment, the invention comprises an isolated nucleic acid molecule having a nucleic acid sequence encoding a polypeptide comprising an amino acid sequence selected from the group consisting of a mature form of the amino acid sequence given SEQ ID NOs:122, 124, 126, 128, 130, 132, and SEQ ID NO:2n, wherein n is an integer between 1 and 39, wherein the nucleic acid molecule comprises the nucleotide sequence of a naturally occurring allelic nucleic acid variant.

In another embodiment, the invention involves an isolated nucleic acid molecule including a nucleic acid sequence encoding a polypeptide having an amino acid sequence selected from the group consisting of a mature form of the amino acid sequence given SEQ ID NOs:122, 124, 126, 128, 130, 132, and SEQ ID NO:2n, wherein n is an integer between 1 and 39 that encodes a variant polypeptide, wherein the variant polypeptide has the polypeptide sequence of a naturally occurring polypeptide variant.

In another embodiment, the invention comprises an isolated nucleic acid molecule having a nucleic acid sequence encoding a polypeptide comprising an amino acid sequence selected from the group consisting of a mature form of the amino acid sequence given SEQ ID NOs:122, 124, 126, 128, 130, 132, and SEQ ID NO:2n, wherein n is an integer between 1 and 39, wherein the nucleic acid molecule differs by a single nucleotide from a nucleic acid sequence selected from the group consisting of SEQ ID NOS: 121, 123, 125, 127, 129, 131, and 2n–1, wherein n is an integer between 1 and 39.

In another embodiment, the invention includes an isolated nucleic acid molecule having a nucleic acid sequence encoding a polypeptide including an amino acid sequence selected from the group consisting of a mature form of the amino acid sequence given SEQ ID NOs:122, 124, 126, 128, 130, 132, and SEQ ID NO:2n, wherein n is an integer between 1 and 39, wherein the nucleic acid molecule comprises a nucleotide sequence selected from the group consisting of the nucleotide sequence selected from the group consisting of SEQ ID NO:121, 123, 125, 127, 129, 131, and 2n–1, wherein n is an integer between 1 and 39; a nucleotide sequence wherein one or more nucleotides in the nucleotide sequence selected from the group consisting of SEQ ID NOs:121, 123, 125, 127, 129, 131, and SEQ ID NO:2n–1, wherein n is an integer between 1 and 39, is changed from that selected from the group consisting of the chosen sequence to a different nucleotide provided that no more than 15% of the nucleotides are so changed; a nucleic acid fragment of the sequence selected from the group consisting of SEQ ID NOs:121, 123, 125, 127, 129, 131, and SEQ ID NO:2n–1, wherein n is an integer between 1 and 39; and a nucleic acid fragment wherein one or more nucleotides in the nucleotide sequence selected from the group consisting of SEQ ID NOs:121, 123, 125, 127, 129, 131, and SEQ ID NO:2n–1, wherein n is an integer between 1 and 39, is changed from that selected from the group consisting of the chosen sequence to a different nucleotide provided that no more than 15% of the nucleotides are so changed.

In another embodiment, the invention includes an isolated nucleic acid molecule having a nucleic acid sequence encoding a polypeptide including an amino acid sequence selected from the group consisting of a mature form of the amino acid sequence given SEQ ID NOs:122, 124, 126, 128, 130, 132, and SEQ ID NO:2n, wherein n is an integer between 1 and 39, wherein the nucleic acid molecule hybridizes under stringent conditions to the nucleotide sequence selected from the group consisting of SEQ ID NOs:121, 123, 125, 127, 129, 131, and SEQ ID NO:2n–1, wherein n is an integer between 1 and 39, or a complement of the nucleotide sequence.

In another embodiment, the invention includes an isolated nucleic acid molecule having a nucleic acid sequence encoding a polypeptide including an amino acid sequence selected from the group consisting of a mature form of the amino acid sequence given SEQ ID NOs:122, 124, 126, 128, 130, 132, and SEQ ID NO:2n, wherein n is an integer between 1 and 39, wherein the nucleic acid molecule has a nucleotide sequence in which any nucleotide specified in the coding sequence of the chosen nucleotide sequence is changed from that selected from the group consisting of the chosen sequence to a different nucleotide provided that no more than 15% of the nucleotides in the chosen coding sequence are so changed, an isolated second polynucleotide that is a complement of the first polynucleotide, or a fragment of any of them.

In another embodiment, the invention includes a vector involving the nucleic acid molecule having a nucleic acid sequence encoding a polypeptide including an amino acid sequence selected from the group consisting of a mature form of the amino acid sequence given SEQ ID NOs:122, 124, 126, 128, 130, 132, and SEQ ID NO:2n, wherein n is an integer between 1 and 39. This vector can have a promoter operably linked to the nucleic acid molecule. This vector can be located within a cell.

In another embodiment, the invention involves a method for determining the presence or amount of a nucleic acid molecule having a nucleic acid sequence encoding a polypeptide including an amino acid sequence selected from the group consisting of a mature form of the amino acid sequence given SEQ ID NOs:122, 124, 126, 128, 130, 132, and SEQ ID NO:2n, wherein n is an integer between 1 and 39 in a sample, the method including providing the sample; introducing the sample to a probe that binds to the nucleic acid molecule; and determining the presence or amount of the probe bound to the nucleic acid molecule, thereby determining the presence or amount of the nucleic acid molecule in the sample. The presence or amount of the nucleic acid molecule is used as a marker for cell or tissue type. The cell type can be cancerous.

In another embodiment, the invention involves a method for determining the presence of or predisposition for a disease associated with altered levels of a nucleic acid molecule having a nucleic acid sequence encoding a polypeptide including an amino acid sequence selected from the group consisting of a mature form of the amino acid sequence given SEQ ID NOs:122, 124, 126, 128, 130, 132, and SEQ ID NO:2n, wherein n is an integer between 1 and 39 in a first mammalian subject, the method including measuring the amount of the nucleic acid in a sample from the first mammalian subject; and comparing the amount of the nucleic acid in the sample of step (a) to the amount of the nucleic acid present in a control sample from a second mammalian subject known not to have or not be predisposed to, the disease; wherein an alteration in the level of the nucleic acid in the first subject as compared to the control sample indicates the presence of or predisposition to the disease.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

The present invention provides novel nucleotides and polypeptides encoded thereby. Included in the invention are the novel nucleic acid sequences, their encoded polypeptides, antibodies, and other related compounds. The sequences are collectively referred to herein as "NOVX nucleic acids" or "NOVX polynucleotides" and the corresponding encoded polypeptides are referred to as "NOVX polypeptides" or "NOVX proteins." Unless indicated otherwise, "NOVX" is meant to refer to any of the novel sequences disclosed herein. Table 1 provides a summary of the NOVX nucleic acids and their encoded polypeptides.

TABLE 1

Sequences and Corresponding SEQ ID Numbers

| NOVX ASSIGNMENT | INTERNAL IDENTIFICATION | SEQ ID NO (nucleic acid) | SEQ ID NO (polypeptide) | HOMOLOGY |
|---|---|---|---|---|
| 1a | CG101926-01 | 1 | 2 | Osteoglycin |
| 1b | 207639361 | 3 | 4 | Osteoglycin |
| 2a | CG109754-02 | 5 | 6 | Bioactive Peptide Thymosin beta-10 |
| 2b | CG109754-01 | 121 | 122 | Thymosin beta-10 |
| 3a | CG114834-02 | 7 | 8 | Bioactive Peptide Thymosin alpha |
| 3b | CG114834-01 | 123 | 124 | Thymosin beta-10 |
| 4a | CG124728-02 | 9 | 10 | Complement-C1q tumor necrosis factor-related protein like *homo sapiens* |
| 4b | CG124728-03 | 11 | 12 | Complement-C1q tumor necrosis factor-related protein like *homo sapiens* |
| 4c | 263479529 | 13 | 14 | Complement-C1Q-like Proteins |
| 4d | 271674589 | 15 | 16 | Complement-C1Q-like Proteins |
| 5a | CG127616-01 | 17 | 18 | Erythropoietin like *homo sapiens* |
| 5b | CG127616-02 | 19 | 20 | Erythropoietin splice variant-like Proteins, derived Peptides, and Nucleic Acids Encoding Same |
| 5c | 214374151 | 21 | 22 | Erythropoietin splice variant-like Proteins, derived Peptides, and Nucleic Acids Encoding Same |
| 5d | 219936857 | 23 | 24 | Erythropoietin |
| 5e | 259333914 | 25 | 26 | Erythropoietin |
| 5f | 219936857 | 27 | 28 | Erythropoietin IFC |
| 6a | CG128348-01 | 29 | 30 | Apolipoprotein E Precursor like *homo sapiens* |
| 6b | CG128348-02 | 31 | 32 | Apolipoprotein E Precursor like *homo sapiens* |
| 6c | CG128348-03 | 33 | 34 | Apolipoprotein E Precursor like *homo sapiens* |
| 6d | 278480724 | 35 | 36 | Apolipoprotein E Precursor-like |
| 6e | 278480754 | 37 | 38 | Apolipoprotein E Precursor-like |
| 6f | 278480861 | 39 | 40 | Apolipoprotein E Precursor-like |
| 6g | 278876278 | 41 | 42 | Apolipoprotein E Precursor |
| 6h | 278876445 | 43 | 44 | Apolipoprotein E Precursor |
| 6i | 278876664 | 45 | 46 | Apolipoprotein E Precursor |
| 7a | CG129136-01 | 47 | 48 | 4-1BB Ligand like *homo sapiens* |

TABLE 1-continued

Sequences and Corresponding SEQ ID Numbers

| NOVX ASSIGNMENT | INTERNAL IDENTIFICATION | SEQ ID NO (nucleic acid) | SEQ ID NO (polypeptide) | HOMOLOGY |
|---|---|---|---|---|
| 7b | CG129136-03 | 49 | 50 | Novel 4-1BB Ligand-like Proteins and Nucleic Acids Encoding Same |
| 7c | 278876545 | 51 | 52 | IFC-4-1BB Ligand |
| 7d | 278876597 | 53 | 54 | IFC-4-1BB Ligand |
| 8a | CG133483-01 | 55 | 56 | Win4 like *homo sapiens* |
| 9a | CG135316-01 | 57 | 58 | splice variant of FGF14 like *homo sapiens* |
| 10a | CG53473-03 | 59 | 60 | Bioactive Peptide Neuromedin |
| 10b | CG53473-01 | 125 | 126 | Neuromedin |
| 11a | CG54725-03 | 61 | 62 | Bioactive Peptide Thymosin beta-10 |
| 11b | CG54725-01 | 127 | 128 | Thymosin beta-10 |
| 12a | CG56983-02 | 63 | 64 | Bioactive Peptide YY |
| 12b | CG56983-03 | 65 | 66 | Bioactive Peptide YY |
| 12c | CG56983-04 | 67 | 68 | Bioactive Peptide YY |
| 12d | CG56983-01 | 129 | 130 | YY Peptide |
| 13a | CG57666-02 | 69 | 70 | Bioactive Peptide MHC Class I |
| 14a | CG59651-03 | 71 | 72 | Growth/differentiation factor-15 |
| 14b | 207775400 | 73 | 74 | Growth/differentiation factor-15 |
| 14c | 207775387 | 75 | 76 | Prostate differentiation factor-like Proteins, derived Peptides, and Nucleic Acids Encoding Same |
| 15a | CG89614-04 | 77 | 78 | Bioactive Peptide Oxytocin |
| 15b | CG89614-01 | 131 | 132 | Oxytocin |

Table 1 indicates homology of NOVX nucleic acids to known protein families. Thus, the nucleic acids and polypeptides, antibodies and related compounds according to the invention corresponding to a NOVX as identified in column 1 of Table 1 will be useful in therapeutic and diagnostic applications implicated in, for example, pathologies and disorders associated with the known protein families identified in column 5 of Table 1.

NOVX nucleic acids and their encoded polypeptides are useful in a variety of applications and contexts. The various NOVX nucleic acids and polypeptides according to the invention are useful as novel members of the protein families according to the presence of domains and sequence relatedness to previously described proteins. Additionally, NOVX nucleic acids and polypeptides can also be used to identify proteins that are members of the family to which the NOVX polypeptides belong.

Consistent with other known members of the family of proteins, identified in column 5 of Table 1, the NOVX polypeptides of the present invention show homology to, and contain domains that are characteristic of, other members of such protein families. Details of the sequence relatedness and domain analysis for each NOVX are presented in Example A.

The NOVX nucleic acids and polypeptides can also be used to screen for molecules, which inhibit or enhance NOVX activity or function. Specifically, the nucleic acids and polypeptides according to the invention may be used as targets for the identification of small molecules that modulate or inhibit diseases associated with the protein families listed in Table 1.

The NOVX nucleic acids and polypeptides are also useful for detecting specific cell types. Details of the expression analysis for each NOVX are presented in Example C. Accordingly, the NOVX nucleic acids, polypeptides, antibodies and related compounds according to the invention will have diagnostic and therapeutic applications in the detection of a variety of diseases with differential expression in normal vs. diseased tissues, e.g. a variety of cancers.

Additional utilities for NOVX nucleic acids and polypeptides according to the invention are disclosed herein.

NOVX Clones

NOVX nucleic acids and their encoded polypeptides are useful in a variety of applications and contexts. The various NOVX nucleic acids and polypeptides according to the invention are useful as novel members of the protein families according to the presence of domains and sequence relatedness to previously described proteins. Additionally, NOVX nucleic acids and polypeptides can also be used to identify proteins that are members of the family to which the NOVX polypeptides belong.

The NOVX genes and their corresponding encoded proteins are useful for preventing, treating or ameliorating medical conditions, e.g., by protein or gene therapy. Pathological conditions can be diagnosed by determining the amount of the new protein in a sample or by determining the presence of mutations in the new genes. Specific uses are described for each of the NOVX genes, based on the tissues in which they are most highly expressed. Uses include developing products for the diagnosis or treatment of a variety of diseases and disorders.

The NOVX nucleic acids and proteins of the invention are useful in potential diagnostic and therapeutic applications and as a research tool. These include serving as a specific or selective nucleic acid or protein diagnostic and/or prognostic marker, wherein the presence or amount of the nucleic acid or the protein are to be assessed, as well as potential therapeutic applications such as the following: (i) a protein therapeutic, (ii) a small molecule drug target, (iii) an antibody target (therapeutic, diagnostic, drug targeting/ cytotoxic antibody), (iv) a nucleic acid useful in gene therapy (gene delivery/gene ablation), and (v) a composition promoting tissue regeneration in vitro and in vivo (vi) biological defense weapon.

In one specific embodiment, the invention includes an isolated polypeptide comprising an amino acid sequence selected from the group consisting of: (a) a mature form of the amino acid sequence selected from the group consisting of SEQ ID NOs:122, 124, 126, 128, 130, 132, and SEQ ID NO:2n, wherein n is an integer between 1 and 39; (b) a variant of a mature form of the amino acid sequence selected from the group consisting of SEQ ID NOs:122, 124, 126, 128, 130, 132, and SEQ ID NO:2n, wherein n is an integer between 1 and 39, wherein any amino acid in the mature form is changed to a different amino acid, provided that no more than 15% of the amino acid residues in the sequence of the mature form are so changed; (c) an amino acid sequence selected from the group consisting of SEQ ID NOs:122, 124, 126, 128, 130, 132, and SEQ ID NO:2n, wherein n is an integer between 1 and 39; (d) a variant of the amino acid sequence selected from the group consisting of SEQ ID NOs:122, 124, 126, 128, 130, 132, and SEQ ID NO:2n, wherein n is an integer between 1 and 39, wherein any amino acid specified in the chosen sequence is changed to a different amino acid, provided that no more than 15% of the amino acid residues in the sequence are so changed; and (e) a fragment of any of (a) through (d).

In another specific embodiment, the invention includes an isolated nucleic acid molecule comprising a nucleic acid sequence encoding a polypeptide comprising an amino acid sequence selected from the group consisting of: (a) a mature form of the amino acid sequence given, SEQ ID NOs:122, 124, 126, 128, 130, 132, and SEQ ID NOs:122, 124, 126, 128, 130, 132, and SEQ ID NO:2n, wherein n is an integer between 1 and 39; (b) a variant of a mature form of the amino acid sequence selected from the group consisting of SEQ ID NOs:122, 124, 126, 128, 130, 132, and SEQ ID NO:2n, wherein n is an integer between 1 and 39, wherein any amino acid in the mature form of the chosen sequence is changed to a different amino acid, provided that no more than 15% of the amino acid residues in the sequence of the mature form are so changed; (c) the amino acid sequence selected from the group consisting of SEQ ID NOs:122, 124, 126, 128, 130, 132, and SEQ ID NO:2n, wherein n is an integer between 1 and 39; (d) a variant of the amino acid sequence selected from the group consisting of SEQ ID NOs:122, 124, 126, 128, 130, 132, and SEQ ID NO:2n, wherein n is an integer between 1 and 39, in which any amino acid specified in the chosen sequence is changed to a different amino acid, provided that no more than 15% of the amino acid residues in the sequence are so changed; (e) a nucleic acid fragment encoding at least a portion of a polypeptide comprising the amino acid sequence selected from the group consisting of SEQ ID NOs:122, 124, 126, 128, 130, 132, and SEQ ID NO:2n, wherein n is an integer between 1 and 39, or any variant of said polypeptide wherein any amino acid of the chosen sequence is changed to a different amino acid, provided that no more than 10% of the amino acid residues in the sequence are so changed; and (f) the complement of any of said nucleic acid molecules.

In yet another specific embodiment, the invention includes an isolated nucleic acid molecule, wherein said nucleic acid molecule comprises a nucleotide sequence selected from the group consisting of: (a) the nucleotide sequence selected from the group consisting of SEQ ID NOs:121, 123, 125, 127, 129, 131, and SEQ ID NO:2n–1, wherein n is an integer between 1 and 39; (b) a nucleotide sequence wherein one or more nucleotides in the nucleotide sequence selected from the group consisting of SEQ ID NOs:121, 123, 125, 127, 129, 131, and SEQ ID NO:2n–1, wherein n is an integer between 1 and 39, is changed from that selected from the group consisting of the chosen sequence to a different nucleotide provided that no more than 15% of the nucleotides are so changed; (c) a nucleic acid fragment of the sequence selected from the group consisting of SEQ ID NOs:121, 123, 125, 127, 129, 131, and SEQ ID NO:2n–1, wherein n is an integer between 1 and 39; and (d) a nucleic acid fragment wherein one or more nucleotides in the nucleotide sequence selected from the group consisting of SEQ ID NOs:121, 123, 125, 127, 129, 131, and SEQ ID NO:2n–1, wherein n is an integer between 1 and 39, is changed from that selected from the group consisting of the chosen sequence to a different nucleotide provided that no more than 15% of the nucleotides are so changed.

NOVX Nucleic Acids and Polypeptides

One aspect of the invention pertains to isolated nucleic acid molecules that encode NOVX polypeptides or biologically active portions thereof. Also included in the invention are nucleic acid fragments sufficient for use as hybridization probes to identify NOVX-encoding nucleic acids (e.g., NOVX mRNAs) and fragments for use as PCR primers for the amplification and/or mutation of NOVX nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule may be single-stranded or double-stranded, but preferably is comprised double-stranded DNA.

A NOVX nucleic acid can encode a mature NOVX polypeptide. As used herein, a "mature" form of a polypeptide or protein disclosed in the present invention is the product of a naturally occurring polypeptide, precursor form, or proprotein. The naturally occurring polypeptide, precursor or proprotein includes, by way of nonlimiting example, the full-length gene product encoded by the corresponding gene. Alternatively, it may be defined as the polypeptide, precursor or proprotein encoded by an ORF described herein. The product "mature" form arises, by way of nonlimiting example, as a result of one or more naturally occurring processing steps that may take place within the cell (host cell) in which the gene product arises. Examples of such processing steps leading to a "mature" form of a polypeptide or protein include the cleavage of the N-terminal methionine residue encoded by the initiation codon of an ORF or the proteolytic cleavage of a signal peptide or leader sequence. Thus a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

The term "probe", as utilized herein, refers to nucleic acid sequences of variable length, preferably between at least about 10 nucleotides (nt), and 100 nt, or as many as approximately, e.g., 6,000 nt, depending upon the specific use. Probes are used in the detection of identical, similar, or complementary nucleic acid sequences. Longer length probes are generally obtained from a natural or recombinant source, are highly specific, and much slower to hybridize than shorter-length oligomer probes. Probes may be single- or double-stranded and designed to have specificity in PCR, membrane-based hybridization technologies, or ELISA-like technologies.

The term "isolated" nucleic acid molecule, as used herein, is a nucleic acid which is separated from other nucleic acid molecules which are present in the natural source of the nucleic acid. Preferably, an "isolated" nucleic acid is free of sequences which naturally flank the nucleic acid (i.e., sequences located at the 5'- and 3'-termini of the nucleic acid) in the genomic DNA of the organism from which the nucleic acid is derived. For example, in various embodiments, the isolated NOVX nucleic acid molecules can contain less than about 5 kb, 4 kb, 3 kb, 2 kb, 1 kb, 0.5 kb, 0.1 kb, or less of nucleotide sequences which naturally flank the nucleic acid molecule in genomic DNA of the cell/tissue from which the nucleic acid is derived (e.g., brain, heart, liver, spleen, etc.). Moreover, an "isolated" nucleic acid molecule, such as a cDNA molecule, can be substantially free of other cellular material, culture medium, or of chemical precursors or other chemicals.

A nucleic acid molecule of the invention, e.g., a nucleic acid molecule having the nucleotide sequence SEQ ID NOS: 121, 123, 125, 127, 129, 131, and SEQ ID NOs: 2n−1, wherein n is an integer between 1 and 39, or a complement of this nucleotide sequence, can be isolated using standard molecular biology techniques and the sequence information provided herein. Using all or a portion of the nucleic acid sequence of SEQ ID NOS: 121, 123, 125, 127, 129, 131, and SEQ ID NOs: 2n−1, wherein n is an integer between 1 and 39, as a hybridization probe, NOVX molecules can be isolated using standard hybridization and cloning techniques (e.g., as described in Sambrook, et al., (eds.), Molecular Cloning: A Laboratory Manual $2^{nd}$ Ed., Cold Spring Harbor Laboratory Press, Cold Spring Harbor, N.Y., 1989; and Ausubel, et al., (eds.), CURRENT PROTOCOLS IN MOLECULAR BIOLOGY, John Wiley & Sons, New York, N.Y., 1993).

A nucleic acid of the invention can be amplified using cDNA, mRNA or, alternatively, genomic DNA as a template with appropriate oligonucleotide primers according to standard PCR amplification techniques. The nucleic acid so amplified can be cloned into an appropriate vector and characterized by DNA sequence analysis. Furthermore, oligonucleotides corresponding to NOVX nucleotide sequences can be prepared by standard synthetic techniques, e.g., using an automated DNA synthesizer.

As used herein, the term "oligonucleotide" refers to a series of linked nucleotide residues. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise a nucleic acid sequence having about 10 nt, 50 nt, or 100 nt in length, preferably about 15 nt to 30 nt in length. In one embodiment of the invention, an oligonucleotide comprising a nucleic acid molecule less than 100 nt in length would further comprise at least 6 contiguous nucleotides of SEQ ID NOS: 121, 123, 125, 127, 129, 131, and SEQ ID NOs: 2n−1, wherein n is an integer between 1 and 39, or a complement thereof. Oligonucleotides may be chemically synthesized and may also be used as probes.

In another embodiment, an isolated nucleic acid molecule of the invention comprises a nucleic acid molecule that is a complement of the nucleotide sequence shown in SEQ ID NOS: 121, 123, 125, 127, 129, 131, and SEQ ID NOs: 2n−1, wherein n is an integer between 1 and 39, or a portion of this nucleotide sequence (e.g., a fragment that can be used as a probe or primer or a fragment encoding a biologically-active portion of a NOVX polypeptide). A nucleic acid molecule that is complementary to the nucleotide sequence shown SEQ ID NOS: 121, 123, 125, 127, 129, 131, and SEQ ID NOs:2n−1, wherein n is an integer between 1 and 39, is one that is sufficiently complementary to the nucleotide sequence shown SEQ ID NOS: 121, 123, 125, 127, 129, 131, and SEQ ID NOs:2n−1, wherein n is an integer between 1 and 39, that it can hydrogen bond with few or no mismatches to the nucleotide sequence shown SEQ ID NOS: 121, 123, 125, 127, 129, 131, and SEQ ID NOs:2n−1, wherein n is an integer between 1 and 39, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, van der Waals, hydrophobic interactions, and the like. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

"Fragments" provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, and are at most some portion less than a full length sequence. Fragments may be derived from any contiguous portion of a nucleic acid or amino acid sequence of choice.

A full-length NOVX clone is identified as containing an ATG translation start codon and an in-frame stop codon. Any disclosed NOVX nucleotide sequence lacking an ATG start codon therefore encodes a truncated C-terminal fragment of the respective NOVX polypeptide, and requires that the corresponding full-length cDNA extend in the 5' direction of the disclosed sequence. Any disclosed NOVX nucleotide sequence lacking an in-frame stop codon similarly encodes a truncated N-terminal fragment of the respective NOVX polypeptide, and requires that the corresponding full-length cDNA extend in the 3' direction of the disclosed sequence.

"Derivatives" are nucleic acid sequences or amino acid sequences formed from the native compounds either directly, by modification, or by partial substitution. "Analogs" are nucleic acid sequences or amino acid sequences that have a structure similar to, but not identical to, the native compound, e.g. they differ from it in respect to certain components or side chains. Analogs may be synthetic or derived from a different evolutionary origin and may have a similar or opposite metabolic activity compared to wild type. Homologs are nucleic acid sequences or amino acid sequences of a particular gene that are derived from different species.

Derivatives and analogs may be full length or other than full length. Derivatives or analogs of the nucleic acids or proteins of the invention include, but are not limited to, molecules comprising regions that are substantially homologous to the nucleic acids or proteins of the invention, in various embodiments, by at least about 70%, 80%, or 95% identity (with a preferred identity of 80–95%) over a nucleic acid or amino acid sequence of identical size or when compared to an aligned sequence in which the alignment is done by a computer homology program known in the art, or whose encoding nucleic acid is capable of hybridizing to the complement of a sequence encoding the proteins of the invention under stringent, moderately stringent, or low stringent conditions. See e.g. Ausubel, et al., CURRENT PROTOCOLS IN MOLECULAR BIOLOGY, John Wiley & Sons, New York, N.Y., 1993, and below.

A "homologous nucleic acid sequence" or "homologous amino acid sequence," or variations thereof, refer to sequences characterized by a homology at the nucleotide level or amino acid level as discussed above. Homologous nucleotide sequences include those sequences coding for isoforms of NOVX polypeptides. Isoforms can be expressed in different tissues of the same organism as a result of, for example, alternative splicing of RNA. Alternatively, isoforms can be encoded by different genes. In the invention, homologous nucleotide sequences include nucleotide sequences encoding for a NOVX polypeptide of species other than humans, including, but not limited to vertebrates, and thus can include, e.g., frog, mouse, rat, rabbit, dog, cat, cow, horse, and other organisms. Homologous nucleotide sequences also include, but are not limited to, naturally occurring allelic variations and mutations of the nucleotide sequences set forth herein. A homologous nucleotide sequence does not, however, include the exact nucleotide sequence encoding a human NOVX protein. Homologous nucleic acid sequences include those nucleic acid sequences that encode conservative amino acid substitutions (see below) in SEQ ID NOS: 121, 123, 125, 127, 129, 131, and SEQ ID NOs:2n–1, wherein n is an integer between 1 and 39, as well as a polypeptide possessing NOVX biological activity. Various biological activities of the NOVX proteins are described below.

A NOVX polypeptide is encoded by the open reading frame ("ORF") of a NOVX nucleic acid. An ORF corresponds to a nucleotide sequence that could potentially be translated into a polypeptide. A stretch of nucleic acids comprising an ORF is uninterrupted by a stop codon. An ORF that represents the coding sequence for a full protein begins with an ATG "start" codon and terminates with one of the three "stop" codons, namely, TAA, TAG, or TGA. For the purposes of this invention, an ORF may be any part of a coding sequence, with or without a start codon, a stop codon, or both. For an ORF to be considered as a good candidate for coding for a bona fide cellular protein, a minimum size requirement is often set, e.g., a stretch of DNA that would encode a protein of 50 amino acids or more.

The nucleotide sequences determined from the cloning of the human NOVX genes allows for the generation of probes and primers designed for use in identifying and/or cloning NOVX homologues in other cell types, e.g. from other tissues, as well as NOVX homologues from other vertebrates. The probe/primer typically comprises a substantially purified oligonucleotide. The oligonucleotide typically comprises a region of nucleotide sequence that hybridizes under stringent conditions to at least about 12, 25, 50, 100, 150, 200, 250, 300, 350 or 400 consecutive sense strand nucleotide sequence of SEQ ID NOS: 121, 123, 125, 127, 129, 131, and SEQ ID NOs:2n–1, wherein n is an integer between 1 and 39; or an anti-sense strand nucleotide sequence of SEQ ID NOS: 121, 123, 125, 127, 129, 131, and SEQ ID NOs:2n–1, wherein n is an integer between 1 and 39; or of a naturally occurring mutant of SEQ ID NOS: 121, 123, 125, 127, 129, 131, and SEQ ID NOs:2n–1, wherein n is an integer between 1 and 39.

Probes based on the human NOVX nucleotide sequences can be used to detect transcripts or genomic sequences encoding the same or homologous proteins. In various embodiments, the probe has a detectable label attached, e.g. the label can be a radioisotope, a fluorescent compound, an enzyme, or an enzyme co-factor. Such probes can be used as a part of a diagnostic test kit for identifying cells or tissues which mis-express a NOVX protein, such as by measuring a level of a NOVX-encoding nucleic acid in a sample of cells from a subject e.g., detecting NOVX mRNA levels or determining whether a genomic NOVX gene has been mutated or deleted.

"A polypeptide having a biologically-active portion of a NOVX polypeptide" refers to polypeptides exhibiting activity similar, but not necessarily identical, an activity of a polypeptide of the invention, including mature forms, as measured in a particular biological assay, with or without dose dependency. A nucleic acid fragment encoding a "biologically-active portion of NOVX" can be prepared by isolating a portion SEQ ID NOS: 121, 123, 125, 127, 129, 131, and SEQ ID NOs:2n–1, wherein n is an integer between 1 and 39, that encodes a polypeptide having a NOVX biological activity (the biological activities of the NOVX proteins are described below), expressing the encoded portion of NOVX protein (e.g., by recombinant expression in vitro) and assessing the activity of the encoded portion of NOVX.

NOVX Nucleic Acid and Polypeptide Variants

The invention further encompasses nucleic acid molecules that differ from the nucleotide sequences shown in SEQ ID NOS: 121, 123, 125, 127, 129, 131, and SEQ ID NOs:2n–1, wherein n is an integer between 1 and 39, due to degeneracy of the genetic code and thus encode the same NOVX proteins as that encoded by the nucleotide sequences shown in SEQ ID NOS: 121, 123, 125, 127, 129, 131, and SEQ ID NOs:2n–1, wherein n is an integer between 1 and 39. In another embodiment, an isolated nucleic acid molecule of the invention has a nucleotide sequence encoding a protein having an amino acid sequence shown in SEQ ID NOS: 122, 124, 126, 128, 130, 132, and SEQ ID NOs:2n, wherein n is an integer between 1 and 39.

In addition to the human NOVX nucleotide sequences shown in SEQ ID NOS: 121, 123, 125, 127, 129, 131, and SEQ ID NOs:2n–1, wherein n is an integer between 1 and 39, it will be appreciated by those skilled in the art that DNA sequence polymorphisms that lead to changes in the amino acid sequences of the NOVX polypeptides may exist within a population (e.g., the human population). Such genetic polymorphism in the NOVX genes may exist among individuals within a population due to natural allelic variation. As used herein, the terms "gene" and "recombinant gene" refer to nucleic acid molecules comprising an open reading frame (ORF) encoding a NOVX protein, preferably a vertebrate NOVX protein. Such natural allelic variations can typically result in 1–5% variance in the nucleotide sequence of the NOVX genes. Any and all such nucleotide variations and resulting amino acid polymorphisms in the NOVX polypeptides, which are the result of natural allelic variation and that do not alter the functional activity of the NOVX polypeptides, are intended to be within the scope of the invention.

Moreover, nucleic acid molecules encoding NOVX proteins from other species, and thus that have a nucleotide sequence that differs from the human SEQ ID NOS: 121, 123, 125, 127, 129, 131, and SEQ ID NOs:2n−1, wherein n is an integer between 1 and 39, are intended to be within the scope of the invention. Nucleic acid molecules corresponding to natural allelic variants and homologues of the NOVX cDNAs of the invention can be isolated based on their homology to the human NOVX nucleic acids disclosed herein using the human cDNAs, or a portion thereof, as a hybridization probe according to standard hybridization techniques under stringent hybridization conditions.

Accordingly, in another embodiment, an isolated nucleic acid molecule of the invention is at least 6 nucleotides in length and hybridizes under stringent conditions to the nucleic acid molecule comprising the nucleotide sequence of SEQ ID NOS: 121, 123, 125, 127, 129, 131, and SEQ ID NOs:2n−1, wherein n is an integer between 1 and 39. In another embodiment, the nucleic acid is at least 10, 25, 50, 100, 250, 500, 750, 1000, 1500, 2000 or more nucleotides in length. In yet another embodiment, an isolated nucleic acid molecule of the invention hybridizes to the coding region. As used herein, the term "hybridizes under stringent conditions" is intended to describe conditions for hybridization and washing under which nucleotide sequences at least about 65% homologous to each other typically remain hybridized to each other.

Homologs (i.e., nucleic acids encoding NOVX proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in Ausubel, et al., (eds.), CURRENT PROTOCOLS IN MOLECULAR BIOLOGY, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions are hybridization in a high salt buffer comprising 6×SSC, 50 mM Tris-HCl (pH 7.5), 1 mM EDTA, 0.02% PVP, 0.02% Ficoll, 0.2% BSA, and 500 mg/ml denatured salmon sperm DNA at 65° C., followed by one or more washes in 0.2×SSC, 0.01% BSA at 50° C. An isolated nucleic acid molecule of the invention that hybridizes under stringent conditions to the sequences SEQ ID NOS: 121, 123, 125, 127, 129, 131, and SEQ ID NOs:2n−1, wherein n is an integer between 1 and 39, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NOS: 121, 123, 125, 127, 129, 131, and SEQ ID NOs:2n−1, wherein n is an integer between 1 and 39, or fragments, analogs or derivatives thereof, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well-known within the art. See, e.g., Ausubel, et al. (eds.), 1993, CURRENT PROTOCOLS IN MOLECULAR BIOLOGY, John Wiley & Sons, New York, and Kriegler, 1990; GENE TRANSFER AND EXPRESSION, A LABORATORY MANUAL, Stockton Press, New York.

In a third embodiment, a nucleic acid that is hybridizable to the nucleic acid molecule comprising the nucleotide sequences SEQ ID NOS: 121, 123, 125, 127, 129, 131, and SEQ ID NOs:2n−1, wherein n is an integer between 1 and 39, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel, et al. (eds.), 1993, CURRENT PROTOCOLS IN MOLECULAR BIOLOGY, John Wiley & Sons, New York , and Kriegler, 1990, GENE TRANSFER AND :EXPRESSION, A LABORATORY MANUALStockton Press, New York ; Shilo and Weinberg, 1981. *Proc Natl Acad Sci USA* 78: 6789–6792.

Conservative Mutations

In addition to naturally-occurring allelic variants of NOVX sequences that may exist in the population, the skilled artisan will further appreciate that changes can be introduced by mutation into the nucleotide sequences SEQ ID NOS: 121, 123, 125, 127, 129, 131, and SEQ ID NOs:2n−1, wherein n is an integer between 1 and 39, thereby leading to changes in the amino acid sequences of the encoded NOVX proteins, without altering the functional ability of the NOVX proteins. For example, nucleotide substitutions leading to amino acid substitutions at "non-essential" amino acid residues can be made in the sequence SEQ ID NOS:122, 124, 126, 128, 130, 132 and 2n, wherein n is an integer between 1 and 39. A "non-essential" amino acid residue is a residue that can be altered from the wild-type sequences of the NOVX proteins without altering their biological activity, whereas an "essential" amino acid residue is required for such biological activity. For example, amino acid residues that are conserved among the NOVX proteins of the invention are predicted to be particularly non-amenable to alteration. Amino acids for which conservative substitutions can be made are well known within the art.

Another aspect of the invention pertains to nucleic acid molecules encoding NOVX proteins that contain changes in amino acid residues that are not essential for activity. Such NOVX proteins differ in amino acid sequence from SEQ ID NOS: 121, 123, 125, 127, 129, 131, and SEQ ID NOs:2n−1, wherein n is an integer between 1 and 39, yet retain biological activity. In one embodiment, the isolated nucleic acid molecule comprises a nucleotide sequence encoding a protein, wherein the protein comprises an amino acid sequence at least about 40% homologous to the amino acid sequences SEQ ID NOS:122, 124, 126, 128, 130, 132, and 2n, wherein n is an integer between 1 and 39. Preferably, the protein encoded by the nucleic acid molecule is at least about 60% homologous to SEQ ID NOS:122, 124, 126, 128, 130, 132, and 2n, wherein n is an integer between 1 and 39; more preferably at least about 70% homologous SEQ ID NOS:122, 124, 126, 128, 130, 132, and 2n, wherein n is an integer between 1 and 39; still more preferably at least about 80% homologous to SEQ ID NOS:122, 124, 126, 128, 130, 132, and 2n, wherein n is an integer between 1 and 39; even more preferably at least about 90% homologous to SEQ ID NOS:122, 124, 126, 128, 130, 132, and 2n, wherein n is an integer between 1 and 39; and most preferably at least about 95% homologous to SEQ ID NOS:122, 124, 126, 128, 130, 132, and 2n, wherein n is an integer between 1 and 39.

An isolated nucleic acid molecule encoding a NOVX protein homologous to the protein of SEQ ID NOS:122, 124, 126, 128, 130, 132, and 2n, wherein n is an integer between 1 and 39, can be created by introducing one or more nucleotide substitutions, additions or deletions into the nucleotide sequence of SEQ ID NOS:121, 123, 125, 127, 129, 131, and 2n−1, wherein n is an integer between 1 and 39, such that one or more amino acid substitutions, additions or deletions are introduced into the encoded protein.

Mutations can be introduced into SEQ ID NOS:121, 123, 125, 127, 129, 131, and 2n−1, wherein n is an integer between 1 and 39, by standard techniques, such as site-directed mutagenesis and PCR-mediated mutagenesis. Preferably, conservative amino acid substitutions are made at one or more predicted, non-essential amino acid residues. A "conservative amino acid substitution" is one in which the amino acid residue is replaced with an amino acid residue having a similar side chain. Families of amino acid residues having similar side chains have been defined within the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in the NOVX protein is replaced with another amino acid residue from the same side chain family. Alternatively, in another embodiment, mutations can be introduced randomly along all or part of a NOVX coding sequence, such as by saturation mutagenesis, and the resultant mutants can be screened for NOVX biological activity to identify mutants that retain activity. Following mutagenesis SEQ ID NOS:121, 123, 125, 127, 129, 131, and SEQ ID NOS: 2n−1, wherein n is an integer between 1 and 39, the encoded protein can be expressed by any recombinant technology known in the art and the activity of the protein can be determined.

The relatedness of amino acid families may also be determined based on side chain interactions. Substituted amino acids may be fully conserved "strong" residues or fully conserved "weak" residues. The "strong" group of conserved amino acid residues may be any one of the following groups: STA, NEQK, NHQK, NDEQ, QHRK, MILV, MILF, HY, FYW, wherein the single letter amino acid codes are grouped by those amino acids that may be substituted for each other. Likewise, the "weak" group of conserved residues may be any one of the following: CSA, ATV, SAG, STNK, STPA, SGND, SNDEQK, NDEQHK, NEQHRK, HFY, wherein the letters within each group represent the single letter amino acid code.

In one embodiment, a mutant NOVX protein can be assayed for (i) the ability to form protein:protein interactions with other NOVX proteins, other cell-surface proteins, or biologically-active portions thereof, (ii) complex formation between a mutant NOVX protein and a NOVX ligand; or (iii) the ability of a mutant NOVX protein to bind to an intracellular target protein or biologically-active portion thereof; (e.g. avidin proteins).

In yet another embodiment, a mutant NOVX protein can be assayed for the ability to regulate a specific biological function (e.g., regulation of insulin release).

Antisense Nucleic Acids

Another aspect of the invention pertains to isolated antisense nucleic acid molecules that are hybridizable to or complementary to the nucleic acid molecule comprising the nucleotide sequence of SEQ ID NOS: 121, 123, 125, 127, 129, 131, and SEQ ID NOS: 2n−1, wherein n is an integer between 1 and 39, or fragments, analogs or derivatives thereof. An "antisense" nucleic acid comprises a nucleotide sequence that is complementary to a "sense" nucleic acid encoding a protein (e.g., complementary to the coding strand of a double-stranded cDNA molecule or complementary to an mRNA sequence). In specific aspects, antisense nucleic acid molecules are provided that comprise a sequence complementary to at least about 10, 25, 50, 100, 250 or 500 nucleotides or an entire NOVX coding strand, or to only a portion thereof. Nucleic acid molecules encoding fragments, homologs, derivatives and analogs of a NOVX protein of SEQ ID NOS:122, 124, 126, 128, 130, 132, and 2n, wherein n is an integer between 1 and 39, or antisense nucleic acids complementary to a NOVX nucleic acid sequence of SEQ ID NOS: 121, 123, 125, 127, 129, 131, and SEQ ID NOS: 2n−1, wherein n is an integer between 1 and 39, are additionally provided.

In one embodiment, an antisense nucleic acid molecule is antisense to a "coding region" of the coding strand of a nucleotide sequence encoding a NOVX protein. The term "coding region" refers to the region of the nucleotide sequence comprising codons, which are translated into amino acid residues. In another embodiment, the antisense nucleic acid molecule is antisense to a "noncoding region" of the coding strand of a nucleotide sequence encoding the NOVX protein. The term "noncoding region" refers to 5' and 3' sequences, which flank the coding region that are not translated into amino acids (i.e., also referred to as 5' and 3' untranslated regions).

Given the coding strand sequences encoding the NOVX protein disclosed herein, antisense nucleic acids of the invention can be designed according to the rules of Watson and Crick or Hoogsteen base pairing. The antisense nucleic acid molecule can be complementary to the entire coding region of NOVX mRNA, but more preferably is an oligonucleotide that is antisense to only a portion of the coding or noncoding region of NOVX mRNA. For example, the antisense oligonucleotide can be complementary to the region surrounding the translation start site of NOVX mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids (e.g., phosphorothioate derivatives and acridine substituted nucleotides can be used).

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, beta-D-mannosylqueosine, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a NOVX protein to thereby inhibit expression of the protein (e.g., by inhibiting transcription and/or translation). The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface (e.g., by linking the antisense nucleic acid molecules to peptides or antibodies that bind to cell surface receptors or antigens). The antisense nucleic acid molecules can also be delivered to cells using the vectors described herein. To achieve sufficient nucleic acid molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. A α-anomeric nucleic acid molecule forms specific double-stranded hybrids with complementary RNA in which, contrary to the usual β-units, the strands run parallel to each other. See, e.g., Gaultier, et al., 1987. *Nucl. Acids Res.* 15: 6625–6641. The antisense nucleic acid molecule can also comprise a 2'-o-methylribonucleotide (See, e.g., Inoue, et al. 1987. *Nucl. Acids Res.* 15: 6131–6148) or a chimeric RNA-DNA analogue (See, e.g., Inoue, et al., 1987. *FEBS Lett.* 215: 327–330.

Ribozymes and PNA Moieties

Nucleic acid modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

In one embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes as described in Haselhoff and Gerlach 1988. *Nature* 334: 585–591) can be used to catalytically cleave NOVX mRNA transcripts to thereby inhibit translation of NOVX mRNA. A ribozyme having specificity for a NOVX-encoding nucleic acid can be designed based upon the nucleotide sequence of a NOVX cDNA disclosed herein (i.e., SEQ ID NOS: 121, 123, 125, 127, 129, 131, and SEQ ID NOS: 2n−1, wherein n is an integer between 1 and 39). For example, a derivative of a *Tetrahymena* L-19 IVS RNA can be constructed in which the nucleotide sequence of the active site is complementary to the nucleotide sequence to be cleaved in a NOVX-encoding mRNA. See, e.g., U.S. Pat. No. 4,987,071 to Cech, et al. and U.S. Pat. No. 5,116,742 to Cech, et al. NOVX mRNA can also be used to select a catalytic RNA having a specific ribonuclease activity from a pool of RNA molecules. See, e.g., Bartel et al., (1993) *Science* 261:1411–1418.

Alternatively, NOVX gene expression can be inhibited by targeting nucleotide sequences complementary to the regulatory region of the NOVX nucleic acid (e.g., the NOVX promoter and/or enhancers) to form triple helical structures that prevent transcription of the NOVX gene in target cells. See, e.g., Helene, 1991. *Anticancer Drug Des.* 6: 569–84; Helene, et al. 1992. *Ann. N.Y. Acad. Sci.* 660: 27–36; Maher, 1992. *Bioassays* 14: 807–15.

In various embodiments, the NOVX nucleic acids can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids. See, e.g., Hyrup, et al., 1996. *Bioorg Med Chem* 4: 5–23. As used herein, the terms "peptide nucleic acids" or "PNAs" refer to nucleic acid mimics (e.g., DNA mimics) in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup, et al., 1996. supra; Perry-O'Keefe, et al., 1996. *Proc. Natl. Acad. Sci. USA* 93: 14670–14675.

PNAs of NOVX can be used in therapeutic and diagnostic applications. For example, PNAs can be used as antisense or antigene agents for sequence-specific modulation of gene expression by, e.g., inducing transcription or translation arrest or inhibiting replication. PNAs of NOVX can also be used, for example, in the analysis of single base pair mutations in a gene (e.g., PNA directed PCR clamping; as artificial restriction enzymes when used in combination with other enzymes, e.g., $S_1$ nucleases (See, Hyrup, et al., 1996.supra); or as probes or primers for DNA sequence and hybridization (See, Hyrup, et al., 1996, supra; Perry-O'Keefe, et al., 1996. supra).

In another embodiment, PNAs of NOVX can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of NOVX can be generated that may combine the advantageous properties of PNA and DNA. Such chimeras allow DNA recognition enzymes (e.g., RNase H and DNA polymerases) to interact with the DNA portion while the PNA portion would provide high binding affinity and specificity. PNA-DNA chimeras can be linked using linkers of appropriate lengths selected in terms of base stacking, number of bonds between the nucleobases, and orientation (see, Hyrup, et al., 1996. supra). The synthesis of PNA-DNA chimeras can be performed as described in Hyrup, et al., 1996. supra and Finn, et al., 1996. *Nucl Acids Res* 24: 3357–3363. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA. See, e.g., Mag, et al., 1989. *Nucl Acid Res* 17: 5973–5988. PNA monomers are then coupled in a stepwise manner to produce a chimeric molecule with a 5' PNA segment and a 3' DNA segment. See, e.g., Finn, et al., 1996. supra. Alternatively, chimeric molecules can be synthesized with a 5' DNA segment and a 3' PNA segment. See, e.g., Petersen, et al., 1975. *Bioorg. Med. Chem. Lett.* 5: 1119–11124.

In other embodiments, the oligonucleotide may include other appended groups such as peptides (e.g., for targeting host cell receptors in vivo), or agents facilitating transport across the cell membrane (see, e.g., Letsinger, et al., 1989. *Proc. Natl. Acad. Sci. U.S.A.* 86: 6553–6556; Lemaitre, et al., 1987. *Proc. Natl. Acad. Sci.* 84: 648–652; PCT Publication No. WO88/09810) or the blood-brain barrier (see, e.g., PCT Publication No. WO 89/10134). In addition, oligonucleotides can be modified with hybridization triggered cleavage agents (see, e.g., Krol, et al., 1988. *BioTechniques* 6:958–976) or intercalating agents (see, e.g., Zon, 1988. *Pharm. Res.* 5: 539–549). To this end, the oligonucleotide may be conjugated to another molecule, e.g., a peptide, a hybridization triggered cross-linking agent, a transport agent, a hybridization-triggered cleavage agent, and the like.

NOVX Polypeptides

A polypeptide according to the invention includes a polypeptide including the amino acid sequence of NOVX polypeptides whose sequences are provided in SEQ ID NOS:122, 124, 126, 128, 130, 132, and 2n, wherein n is an integer between 1 and 39. The invention also includes a mutant or variant protein any of whose residues may be changed from the corresponding residues shown in SEQ ID NOS:122, 124, 126, 128, 130, 132, and 2n, wherein n is an integer between 1 and 39, while still encoding a protein that maintains its NOVX activities and physiological functions, or a functional fragment thereof.

In general, a NOVX variant that preserves NOVX-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated NOVX proteins, and biologically-active portions thereof, or derivatives, fragments, analogs or homologs thereof. Also provided are polypeptide fragments suitable for use as immunogens to raise anti-NOVX antibodies. In one embodiment, native NOVX proteins can be isolated from cells or tissue sources by an appropriate purification scheme using standard protein purification techniques. In another embodiment, NOVX proteins are produced by recombinant DNA techniques. Alternative to recombinant expression, a NOVX protein or polypeptide can be synthesized chemically using standard peptide synthesis techniques.

An "isolated" or "purified" polypeptide or protein or biologically-active portion thereof is substantially free of cellular material or other contaminating proteins from the cell or tissue source from which the NOVX protein is derived, or substantially free from chemical precursors or other chemicals when chemically synthesized. The language "substantially free of cellular material" includes preparations of NOVX proteins in which the protein is separated from cellular components of the cells from which it is isolated or recombinantly-produced. In one embodiment, the language "substantially free of cellular material" includes preparations of NOVX proteins having less than about 30% (by dry weight) of non-NOVX proteins (also referred to herein as a "contaminating protein"), more preferably less than about 20% of non-NOVX proteins, still more preferably less than about 10% of non-NOVX proteins, and most preferably less than about 5% of non-NOVX proteins. When the NOVX protein or biologically-active portion thereof is recombinantly-produced, it is also preferably substantially free of culture medium, i.e., culture medium represents less than about 20%, more preferably less than about 10%, and most preferably less than about 5% of the volume of the NOVX protein preparation.

The language "substantially free of chemical precursors or other chemicals" includes preparations of NOVX proteins in which the protein is separated from chemical precursors or other chemicals that are involved in the synthesis of the protein. In one embodiment, the language "substantially free of chemical precursors or other chemicals" includes preparations of NOVX proteins having less than about 30% (by dry weight) of chemical precursors or non-NOVX chemicals, more preferably less than about 20% chemical precursors or non-NOVX chemicals, still more preferably less than about 10% chemical precursors or non-NOVX chemicals, and most preferably less than about 5% chemical precursors or non-NOVX chemicals.

Biologically-active portions of NOVX proteins include peptides comprising amino acid sequences sufficiently homologous to or derived from the amino acid sequences of the NOVX proteins (e.g., the amino acid sequence shown in SEQ ID NOS:122, 124, 126, 128, 130, 132, and 2n, wherein n is an integer between 1 and 39) that include fewer amino acids than the full-length NOVX proteins, and exhibit at least one activity of a NOVX protein. Typically, biologically-active portions comprise a domain or motif with at least one activity of the NOVX protein. A biologically-active portion of a NOVX protein can be a polypeptide which is, for example, 10, 25, 50, 100 or more amino acid residues in length.

Moreover, other biologically-active portions, in which other regions of the protein are deleted, can be prepared by recombinant techniques and evaluated for one or more of the functional activities of a native NOVX protein.

In an embodiment, the NOVX protein has an amino acid sequence shown SEQ ID NOS:122, 124, 126, 128, 130, 132, and 2n, wherein n is an integer between 1 and 39. In other embodiments, the NOVX protein is substantially homologous to SEQ ID NOS:122, 124, 126, 128, 130, 132, and 2n, wherein n is an integer between 1 and 39, and retains the functional activity of the protein of SEQ ID NOS:122, 124, 126, 128, 130, 132, and 2n, wherein n is an integer between 1 and 39, yet differs in amino acid sequence due to natural allelic variation or mutagenesis, as described in detail, below. Accordingly, in another embodiment, the NOVX protein is a protein that comprises an amino acid sequence at least about 45% homologous to the amino acid sequence SEQ ID NOS:122, 124, 126, 128, 130, 132, and 2n, wherein n is an integer between 1 and 39, and retains the functional activity of the NOVX proteins of SEQ ID NOS:122, 124, 126, 128, 130, 132, and 2n, wherein n is an integer between 1 and 39.

Determining Homology Between Two or More Sequences

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch, 1970. *J Mol Biol* 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NOS: 121, 123, 125, 127, 129, 131, and SEQ ID NOS: 2n–1, wherein n is an integer between 1 and 39.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

Chimeric and Fusion Proteins

The invention also provides NOVX chimeric or fusion proteins. As used herein, a NOVX "chimeric protein" or "fusion protein" comprises a NOVX polypeptide operatively-linked to a non-NOVX polypeptide. An "NOVX polypeptide" refers to a polypeptide having an amino acid sequence corresponding to a NOVX protein SEQ ID NOS:122, 124, 126, 128, 130, 132, and 2n, wherein n is an integer between 1 and 39, whereas a "non-NOVX polypeptide" refers to a polypeptide having an amino acid sequence corresponding to a protein that is not substantially homologous to the NOVX protein, e.g., a protein that is different from the NOVX protein and that is derived from the same or a different organism. Within a NOVX fusion protein the NOVX polypeptide can correspond to all or a portion of a NOVX protein. In one embodiment, a NOVX fusion protein comprises at least one biologically active portion of a NOVX protein. In another embodiment, a NOVX fusion protein comprises at least two biologically active portions of a NOVX protein. In yet another embodiment, a NOVX fusion protein comprises at least three biologically active portions of a NOVX protein. Within the fusion protein, the term "operatively-linked" is intended to indicate that the NOVX polypeptide and the non-NOVX polypeptide are fused in-frame with one another. The non-NOVX polypeptide can be fused to the N-terminus or C-terminus of the NOVX polypeptide.

In one embodiment, the fusion protein is a GST-NOVX fusion protein in which the NOVX sequences are fused to the C-terminus of the GST (glutathione S-transferase) sequences. Such fusion proteins can facilitate the purification of recombinant NOVX polypeptides.

In another embodiment, the fusion protein is a NOVX protein containing a heterologous signal sequence at its N-terminus. In certain host cells (e.g., mammalian host cells), expression and/or secretion of NOVX can be increased through use of a heterologous signal sequence.

In yet another embodiment, the fusion protein is a NOVX-immunoglobulin fusion protein in which the NOVX sequences are fused to sequences derived from a member of the immunoglobulin protein family. The NOVX-immunoglobulin fusion proteins of the invention can be incorporated into pharmaceutical compositions and administered to a subject to inhibit an interaction between a NOVX ligand and a NOVX protein on the surface of a cell, to thereby suppress NOVX-mediated signal transduction in vivo. The NOVX-immunoglobulin fusion proteins can be used to affect the bioavailability of a NOVX cognate ligand. Inhibition of the NOVX ligand/NOVX interaction may be useful therapeutically for both the treatment of proliferative and differentiative disorders, as well as modulating (e.g. promoting or inhibiting) cell survival. Moreover, the NOVX-immunoglobulin fusion proteins of the invention can be used as immunogens to produce anti-NOVX antibodies in a subject, to purify NOVX ligands, and in screening assays to identify molecules that inhibit the interaction of NOVX with a NOVX ligand.

A NOVX chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel, et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A NOVX-encoding nucleic acid can be cloned into such an expression vector such that the fusion moiety is linked in-frame to the NOVX protein.

NOVX Agonists and Antagonists

The invention also pertains to variants of the NOVX proteins that function as either NOVX agonists (i.e., mimetics) or as NOVX antagonists. Variants of the NOVX protein can be generated by mutagenesis (e.g., discrete point mutation or truncation of the NOVX protein). An agonist of the NOVX protein can retain substantially the same, or a subset of, the biological activities of the naturally occurring form of the NOVX protein. An antagonist of the NOVX protein can inhibit one or more of the activities of the naturally occurring form of the NOVX protein by, for example, competitively binding to a downstream or upstream member of a cellular signaling cascade, which includes the NOVX protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the NOVX proteins.

Variants of the NOVX proteins that function as either NOVX agonists (i.e., mimetics) or as NOVX antagonists can be identified by screening combinatorial libraries of mutants (e.g., truncation mutants) of the NOVX proteins for NOVX protein agonist or antagonist activity. In one embodiment, a variegated library of NOVX variants is generated by combinatorial mutagenesis at the nucleic acid level and is encoded by a variegated gene library. A variegated library of NOVX variants can be produced by, for example, enzymatically ligating a mixture of synthetic oligonucleotides into gene sequences such that a degenerate set of potential NOVX sequences is expressible as individual polypeptides, or alternatively, as a set of larger fusion proteins (e.g., for phage display) containing the set of NOVX sequences therein. There are a variety of methods, which can be used to produce libraries of potential NOVX variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential NOVX sequences. Methods for synthesizing degenerate oligonucleotides are well known within the art. See, e.g., Narang, 1983. *Tetrahedron* 39: 3; Itakura, et al., 1984. *Annu. Rev. Biochem.* 53: 323; Itakura, et al., 1984. *Science* 198: 1056; Ike, et al., 1983. *Nucl. Acids Res.* 11:477.

Polypeptide Libraries

In addition, libraries of fragments of the NOVX protein coding sequences can be used to generate a variegated population of NOVX fragments for screening and subsequent selection of variants of a NOVX protein. In one embodiment, a library of coding sequence fragments can be generated by treating a double stranded PCR fragment of a NOVX coding sequence with a nuclease under conditions wherein nicking occurs only about once per molecule, denaturing the double stranded DNA, renaturing the DNA to form double-stranded DNA that can include sense/antisense pairs from different nicked products, removing single stranded portions from reformed duplexes by treatment with $S_1$ nuclease, and ligating the resulting fragment library into an expression vector. By this method, expression libraries can be derived which encodes N-terminal and internal fragments of various sizes of the NOVX proteins.

Various techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of NOVX proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify NOVX variants. See, e.g., Arkin and Youvan, 1992. *Proc. Natl. Acad. Sci. USA* 89: 7811–7815; Delgrave, et al., 1993. *Protein Engineering* 6:327–331.

NOVX Antibodies

The term "antibody" as used herein refers to immunoglobulin molecules and immunologically active portions of immunoglobulin (Ig) molecules, i.e., molecules that contain an antigen-binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. In general, antibody molecules obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

An isolated protein of the invention intended to serve as an antigen, or a portion or fragment thereof, can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein, such as an amino acid sequence shown in SEQ ID NOs: 122, 124, 126, 128, 130, 132, and 2n, wherein n is an integer between 1 and 39, and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the invention, at least one epitope encompassed by the antigenic peptide is a region of NOVX that is located on the surface of the protein, e.g., a hydrophilic region. A hydrophobicity analysis of the human NOVX protein sequence will indicate which regions of a NOVX polypeptide are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci. USA* 78: 3824–3828; Kyte and Doolittle 1982, *J. Mol. Biol.* 157: 105–142, each incorporated herein by reference in their entirety. Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow E, and Lane D, 1988, Cold Spring Harbor Laboratory Press, Cold Spring Harbor, N.Y., incorporated herein by reference). Some of these antibodies are discussed below.

Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and *Corynebacterium parvum*, or similar immunostimulatory agents. Additional examples of adjuvants which can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25–28).

Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.*, 133:3001 (1984); Brodeur et al.,

*Monoclonal Antibody Production Techniques and Applications,* Marcel Dekker, Inc., New York, (1987) pp. 51–63].

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980). It is an objective, especially important in therapeutic applications of monoclonal antibodies, to identify antibodies having a high degree of specificity and a high binding affinity for the target antigen.

After the desired hybridoma cells are identified, the clones can be subcloned by limiting dilution procedures and grown by standard methods (Goding,1986). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, *Nature* 368, 812–13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Humanized Antibodies

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., *Nature,* 321:522–525 (1986); Riechmann et al., *Nature,* 332:323–327 (1988); Verhoeyen et al., *Science,* 239:1534–1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, *Curr. Op. Struct. Biol.,* 2:593–596 (1992)).

Human Antibodies

Fully human antibodies essentially relate to antibody molecules in which the entire sequence of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77–96). Human monoclonal antibodies may be utilized in the practice of the present invention and may be produced by using human hybridomas (see Cote, et al., 1983. Proc Natl Acad Sci USA 80: 2026–2030) or by transforming human B-cells with Epstein Barr Virus in vitro (see Cole, et al., 1985 In: MONOCLONAL ANTIBODIES AND CANCER THERAPY, Alan R. Liss, Inc., pp. 77–96).

In addition, human antibodies can also be produced using additional techniques, including phage display libraries (Hoogenboom and Winter, *J. Mol. Biol.,* 227:381 (1991); Marks et al., *J. Mol. Biol.,* 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in Marks et al. (*Bio/Technology* 10, 779–783 (1992)); Lonberg et al. (*Nature* 368 856–859 (1994)); Morrison (*Nature* 368, 812–13 (1994)); Fishwild et al,(*Nature Biotechnology* 14, 845–51 (1996)); Neuberger (*Nature Biotechnology* 14, 826 (1996)); and Lonberg and Huszar (*Intern. Rev. Immunol.* 13 65–93 (1995)).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

$F_{ab}$ Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275–1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537–539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J., 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from *E. coli* and chemically coupled to form bispecific antibodies. Shalaby et al., *J. Exp. Med.* 175:217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. For example, trispecific antibodies can be prepared. Tutt et al., *J. Immunol.* 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., *J. Exp Med.*, 176: 1191–1195 (1992) and Shopes, *J. Immunol.*, 148: 2918–2922 (1992). Homodimeric antibodies with enhanced anti-tumor activity can also be prepared using heterobifunctional cross-linkers as described in Wolff et al. *Cancer Research*, 53: 2560–2565 (1993). Alternatively, an antibody can be engineered that has dual Fc regions and can thereby have enhanced complement lysis and ADCC capabilities. See Stevenson et al., *Anti-Cancer Drug Design*, 3: 219–230 (1989).

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-disocyanate), and bisactive fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

Immunoliposomes

The antibodies disclosed herein can also be formulated as immunoliposomes. Liposomes containing the antibody are prepared by methods known in the art, such as described in Epstein et al., *Proc. Natl. Acad. Sci. USA*, 82: 3688 (1985); Hwang et al., *Proc. Natl Acad. Sci. USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.*, 257: 286–288 (1982) via a disulfide-interchange reaction. A chemotherapeutic agent (such as Doxorubicin) is optionally contained within the liposome. See Gabizon et al., *J. National Cancer Inst.*, 81(19): 1484 (1989).

Diagnostic Applications of Antibodies Directed Against the Proteins of the Invention Antibodies directed against a protein of the invention may be used in methods known within the art relating to the localization and/or quantitation of the protein (e.g., for use in measuring levels of the protein within appropriate physiological samples, for use in diagnostic methods, for use in imaging the protein, and the like). In a given embodiment, antibodies against the proteins, or derivatives, fragments, analogs or homologs thereof, that contain the antigen binding domain, are utilized as pharmacologically-active compounds (see below).

An antibody specific for a protein of the invention can be used to isolate the protein by standard techniques, such as immunoaffinity chromatography or immunoprecipitation. Such an antibody can facilitate the purification of the natural protein antigen from cells and of recombinantly produced antigen expressed in host cells. Moreover, such an antibody can be used to detect the antigenic protein (e.g., in a cellular lysate or cell supernatant) in order to evaluate the abundance and pattern of expression of the antigenic protein. Antibodies directed against the protein can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Therapeutics

Antibodies of the invention, including polyclonal, monoclonal, humanized and fully human antibodies, may used as therapeutic agents. Such agents will generally be employed to treat or prevent a disease or pathology in a subject. An antibody preparation, preferably one having high specificity and high affinity for its target antigen, is administered to the subject and will generally have an effect due to its binding with the target. Such an effect may be one of two kinds, depending on the specific nature of the interaction between the given antibody molecule and the target antigen in question. In the first instance, administration of the antibody may abrogate or inhibit the binding of the target with an endogenous ligand to which it naturally binds. In this case, the antibody binds to the target and masks a binding site of the naturally occurring ligand, wherein the ligand serves as an effector molecule. Thus the receptor mediates a signal transduction pathway for which ligand is responsible.

Alternatively, the effect may be one in which the antibody elicits a physiological result by virtue of binding to an effector binding site on the target molecule. In this case the target, a receptor having an endogenous ligand which may be absent or defective in the disease or pathology, binds the antibody as a surrogate effector ligand, initiating a receptor-based signal transduction event by the receptor.

A therapeutically effective amount of an antibody of the invention relates generally to the amount needed to achieve a therapeutic objective. As noted above, this may be a binding interaction between the antibody and its target antigen that, in certain cases, interferes with the functioning of the target, and in other cases, promotes a physiological response. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Pharmaceutical Compositions of Antibodies

Antibodies specifically binding a protein of the invention, as well as other molecules identified by the screening assays disclosed herein, can be administered for the treatment of various disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

If the antigenic protein is intracellular and whole antibodies are used as inhibitors, internalizing antibodies are preferred. However, liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., Proc. Natl. Acad. Sci. USA, 90: 7889–7893 (1993). The formulation herein can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

ELISA Assay

An agent for detecting an analyte protein is an antibody capable of binding to an analyte protein, preferably an antibody with a detectable label. Antibodies can be polyclonal, or more preferably, monoclonal. An intact antibody, or a fragment thereof (e.g., $F_{ab}$ or $F_{(ab)2}$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Thory of Enzyme Immunoassays", P. Tijssen, Elsevier Science Publishers, Amsterdam, 1985. Furthermore, in vivo techniques for detection of an analyte protein include introducing into a subject a labeled anti-an analyte protein antibody. For example, the antibody can be labeled with a radioactive marker whose presence and location in a subject can be detected by standard imaging techniques.

NOVX Recombinant Expression Vectors and Host Cells

Another aspect of the invention pertains to vectors, preferably expression vectors, containing a nucleic acid encoding a NOVX protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., NOVX proteins, mutant forms of NOVX proteins, fusion proteins, etc.).

The recombinant expression vectors of the invention can be designed for expression of NOVX proteins in prokaryotic or eukaryotic cells. For example, NOVX proteins can be expressed in bacterial cells such as *Escherichia coli,* insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301–315) and pET 11d (Studier et al., GENE EXPRESSION TECHNOLOGY: METHODS IN ENZYMOLOGY 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111–2118). Such alteration of nucleic acid sequences of the invention can be carried out by standard DNA synthesis techniques.

In another embodiment, the NOVX expression vector is a yeast expression vector. Examples of vectors for expression in yeast *Saccharomyces cerivisae* include pYepSec1 (Baldari, et al., 1987. *EMBO J.* 6: 229–234), pMFa (Kurjan and Herskowitz, 1982. *Cell* 30: 933–943), pJRY88 (Schultz et al., 1987. *Gene* 54: 113–123), pYES2 (Invitrogen Corporation, San Diego, Calif.), and picZ (InVitrogen Corp, San Diego, Calif.).

Alternatively, NOVX can be expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156–2165) and the pVL series (Lucklow and Summers, 1989. *Virology* 170: 31–39).

In yet another embodiment, a nucleic acid of the invention is expressed in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187–195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268–277), lymphoid-specific promoters (Calame and Eaton, 1988. *Adv. Immunol.* 43: 235–275), in particular promoters of T cell receptors (Winoto and Baltimore, 1989. *EMBO J.* 8: 729–733) and immunoglobulins (Banerji, et al., 1983. *Cell* 33: 729–740; Queen and Baltimore, 1983. *Cell* 33: 741–748), neuron-specific promoters (e.g., the neurofilament promoter; Byrne and Ruddle, 1989. *Proc. Natl. Acad. Sci. USA* 86: 5473–5477), pancreas-specific promoters (Edlund, et al., 1985. *Science* 230: 912–916), and mammary gland-specific promoters (e.g., milk whey promoter; U.S. Pat. No. 4,873, 316 and European Application Publication No. 264,166). Developmentally-regulated promoters are also encompassed, e.g., the murine hox promoters (Kessel and Gruss, 1990. *Science* 249: 374–379) and the α-fetoprotein promoter (Campes and Tilghman, 1989. *Genes Dev.* 3: 537–546).

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to NOVX mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," *Reviews—Trends in Genetics,* Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, NOVX protein can be expressed in bacterial cells such as *E. coli,* insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding NOVX or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) NOVX protein. Accordingly, the invention further provides methods for producing NOVX protein using the host cells of the invention. In one embodiment, the method comprises culturing the host cell of invention (into which a recombinant expression vector encoding NOVX protein has been introduced) in a suitable medium such that NOVX protein is produced. In another embodiment, the method further comprises isolating NOVX protein from the medium or the host cell.

Transgenic NOVX Animals

The host cells of the invention can also be used to produce non-human transgenic animals. For example, in one embodiment, a host cell of the invention is a fertilized oocyte or an embryonic stem cell into which NOVX protein-coding sequences have been introduced. Such host cells can then be used to create non-human transgenic animals in which exogenous NOVX sequences have been introduced into their genome or homologous recombinant animals in which endogenous NOVX sequences have been altered. Such animals are useful for studying the function and/or activity of NOVX protein and for identifying and/or evaluating modulators of NOVX protein activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous NOVX gene has been altered by homologous recombination between the endogenous gene and an exogenous DNA molecule introduced into a cell of the animal, e.g., an embryonic cell of the animal, prior to development of the animal.

A transgenic animal of the invention can be created by introducing NOVX-encoding nucleic acid into the male pronuclei of a fertilized oocyte (e.g., by microinjection, retroviral infection) and allowing the oocyte to develop in a pseudopregnant female foster animal. The human NOVX cDNA sequences SEQ ID NOS: 121, 123, 125, 127, 129, 131, and SEQ ID NOS: 2n−1, wherein n is an integer between 1 and 39, can be introduced as a transgene into the genome of a non-human animal. Alternatively, a non-human homologue of the human NOVX gene, such as a mouse NOVX gene, can be isolated based on hybridization to the human NOVX cDNA (described further supra) and used as a transgene. Intronic sequences and polyadenylation signals can also be included in the transgene to increase the efficiency of expression of the transgene. A tissue-specific regulatory sequence(s) can be operably-linked to the NOVX transgene to direct expression of NOVX protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan, 1986. In: Manipulating The Mouse Embryo, Cold Spring Harbor Laboratory Press, Cold Spring Harbor, N.Y. Similar methods are used for production of other transgenic animals. A transgenic founder animal can be identified based upon the presence of the NOVX transgene in its genome and/or expression of NOVX mRNA in tissues or cells of the animals. A transgenic founder animal can then be used to breed additional animals carrying the transgene. Moreover, transgenic animals carrying a transgene-encoding NOVX protein can further be bred to other transgenic animals carrying other transgenes.

To create a homologous recombinant animal, a vector is prepared which contains at least a portion of a NOVX gene into which a deletion, addition or substitution has been introduced to thereby alter, e.g., functionally disrupt, the NOVX gene. The NOVX gene can be a human gene (e.g., the cDNA of SEQ ID NOS: 121, 123, 125, 127, 129, 131, and SEQ ID NOS: 2n−1, wherein n is an integer between 1 and 39), but more preferably, is a non-human homologue of a human NOVX gene. For example, a mouse homologue of human NOVX gene of SEQ ID NOS: 121, 123, 125, 127, 129, 131, and SEQ ID NOS: 2n−1, wherein n is an integer between 1 and 39, can be used to construct a homologous recombination vector suitable for altering an endogenous NOVX gene in the mouse genome. In one embodiment, the vector is designed such that, upon homologous recombination, the endogenous NOVX gene is functionally disrupted (i.e., no longer encodes a functional protein; also referred to as a "knock out" vector).

Alternatively, the vector can be designed such that, upon homologous recombination, the endogenous NOVX gene is mutated or otherwise altered but still encodes functional protein (e.g., the upstream regulatory region can be altered to thereby alter the expression of the endogenous NOVX protein). In the homologous recombination vector, the altered portion of the NOVX gene is flanked at its 5'- and 3'-termini by additional nucleic acid of the NOVX gene to allow for homologous recombination to occur between the exogenous NOVX gene carried by the vector and an endogenous NOVX gene in an embryonic stem cell. The additional flanking NOVX nucleic acid is of sufficient length for successful homologous recombination with the endogenous gene. Typically, several kilobases of flanking DNA (both at the 5'- and 3'-termini) are included in the vector. See, e.g., Thomas, et al., 1987. *Cell* 51: 503 for a description of homologous recombination vectors. The vector is ten introduced into an embryonic stem cell line (e.g., by electroporation) and cells in which the introduced NOVX gene has homologously-recombined with the endogenous NOVX gene are selected. See, e.g., Li, et al., 1992. *Cell* 69: 915.

The selected cells are then injected into a blastocyst of an animal (e.g., a mouse) to form aggregation chimeras. See, e.g., Bradley, 1987. In: TERATOCARCINOMAS And EMBRYONIC STEM CELLS: A PRACTICAL APPROACH, Robertson, ed. IRL, Oxford, pp. 113–152. A chimeric embryo can then be implanted into a suitable pseudopregnant female foster animal and the embryo brought to term. Progeny harboring the homologously-recombined DNA in their germ cells can be used to breed animals in which all cells of the animal contain the homologously-recombined DNA by germline transmission of the transgene. Methods for constructing homologous recombination vectors and homologous recombinant animals are described further in Bradley, 1991. *Curr. Opin. Biotechnol.* 2: 823–829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, See, e.g., Lakso, et al., 1992. *Proc. Natl. Acad. Sci. USA* 89: 6232–6236. Another example of a recombinase system is the FLP recombinase system of *Saccharomyces cerevisiae*. See, O'Gorman, et al., 1991. *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, et al., 1997. *Nature* 385: 810–813. In brief, a cell (e.g., a somatic cell) from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell (e.g., the somatic cell) is isolated.

Pharmaceutical Compositions

The NOVX nucleic acid molecules, NOVX proteins, and anti-NOVX antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a NOVX protein or anti-NOVX antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad. Sci. USA* 91: 3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

Screening and Detection Methods

The isolated nucleic acid molecules of the invention can be used to express NOVX protein (e.g., via a recombinant expression vector in a host cell in gene therapy applications), to detect NOVX mRNA (e.g., in a biological sample) or a genetic lesion in a NOVX gene, and to modulate NOVX activity, as described further, below. In addition, the NOVX proteins can be used to screen drugs or compounds that modulate the NOVX protein activity or expression as well as to treat disorders characterized by insufficient or excessive production of NOVX protein or production of NOVX protein forms that have decreased or aberrant activity compared to NOVX wild-type protein (e.g.; diabetes (regulates insulin release); obesity (binds and transport lipids); metabolic disturbances associated with obesity, the metabolic syndrome X as well as anorexia and wasting disorders associated with chronic diseases and various cancers, and infectious disease (possesses anti-microbial activity) and the various dyslipidemias. In addition, the anti-NOVX antibodies of the invention can be used to detect and isolate NOVX proteins and modulate NOVX activity. In yet a further aspect, the invention can be used in methods to influence appetite, absorption of nutrients and the disposition of metabolic substrates in both a positive and negative fashion.

The invention further pertains to novel agents identified by the screening assays described herein and uses thereof for treatments as described, supra.

Screening Assays

The invention provides a method (also referred to herein as a "screening assay") for identifying modulators, i.e., candidate or test compounds or agents (e.g., peptides, peptidomimetics, small molecules or other drugs) that bind to NOVX proteins or have a stimulatory or inhibitory effect on, e.g., NOVX protein expression or NOVX protein activity. The invention also includes compounds identified in the screening assays described herein.

In one embodiment, the invention provides assays for screening candidate or test compounds which bind to or modulate the activity of the membrane-bound form of a NOVX protein or polypeptide or biologically-active portion thereof. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g., Lam, 1997. *Anticancer Drug Design* 12: 145.

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. *Proc. Natl. Acad. Sci. U.S.A.* 90: 6909; Erb, et al., 1994. *Proc. Natl. Acad. Sci. U.S.A.* 91: 11422; Zuckermann, et al., 1994. *J. Med. Chem.* 37: 2678; Cho, et al., 1993. *Science* 261: 1303; Carrell, et al., 1994. *Angew. Chem. Int. Ed. Engl.* 33: 2059; Carell, et al., 1994. *Angew. Chem. Int. Ed. Engl.* 33: 2061; and Gallop, et al., 1994. *J. Med. Chem.* 37: 1233.

Libraries of compounds may be presented in solution (e.g., Houghten, 1992. *Biotechniques* 13: 412–421), or on beads (Lam, 1991. *Nature* 354: 82–84), on chips (Fodor, 1993. *Nature* 364: 555–556), bacteria (Ladner, U.S. Pat. No. 5,223,409), spores (Ladner, U.S. Pat. No. 5,233,409), plasmids (Cull, et al., 1992. *Proc. Natl. Acad. Sci. USA* 89: 1865–1869) or on phage (Scott and Smith, 1990. *Science* 249: 386–390; Devlin, 1990. *Science* 249: 404–406; Cwirla, et al., 1990. *Proc. Natl. Acad. Sci. U.S.A.* 87: 6378–6382; Felici, 1991. *J. Mol. Biol.* 222: 301–310; Ladner, U.S. Pat. No. 5,233,409.).

In one embodiment, an assay is a cell-based assay in which a cell which expresses a membrane-bound form of NOVX protein, or a biologically-active portion thereof, on the cell surface is contacted with a test compound and the ability of the test compound to bind to a NOVX protein determined. The cell, for example, can of mammalian origin or a yeast cell. Determining the ability of the test compound to bind to the NOVX protein can be accomplished, for example, by coupling the test compound with a radioisotope or enzymatic label such that binding of the test compound to the NOVX protein or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of NOVX protein, or a biologically-active portion thereof, on the cell surface with a known compound which binds NOVX to form an assay mixture, contacting the assay mixture with a test compound, and determining the ability of the test compound to interact with a NOVX protein, wherein determining the ability of the test compound to interact with a NOVX protein comprises determining the ability of the test compound to preferentially bind to NOVX protein or a biologically-active portion thereof as compared to the known compound.

In another embodiment, an assay is a cell-based assay comprising contacting a cell expressing a membrane-bound form of NOVX protein, or a biologically-active portion thereof, on the cell surface with a test compound and determining the ability of the test compound to modulate (e.g., stimulate or inhibit) the activity of the NOVX protein or biologically-active portion thereof. Determining the ability of the test compound to modulate the activity of NOVX or a biologically-active portion thereof can be accomplished, for example, by determining the ability of the NOVX protein to bind to or interact with a NOVX target molecule. As used herein, a "target molecule" is a molecule with which a NOVX protein binds or interacts in nature, for example, a molecule on the surface of a cell which expresses a NOVX interacting protein, a molecule on the surface of a second cell, a molecule in the extracellular milieu, a molecule associated with the internal surface of a cell membrane or a cytoplasmic molecule. A NOVX target molecule can be a non-NOVX molecule or a NOVX protein or polypeptide of the invention. In one embodiment, a NOVX target molecule is a component of a signal transduction pathway that facilitates transduction of an extracellular signal (e.g. a signal generated by binding of a compound to a membrane-bound NOVX molecule) through the cell membrane and into the cell. The target, for example, can be a second intercellular protein that has catalytic activity or a protein that facilitates the association of downstream signaling molecules with NOVX.

Determining the ability of the NOVX protein to bind to or interact with a NOVX target molecule can be accomplished by one of the methods described above for determining direct binding. In one embodiment, determining the ability of the NOVX protein to bind to or interact with a NOVX target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a NOVX-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the invention is a cell-free assay comprising contacting a NOVX protein or biologically-active portion thereof with a test compound and determining the ability of the test compound to bind to the NOVX protein or biologically-active portion thereof. Binding of the test compound to the NOVX protein can be determined either directly or indirectly as described above. In one such embodiment, the assay comprises contacting the NOVX protein or biologically-active portion thereof with a known compound which binds NOVX to form an assay mixture, contacting the assay mixture with a test compound, and determining the ability of the test compound to interact with a NOVX protein, wherein determining the ability of the test compound to interact with a NOVX protein comprises determining the ability of the test compound to preferentially bind to NOVX or biologically-active portion thereof as compared to the known compound.

In still another embodiment, an assay is a cell-free assay comprising contacting NOVX protein or biologically-active portion thereof with a test compound and determining the ability of the test compound to modulate (e.g. stimulate or inhibit) the activity of the NOVX protein or biologically-active portion thereof. Determining the ability of the test compound to modulate the activity of NOVX can be accomplished, for example, by determining the ability of the NOVX protein to bind to a NOVX target molecule by one of the methods described above for determining direct binding. In an alternative embodiment, determining the ability of the test compound to modulate the activity of NOVX protein can be accomplished by determining the ability of the NOVX protein further modulate a NOVX target molecule. For example, the catalytic/enzymatic activity of the target molecule on an appropriate substrate can be determined as described, supra.

In yet another embodiment, the cell-free assay comprises contacting the NOVX protein or biologically-active portion thereof with a known compound which binds NOVX protein to form an assay mixture, contacting the assay mixture with a test compound, and determining the ability of the test compound to interact with a NOVX protein, wherein determining the ability of the test compound to interact with a NOVX protein comprises determining the ability of the NOVX protein to preferentially bind to or modulate the activity of a NOVX target molecule.

The cell-free assays of the invention are amenable to use of both the soluble form or the membrane-bound form of NOVX protein. In the case of cell-free assays comprising the membrane-bound form of NOVX protein, it may be desirable to utilize a solubilizing agent such that the membrane-bound form of NOVX protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl)dimethylamminiol-1-propane sulfonate (CHAPS), or 3-(3-cholamidopropyl)dimethylamminiol-2-hydroxy-1-propane sulfonate (CHAPSO).

In more than one embodiment of the above assay methods of the invention, it may be desirable to immobilize either NOVX protein or its target molecule to facilitate separation of complexed from uncomplexed forms of one or both of the proteins, as well as to accommodate automation of the assay. Binding of a test compound to NOVX protein, or interaction of NOVX protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-NOVX fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or NOVX protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, supra. Alternatively, the complexes can be dissociated from the matrix, and the level of NOVX protein binding or activity determined using standard techniques.

Other techniques for immobilizing proteins on matrices can also be used in the screening assays of the invention. For example, either the NOVX protein or its target molecule can be immobilized utilizing conjugation of biotin and streptavidin. Biotinylated NOVX protein or target molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with NOVX protein or target molecules, but which do not interfere with binding of the NOVX protein to its target molecule, can be derivatized to the wells of the plate, and unbound target or NOVX protein trapped in the wells by antibody conjugation. Methods for detecting such complexes, in addition to those described above for the GST-immobilized complexes, include immunodetection of complexes using antibodies reactive with the NOVX protein or target molecule, as well as enzyme-linked assays that rely on detecting an enzymatic activity associated with the NOVX protein or target molecule.

In another embodiment, modulators of NOVX protein expression are identified in a method wherein a cell is contacted with a candidate compound and the expression of NOVX mRNA or protein in the cell is determined. The level of expression of NOVX mRNA or protein in the presence of the candidate compound is compared to the level of expression of NOVX mRNA or protein in the absence of the candidate compound. The candidate compound can then be identified as a modulator of NOVX mRNA or protein expression based upon this comparison. For example, when expression of NOVX mRNA or protein is greater (i.e., statistically significantly greater) in the presence of the candidate compound than in its absence, the candidate compound is identified as a stimulator of NOVX mRNA or protein expression. Alternatively, when expression of NOVX mRNA or protein is less (statistically significantly less) in the presence of the candidate compound than in its absence, the candidate compound is identified as an inhibitor of NOVX mRNA or protein expression. The level of NOVX mRNA or protein expression in the cells can be determined by methods described herein for detecting NOVX mRNA or protein.

In yet another aspect of the invention, the NOVX proteins can be used as "bait proteins" in a two-hybrid assay or three hybrid assay (see, e.g., U.S. Pat. No. 5,283,317; Zervos, et al., 1993. *Cell* 72: 223–232; Madura, et al., 1993. *J. Biol. Chem.* 268: 12046–12054; Bartel, et al., 1993. *Biotechniques* 14: 920–924; Iwabuchi, et al., 1993. *Oncogene* 8: 1693–1696; and Brent WO 94/10300), to identify other proteins that bind to or interact with NOVX ("NOVX-binding proteins" or "NOVX-bp") and modulate NOVX activity. Such NOVX-binding proteins are also likely to be involved in the propagation of signals by the NOVX proteins as, for example, upstream or downstream elements of the NOVX pathway.

The two-hybrid system is based on the modular nature of most transcription factors, which consist of separable DNA-binding and activation domains. Briefly, the assay utilizes two different DNA constructs. In one construct, the gene that codes for NOVX is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a NOVX-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with NOVX.

The invention further pertains to novel agents identified by the aforementioned screening assays and uses thereof for treatments as described herein.

Detection Assays

Portions or fragments of the cDNA sequences identified herein (and the corresponding complete gene sequences) can be used in numerous ways as polynucleotide reagents. By way of example, and not of limitation, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. Some of these applications are described in the subsections, below.

Chromosome Mapping

Once the sequence (or a portion of the sequence) of a gene has been isolated, this sequence can be used to map the location of the gene on a chromosome. This process is called chromosome mapping. Accordingly, portions or fragments of the NOVX sequences, SEQ ID NOS: 121, 123, 125, 127, 129, 131, and SEQ ID NOS: 2n–1, wherein n is an integer between 1 and 39, or fragments or derivatives thereof, can be used to map the location of the NOVX genes, respectively, on a chromosome. The mapping of the NOVX sequences to chromosomes is an important first step in correlating these sequences with genes associated with disease.

Briefly, NOVX genes can be mapped to chromosomes by preparing PCR primers (preferably 15–25 bp in length) from the NOVX sequences. Computer analysis of the NOVX, sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the NOVX sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. See, e.g., D'Eustachio, et al., 1983. *Science* 220: 919–924. Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the NOVX sequences to design oligonucleotide primers, sub-localization can be achieved with panels of fragments from specific chromosomes.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases, will suffice to get good results at a reasonable amount of time. For a review of this technique, see, Verma, et al., Human Chromosomes: A Manual Of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. Such data are found, e.g., in McKusick, Mendelian Inheritance In Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland, et al., 1987. *Nature*, 325: 783–787.

Moreover, differences in the DNA sequences between individuals affected and unaffected with a disease associated with the NOVX gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

The NOVX sequences of the invention can also be used to identify individuals from minute biological samples. In this technique, an individual's genomic DNA is digested with one or more restriction enzymes, and probed on a Southern blot to yield unique bands for identification. The sequences of the invention are useful as additional DNA markers for RFLP ("restriction fragment length polymorphisms," described in U.S. Pat. No. 5,272,057).

Furthermore, the sequences of the invention can be used to provide an alternative technique that determines the actual base-by-base DNA sequence of selected portions of an individual's genome. Thus, the NOVX sequences described herein can be used to prepare two PCR primers from the 5'- and 3'-termini of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the invention can be used to obtain such identification sequences from individuals and from tissue. The NOVX sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Much of the allelic variation is due to single nucleotide polymorphisms (SNPs), which include restriction fragment length polymorphisms (RFLPs).

Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences can comfortably provide positive individual identification with a panel of perhaps 10 to 1,000 primers that each yield a noncoding amplified sequence of 100 bases. If predicted coding sequences, such as those in SEQ ID NOS: 121, 123, 125, 127, 129, 131, and SEQ ID NOS: 2n–1, wherein n is an integer between 1 and 39, are used, a more appropriate number of primers for positive individual identification would be 500–2,000.

Predictive Medicine

The invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the invention relates to diagnostic assays for determining NOVX protein and/or nucleic acid expression as well as NOVX activity, in the context of a biological sample (e.g., blood, serum, cells, tissue) to thereby determine whether an individual is afflicted with a disease or disorder, or is at risk of developing a disorder, associated with aberrant NOVX expression or activity. The disorders include metabolic disorders, diabetes, obesity, infectious disease, anorexia, cancer-associated cachexia, cancer, neurodegenerative disorders, Alzheimer's Disease, Parkinson's Disorder, immune disorders, and hematopoietic disorders, and the various dyslipidemias, metabolic disturbances associated with obesity, the metabolic syndrome X and wasting disorders associated with chronic diseases and various cancers. The invention also provides for prognostic (or predictive) assays for determining whether an individual is at risk of developing a disorder associated with NOVX protein, nucleic acid expression or activity. For example, mutations in a NOVX gene can be assayed in a biological sample. Such assays can be used for prognostic or predictive purpose to thereby prophylactically treat an individual prior to the onset of a disorder characterized by or associated with NOVX protein, nucleic acid expression, or biological activity.

Another aspect of the invention provides methods for determining NOVX protein, nucleic acid expression or activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs, compounds) on the expression or activity of NOVX in clinical trials.

These and other agents are described in further detail in the following sections.

Diagnostic Assays

An exemplary method for detecting the presence or absence of NOVX in a biological sample involves obtaining a biological sample from a test subject and contacting the biological sample with a compound or an agent capable of detecting NOVX protein or nucleic acid (e.g., mRNA, genomic DNA) that encodes NOVX protein such that the presence of NOVX is detected in the biological sample. An agent for detecting NOVX mRNA or genomic DNA is a labeled nucleic acid probe capable of hybridizing to NOVX mRNA or genomic DNA. The nucleic acid probe can be, for example, a full-length NOVX nucleic acid, such as the nucleic acid of SEQ ID NOS: 121, 123, 125, 127, 129, 131, and SEQ ID NOS: 2n–1, wherein n is an integer between 1 and 39, or a portion thereof, such as an oligonucleotide of at least 15, 30, 50, 100, 250 or 500 nucleotides in length and sufficient to specifically hybridize under stringent conditions to NOVX mRNA or genomic DNA. Other suitable probes for use in the diagnostic assays of the invention are described herein.

An agent for detecting NOVX protein is an antibody capable of binding to NOVX protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect NOVX mRNA, protein, or genomic DNA in a biological sample in vitro as well as in vivo. For example, in vitro techniques for detection of NOVX mRNA include Northern hybridizations and in situ hybridizations. In vitro techniques for detection of NOVX protein include enzyme linked immunosorbent assays (ELISAs), Western blots, immunoprecipitations, and immunofluorescence. In vitro techniques for detection of NOVX genomic DNA include Southern hybridizations. Furthermore, in vivo techniques for detection of NOVX protein include introducing into a subject a labeled anti-NOVX antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting NOVX protein, mRNA, or genomic DNA, such that the presence of NOVX protein, mRNA or genomic DNA is detected in the biological sample, and comparing the presence of NOVX protein, mRNA or genomic DNA in the control sample with the presence of NOVX protein, mRNA or genomic DNA in the test sample.

The invention also encompasses kits for detecting the presence of NOVX in a biological sample. For example, the kit can comprise: a labeled compound or agent capable of detecting NOVX protein or mRNA in a biological sample; means for determining the amount of NOVX in the sample; and means for comparing the amount of NOVX in the sample with a standard. The compound or agent can be packaged in a suitable container. The kit can further comprise instructions for using the kit to detect NOVX protein or nucleic acid.

Prognostic Assays

The diagnostic methods described herein can furthermore be utilized to identify subjects having or at risk of developing a disease or disorder associated with aberrant NOVX expression or activity. For example, the assays described herein, such as the preceding diagnostic assays or the following assays, can be utilized to identify a subject having or at risk of developing a disorder associated with NOVX protein, nucleic acid expression or activity. Alternatively, the prognostic assays can be utilized to identify a subject having or at risk for developing a disease or disorder. Thus, the invention provides a method for identifying a disease or disorder associated with aberrant NOVX expression or activity in which a test sample is obtained from a subject and NOVX protein or nucleic acid (e.g., mRNA, genomic DNA) is detected, wherein the presence of NOVX protein or nucleic acid is diagnostic for a subject having or at risk of developing a disease or disorder associated with aberrant NOVX expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant NOVX expression or activity. For example, such methods can be used to determine whether a subject can be effectively treated with an agent for a disorder. Thus, the invention provides methods for determining whether a subject can be effectively treated with an agent for a disorder associated with aberrant NOVX expression or activity in which a test sample is obtained and NOVX protein or nucleic acid is detected (e.g., wherein the presence of NOVX protein or nucleic acid is diagnostic for a subject that can be administered the agent to treat a disorder associated with aberrant NOVX expression or activity).

The methods of the invention can also be used to detect genetic lesions in a NOVX gene, thereby determining if a subject with the lesioned gene is at risk for a disorder characterized by aberrant cell proliferation and/or differentiation. In various embodiments, the methods include detecting, in a sample of cells from the subject, the presence or absence of a genetic lesion characterized by at least one of an alteration affecting the integrity of a gene encoding a NOVX-protein, or the misexpression of the NOVX gene. For example, such genetic lesions can be detected by ascertaining the existence of at least one of: (i) a deletion of one or more nucleotides from a NOVX gene; (ii) an addition of one or more nucleotides to a NOVX gene; (iii) a substitution of one or more nucleotides of a NOVX gene, (iv) a chromosomal rearrangement of a NOVX gene; (v) an alteration in the level of a messenger RNA transcript of a NOVX gene, (vi) aberrant modification of a NOVX gene, such as of the methylation pattern of the genomic DNA, (vii) the presence of a non-wild-type splicing pattern of a messenger RNA transcript of a NOVX gene, (viii) a non-wild-type level of a NOVX protein, (ix) allelic loss of a NOVX gene, and (x) inappropriate post-translational modification of a NOVX protein. As described herein, there are a large number of assay techniques known in the art which can be used for detecting lesions in a NOVX gene. A preferred biological sample is a peripheral blood leukocyte sample isolated by conventional means from a subject. However, any biological sample containing nucleated cells may be used, including, for example, buccal mucosal cells.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran, et al., 1988. *Science* 241: 1077–1080; and Nakazawa, et al., 1994. *Proc. Natl. Acad. Sci. USA* 91: 360–364), the latter of which can be particularly useful for detecting point mutations in the NOVX-gene (see, Abravaya, et al., 1995. *Nucl. Acids Res.* 23: 675–682). This method can include the steps of collecting a sample of cells from a patient, isolating nucleic acid (e.g., genomic, mRNA or both) from the cells of the sample, contacting the nucleic acid sample with one or more primers that specifically hybridize to a NOVX gene under conditions such that hybridization and amplification of the NOVX gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (see, Guatelli, et al., 1990. *Proc. Natl. Acad. Sci. USA* 87: 1874–1878), transcriptional amplification system (see, Kwoh, et al., 1989. *Proc. Natl. Acad. Sci. USA* 86: 1173–1177); Qβ Replicase (see, Lizardi, et al, 1988. *BioTechnology* 6: 1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a NOVX gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,493,531) can be used to score for the presence of specific mutations by development or loss of a ribozyme cleavage site.

In other embodiments, genetic mutations in NOVX can be identified by hybridizing a sample and control nucleic acids, e.g., DNA or RNA, to high-density arrays containing hundreds or thousands of oligonucleotides probes. See, e.g., Cronin, et al., 1996. *Human Mutation* 7: 244–255; Kozal, et al., 1996. *Nat. Med.* 2: 753–759. For example, genetic mutations in NOVX can be identified in two dimensional arrays containing light-generated DNA probes as described in Cronin, et al., supra. Briefly, a first hybridization array of probes can be used to scan through long stretches of DNA in a sample and control to identify base changes between the sequences by making linear arrays of sequential overlapping probes. This step allows the identification of point mutations. This is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the NOVX gene and detect mutations by comparing the sequence of the sample NOVX with the corresponding wild-type (control) sequence. Examples of sequencing reactions include those based on techniques developed by Maxim and Gilbert, 1977. *Proc. Natl. Acad. Sci. USA* 74: 560 or Sanger, 1977. *Proc. Natl. Acad. Sci. USA* 74: 5463. It is also contemplated that any of a variety of automated sequencing procedures can be utilized when performing the diagnostic assays (see, e.g., Naeve, et al., 1995. *Biotechniques* 19: 448), including sequencing by mass spectrometry (see, e.g., PCT International Publication No. WO 94/16101; Cohen, et al., 1996. *Adv. Chromatography* 36: 127–162; and Griffin, et al., 1993. *Appl. Biochem. Biotechnol.* 38: 147–159).

Other methods for detecting mutations in the NOVX gene include methods in which protection from cleavage agents is used to detect mismatched bases in RNA/RNA or RNA/DNA heteroduplexes. See, e.g., Myers, et al., 1985. *Science* 230: 1242. In general, the art technique of "mismatch cleavage" starts by providing heteroduplexes of formed by hybridizing (labeled) RNA or DNA containing the wild-type NOVX sequence with potentially mutant RNA or DNA obtained from a tissue sample. The double-stranded duplexes are treated with an agent that cleaves single-stranded regions of the duplex such as which will exist due to basepair mismatches between the control and sample strands. For instance, RNA/DNA duplexes can be treated with RNase and DNA/DNA hybrids treated with $S_1$ nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton, et al., 1988. *Proc. Natl. Acad. Sci. USA* 85: 4397; Saleeba, et al., 1992. *Methods Enzymol.* 217: 286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in NOVX cDNAs obtained from samples of cells. For example, the mutY enzyme of *E. coli* cleaves A at G/A mismatches and the thymidine DNA glycosylase from HeLa cells cleaves T at G/T mismatches. See, e.g., Hsu, et al., 1994. *Carcinogenesis* 15: 1657–1662. According to an exemplary embodiment, a probe based on a NOVX sequence, e.g., a wild-type NOVX sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in NOVX genes. For example, single strand conformation polymorphism (SSCP) may be used to detect differences in electrophoretic mobility between mutant and wild type nucleic acids. See, e.g., Orita, et al., 1989. *Proc. Natl. Acad. Sci. USA:* 86: 2766; Cotton, 1993. *Mutat. Res.* 285: 125–144; Hayashi, 1992. *Genet. Anal. Tech. Appl.* 9: 73–79. Single-stranded DNA fragments of sample and control NOVX nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility. See, e.g., Keen, et al., 1991. *Trends Genet.* 7: 5.

In yet another embodiment, the movement of mutant or wild-type fragments in polyacrylamide gels containing a gradient of denaturant is assayed using denaturing gradient gel electrophoresis (DGGE). See, e.g., Myers, et al., 1985. *Nature* 313: 495. When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA. See, e.g., Rosenbaum and Reissner, 1987. *Biophys. Chem.* 265: 12753.

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found. See, e.g., Saiki, et al., 1986. *Nature* 324: 163; Saiki, et al., 1989. *Proc. Natl. Acad. Sci. USA* 86: 6230. Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization; see, e.g., Gibbs, et al., 1989. *Nucl. Acids Res.* 17: 2437–2448) or at the extreme 3'-terminus of one primer where, under appropriate conditions, mismatch can prevent, or reduce polymerase extension (see, e.g., Prossner, 1993. *Tibtech.* 11: 238). In addition it may be desirable to introduce a novel restriction site in the region of the mutation to create cleavage-based detection. See, e.g., Gasparini, et al., 1992. *Mol. Cell Probes* 6: 1. It is anticipated that in certain embodiments amplification may also be performed using Taq ligase for amplification. See, e.g., Barany, 1991. *Proc. Natl. Acad. Sci. USA* 88: 189. In such cases, ligation will occur only if there is a perfect match at the 3'-terminus of the 5' sequence, making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a NOVX gene.

Furthermore, any cell type or tissue, preferably peripheral blood leukocytes, in which NOVX is expressed may be utilized in the prognostic assays described herein. However, any biological sample containing nucleated cells may be used, including, for example, buccal mucosal cells.

Pharmacogenomics

Agents, or modulators that have a stimulatory or inhibitory effect on NOVX activity (e.g., NOVX gene expression), as identified by a screening assay described herein can be administered to individuals to treat (prophylactically or therapeutically) disorders (The disorders include metabolic disorders, diabetes, obesity, infectious disease, anorexia, cancer-associated cachexia, cancer, neurodegenerative disorders, Alzheimer's Disease, Parkinson's Disorder, immune disorders, and hematopoietic disorders, and the various dyslipidemias, metabolic disturbances associated with obesity, the metabolic syndrome X and wasting disorders associated with chronic diseases and various cancers.) In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of NOVX protein, expression of NOVX nucleic acid, or mutation content of NOVX genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum, 1996. *Clin. Exp. Pharmacol. Physiol.,* 23: 983–985; Linder, 1997. *Clin. Chem.,* 43: 254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome Pregnancy Zone Protein Precursor enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. At the other extreme are the so called ultra-rapid metabolizers who do not respond to standard doses. Recently, the molecular basis of ultra-rapid metabolism has been identified to be due to CYP2D6 gene amplification.

Thus, the activity of NOVX protein, expression of NOVX nucleic acid, or mutation content of NOVX genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a NOVX modulator, such as a modulator identified by one of the exemplary screening assays described herein.

Monitoring of Effects During Clinical Trials

Monitoring the influence of agents (e.g., drugs, compounds) on the expression or activity of NOVX (e.g., the ability to modulate aberrant cell proliferation and/or differentiation) can be applied not only in basic drug screening, but also in clinical trials. For example, the effectiveness of an agent determined by a screening assay as described herein to increase NOVX gene expression, protein levels, or upregulate NOVX activity, can be monitored in clinical trails of subjects exhibiting decreased NOVX gene expression, protein levels, or downregulated NOVX activity. Alternatively, the effectiveness of an agent determined by a screening assay to decrease NOVX gene expression, protein levels, or downregulate NOVX activity, can be monitored in clinical trails of subjects exhibiting increased NOVX gene expression, protein levels, or upregulated NOVX activity. In such clinical trials, the expression or activity of NOVX and, preferably, other genes that have been implicated in, for example, a cellular proliferation or immune disorder can be used as a "read out" or markers of the immune responsiveness of a particular cell.

By way of example, and not of limitation, genes, including NOVX, that are modulated in cells by treatment with an agent (e.g., compound, drug or small molecule) that modulates NOVX activity (e.g., identified in a screening assay as described herein) can be identified. Thus, to study the effect of agents on cellular proliferation disorders, for example, in a clinical trial, cells can be isolated and RNA prepared and analyzed for the levels of expression of NOVX and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of NOVX or other genes. In this manner, the gene expression pattern can serve as a marker, indicative of the physiological response of the cells to the agent. Accordingly, this response state may be determined before, and at various points during, treatment of the individual with the agent.

In one embodiment, the invention provides a method for monitoring the effectiveness of treatment of a subject with an agent (e.g., an agonist, antagonist, protein, peptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of a NOVX protein, mRNA, or genomic DNA in the preadministration sample; (iii) obtaining one or more post-administration samples from the subject; (iv) detecting the level of expression or activity of the NOVX protein, mRNA, or genomic DNA in the post-administration samples; (v) comparing the level of expression or activity of the NOVX protein, mRNA, or genomic DNA in the pre-administration sample with the NOVX protein, mRNA, or genomic DNA in the post administration sample or samples; and (vi) altering the administration of the agent to the subject accordingly. For example, increased administration of the agent may be desirable to increase the expression or activity of NOVX to higher levels than detected, i.e., to increase the effectiveness of the agent. Alternatively, decreased administration of the agent may be desirable to decrease expression or activity of NOVX to lower levels than detected, i.e., to decrease the effectiveness of the agent.

Methods of Treatment

The invention provides for both prophylactic and therapeutic methods of treating a subject at risk of (or susceptible to) a disorder or having a disorder associated with aberrant NOVX expression or activity. The disorders include cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, tuberous sclerosis, scleroderma, obesity, transplantation, adrenoleukodystrophy, congenital adrenal hyperplasia, prostate cancer, neoplasm; adenocarcinoma, lymphoma, uterus cancer, fertility, hemophilia, hypercoagulation, idiopathic thrombocytopenic purpura, immunodeficiencies, graft versus host disease, AIDS, bronchial asthma, Crohn's disease; multiple sclerosis, treatment of Albright Hereditary Ostoeodystrophy, and other diseases, disorders and conditions of the like.

These methods of treatment will be discussed more fully, below.

Diseases and Disorders

Diseases and disorders that are characterized by increased (relative to a subject not suffering from the disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to: (i) an aforementioned peptide, or analogs, derivatives, fragments or homologs thereof; (ii) antibodies to an aforementioned peptide; (iii) nucleic acids encoding an aforementioned peptide; (iv) administration of antisense nucleic acid and nucleic acids that are "dysfunctional" (i.e., due to a heterologous insertion within the coding sequences of coding sequences to an aforementioned peptide) that are utilized to "knockout" endogenous function of an aforementioned peptide by homologous recombination (see, e.g., Capecchi, 1989. Science 244:1288–1292); or (v) modulators (i.e., inhibitors, agonists and antagonists, including additional peptide mimetic of the invention or antibodies specific to a peptide of the invention) that alter the interaction between an aforementioned peptide and its binding partner.

Diseases and disorders that are characterized by decreased (relative to a subject not suffering from the disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, an aforementioned peptide, or analogs, derivatives, fragments or homologs thereof; or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of an aforementioned peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, and the like).

Prophylactic Methods

In one aspect, the invention provides a method for preventing, in a subject, a disease or condition associated with an aberrant NOVX expression or activity, by administering to the subject an agent that modulates NOVX expression or at least one NOVX activity. Subjects at risk for a disease that is caused or contributed to by aberrant NOVX expression or activity can be identified by, for example, any or a combination of diagnostic or prognostic assays as described herein. Administration of a prophylactic agent can occur prior to the manifestation of symptoms characteristic of the NOVX aberrancy, such that a disease or disorder is prevented or, alternatively, delayed in its progression. Depending upon the type of NOVX aberrancy, for example, a NOVX agonist or NOVX antagonist agent can be used for treating the subject. The appropriate agent can be determined based on screening assays described herein. The prophylactic methods of the invention are further discussed in the following subsections.

Therapeutic Methods

Another aspect of the invention pertains to methods of modulating NOVX expression or activity for therapeutic purposes. The modulatory method of the invention involves contacting a cell with an agent that modulates one or more of the activities of NOVX protein activity associated with the cell. An agent that modulates NOVX protein activity can be an agent as described herein, such as a nucleic acid or a protein, a naturally-occurring cognate ligand of a NOVX protein, a peptide, a NOVX peptidomimetic, or other small molecule. In one embodiment, the agent stimulates one or more NOVX protein activity. Examples of such stimulatory agents include active NOVX protein and a nucleic acid molecule encoding NOVX that has been introduced into the cell. In another embodiment, the agent inhibits one or more NOVX protein activity. Examples of such inhibitory agents include antisense NOVX nucleic acid molecules and anti-NOVX antibodies. These modulatory methods can be performed in vitro (e.g., by culturing the cell with the agent) or, alternatively, in vivo (e.g., by administering the agent to a subject). As such, the invention provides methods of treating an individual afflicted with a disease or disorder characterized by aberrant expression or activity of a NOVX protein or nucleic acid molecule. In one embodiment, the method involves administering an agent (e.g., an agent identified by a screening assay described herein), or combination of agents that modulates (e.g., up-regulates or down-regulates) NOVX expression or activity. In another embodiment, the method involves administering a NOVX protein or nucleic acid molecule as therapy to compensate for reduced or aberrant NOVX expression or activity.

Stimulation of NOVX activity is desirable in situations in which NOVX is abnormally downregulated and/or in which increased NOVX activity is likely to have a beneficial effect. One example of such a situation is where a subject has a disorder characterized by aberrant cell proliferation and/or differentiation (e.g., cancer or immune associated disorders). Another example of such a situation is where the subject has a gestational disease (e.g., preclampsia).

Determination of the Biological Effect of the Therapeutic

In various embodiments of the invention, suitable in vitro or in vivo assays are performed to determine the effect of a specific Therapeutic and whether its administration is indicated for treatment of the affected tissue.

In various specific embodiments, in vitro assays may be performed with representative cells of the type(s) involved in the patient's disorder, to determine if a given Therapeutic exerts the desired effect upon the cell type(s). Compounds for use in therapy may be tested in suitable animal model systems including, but not limited to rats, mice, chicken, cows, monkeys, rabbits, and the like, prior to testing in human subjects. Similarly, for in vivo testing, any of the animal model system known in the art may be used prior to administration to human subjects.

Prophylactic and Therapeutic Uses of the Compositions of the Invention

The NOVX nucleic acids and proteins of the invention are useful in potential prophylactic and therapeutic applications implicated in a variety of disorders including, but not limited to: metabolic disorders, diabetes, obesity, infectious disease, anorexia, cancer-associated cancer, neurodegenerative disorders, Alzheimer's Disease, Parkinson's Disorder, immune disorders, hematopoietic disorders, and the various dyslipidemias, metabolic disturbances associated with obesity, the metabolic syndrome X and wasting disorders associated with chronic diseases and various cancers.

As an example, a cDNA encoding the NOVX protein of the invention may be useful in gene therapy, and the protein may be useful when administered to a subject in need thereof. By way of non-limiting example, the compositions of the invention will have efficacy for treatment of patients suffering from: metabolic disorders, diabetes, obesity, infectious disease, anorexia, cancer-associated cachexia, cancer, neurodegenerative disorders, Alzheimer's Disease, Parkinson's Disorder, immune disorders, hematopoietic disorders, and the various dyslipidemias.

Both the novel nucleic acid encoding the NOVX protein, and the NOVX protein of the invention, or fragments thereof, may also be useful in diagnostic applications, wherein the presence or amount of the nucleic acid or the protein are to be assessed. A further use could be as an anti-bacterial molecule (i.e., some peptides have been found to possess anti-bacterial properties). These materials are further useful in the generation of antibodies, which immunospecifically-bind to the novel substances of the invention for use in therapeutic or diagnostic methods.

The invention will be further described in the following examples, which do not limit the scope of the invention described in the claims.

EXAMPLES

Example A

Polynucleotide and Polypeptide Sequences, and Homology Data

Example 1

The NOV1 clone was analyzed, and the nucleotide and encoded polypeptide sequences are shown in Table 1A.

TABLE 1A

NOV1 Sequence Analysis

| | | |
|---|---|---|
| NOV1a, CG101926-01 DNA Sequence | SEQ ID NO:1 | 975 bp |
| | AGCAGGCCACTAGTTTATTAACTTCCAGCCACCTTGATTTTTGCTAAAATGAAGACTC | |
| | TGCAGTCTACACTTCTCCTATTACTGCTTGTGCCTCTGATAAAGCCAGCACCACCAAC | |
| | CCAGCAGGACTCACGCATTATCTATGATTATGGAACAGATAATTTTGAAGAATCCATA | |
| | TTTAGCCAAGATTATGAGGATAAATACCTGGATGGAAAAAATATTAAGGAAAAAGAAA | |

TABLE 1A-continued

NOV1 Sequence Analysis

```
CTGTGATAATACCCAATGAGAAAAGTCTTCAATTACAAAAAGATGAGGCAATAACACC
ATTACCTCCCAAGAAAGAAAATGATGAAATGCCCACGTGTCTGCTGTGTGTTTGTTTA
AGTGGCTCTGTATACTGTGAAGAAGTTGACATTGATGCTGTACCACCCTTACCAAGG
AATCAGCCTATCTTTACGCACGATTCAACAAAATTAAAAAGCTGACTGCCAAAGATTT
TGCAGACATACCTAACTTAAGAAGACTCGATTTTACAGGAAATTTGATAGAAGATATA
GAAGATGGTACTTTTTCAAAACTTTCTCTGTTAGAAGAACTTTCACTTGCTGAAAATC
AACTACTAAAACTTCCAGTTCTTCCTCCCAAGCTCACTTTATTTAATGCAAAATACAA
CAAAATCAAGAGTAGGGGAATCAAAGCAAATGCATTCAAAAAACTGAATAACCTCACC
TTCCTCTGCTTGGACCATAATGCCCTGGAATCCGTGCCTCTTAATTTACCAGAAAGTC
TACGTGTAATTCATCTTCAGTTCAACAACATAGCTTCAATTACAGATGACACATTCTG
CAAGGCTAATGACACCAGTTACATCCGGGACCGCATTGAAGAGATACGCCTGGAGGGC
AATCCAATCGTCCTGGGAAAGCATCCAAACAGTTTTATTTGCTTAAAAAGATTACCGA
TAGGGTCATACTTTTAACCTCTATTGGTACAACATATAAATGAAAGT
```

NOV1a,
CG101926-01
Protein Sequence

ORF Start: ATG at 49    ORF Stop: TAA at 943
SEQ ID NO:2             298 aa MW at 33861.6 kD MKTLQSTLLLLLVPLIKPAPPTQQDSRIIYDYGTDNFEESIFSQDYEDKYLDGKNIK
EKETVIIPNEKSLQLQKDEAITPLPPKKENDEMPTCLLCVCLSGSVYCEEVDIDAVPP
LPKESAYLYARFNKIKKLTAKDFADIPNLRRLDFTGNLIEDIEDGTFSKLSLLEELSL
AENQLLKLPVLPPKLTLFNAKYNKIKSRGIKANAFKKLNNLTFLCLDHNALESVPLNL
PESLRVIHLQFNNIASITDDTFCKANDTSYIRDRIEEIRLEGNPIVLGKHPNSFICLK
RLPIGSYF NOV1b,
207639361 DNA
Sequence SEQ ID NO:3             849 bp

GGATCCGCACCACCAACCCAGCAGGACTCACGCATTATCTATGATTATGGAACAGATA
ATTTTGAAGAATCCATATTTAGCCAAGATTATGAGGATAAATACCTGGATGGAAAAAA
TATTAAGGAAAAAGAAACTGTGATAATACCCAATGAGAAAAGTCTTCAATTACAAAAA
GATGAGGCAATAACACCATTACCTCCCAAGAAAGAAAATGATGAAATGCCCACGTGTC
TGCTGTGTGTTTGTTTAAGTGGCTCTGTATACTGTGAAGAAGTTGACATTGATGCTGT
ACCACCCTTACCAAAGGAATCAGCCTATCTTTACGCACGATTCAACAAAATTAAAAAG
CTGACTGCCAAAGATTTTGCAGACATACCTAACTTAAGAAGACTCGATTTTACAGGAA
ATTTGATAGAAGATATAGAAGATGGTACTTTTTCAAAACTTTCTCTGTTAGAAGAACT
TTCACTTGCTGAAAATCAACTACTAAAACTTCCAGTTCTTCCTCCCAAGCTCACTTTA
TTTAATGCAAAATACAACAAAATCAAGAGTAGGGGAATCAAAGCAAATGCATTCAAAA
AACTGAATAACCTCACCTTCCTCTGCTTGGACCATAATGCCCTGGAATCCGTGCCTCT
TAATTTACCAGAAAGTCTACGTGTAATTCATCTTCAGTTCAACAACATAGCTTCAATT
ACAGATGACACATTCTGCAAGGCTAACGACACCAGTTACATCCGGGACCGCATTGAAG
AGATACGCCTGGAGGGCAATCCAATCGTCCTGGGAAAGCATCCAAACAGTTTTATTTG
CTTAAAAAGATTACCGATAGGGTCATACTTTCTCGAG

NOV1b,
207639361
Protein Sequence

ORF Start: at 1         ORF Stop: end of sequence
SEQ ID NO:4             283 aa MW at 32131.3 kD GSAPPTQQDSRIIYDYGTDNFEESIFSQDYEDKYLDGKNIKEKETVIIPNEKSLQLQK
DEAITPLPPKKENDEMPTCLLCVCLSGSVYCEEVDIDAVPPLPKESAYLYARFNKIKK

TABLE 1A-continued

NOV1 Sequence Analysis

LTAKDFADIPNLRRLDFTGNLIEDIEDGTFSKLSLLEELSLAENQLLKLPVLPPKLTL

FNAKYNKIKSRGIKANAFKKLNNLTFLCLDHNALESVPLNLPESLRVIHLQFNNIASI

TDDTFCKANDTSYIRDRIEEIRLEGNPIVLGKHPNSFICLKRLPIGSYFLE

Sequence comparison of the above protein sequences yields the following sequence relationships shown in Table 1B.

TABLE 1B

Comparison of NOV1a against NOV1b.

| Protein Sequence | NOV1a Residues/ Match Residues | Identities/ Similarities for the Matched Region |
|---|---|---|
| NOV1b | 20 ... 298 | 251/279 (89%) |
|  | 3 ... 281 | 251/279 (89%) |

Further analysis of the NOV1a protein yielded the following properties shown in Table 1C.

TABLE 1C

Protein Sequence Properties NOV1a

| PSort analysis: | 0.4610 probability located in outside; 0.1900 probability located in lysosome (lumen); 0.1000 probability located in endoplasmic reticulum (membrane); 0.1000 probability located in endoplasmic reticulum (lumen) |
|---|---|
| SignalP analysis: | Cleavage site between residues 20 and 21 |

A search of the NOV1a protein against the Geneseq database, a proprietary database that contains sequences published in patents and patent publications, yielded several homologous proteins shown in Table 1D.

TABLE 1D

Geneseq Results for NOV1a

| Geneseq Identifier | Protein/Organism/Length [Patent #, Date] | NOV1a Residues/ Match Residues | Identities/ Similarities for the Matched Region | Expect Value |
|---|---|---|---|---|
| AAB90583 | Human secreted protein, SEQ ID NO: 121 - *Homo sapiens*, 298 aa. [WO200121658-A1, Mar. 29, 2001] | 1 ... 298<br>1 ... 298 | 297/298 (99%)<br>297/298 (99%) | e-171 |
| AAB90549 | Human secreted protein, SEQ ID NO: 87 - *Homo sapiens*, 298 aa. [WO200121658-A1, Mar. 29, 2001] | 1 ... 298<br>1 ... 298 | 297/298 (99%)<br>297/298 (99%) | e-171 |
| AAE03780 | Human gene 17 encoded secreted protein HSDEE58, SEQ ID NO: 50 - *Homo sapiens*, 298 aa. [WO200132837-A1, May 10, 2001] | 1 ... 298<br>1 ... 298 | 297/298 (99%)<br>297/298 (99%) | e-171 |
| AAM38687 | Human polypeptide SEQ ID NO 1832 - *Homo sapiens*, 298 aa. [WO200153312-A1, Jul. 26, 2001] | 1 ... 298<br>1 ... 298 | 297/298 (99%)<br>297/298 (99%) | e-171 |
| AAM40473 | Human polypeptide SEQ ID NO 5404 - *Homo sapiens*, 307 aa. [WO200153312-A1, Jul. 26, 2001] | 1 ... 298<br>10 ... 307 | 296/298 (99%)<br>297/298 (99%) | e-170 |

In a BLAST search of public sequence datbases, the NOV1a protein was found to have homology to the proteins shown in the BLASTP data in Table 1E.

TABLE 1E

Public BLASTP Results for NOV1a

| Protein Accession Number | Protein/Organism/Length | NOV1a Residues/ Match Residues | Identities/ Similarities for the Matched Portion | Expect Value |
|---|---|---|---|---|
| P20774 | Osteoinductive factor precursor (OIF) (Osteoglycin) (Mimecan) - Homo sapiens (Human), 298 aa. | 1 ... 298<br>1 ... 298 | 297/298 (99%)<br>297/298 (99%) | e-170 |
| P19879 | Osteoinductive factor precursor (OIF) (Osteoglycin) - Bos taurus (Bovine), 299 aa. | 1 ... 297<br>1 ... 298 | 276/298 (92%)<br>287/298 (95%) | e-160 |
| O18818 | MIMECAN - Bos taurus (Bovine), 299 aa. | 1 ... 297<br>1 ... 298 | 275/298 (92%)<br>286/298 (95%) | e-159 |
| AAM46865 | Osteoglycin - Oryctolagus cuniculus (Rabbit), 298 aa. | 1 ... 298<br>1 ... 298 | 261/298 (87%)<br>280/298 (93%) | e-152 |
| Q62000 | Osteoglycin precursor - Mus musculus (Mouse), 298 aa. | 1 ... 298<br>1 ... 298 | 253/298 (84%)<br>273/298 (90%) | e-145 |

PFam analysis predicts that the NOV1a protein contains the domains shown in the Table 1F.

TABLE 1F

Domain Analysis of NOV1a

| Pfam Domain | NOV1a Match Region | Identities/ Similarities for the Matched Region | Expect Value |
|---|---|---|---|
| LRR | 144 ... 167 | 7/25 (28%)<br>21/25 (84%) | 0.0073 |
| LRR | 235 ... 258 | 6/25 (24%)<br>20/25 (80%) | 0.64 |

Example 2

The NOV2 clone was analyzed, and the nucleotide and encoded polypeptide sequences are shown in Table 2A.

Further analysis of the NOV2a protein yielded the following properties shown in Table 2B.

TABLE 2B

Protein Sequence Properties NOV2a

| PSort analysis: | 0.5600 probability located in nucleus; 0.3000 probability located in microbody (peroxisome); 0.1000 probability located in mitochondrial matrix space; 0.1000 probability located in lysosome (lumen) |
|---|---|
| SignalP analysis: | No Known Signal Sequence Predicted |

A search of the NOV2a protein against the Geneseq database, a proprietary database that contains sequences published in patents and patent publications, yielded several homologous proteins shown in Table 2C.

TABLE 2A

NOV2 Sequence Analysis

| NOV2a, CG109754-02 DNA Sequence | SEQ ID NO:5      126 bp<br>GCAGACAAACCAGACGTGGGGGGAATCGCCAGCTTCAATAGGGCCAAGCTGAAGAAAA<br>CGGAGACGCAGGAGAAGAACACCCTGCCGACCAAAGAGACCACTGGGCAGAAGCGGAG<br>TGAAATTTCC |
|---|---|
| NOV2a, CG109754-02 Protein Sequence | ORF Start: at 1      ORF Stop: end of sequence<br>SEQ ID NO:6      42 aa MW at 4604.1 kD<br>ADKPDVGGIASFNRAKLKKTETQEKNTLPTKETTGQKRSEIS |

TABLE 2C

Geneseq Results for NOV2a

| Geneseq Identifier | Protein/Organism/Length [Patent #, Date] | NOV2a Residues/ Match Residues | Identities/ Similarities for the Matched Region | Expect Value |
|---|---|---|---|---|
| AAY80267 | Thymosin beta 4 peptide isoform Tbeta10 - Unidentified, 43 aa. [WO200006190-A1, Feb. 10, 2000] | 1 . . . 42<br>1 . . . 43 | 36/43 (83%)<br>39/43 (89%) | 4e-12 |
| AAR96932 | Thymosin beta 10 - Synthetic, 43 aa. [WO9611016-A1, Apr. 18, 1996] | 1 . . . 42<br>1 . . . 43 | 36/43 (83%)<br>39/43 (89%) | 4e-12 |
| AAR27109 | N-terminus of thymosin beta peptide - Synthetic, 43 aa. [JP04234325-A, Aug. 24, 1992] | 1 . . . 42<br>1 . . . 43 | 35/43 (81%)<br>39/43 (90%) | 9e-12 |
| AAY80270 | Thymosin beta 4 peptide isoform Tbeta13 - Unidentified, 41 aa. [W0200006190-A1, Feb. 10, 2000] | 1 . . . 38<br>1 . . . 38 | 30/38 (78%)<br>35/38 (91%) | 1e-10 |
| AAR96935 | Thymosin beta 13 - Synthetic, 41 aa. [WO9611016-A1, Apr. 18, 1996] | 1 . . . 38<br>1 . . . 38 | 30/38 (78%)<br>35/38 (91%) | 1e-10 |

In a BLAST search of public sequence datbases, the NOV2a protein was found to have homology to the proteins shown in the BLASTP data in Table 2D.

TABLE 2D

Public BLASTP Results for NOV2a

| Protein Accession Number | Protein/Organism/Length | NOV2a Residues/ Match Residues | Identities/ Similarities for the Matched Portion | Expect Value |
|---|---|---|---|---|
| AAM34215 | Thymosin beta 10 - *Equus caballus* (Horse), 44 aa. | 1 . . . 42<br>2 . . . 44 | 36/43 (83%)<br>39/43 (89%) | 9e-12 |
| P13472 | Thymosin beta-10 - *Homo sapiens* (Human),, 43 aa. | 1 . . . 42<br>1 . . . 43 | 36/43 (83%)<br>39/43 (89%) | 9e-12 |
| P21753 | Thymosin beta-9 - *Sus scrofa* (Pig), 41 aa. | 1 . . . 38<br>1 . . . 38 | 29/38 (76%)<br>34/38 (89%) | 1e-09 |
| P21752 | Thymosin beta-9 (Thymosin beta-10) [Contains: Thymosin beta-8] - *Bos taurus* (Bovine), 41 aa. | 1 . . . 38<br>1 . . . 38 | 29/38 (76%)<br>34/38 (89%) | 1e-09 |
| O76538 | Thymosin beta - *Strongylocentrotus purpuratus* (Purple sea urchin), 41 aa. | 1 . . . 39<br>2 . . . 40 | 26/39 (66%)<br>34/39 (86%) | 4e-09 |

PFam analysis predicts that the NOV2a protein contains the domains shown in the Table 2E.

TABLE 2E

Domain Analysis of NOV2a

| Pfam Domain | NOV2a Match Region | Identities/ Similarities for the Matched Region | Expect Value |
|---|---|---|---|
| Thymosin | 1 . . . 40 | 29/41 (71%)<br>36/41 (88%) | 1.8e-16 |

Example 3

The NOV3 clone was analyzed, and the nucleotide and encoded polypeptide sequences are shown in Table 3A.

TABLE 3A

NOV3 Sequence Analysis

| | | |
|---|---|---|
| NOV3a, CG114834-02 DNA Sequence | SEQ ID NO:7 | 84 bp |
| | TCAGATGCAGCTGTAGACACCAGCTCTGAAATCATTGCCAAGGACTTAAAGGAGAAGA AGGAAGTTGTGAAAGAGGCGGAAAAT | |
| NOV3a, CG114834-02 Protein Sequence | ORF Start: at 1 | ORF Stop: end of sequence |
| | SEQ ID NO:8 | 28 aa MW at 3047.3 kD |
| | SDAAVDTSSEIIAKDLKEKKEVVKEAEN | |

Further analysis of the NOV3a protein yielded the following properties shown in Table 3B.

TABLE 3B

Protein Sequence Properties NOV3a

| | |
|---|---|
| PSort analysis: | 0.6500 probability located in cytoplasm; 0.1000 probability located in mitochondrial matrix space; 0.1000 probability located in lysosome (lumen); 0.0000 probability located in endoplasmic reticulum (membrane) |
| SignalP analysis: | No Known Signal Sequence Predicted |

A search of the NOV3a protein against the Geneseq database, a proprietary database that contains sequences published in patents and patent publications, yielded several homologous proteins shown in Table 3C.

TABLE 3C

Geneseq Results for NOV3a

| Geneseq Identifier | Protein/Organism/Length [Patent #, Date] | NOV3a Residues/ Match Residues | Identities/ Similarities for the Matched Region | Expect Value |
|---|---|---|---|---|
| AAB67858 | Amino acid sequence of a human polypeptide designated PTMA-1- Homo sapiens, 109 aa. [WO200123572-A2, Apr. 5, 2001] | 1...28 2...29 | 28/28 (100%) 28/28 (100%) | 6e-08 |
| AAM03072 | Peptide #1754 encoded by probe for measuring breast gene expression - Homo sapiens, 70 aa. [WO200157270-A2, Aug. 9, 2001] | 1...28 2...29 | 28/28 (100%) 28/28 (100%) | 6e-08 |
| AAM27792 | Peptide #1829 encoded by probe for measuring placental gene expression - Homo sapiens, 70 aa. [WO200157272-A2, Aug. 9, 2001] | 1...28 2...29 | 28/28 (100%) 28/28 (100%) | 6e-08 |
| AAM15317 | Peptide #1751 encoded by probe for measuring cervical gene expression - Homo sapiens, 70 aa. [WO200157278-A2, Aug. 9, 2001] | 1...28 2...29 | 28/28 (100%) 28/28 (100%) | 6e-08 |
| AAM67501 | Human bone marrow expressed probe encoded protein SEQ ID NO: 27807 - Homo sapiens, 70 aa. [WO200157276-A2, Aug. 9, 2001] | 1...28 2...29 | 28/28 (100%) 28/28 (100%) | 6e-08 |

In a BLAST search of public sequence datbases, the NOV3a protein was found to have homology to the proteins shown in the BLASTP data in Table 3D.

TABLE 3D

Public BLASTP Results for NOV3a

| Protein Accession Number | Protein/Organism/Length | NOV3a Residues/ Match Residues | Identities/ Similarities for the Matched Portion | Expect Value |
|---|---|---|---|---|
| S15073 | prothymosin alpha - mouse, 111 aa. | 1 . . . 28<br>2 . . . 29 | 25/28 (89%)<br>26/28 (92%) | 4e-06 |
| C33356 | prothymosin alpha homolog (clone 32) - human, 59 aa (fragment). | 1 . . . 28<br>2 . . . 29 | 25/28 (89%)<br>26/28 (92%) | 4e-06 |
| TNRTA | prothymosin alpha - rat, 112 aa. | 1 . . . 28<br>2 . . . 29 | 25/28 (89%)<br>26/28 (92%) | 4e-06 |
| AAK30146 | Prothymosin alpha - *Homo sapiens* (Human), 110 aa. | 1 . . . 28<br>2 . . . 29 | 25/28 (89%)<br>26/28 (92%) | 4e-06 |
| AAA63238 | HUMAN PROTHYMOSIN-ALPHA PSEUDOGENE, COMPLETE SEQUENCE - *Homo sapiens* (Human), 109 aa. | 1 . . . 28<br>2 . . . 29 | 25/28 (89%)<br>26/28 (92%) | 4e-06 |

PFam analysis predicts that the NOV3a protein contains the domains shown in the Table 3E.

TABLE 3E

Domain Analysis of NOV3a

| Pfam Domain | NOV3a Match Region | Identities/ Similarities for the Matched Region | Expect Value |
|---|---|---|---|

Example 4

The NOV4 clone was analyzed, and the nucleotide and encoded polypeptide sequences are shown in Table 4A.

TABLE 4A

NOV4 Sequence Analysis

NOV4a, CG124728-02 DNA Sequence

SEQ ID NO:9  657 bp

```
CCGGTGCCAGCGCTATGAGGCCACTCCTCGTCCTGCTGCTCCTGGGCCTGGCGGCCGG
CTCGCCCCCACTGGACGACAACAAGATCCCCAGCCTCTGCCCGGGGCACCCCGGCCTT
CCAGGACTGCCGGGACCTCGAGGGGACCCCGGGCCGCGAGGAGAGGCGGGACCCGCGG
GGCCCACCGGGCCTGCCGGGGAGTGCTCGGTGCCTCCGCGATCCGCCTTCAGCGCCAA
GCGCTCCGAGAGCCGGGTGCCTCCGCCGTCTGACGCACCCTTGCCCTTCGACCGCGTG
CTGGTGAACGAGCAGGGACATTACGACGCCGTCACCGGCAAGTTCACCTGCCAGGTGC
CTGGGGTCTACTACTTCGCCGTCCATGCCACCGTCTACCGGGCCAGCCTGCAGTTTGA
TCTGGTGAAGAATGGCGAATCCATTGCCTCTTTCTTCCAGTTTTTCGGGGGGTGGCCC
AAGCCAGCCTCGCTCTCGGGGGGGCCATGGTGAGGCTGGAGCCTGAGGACCAAGTGT
GGGTGCAGGTGGGTGTGGGTGACTACATTGGCATCTATGCCAGCATCAAGACAGACAG
CACCTTCTCCGGATTTCTGGTGTACTCCGACTGGCGCAGCTCCCCAGTCTTTGCTTAG
TGCCCACTGCAAAGTGAGC
```

ORF Start: ATG at 15  ORF Stop: TAG at 636
SEQ ID NO:10  207 aa MW at 21887.6 kD NOV4a, CG124728-02 Protein Sequence

```
MRPLLVLLLLGLAAGSPPLDDNKIPSLCPGHPGLPGLPGPRGDPGPRGEAGPAGPTGP
AGECSVPPRSAFSAKRSESRVPPPSDAPLPFDRVLVNEQGHYDAVTGKFTCQVPGVYY
FAVHATVYRASLQFDLVKNGESIASFFQFFGGWPKPASLSGGAMVRLEPEDQVWVQVG
```

TABLE 4A-continued

NOV4 Sequence Analysis

|  |  |
|---|---|
| | VGDYIGIYASIKTDSTFSGFLVYSDWRSSPVFA |
| NOV4b, CG124728-03 DNA Sequence | SEQ ID NO:11      643 bp<br>CACCGGATCCACCATGAGGCCACTCCTCGTCCTGCTGCTCCTGGGCCTGGCGGCCGGC<br>TCGCCCCCACTGGACGACAACAAGATCCCCAGCCTCTGCCCGGGGCACCCCGGCCTTC<br>CAGGACTGCCGGGACCTCGAGGGGACCCCGGGCCGCGAGGAGAGGCGGGACCCGCGGG<br>GCCCACCGGGCCTGCCGGGGAGTGCTCGGTGCCTCCGCGATCCGCCTTCAGCGCCAAG<br>CGCTCCGAGAGCCGGGTGCCTCCGCCGTCTGACGCACCCTTGCCCTTCGACCGCGTGC<br>TGGTGAACGAGCAGGGACATTACGACGCCGTCACCGGCAAGTTCACCTGCCAGGTGCC<br>TGGGGTCTACTACTTCGCCGTCCATGCCACCGTCTACCGGGCCAGCCTGCAGTTTGAT<br>CTGGTGAAGAATGGCGAATCCATTGCCTCTTTCTTCCAGTTTTTCGGGGGGTGGCCCA<br>AGCCAGCCTCGCTCTCGGGGGGGCCATGGTGAGGCTGGAGCCTGAGGACCAAGTGTG<br>GGTGCAGGTGGGTGTGGGTGACTACATTGGCATCTATGCCAGCATCAAGACAGACAGC<br>ACCTTCTCCGGATTTCTGGTGTACTCCGACTGGCGCAGCTCCCCAGTCTTTGCTGTCG<br><br>ACGGC |
| NOV4b, CG124728-03 Protein Sequence | ORF Start: ATG at 14      ORF Stop: at 635<br>SEQ ID NO:12      207 aa MW at 21887.6 kD<br>MRPLLVLLLLGLAAGSPPLDDNKIPSLCPGHPGLPGLPGPRGDPGPRGEAGPAGPTGP<br>AGECSVPPRSAFSAKRSESRVPPPSDAPLPFDRVLVNEQGHYDAVTGKFTCQVPGVYY<br>FAVHATVYRASLQFDLVKNGESIASFFQFFGGWPKPASLSGGAMVRLEPEDQVWVQVG<br>VGDYIGIYASIKTDSTFSGFLVYSDWRSSPVFA |
| NOV4c, 263479529 DNA Sequence | SEQ ID NO:13      643 bp<br>CACCGGATCCACCATGAGGCCACTCCTCGTCCTGCTGCTCCTGGGCCTGGCGGCCGGC<br>TCGCCCCCACTGGACGACAACAAGATCCCCAGCCTCTGCCCGGGGCACCCCGGCCTTC<br>CAGGACTGCCGGGACCTCGAGGGGACCCCGGGCCGCGAGGAGAGGCGGGACCCGCGGG<br>GCCCACCGGGCCTGCCGGGGAGTGCTCGGTGCCTCCGCGATCCGCCTTCAGCGCCAAG<br>CGCTCCGAGAGCCGGGTGCCTCCGCCGTCTGACGCACCCTTGCCCTTCGACCGCGTGC<br>TGGTGAACGAGCAGGGACATTACGACGCCGTCACCGGCAAGTTCACCTGCCAGGTGCC<br>TGGGGTCTACTACTTCGCCGTCCATGCCACCGTCTACCGGGCCAGCCTGCAGTTTGAT<br>CTGGTGAAGAATGGCGAATCCATTGCCTCTTTCTTCCAGTTTTTCGGGGGGTGGCCCA<br>AGCCAGCCTCGCTCTCGGGGGGGCCATGGTGAGGCTGGAGCCTGAGGACCAAGTGTG<br>GGTGCAGGTGGGTGTGGGTGACTACATTGGCATCTATGCCAGCATCAAGACAGACAGC<br>ACCTTCTCCGGATTTCTGGTGTACTCCGACTGGCGCAGCTCCCCAGTCTTTGCTGTCG<br><br>ACGGC |
| NOV4c, 263479529 Protein Sequence | ORF Start: at 2      ORF Stop: end of sequence<br>SEQ ID NO:14      214 aa MW at 22505.2 kD<br>TGSTMRPLLVLLLLGLAAGSPPLDDNKIPSLCPGHPGLPGLPGPRGDPGPRGEAGPAG<br>PTGPAGECSVPPRSAFSAKRSESRVPPPSDAPLPFDRVLVNEQGHYDAVTGKFTCQVP<br>GVYYFAVHATVYRASLQFDLVKNGESIASFFQFFGGWPKPASLSGGAMVRLEPEDQVW<br>VQVGVGDYIGIYASIKTDSTFSGFLVYSDWRSSPVFAVDG |
| NOV4d, 271674589 DNA Sequence | SEQ ID NO:15      595 bp<br>CACCGGATCCTCGCCCCCACTGGACGACAACAAGATCCCCAGCCTCTGCCCGGGGCAC<br>CCCGGCCTTCCAGGACTGCCGGGACCTCGAGGGGACCCCGGGCCGCGAGGAGAGGCGG |

TABLE 4A-continued

NOV4 Sequence Analysis

```
                GACCCGCGGGCCCACCGGGCCTGCCGGGGAGTGCTCGGTGCCTCCGCGATCCGCCTT

CAGCGCCAAGCGCTCCGAGAGCCGGGTGCCTCCGCCGTCTGACGCACCCTTGCCCTTC

GACCGCGTGCTGGTGAACGAGCAGGGACATTACGACGCCGTCACCGGCAAGTTCACCT

GCCAGGTGCCTGGGGTCTACTACTTCGCCGTCCATGCCACCGTCTACCGGGCCAGCCT

GCAGTTTGATCTGGTGAAGAATGGCGAATCCATTGCCTCTTTCTTCCAGTTTTTCGGG

GGGTGGCCCAAGCCAGCCTCGCTCTCGGGGGGGGCCATGGTGAGGCTGGAGCCTGAGG

ACCAAGTGTGGGTGCAGGTGGGTGTGGGTGACTACATTGGCATCTATGCCAGCATCAA

GACAGACAGCACCTTCTCCGGATTTCTGGTGTACTCCGACTGGCGCAGCTCCCCAGTC

TTTGCTGTCGACGGC

ORF Start: at 2          ORF Stop: end of sequence
                SEQ ID NO:16             198 aa MW at 20872.2 kD
NOV4d,          TGSSPPLDDNKIPSLCPGHPGLPGLPGPRGDPGPRGEAGPAGPTGPAGECSVPPRSAF
271674589
Protein Sequence SAKRSESRVPPPSDAPLPFDRVLVNEQGHYDAVTGKFTCQVPGVYYFAVHATVYRASL

QFDLVKNGESIASFFQFFGGWPKPASLSGGAMVRLEPEDQVWVQVGVGDYIGIYASIK

TDSTFSGFLVYSDWRSSPVFAVDG
```

Sequence comparison of the above protein sequences yields the following sequence relationships shown in Table 4B.

TABLE 4B

Comparison of NOV4a against NOV4b through NOV4d.

| Protein Sequence | NOV4a Residues/ Match Residues | Identities/ Similarities for the Matched Region |
|---|---|---|
| NOV4b | 61 ... 207 | 147/147 (100%) |
|  | 61 ... 207 | 147/147 (100%) |
| NOV4c | 61 ... 207 | 147/147 (100%) |
|  | 65 ... 211 | 147/147 (100%) |
| NOV4d | 16 ... 207 | 156/192 (81%) |
|  | 4 ... 195 | 156/192 (81%) |

Further analysis of the NOV4a protein yielded the following properties shown in Table 4C.

TABLE 4C

Protein Sequence Properties NOV4a

| PSort analysis: | 0.6042 probability located in outside; 0.2159 probability located in microbody (peroxisome); 0.1000 probability located in endoplasmic reticulum (membrane); 0.1000 probability located in endoplasmic reticulum (lumen) |
|---|---|
| SignalP analysis: | Cleavage site between residues 16 and 17 |

A search of the NOV4a protein against the Geneseq database, a proprietary database that contains sequences published in patents and patent publications, yielded several homologous proteins shown in Table 4D.

TABLE 4D

Geneseq Results for NOV4a

| Geneseq Identifier | Protein/Organism/Length [Patent #, Date] | NOV4a Residues/ Match Residues | Identities/ Similarities for the Matched Region | Expect Value |
|---|---|---|---|---|
| AAB49599 | Human adipocyte complement related protein homolog zsig39 - Homo sapiens, 243 aa. [WO200073446-A2, Dec. 7, 2000] | 1 ... 207<br>1 ... 243 | 206/243 (84%)<br>206/243 (84%) | e-116 |
| AAB49593 | Human adipocyte complement related protein homolog zsig39 - Homo sapiens, 243 aa. [WO200073444-A1, Dec. 7, 2000] | 1 ... 207<br>1 ... 243 | 206/243 (84%)<br>206/243 (84%) | e-116 |
| AAB65888 | Human secreted protein related protein SEQ ID NO: 102 - Homo sapiens, 243 aa. [WO200078808-A1, Dec. 28, 2000] | 1 ... 207<br>1 ... 243 | 206/243 (84%)<br>206/243 (84%) | e-116 |

TABLE 4D-continued

Geneseq Results for NOV4a

| Geneseq Identifier | Protein/Organism/Length [Patent #, Date] | NOV4a Residues/ Match Residues | Identities/ Similarities for the Matched Region | Expect Value |
|---|---|---|---|---|
| AAB65815 | Human TANGO 253 SEQ ID NO: 3 - *Homo sapiens*, 243 aa. [WO200078808-A1, Dec. 28, 2000] | 1 . . . 207<br>1 . . . 243 | 206/243 (84%)<br>206/243 (84%) | e-116 |
| AAB65816 | Human mature TANGO 253 SEQ ID NO: 4 - *Homo sapiens*, 228 aa. [WO200078808-A1, Dec. 28, 2000] | 16 . . . 207<br>1 . . . 228 | 191/228 (83%)<br>191/228 (83%) | e-108 |

In a BLAST search of public sequence datbases, the NOV4a protein was found to have homology to the proteins shown in the BLASTP data in Table 4E.

TABLE 4E

Public BLASTP Results for NOV4a

| Protein Accession Number | Protein/Organism/Length | NOV4a Residues/ Match Residues | Identities/ Similarities for the Matched Portion | Expect Value |
|---|---|---|---|---|
| AAH29485 | C1q and tumor necrosis factor related protein 5 - *Homo sapiens* (Human), 243 aa. | 1 . . . 207<br>1 . . . 243 | 206/243 (84%)<br>206/243 (84%) | e-116 |
| Q9BXJ0 | Complement-c1q tumor necrosis factor-related protein 5 precursor - *Homo sapiens* (Human), 243 aa. | 1 . . . 207<br>1 . . . 243 | 206/243 (84%)<br>206/243 (84%) | e-116 |
| Q8R002 | Similar to DKFZP586B0621 protein (Hypothetical 25.4 kDa protein) - *Mus musculus* (Mouse), 243 aa. | 1 . . . 207<br>1 . . . 243 | 190/243 (78%)<br>197/243 (80%) | e-107 |
| T14782 | hypothetical protein DKFZp586B0621.1 - human, 219 aa (fragment). | 25 . . . 207<br>1 . . . 219 | 182/219 (83%)<br>182/219 (83%) | e-102 |
| BAB84561 | Otolin-1 - *Oncorhynchus keta* (Chum salmon), 508 aa. | 30 . . . 199<br>338 . . . 505 | 74/171 (43%)<br>104/171 (60%) | 2e-31 |

PFam analysis predicts that the NOV4a protein contains the domains shown in the Table 4F.

TABLE 4F

Domain Analysis of NOV4a

| Pfam Domain | NOV4a Match Region | Identities/ Similarities for the Matched Region | Expect Value |
|---|---|---|---|
| Collagen | 15 . . . 74 | 24/60 (40%)<br>37/60 (62%) | 0.012 |
| C1q | 69 . . . 196 | 50/138 (36%)<br>90/138 (65%) | 2.1e-34 |

Example 5

The NOV5 clone was analyzed, and the nucleotide and encoded polypeptide sequences are shown in Table 5A.

TABLE 5A

NOV5 Sequence Analysis

| | | |
|---|---|---|
| NOV5a,<br>CG127616-01<br>DNA Sequence | SEQ ID NO:17 | 500 bp |
| | <u>CCCGGAGCCGGACCGGGGCCACCGCGCCCGCTCTGCTCCGACACCGCGCCCCCTGGAC</u> | |
| | <u>AGCCGCCCTCTCCTCCAGGCCCGTGGGGCTGGCCCTGCACCGCCGAGCTTCCCGGGAT</u> | |
| | <u>GAGGGCCCCCGGTGTGGTCACCCGGCGCGCCCCAGGTCGCTGAGGGACCCCGGCCAGG</u> | |
| | <u>CGCGGAGATGGGGGTGCACGAATGTCCTGCCTGGCTGTGGCTTCTCCTGTCCCTGCTG</u> | |
| | TCGCTCCCTCTGGGCCTCCCAGTCCTGGGCGCCCCACCACGCCTCATCTGTGACAGCC | |
| | GAGTCCTGGAGAGGTACCTCTTGGAGGCCAAGGAGGCCGAGAATATCACGAAGGAAGC | |
| | CATCTCCCCTCCAGATGCGGCCTCAGCTGCTCCACTCCGAACAATCACTGCTGACACT | |
| | TTCCGCAAACTCTTCCGAGTCTACTCCAATTTCCTCCGGGGAAAGCTGAAGCTGTACA | |
| | CAGGGGAGGCCTGCAGGACAGGGGACAGATGA<u>CCAG</u> | |
| NOV5a,<br>CG127616-01<br>Protein Sequence | ORF Start: ATG at 182<br>SEQ ID NO:18<br>MGVHECPAWLWLLLSLLSLPLGLPVLGAPPRLICDSRVLERYLLEAKEAENITKEAIS<br>PPDAASAAPLRTITADTFRKLFRVYSNFLRGKLKLYTGEACRTGDR | ORF Stop: TGA at 494<br>104 aa MW at 11567.4 kD |
| NOV5b,<br>CG127616-02<br>DNA Sequence | SEQ ID NO:19 | 324 bp |
| | <u>CCTGG</u>CTATCTGTTCTAGAATGTCCTGCCTGGCTGTGGCTTCTCCTGTCCCTGCTGTC | |
| | GCTCCCTCTGGGCCTCCCAGTCCTGGGCGCCCCACCACGCCTCATCTGTGACAGCCGA | |
| | GTCCTGGAGAGGTACCTCTTGGAGGCCAAGGAGGCCGAGAATATCACGAAGGAAGCCA | |
| | TCTCCCCTCCAGATGCGGCCTCAGCTGCTCCACTCCGAACAATCACTGCTGACACTTT | |
| | CCGCAAACTCTTCCGAGTCTACTCCAATTTCCTCCGGGGAAAGCTGAAGCTGTACACA | |
| | GGGGAGGCCTGCAGGACAGGGGACAGATGA<u>CCAG</u> | |
| NOV5b,<br>CG127616-02<br>Protein Sequence | ORF Start: at 3<br>SEQ ID NO:20<br>WLSVLECPAWLWLLLSLLSLPLGLPVLGAPPRLICDSRVLERYLLEAKEAENITKEAI<br>SPPDAASAAPLRTITADTFRKLFRVYSNFLRGKLKLYTGEACRTGDR | ORF Stop: TGA at 318<br>105 aa MW at 11741.6 kD |
| NOV5c,<br>214374151 DNA<br>Sequence | SEQ ID NO:21 | 282 bp |
| | GGATCCTGGCTTCTCCTGTCCCTGCTGTCGCTCCCTCTGGGCCTCCCAGTCCTGGGCG | |
| | CCCCACCACGCCTCATCTGTGACAGCCGAGTCCTGGAGAGGTACCTCTTGGAGGCCAA | |
| | GGAGGCCGAGAATATCACGAAGGAAGCCATCTCCCCTCCAGATGCGGCCTCAGCTGCT | |
| | CCACTCCGAACAATCACTGCTGACACTTTCCGCAAACTCTTCCGAGTCTACTCCAATT | |
| | TCCTCCGGGGAAAGCTGAAGCTGTACACAGGGGAGGCCTGCAGGCTCGAG | |
| NOV5c,<br>214374151<br>Protein Sequence | ORF Start: at 1<br>SEQ ID NO:22<br>GSWLLLSLLSLPLGLPVLGAPPRLICDSRVLERYLLEAKEAENITKEAISPPDAASAA<br>PLRTITADTFRKLFRVYSNFLRGKLKLYTGEACRLE | ORF Stop: end of sequence<br>94 aa MW at 10400.0 kD |
| NOV5d,<br>219936857 DNA<br>Sequence | SEQ ID NO:23 | 333 bp |
| | CGCGGATCCATGGGGGTGCACGAATGTCCTGCCTGGCTGTGGCTTCTCCTGTCCCTGC | |
| | TGTCGCTCCCTCTGGGCCTCCCAGTCCTGGGCGCCCCACCACGCCTCATCTGTGACAG | |
| | CCGAGTCCTGGAGAGGTACCTCTTGGAGGCCAAGGAGGCCGAGAATATCACGAAGGAA | |
| | GCCATCTCCCCTCCAGATGCGGCCTCAGCTGCTCCACTCCGAACAATCACTGCTGACA | |
| | CTTTCCGCAAACTCTTCCGAGTCTACTCCAATTTCCTCCGGGGAAAGCTGAAGCTGTA | |

TABLE 5A-continued

NOV5 Sequence Analysis

```
                CACAGGGGAGGCCTGCAGGACAGGGACAGATGACTCGAGCGG

ORF Start: at 1              ORF Stop: TGA at 322
                SEQ ID NO:24                 107 aa    MW at 11867.7 kD
NOV5d,          RGSMGVHECPAWLWLLLSLLSLPLGLPVLGAPPRLICDSRVLERYLLEAKEAENITKE
219936857
Protein Sequence AISPPDAASAAPLRTITADTFRKLFRVYSNFLRGKLKLYTGEACRTGDR SEQ ID NO:25                 330 bp
NOV5e,          CGCGGATCCATGGGGGTGCACGAATGTCCTGCCTGGCTGTGGCTTCTCCTGTCCCTGC
259333914 DNA
Sequence        TGTCGCTCCCTCTGGGCCTCCCAGTCCTGGGCGCCCCACCACGCCTCATCTGTGACAG

CCGAGTCCTGGAGAGGTACCTCTTGGAGGCCAAGGAGGCCGAGAATATCACGAAGGAA

GCCATCTCCCCTCCAGATGCGGCCTCAGCTGCTCCACTCCGAACAATCACTGCTGACA

CTTTCCGCAAACTCTTCCGAGTCTACTCCAATTTCCTCCGGGGAAAGCTGAAGCTGTA

CACAGGGGAGGCCTGCAGGACAGGGACAGACTCGAGCGG

ORF Start: at 1              ORF Stop: end of sequence
                SEQ ID NO:26                 110 aa    MW at 12266.1 kD
NOV5e,          RGSMGVHECPAWLWLLLSLLSLPLGLPVLGAPPRLICDSRVLERYLLEAKEAENITKE
259333914
Protein Sequence AISPPDAASAAPLRTITADTFRKLFRVYSNFLRGKLKLYTGEACRTGDRLER SEQ ID NO:27                 333 bp
NOV5f,          CGCGGATCCATGGGGGTGCACGAATGTCCTGCCTGGCTGTGGCTTCTCCTGTCCCTGC
219936857 DNA
Sequence        TGTCGCTCCCTCTGGGCCTCCCAGTCCTGGGCGCCCCACCACGCCTCATCTGTGACAG

CCGAGTCCTGGAGAGGTACCTCTTGGAGGCCAAGGAGGCCGAGAATATCACGAAGGAA

GCCATCTCCCCTCCAGATGCGGCCTCAGCTGCTCCACTCCGAACAATCACTGCTGACA

CTTTCCGCAAACTCTTCCGAGTCTACTCCAATTTCCTCCGGGGAAAGCTGAAGCTGTA

CACAGGGGAGGCCTGCAGGACAGGGACAGATGACTCGAGCGG

ORF Start: at 1              ORF Stop: TGA at 322
                SEQ ID NO:28                 107 aa    MW at 11867.7 kD
NOV5f,          RGSMGVHECPAWLWLLLSLLSLPLGLPVLGAPPRLICDSRVLERYLLEAKEAENITKE
219936857
Protein Sequence AISPPDAASAAPLRTITADTFRKLFRVYSNFLRGKLKLYTGEACRTGDR
```

Sequence comparison of the above protein sequences yields the following sequence relationships shown in Table 5B.

TABLE 5B

Comparison of NOV5a against NOV5b through NOV5f.

| Protein Sequence | NOV5a Residues/ Match Residues | Identities/ Similarities for the Matched Region |
|---|---|---|
| NOV5b | 33 ... 104 | 60/72 (83%) |
|  | 34 ... 105 | 60/72 (83%) |
| NOV5c | 33 ... 100 | 56/68 (82%) |
|  | 25 ... 92 | 56/68 (82%) |
| NOV5d | 1 ... 104 | 66/104 (63%) |
|  | 4 ... 107 | 66/104 (63%) |
| NOV5e | 1 ... 104 | 66/104 (63%) |
|  | 4 ... 107 | 66/104 (63%) |
| NOV5f | 1 ... 104 | 66/104 (63%) |
|  | 4 ... 107 | 66/104 (63%) |

Further analysis of the NOV5a protein yielded the following properties shown in Table 5C.

TABLE 5C

Protein Sequence Properties NOV5a

| | |
|---|---|
| PSort analysis: | 0.8096 probability located in outside; 0.1000 probability located in endoplasmic reticulum (membrane); 0.1000 probability located in endoplasmic reticulum (lumen); 0.1000 probability located in lysosome (lumen) |
| SignalP analysis: | Cleavage site between residues 28 and 29 |

A search of the NOV5a protein against the Geneseq database, a proprietary database that contains sequences published in patents and patent publications, yielded several homologous proteins shown in Table 5D.

TABLE 5D

Geneseq Results for NOV5a

| Geneseq Identifier | Protein/Organism/Length [Patent #, Date] | NOV5a Residues/ Match Residues | Identities/ Similarities for the Matched Region | Expect Value |
|---|---|---|---|---|
| AAW14143 | Erythropoietin variant JM - *Homo sapiens*, 193 aa. [WO9708307-A1, Mar. 6, 1997] | 1 . . . 54<br>1 . . . 54 | 54/54 (100%)<br>54/54 (100%) | 1e-25 |
| AAE15348 | Human erythropoietin (Epo) N47-Fc fusion protein - *Homo sapiens*, 420 aa. [WO200181405-A2, Nov. 1, 2001] | 1 . . . 53<br>1 . . . 53 | 53/53 (100%)<br>53/53 (100%) | 5e-25 |
| AAE15341 | Human erythropoietin (Epo) protein - *Homo sapiens*, 193 aa. [WO200181405-A2, Nov. 1, 2001] | 1 . . . 53<br>1 . . . 53 | 53/53 (100%)<br>53/53 (100%) | 5e-25 |
| AAB35017 | Chimpanzee erythropoietin fragment SEQ ID NO: 49 - Pan sp, 193 aa. [WO200068376-A1, Nov. 16, 2000] | 1 . . . 53<br>1 . . . 53 | 53/53 (100%)<br>53/53 (100%) | 5e-25 |
| AAB35016 | Chimpanzee erythropoietin fragment SEQ ID NO: 48 - Pan sp, 193 aa. [WO200068376-A1, Nov. 16, 2000] | 1 . . . 53<br>1 . . . 53 | 53/53 (100%)<br>53/53 (100%) | 5e-25 |

In a BLAST search of public sequence datbases, the NOV5a protein was found to have homology to the proteins shown in the BLASTP data in Table 5E.

TABLE 5E

Public BLASTP Results for NOV5a

| Protein Accession Number | Protein/Organism/Length | NOV5a Residues/ Match Residues | Identities/ Similarities for the Matched Portion | Expect Value |
|---|---|---|---|---|
| P01588 | Erythropoietin precursor (Epoetin) - *Homo sapiens* (Human), 193 aa. | 1 . . . 53<br>1 . . . 53 | 53/53 (100%)<br>53/53 (100%) | 1e-24 |
| P07865 | Erythropoietin precursor - *Macaca fascicularis* (Crab eating macaque) (Cynomolgus monkey), 192 aa. | 1 . . . 53<br>1 . . . 53 | 50/53 (94%)<br>52/53 (97%) | 2e-23 |
| Q28513 | Erythropoietin precursor - *Macaca mulatta* (Rhesus macaque), 192 aa. | 1 . . . 53<br>1 . . . 53 | 49/53 (92%)<br>52/53 (97%) | 3e-23 |
| CAC41224 | Sequence 1 from Patent WO0136489 - *Homo sapiens* (Human), 166 aa (fragment). | 41 . . . 104<br>103 . . . 166 | 54/64 (84%)<br>54/64 (84%) | 1e-22 |
| P29676 | Erythropoietin precursor - *Rattus norvegicus* (Rat), 192 aa. | 54 . . . 104<br>142 . . . 192 | 44/51 (86%)<br>46/51 (89%) | 9e-19 |

PFam analysis predicts that the NOV5a protein contains the domains shown in the Table 5F.

TABLE 5F

Domain Analysis of NOV5a

| Pfam Domain | NOV5a Match Region | Identities/ Similarities for the Matched Region | Expect Value |
|---|---|---|---|
| EPO_TPO | 11 . . . 100 | 50/180 (28%)<br>89/180 (49%) | 2.3e-10 |

Example 6

The NOV6 clone was analyzed, and the nucleotide and encoded polypeptide sequences are shown in Table 6A.

TABLE 6A

NOV6 Sequence Analysis

| | | |
|---|---|---|
| NOV6a, CG128348-01 DNA Sequence | SEQ ID NO:29 | 684 bp |
| | <u>CAATCACAGGCAGGAAGATGAAGGTTCTGTGGGCTGCGTTGCTGGTCACATTCCTGGC</u> | |
| | AGGATGCCAGGCCAAGGTGGAGCAAGCGGTGGAGACAGAGCCGGAGCCCGAGCTGCGC | |
| | CAGCAGACCGAGTGGCAGAGCGGCCAGCGCTGGGAACTGGCACTGGGTCGCTTTTGGG | |
| | ATTACCTGCGCTGGGTGCAGACACTGTCTGAGCAGGTGCAGGAGGAGCTGCTCAGCTC | |
| | CCAGGTCACCCAGGAACTGAGGGCGCTGATGGACGAGACCATGAAGGAGTTGAAGGCC | |
| | TACAAATCGGAACTGGAGGAACAACTGACCCCGGTGGCGGAGGAGACGCGGGCACGGC | |
| | TGTCCAAGGAGCTGCAGGCGGCGCAGGCCCGGCTGGGCGCGGACGAGGTGAAGGGGCA | |
| | GGTGGCGGAGGTGCGCGCCAAGCTGGAGGAGCAGGCCCAGCAGATACGCCTGCAGGCC | |
| | GAGGCCTTCCAGGCCCGCCTCAAGAGCTGGTTCGAGCCCCTGGTGGAAGACATGCAGC | |
| | GCCAGTGGGCCGGGCTGGTGGAGAAGGTGCAGGCTGCCGTGGGCACCAGCGCCGCCCC | |
| | TGTGCCCAGCGACAATCACTGA<u>ACGCCGAAGCCTGCAGCCATGCGACCCCACGCCACC</u> | |
| | <u>CCGTGCCTCCTGCCTCCGCGCAGCCTGCAGCGGGAGACCCTGTCCC</u> | |
| | ORF Start: ATG at 18 | ORF Stop: TGA at 600 |
| | SEQ ID NO:30 | 194 aa MW at 22147.9 kD |
| NOV6a, CG128348-01 Protein Sequence | MKVLWAALLVTFLAGCQAKVEQAVETEPEPELRQQTEWQSGQRWELALGRFWDYLRWV | |
| | QTLSEQVQEELLSSQVTQELRALMDETMKELKAYKSELEEQLTPVAEETRARLSKELQ | |
| | AAQARLGADEVKGQVAEVRAKLEEQAQQIRLQAEAFQARLKSWFEPLVEDMQRQWAGL | |
| | VEKVQAAVGTSAAPVPSDNH | |
| NOV6b, CG128348-02 DNA Sequence | SEQ ID NO:31 | 802 bp |
| | <u>CAATCACAGGCAGGAAGATGAAGGTTCTGTGGGCTGCGTTGCTGGTCACATTCCTGGC</u> | |
| | AGGATGCCAGGCCAAGGTGGAGCAAGCGGTGGAGACAGAGCCGGAGCCCGAGCTGCGC | |
| | CAGCAGACCGAGTGGCAGAGCGGCCAGCGCTGGGAACTGGCACTGGGTCGCTTTTGGG | |
| | ATTACCTGCGCTGGGTGCAGACACTGTCTGAGCAGGTGCAGGAGGAGCTGCTCAGCTC | |
| | CCAGGTCACCCAGGAACTGAGGGCGCTGATGGACGAGACCATGAAGGAGTTGAAGGCC | |
| | TACAAATCGGAACTGGAGGAACAACTGACCCCGGTGGCGGAGGAGACGCGGGCACGGC | |
| | TGTCCAAGGAGCTGGGGCCCCTGGTGGAACAGGGCCGCGTGCGGGCCGCCACTGTGGG | |
| | CTTCCTGGCCGGCCAGCCGCTACAGGAGCGGGCCCAGGCCTGGGGCGAGCGGCTGCGC | |
| | GCGCGGATGGAGGAGATGGGCAGCCGGACCCGCGACCGCCTGGACGAGGTGAAGGAGC | |
| | AGGTGGCGGAGGTGCGCGCCAAGCTGGAGGAGCAGGCCCAGCAGATACGCCTGCAGGC | |
| | CGAGGCCTTCCAGGCCCGCCTCAAGAGCTGGTTCGAGCCCCTGGTGGAAGACATGCAG | |
| | CGCCAGTGGGCCGGGCTGGTGGAGAAGGTGCAGGCTGCCGTGGGCACCAGCGCCGCCC | |
| | CTGTGCCCAGCGACAATCACTGA<u>ACGCCGAAGCCTGCAGCCATGCGACCCCACGCCAC</u> | |
| | <u>CCCGTGCCTCCTGCCTCCGCGCAGCCTGCAGCGGGAGACCCTGTCCCT</u> | |
| | ORF Start: ATG at 18 | ORF Stop: TGA at 717 |
| | SEQ ID NO:32 | 233 aa MW at 26743.1 kD |
| NOV6b, CG128348-02 Protein Sequence | MKVLWAALLVTFLAGCQAKVEQAVETEPEPELRQQTEWQSGQRWELALGRFWDYLRWV | |
| | QTLSEQVQEELLSSQVTQELRALMDETMKELKAYKSELEEQLTPVAEETRARLSKELG | |
| | PLVEQGRVRAATVGFLAGQPLQERAQAWGERLRARMEEMGSRTRDRLDEVKEQVAEVR | |

TABLE 6A-continued

NOV6 Sequence Analysis

AKLEEQAQQIRLQAEAFQARLKSWFEPLVEDMQRQWAGLVEKVQAAVGTSAAPVPSDN
H

NOV6c,
CG128348-03
DNA Sequence

SEQ ID NO:33          788 bp
<u>CAATCACAGGCAGGAAGATG</u>AAGGTTCTGTGGGCTGCGTTGCTGGTCACATTCCTGGC

AGGATGCCAGGCCAAGGTGGAGCAAGCGGTGGAGACAGAGCCGGAGCCCGAGCTGCGC

CAGCAGACCGAGTGGCAGAGCGGCCAGCGCTGGGAACTGGCACTGGGTCGCTTTTGGG

ATTACCTGCGCTGGGTGCAGACACTGTCTGAGCAGGTGCAGGAGGAGCTGCTCAGCTC

CCAGGTCACCCAGGAACTGAGGGCGCTGATGGACGAGACCATGAAGGAGTTGAAGGCC

TACAAATCGGAACTGGAGGAACAACTGACCCCGGTGGCGGAGGAGACGCGGGCACGGC

TGTCCAAGGAGCTGCAGGCGGCGCAGGCCCGGCTGGGCGCGGACATGGAGGACGTGCG

CGGCCGCCTGGTGCAGTACCGCGGCGAGGTGCAGGCCATGCTCGGCCAGAGCACCGAG

GAGCTGCGGGTGCGCCTCGCCTCCCACCTGCGCAAGCTGCGTAAGCGGCTCCTCCGCG

ATGCCGATGACCTGGAGGAGCAGGCCCAGCAGATACGCCTGCAGGCCGAGGCCTTCCA

GGCCCGCCTCAAGAGCTGGTTCGAGCCCCTGGTGGAAGACATGCAGCGCCAGTGGGCC

GGGCTGGTGGAGAAGGTGCAGGCTGCCGTGGGCACCAGCGCCGCCCCTGTGCCCAGCG

ACAATCACTTGAACGCCGAAGCCTGCAGCCATGCGACCCCACGCCACCCCGTGCCTCCT

GCCTCCGCGCAGCCTGCAGCGGGAGACCCTGTCC

ORF Start: ATG at 18     ORF Stop: TGA at 705
SEQ ID NO:34             229 aa MW at 26399.7 kD NOV6c,
CG128348-03
Protein Sequence

MKVLWAALLVTFLAGCQAKVEQAVETEPEPELRQQTEWQSGQRWELALGRFWDYLRWV

QTLSEQVQEELLSSQVTQELRALMDETMKELKAYKSELEEQLTPVAEETRARLSKELQ

AAQARLGADMEDVRGRLVQYRGEVQAMLGQSTEELRVRLASHLRKLRKRLLRDADDLE

EQAQQIRLQAEAFQARLKSWFEPLVEDMQRQWAGLVEKVQAAVGTSAAPVPSDNH

NOV6d,
278480724 DNA
Sequence

SEQ ID NO:35          718 bp
<u>CACC</u>GGATCCATGAAGGTTCTGTGGGCTGCGTTGCTGGTCACATTCCTGGCAGGATGC

CAGGCCAAGGTGGAGCAAGCGGTGGAGACAGAGCCGGAGCCCGAGCTGCGCCAGCAGA

CCGAGTGGCAGAGCGGCCAGCGCTGGGAACTGGCACTGGGTCGCTTTTGGGATTACCT

GCGCTGGGTGCAGACACTGTCTGAGCAGGTGCAGGAGGAGCTGCTCAGCTCCCAGGTC

ACCCAGGAACTGAGGGCGCTGATGGACGAGACCATGAAGGAGTTGAAGGCCTACAAAT

CGGAACTGGAGGAACAACTGACCCCGGTGGCGGAGGAGACGCGGGCACGGCTGTCCAA

GGAGCTGGGGCCCCTGGTGGAACAGGGCCGCGTGCGGGCCGCCACTGTGGGCTTCCTG

GCCGGCCAGCCGCTACAGGAGCGGGCCCAGGCCTGGGGCGAGCGGCTGCGCGCGCGGA

TGGAGGAGATGGGCAGCCGGACCCGCGACCGCCTGGACGAGGTGAAGGAGCAGGTGGC

GGAGGTGCGCGCCAAGCTGGAGGAGCAGGCCCAGCAGATACGCCTGCAGGCCGAGGCC

TTCCAGGCCCGCCTCAAGAGCTGGTTCGAGCCCCTGGTGGAAGACATGCAGCGCCAGT

GGGCCGGGCTGGTGGAGAAGGTGCAGGCTGCCGTGGGCACCAGCGCCGCCCCTGTGCC

CAGCGACAATCACCTCGAGGGC

ORF Start: at 2          ORF Stop: end of sequence
SEQ ID NO:36             239 aa MW at 27287.7 kD TABLE 6A-continued NOV6 Sequence Analysis

| | |
|---|---|
| NOV6d,<br>278480724<br>Protein Sequence | TGSMKVLWAALLVTFLAGCQAKVEQAVETEPEPELRQQTEWQSGQRWELALGRFWDYL<br>RWVQTLSEQVQEELLSSQVTQELRALMDETMKELKAYKSELEEQLTPVAEETRARLSK<br>ELGPLVEQGRVRAATVGFLAGQPLQERAQAWGERLRARMEEMGSRTRDRLDEVKEQVA<br>EVRAKLEEQAQQIRLQAEAFQARLKSWFEPLVEDMQRQWAGLVEKVQAAVGTSAAPVP<br>SDNHLEG |
| NOV6e,<br>278480754 DNA<br>Sequence | SEQ ID NO:37　　　　　664 bp<br>CACCGGATCCAAGGTGGAGCAAGCGGTGGAGACAGAGCCGGAGCCCGAGCTGCGCCAG<br>CAGACCGAGTGGCAGAGCGGCCAGCGCTGGGAACTGGCACTGGGTCGCTTTTGGGATT<br>ACCTGCGCTGGGTGCAGACACTGTCTGAGCAGGTGCAGGAGGAGCTGCTCAGCTCCCA<br>GGTCACCCAGGAACTGAGGGCGCTGATGGACGAGACCATGAAGGAGTTGAAGGCCTAC<br>AAATCGGAACTGGAGGAACAACTGACCCCGGTGGCGGAGGAGACGCGGGCACGGCTGT<br>CCAAGGAGCTGGGGCCCCTGGTGGAACAGGGCCGCGTGCGGGCCGCCACTGTGGGCTT<br>CCTGGCCGGCCAGCCGCTACAGGAGCGGGCCCAGGCCTGGGGCGAGCGCCTGCGCGCG<br>CGGATGGAGGAGATGGGCAGCCGGACCCGCGACCGCCTGGACGAGGTGAAGGAGCAGG<br>TGGCGGAGGTGCGCGCCAAGCTGGAGGAGCAGGCCCAGCAGATACGCCTGCAGGCCGA<br>GGCCTTCCAGGCCCGCCTCAAGAGCTGGTTCGAGCCCCTGGTGGAAGACATGCAGCGC<br>CAGTGGGCCGGGCTGGTGGAGAAGGTGCAGGCTGCCGTGGGCACCAGCGCCGCCCCTG<br>TGCCCAGCGACAATCACCTCGAGGGC |
| NOV6e,<br>278480754<br>Protein Sequence | ORF Start: at 2　　　　　ORF Stop: end of sequence<br>SEQ ID NO:38　　　　　221 aa MW at 25370.3 kD<br>TGSKVEQAVETEPEPELRQQTEWQSGQRWELALGRFWDYLRWVQTLSEQVQEELLSSQ<br>VTQELRALMDETMKELKAYKSELEEQLTPVAEETRARLSKELGPLVEQGRVRAATVGF<br>LAGQPLQERAQAWGERLRARMEEMGSRTRDRLDEVKEQVAEVRAKLEEQAQQIRLQAE<br>AFQARLKSWFEPLVEDMQRQWAGLVEKVQAAVGTSAAPVPSDNHLEG |
| NOV6f,<br>278480861 DNA<br>Sequence | SEQ ID NO:39　　　　　616 bp<br>CACCGGATCCAAGGTTCTGTGGGCTGCGTTGCTGGTCACATTCCTGGCAGGATGCCAG<br>GCCAAGGTGGAGCAAGCGGTGGAGACAGAGCCGGAGCCCGAGCTGCGCCAGCAGACCG<br>AGTGGCAGAGCGGCCAGCGCTGGGAACTGGCACTGGGTCGCTTTTGGGATTACCTGCG<br>CTGGGTGCAGACACTGTCTGAGCAGGTGCAGGAGGAGCTGCTCAGCTCCCAGGTCACC<br>CAGGAACTGAGGGCGCTGATGGACGAGACCATGAAGGAGTTGAAGGCCTACAAATCGG<br>AACTGGAGGAACAACTGACCCCGGTGGCGGAGGAGACGCGGGCACGGCTGTCCAAGGA<br>GCTGGGGCCCCTGGTGGAACAGGGCCGCGTGCGGGCCGCCACTGTGGGCTTCCTGGCC<br>GGCCAGCCGCTACAGGAGCGGGCCCAGGCCTGGGGCGAGCGGCTGCGCGCGCGGATGG<br>AGGAGATGGGCAGCCGGACCCGCGACCGCCTGGACGAGGTGAAGGAGCAGGTGGCGGA<br>GGTGCGCGCCAAGCTGGAGGAGCAGGCCCAGCAGATACGCCTGCAGGCCGAGGCCTTC<br>CAGGCCCGCCTCAAGAGCTGGTTCGAGCTCGAGGGC |
| NOV6f,<br>278480861<br>Protein Sequence | ORF Start: at 2　　　　　ORF Stop: end of sequence<br>SEQ ID NO:40　　　　　1205 aa MW at 23672.6 kD<br>TGSKVLWAALLVTFLAGCQAKVEQAVETEPEPELRQQTEWQSGQRWELALGRFWDYLR<br>WVQTLSEQVQEELLSSQVTQELRALMDETMKELKAYKSELEEQLTPVAEETRARLSKE<br>LGPLVEQGRVRAATVGFLAGQPLQERAQAWGERLRARMEEMGSRTRDRLDEVKEQVAE<br>VRAKLEEQAQQIRLQAEAFQARLKSWFELEG |

TABLE 6A-continued

NOV6 Sequence Analysis

NOV6g,
278876278 DNA
Sequence

SEQ ID NO:41 709 bp
CACCGGATCCACCATGAAGGTTCTGTGGGCTGCGTTGCTGGTCACATTCCTGGCAGGA

TGCCAGGCCAAGGTGGAGCAAGCGGTGGAGACAGAGCCGGAGCCCGAGCTGCGCCAGC

AGACCGAGTGGCAGAGCGGCCAGCGCTGGGAACTGGCACTGGGTCGCTTTTGGGATTA

CCTGCGCTGGGTGCAGACACTCTCTGAGCAGGTGCAGGAGGAGCTGCTCAGCTCCCAG

GTCACCCAGGAACTGAGGGCGCTGATGGACGAGACCATGAAGGAGTTGAAGGCCTACA

AATCGGAACTGGAGGAACAACTGACCCCGGTGGCGGAGGAGACGCGGGCACGGCTGTC

CAAGGAGCTGCAGGCGGCGCAGGCCCGGCTGGGCGCGGACATGGAGGACGTGCGCGGC

CGCCTGGTGCAGTACCGCGGCGAGGTGCAGGCCATGCTCGGCCAGAGCACCGAGGAGC

TGCGGGTGCGCCTCGCCTCCCACCTGCGCAAGCTGCGTAAGCGGCTCCTCCGCGATGC

CGATGACCTGGAGGAGCAGGCCCAGCAGATACGCCTGCAGGCCGAGGCCTTCCAGGCC

CGCCTCAAGAGCTGGTTCGAGCCCCTGGTGGAAGACATGCAGCGCCAGTGGGCCGGGC

TGGTGGAGAAGGTGCAGGCTGCCGTGGGCACCAGCGCCGCCCCTGTGCCCAGCGACAA

TCACCTCGAGGGC

ORF Start: at 2                 ORF Stop: end of sequence
SEQ ID NO:42                    236 aa MW at 27045.4 kD NOV6g,
278876278
Protein Sequence

TGSTMKVLWAALLVTFLAGCQAKVEQAVETEPEPELRQQTEWQSGQRWELALGRFWDY

LRWVQTLSEQVQEELLSSQVTQELRALMDETMKELKAYKSELEEQLTPVAEETRARLS

KELQAAQARLGADMEDVRGRLVQYRGEVQAMLGQSTEELRVRLASHLRKLRKRLLRDA

DDLEEQAQQIRLQAEAFQARLKSWFEPLVEDMQRQWAGLVEKVQAAVGTSAAPVPSDN

HLEG

NOV6h,
278876445 DNA
Sequence

SEQ ID NO:43 652 bp
CACCGGATCCAAGGTGGAGCAAGCGGTGGAGACAGAGCCGGAGCCCGAGCTGCGCCAG

CAGACCGAGTGGCAGAGCGGCCAGCGCTGGGAACTGGCACTGGGTCGCTTTTGGGATT

ACCTGCGCTGGGTGCAGACACTGTCTGAGCAGGTGCAGGAGGAGCTGCTCAGCTCCCA

GGTCACCCAGGAACTGAGGGCGCTGATGGACGAGACCATGAAGGAGTTGAAGGCCTAC

AAATCGGAACTGGAGGAACAACTGACCCCGGTGGCGGAGGAGACGCGGGCACGGCTGT

CCAAGGAGCTGCAGGCGGCGCAGGCCCGGCTGGGCGCGGACATGGAGGACGTGCGCGG

CCGCCTGGTGCAGTACCGCGGCGAGGTGCAGGCCATGCTCGGCCAGAGCACCGAGGAG

CTGCGGGTGCGCCTCGCCTCCCACCTGCGCAAGCTGCGTAAGCGGCTCCTCCGCGATG

CCGATGACCTGGAGGAGCAGGCCCAGCAGATACGCCTGCAGGCCGAGGCCTTCCAGGC

CCGCCTCAAGAGCTGGTTCGAGCCCCTGGTGGAAGACATGCAGCGCCAGTGGGCCGGG

CTGGTGGAGAAGGTGCAGGCTGCCGTGGGCACCAGCGCCGCCCCTGTGCCCAGCGACA

ATCACCTCGAGGGC

ORF Start: at 2                 ORF Stop: end of sequence
SEQ ID NO:44                    217 aa MW at 25026.9 kD NOV6h,
278876445
Protein Sequence

TGSKVEQAVETEPEPELRQQTEWQSGQRWELALGRFWDYLRWVQTLSEQVQEELLSSQ

VTQELRALMDETMKELKAYKSELEEQLTPVAEETRARLSKELQAAQARLGADMEDVRG

TABLE 6A-continued

NOV6 Sequence Analysis

|  |  |
|---|---|
|  | RLVQYRGEVQAMLGQSTEELRVRLASHLRKLRKRLLRDADDLEEQAQQIRLQAEAFQA |
|  | RLKSWFEPLVEDMQRQWAGLVEKVQAAVGTSAAPVPSDNHLEG |
| NOV6i, 278876664 DNA Sequence | SEQ ID NO:45       691 bp<br>CACCGGATCCAAGGTTCTGTGGGCTGCGTTGCTGGTCACATTCCTGGCAGGATGCCAG<br><br>GCCAAGGTGGAGCAAGCGGTGGAGACAGAGCCGGAGCCCGAGCTGCGCCAGCAGACCG<br><br>AGTGGCAGAGCGGCCAGCGCTGGGAACTGGCACTGGGTCGCTTTTGGGATTACCTGCG<br><br>CTGGGTGCAGACACTGTCTGAGCAGGTGCAGGAGGAGCTGCTCAGCTCCCAGGTCACC<br><br>CAGGAACTGAGGGCGCTGATGGACGAGACCATGAAGGAGTTGAAGGCCTACAAATCGG<br><br>AACTGGAGGAACAACTGACCCCGGTGGCGGAGGAGACGCGGGCACGGCTGTCCAAGGA<br><br>GCTGCAGGCGGCGCAGGCCCGGCTGGGCGCGGACATGGAGGACGTGCGCGGCCGCCTG<br><br>GTGCAGTACCGCGGCGAGGTGCAGGCCATGCTCGGCCAGAGCACCGAGGAGCTGCGGG<br><br>TGCGCCTCGCCTCCCACCTGCGCAAGCTGCGTAAGCGGCTCCTCCGCGATGCCGATGA<br><br>CCTGGAGGAGCAGGCCCAGCAGATACGCCTGCAGGCCGAGGCCTTCCAGGCCCGCCTC<br><br>AAGAGCTGGTTCGAGCCCCTGGTGGAAGACATGCAGCGCCAGTGGGCCGGGCTGGTGG<br><br>AGAAGGTGCAGGCTGCCGTGGGCACCAGCGCCGCCCCTGTGCCCCTCGAGGGC |
| NOV6i, 278876664 Protein Sequence | ORF Start: at 2      ORF Stop: end of sequence<br>SEQ ID NO:46      230 aa MW at 26359.7 kD<br>TGSKVLWAALLVTFLAGCQAKVEQAVETEPEPELRQQTEWQSGQRWELALGRFWDYLR<br><br>WVQTLSEQVQEELLSSQVTQELRALMDETMKELKAYKSELEEQLTPVAEETRARLSKE<br><br>LQAAQARLGADMEDVRGRLVQYRGEVQAMLGQSTEELRVRLASHLRKLRKRLLRDADD<br><br>LEEQAQQIRLQAEAFQARLKSWFEPLVEDMQRQWAGLVEKVQAAVGTSAAPVPLEG |

Sequence comparison of the above protein sequences yields the following sequence relationships shown in Table 6B.

Further analysis of the NOV6a protein yielded the following properties shown in Table 6C.

TABLE 6B

Comparison of NOV6a against NOV6b through NOV6i.

| Protein Sequence | NOV6a Residues/ Match Residues | Identities/ Similarities for the Matched Region |
|---|---|---|
| NOV6b | 1 . . . 194 | 189/233 (81%) |
|  | 1 . . . 233 | 189/233 (81%) |
| NOV6c | 1 . . . 194 | 185/229 (80%) |
|  | 1 . . . 229 | 191/229 (82%) |
| NOV6d | 1 . . . 194 | 189/233 (81%) |
|  | 4 . . . 236 | 189/233 (81%) |
| NOV6e | 18 . . . 194 | 171/216 (79%) |
|  | 3 . . . 218 | 172/216 (79%) |
| NOV6f | 2 . . . 161 | 145/199 (72%) |
|  | 4 . . . 202 | 150/199 (74%) |
| NOV6g | 1 . . . 194 | 185/229 (80%) |
|  | 5 . . . 233 | 191/229 (82%) |
| NOV6h | 18 . . . 194 | 167/212 (78%) |
|  | 3 . . . 214 | 174/212 (81%) |
| NOV6i | 2 . . . 190 | 180/224 (80%) |
|  | 4 . . . 227 | 186/224 (82%) |

TABLE 6C

Protein Sequence Properties NOV6a

| PSort analysis: | 0.3700 probability located in outside; 0.1000 probability located in endoplasmic reticulum (membrane); 0.1000 probability located in endoplasmic reticulum (lumen); 0.1000 probability located in microbody (peroxisome) |
|---|---|
| SignalP analysis: | Cleavage site between residues 19 and 20 |

A search of the NOV6a protein against the Geneseq database, a proprietary database that contains sequences published in patents and patent publications, yielded several homologous proteins shown in Table 6D.

TABLE 6D

Geneseq Results for NOV6a

| Geneseq Identifier | Protein/Organism/Length [Patent #, Date] | NOV6a Residues/ Match Residues | Identities/ Similarities for the Matched Region | Expect Value |
|---|---|---|---|---|
| AAE13293 | Human apolipoprotein E (apoE) isoprotein, apoE4 - *Homo sapiens*, 317 aa. [WO200177136-A1, Oct. 18, 2001] | 1 ... 172<br>1 ... 178 | 136/178 (76%)<br>154/178 (86%) | 2e-69 |
| AAB80998 | Human ApoE4 - *Homo sapiens*, 317 aa. [JP2001017028-A, Jan. 23, 2001] | 1 ... 172<br>1 ... 178 | 136/178 (76%)<br>154/178 (86%) | 2e-69 |
| AAE13296 | Human apolipoprotein E (apoE) allele, apoE1 - *Homo sapiens*, 317 aa. [WO200177136-A1, Oct. 18, 2001] | 1 ... 169<br>1 ... 175 | 135/175 (77%)<br>152/175 (86%) | 7e-69 |
| AAE15158 | Human apolipoprotein E (APOE) protein - *Homo sapiens*, 317 aa. [WO200179234-A2, Oct. 25, 2001] | 1 ... 172<br>1 ... 178 | 136/178 (76%)<br>153/178 (85%) | 9e-69 |
| AAE13298 | Human apolipoprotein E (apoE) allele, apoE2** - *Homo sapiens*, 317 aa. [WO200177136-A1, Oct. 18, 2001] | 1 ... 172<br>1 ... 178 | 136/178 (76%)<br>153/178 (85%) | 9e-69 |

In a BLAST search of public sequence datbases, the NOV6a protein was found to have homology to the proteins shown in the BLASTP data in Table 6E.

TABLE 6E

Public BLASTP Results for NOV6a

| Protein Accession Number | Protein/Organism/Length | NOV6a Residues/ Match Residues | Identities/ Similarities for the Matched Portion | Expect Value |
|---|---|---|---|---|
| P02649 | Apolipoprotein E precursor (Apo-E) - *Homo sapiens* (Human), 317 aa. | 1 ... 172<br>1 ... 178 | 136/178 (76%)<br>153/178 (85%) | 2e-68 |
| CAA03641 | SEQUENCE 28 FROM PATENT WO9712992 - unidentified, 220 aa (fragment). | 1 ... 172<br>21 ... 198 | 135/178 (75%)<br>152/178 (84%) | 1e-67 |
| Q9GLM8 | Apolipoprotein E - *Gorilla gorilla* (gorilla), 317 aa. | 1 ... 172<br>1 ... 178 | 134/178 (75%)<br>151/178 (84%) | 2e-67 |
| Q9GLM7 | Apolipoprotein E - *Pongo pygmaeus* (Orangutan), 317 aa. | 1 ... 172<br>1 ... 178 | 133/178 (74%)<br>150/178 (83%) | 6e-67 |
| Q9GJU3 | Apolipoprotein E (Apolipoprotein-E) - *Pan troglodytes* (Chimpanzee), 317 aa. | 1 ... 172<br>1 ... 178 | 131/178 (73%)<br>148/178 (82%) | 8e-66 |

PFam analysis predicts that the NOV6a protein contains the domains shown in the Table 6F.

TABLE 6F

Domain Analysis of NOV6a

| Pfam Domain | NOV6a Match Region | Identities/ Similarities for the Matched Region | Expect Value |
|---|---|---|---|
| Apolipoprotein | 2 ... 193 | 83/283 (29%)<br>170/283 (60%) | 4.4e-27 |

Example 7

The NOV7 clone was analyzed, and the nucleotide and encoded polypeptide sequences are shown in Table 7A.

TABLE 7A

NOV7 Sequence Analysis

| | | |
|---|---|---|
| NOV7a, CG129136-01 DNA Sequence | SEQ ID NO:47 747 bp <u>CATGGAATACGCCTCTGACGCTTCACTGGACCCCGAAGCCCCGTGGCCTCCCGCGCCC CGCGCTCGCGCCTGCCGCGTACTGCCTTGGGCCCTGGTCGCGGGGCTGCTGCTGCTGC TGCTGCTCACTGCCGCCTGCGCCGTCTTCCTCGCCTGCCCCTGGGCCGTGTCCGGGGC TCGCGCCTCGCCCGGCTCCGCGGCCAGCCCGAGACTCCGCGAGGGTCCCGAGCTTTCG CCCGACGATCCCGCCGGCCTCTTGGACCTGCGGCAGGGCATGTTTGCGCAGCTGGTGG CCAAGGCTGGAGTCTACTATGTCTTCTTTCAACTAGAGCTGCGGCGCGTGGTGGCCGG CGAGGGCTCAGGCTCCGTTTCACTTGCGCTGCACCTGCAGCCACTGCGCTCTGCTGCT GGGGCCGCCGCCCTGGCTTTGACCGTGGACCTGCCACCCGCCTCCTCCGAGGCTCGGA ACTCGGCCTTCGGTTTCCAGGGCCGCTTGCTGCACCTGAGTGCCGGCCAGCGCCTGGG CGTCCATCTTCACACTGAGGCCAGGGCACGCCATGCCTGGCAGCTTACCCAGGGCGCC ACAGTCTTGGGACTCTTCCGGGTGACCCCCGAAATCCCAGCCGGACTCCCTTCACCGA GGTCGGAATAACGCCCAGCCTGGGTGCGGCCCACCTGGACAGAGTCCGAATCCTACTC CATCCTTCATGGAGACCCCTGGTGCTGGGTCCCTGCTGCTTTCTCTACCTC</u> |
| NOV7a, CG129136-01 Protein Sequence | ORF Start: ATG at 2     ORF Stop: TAA at 647<br>SEQ ID NO:48     215 aa MW at 22565.7 kD<br>MEYASDASLDPEAPWPPAPRARACRVLPWALVAGLLLLLLTAACAVFLACPWAVSGA RASPGSAASPRLREGPELSPDDPAGLLDLRQGMFAQLVAKAGVYYVFFQLELRRVVAG EGSGSVSLALHLQPLRSAAGAAALALTVDLPPASSEARNSAFGFQGRLLHLSAGQRLG VHLHTEARARHAWQLTQGATVLGLFRVTPEIPAGLPSPRSE |
| NOV7b, CG129136-03 DNA Sequence | SEQ ID NO:49     442 bp<br><u>GTCATGGAATACGCCTCTGACGCTGTCAGGAATACGCCTCTGACGCTGTCATGGAATA CGCCTCTGACGCTGTCATGGAATACGCCTCTGACGCTTCACTGGACCCCGAAGCCCCG TGGCCTCCCGCGCCCCGCGCTCGCGCCTGCCGCGTACTGCCTTGGGCCCTGGTCGCGG GGCTGCTGCTGCTGCTGCTGCTCGCTGCCGGCCAGCGCCTGGGCGTCCATCTTCACAC TGAGGCCAGGGCACGCCATGCCTGGCAGCTTACCCAGGGCGCCACAGTCTTGGGACTC TTCCGGGTGACCCCCGAAATCCCAGCCGGACTCCCTTCACCGAGGTCGGAATAACGCC CAGCCTGGGTGCAGCCCACCTGGACAGAGTCCGAATCCTACTCCATCCTTCATGGAGA CCCCTGGTGCCGGGTCCCTGCTGCTTTCTCTACCTC</u> |
| NOV7b, CG129136-03 Protein Sequence | ORF Start: ATG at 75     ORF Stop: TAA at 342<br>SEQ ID NO:50     89 aa MW at 9594.0 kD<br>MEYASDASLDPEAPWPPAPRARACRVLPWALVAGLLLLLLLAAGQRLGVHLHTEARAR HAWQLTQGATVLGLFRVTPEIPAGLPSPRSE |
| NOV7c, 278876545 DNA Sequence | SEQ ID NO:51     289 bp<br><u>CACCGGATCCACCATGGAATACGCCTCTGACGCTTCACTGGACCCCGAAGCCCCGTGG CCTCCCGCGCCCCGCGCTCGCGCCTGCCGCGTACTGCCTTGGGCCCTGGTCGCGGGGC TGCTGCTGCTGCTGCTCGCTGCCGGCCAGCGCCTGGGCGTCCATCTTCACACTGA GGCCAGGGCACGCCATGCCTGGCAGCTTACCCAGGGCGCCACAGTCTTGGGACTCTTC CGGGTGACCCCCGAAATCCCAGCCGGACTCCCTTCACCGAGGTCGGAACTCGAGGGC</u> |

TABLE 7A-continued

NOV7 Sequence Analysis

| | | |
|---|---|---|
| NOV7c, 278876545 Protein Sequence | ORF Start: at 2<br>SEQ ID NO:52<br>TGSTMEYASDASLDPEAPWPPAPRARACRVLPWALVAGLLLLLLLAAGQRLGVHLHTE<br>ARARHAWQLTQGATVLGLFRVTPEIPAGLPSPRSELEG | ORF Stop: end of sequence<br>96 aa MW at 10239.7 kD |
| NOV7d, 278876597 DNA Sequence | SEQ ID NO:53<br>CACCGGATCCGCCTGCCGCGTACTGCCTTGGGCCCTGGTCGCGGGGCTGCTGCTGCTG<br>CTGCTGCTCGCTGCCGGCCAGCGCCTGGGCGTCCATCTTCACACTGAGGCCAGGGCAC<br>GCCATGCCTGGCAGCTTACCCAGGGCGCCACAGTCTTGGGACTCTTCCGGGTGCTCGA<br>GGGC | 178 bp |
| NOV7d, 278876597 Protein Sequence | ORF Start: at 2<br>SEQ ID NO:54<br>TGSACRVLPWALVAGLLLLLLLAAGQRLGVHLHTEARARHAWQLTQGATVLGLFRVLE<br>G | ORF Stop: end of sequence<br>59 aa MW at 6296.4 kD |

Sequence comparison of the above protein sequences yields the following sequence relationships shown in Table 7B.

TABLE 7B

Comparison of NOV7a against NOV7b through NOV7d.

| Protein Sequence | NOV7a Residues/ Match Residues | Identities/ Similarities for the Matched Region |
|---|---|---|
| NOV7b | 176 ... 215 | 40/40 (100%) |
| | 50 ... 89 | 40/40 (100%) |
| NOV7c | 176 ... 215 | 40/40 (100%) |
| | 54 ... 93 | 40/40 (100%) |
| NOV7d | 176 ... 201 | 26/26 (100%) |
| | 31 ... 56 | 26/26 (100%) |

Further analysis of the NOV7a protein yielded the following properties shown in Table 7C.

TABLE 7C

Protein Sequence Properties NOV7a

| | |
|---|---|
| PSort analysis: | 0.7900 probability located in plasma membrane; 0.3000 probability located in Golgi body; 0.2000 probability located in endoplasmic reticulum (membrane); 0.1732 probability located in microbody (peroxisome) |
| SignalP analysis: | Cleavage site between residues 58 and 59 |

A search of the NOV7a protein against the Geneseq database, a proprietary database that contains sequences published in patents and patent publications, yielded several homologous proteins shown in Table 7D.

TABLE 7D

Geneseq Results for NOV7a

| Geneseq Identifier | Protein/Organism/Length [Patent #, Date] | NOV7a Residues/ Match Residues | Identities/ Similarities for the Matched Region | Expect Value |
|---|---|---|---|---|
| ABB75953 | Human cytokine 4-1BB ligand - Homo sapiens, 254 aa. [US6355779-B1, Mar. 12, 2002] | 1 ... 215<br>1 ... 254 | 214/254 (84%)<br>214/254 (84%) | e-114 |
| AAW26657 | Human 4-1BB ligand - Homo sapiens, 254 aa. [US5674704-A, Oct. 7, 1997] | 1 ... 215<br>1 ... 254 | 214/254 (84%)<br>214/254 (84%) | e-114 |
| AAR64190 | Human 4-1BB-L polypeptide - Homo sapiens, 254 aa. [WO9426290-A, Nov. 24, 1994] | 1 ... 215<br>1 ... 254 | 214/254 (84%)<br>214/254 (84%) | e-114 |
| ABB75952 | Murine cytokine 4-1BB ligand - Mus sp, 309 aa. [US6355779-B1, Mar. 12, 2002] | 10 ... 206<br>65 ... 307 | 70/248 (28%)<br>93/248 (37%) | 2e-06 |
| AAW26656 | Murine 4-1BB ligand - Mus musculus, 309 aa. [US5674704-A, Oct. 7, 1997] | 10 ... 206<br>65 ... 307 | 70/248 (28%)<br>93/248 (37%) | 2e-06 |

In a BLAST search of public sequence datbases, the NOV7a protein was found to have homology to the proteins shown in the BLASTP data in Table 7E.

TABLE 7E

Public BLASTP Results for NOV7a

| Protein Accession Number | Protein/Organism/Length | NOV7a Residues/ Match Residues | Identities/ Similarities for the Matched Portion | Expect Value |
|---|---|---|---|---|
| P41273 | Tumor necrosis factor ligand superfamily member 9 (4-1BB ligand) (4-1BBL) - *Homo sapiens* (Human), 254 aa. | 1 ... 215<br>1 ... 254 | 214/254 (84%)<br>214/254 (84%) | e-113 |
| P41274 | Tumor necrosis factor ligand superfamily member 9 (4-1BB ligand) (4-1BBL) - *Mus musculus* (Mouse), 309 aa. | 10 ... 206<br>65 ... 307 | 70/248 (28%)<br>93/248 (37%) | 5e-06 |
| Q93QG0 | Putative regulator - Brevibacterium sp. HCU, 263 aa. | 13 ... 84<br>53 ... 112 | 29/72 (40%)<br>32/72 (44%) | 0.064 |
| P42514 | Hypothetical protein PA4219 - *Pseudomonas aeruginosa*, 394 aa. | 77 ... 202<br>257 ... 389 | 45/140 (32%)<br>59/140 (42%) | 0.94 |
| Q9PEB0 | UDP-N-acetylmuramoylalanine-D-glutamate ligase - *Xylella fastidiosa*, 468 aa. | 127 ... 185<br>387 ... 447 | 27/62 (43%)<br>33/62 (52%) | 2.8 |

PFam analysis predicts that the NOV7a protein contains the domains shown in the Table 7F.

TABLE 7F

Domain Analysis of NOV7a

| Pfam Domain | NOV7a Match Region | Identities/ Similarities for the Matched Region | Expect Value |
|---|---|---|---|
| TNF | 95 ... 201 | 33/115 (29%)<br>102/115 (89%) | 1.3e-27 |

Example 8

The NOV8 clone was analyzed, and the nucleotide and encoded polypeptide sequences are shown in Table 8A.

TABLE 8A

NOV8 Sequence Analysis

NOV8a,
CG133483-01
DNA Sequence

SEQ ID NO:55      598 bp

GCGGCCGCAGCCGCTGCCCCGGGCCGGGCGCCCGCGGCGGCACCATGAGTCCCCGCTC

GTGCCTGCGTTCGCTGCGCCTCCTCGTCTTCGCCGTCTTCTCAGCCGCCGCGAGCAAC

TGGCTGTACCTGGCCAAGCTGTCGTCGGTGGGGAGCATCTCAGAGGAGGAGACGTGCG

AGAAACTCAAGGGCCTGATCCAGAGGCAGGTGCAGATGTGCAAGCGGAACCTGGAAGT

CATGGACTCGGTGCGCCGCGGTGCCCAGCTGGCCATTGAGGAGTGCCAGTACCAGTTC

CGGAACCGGCGCTGGAACTGCTCCACACTCGACTCCTTGCCCGTCTTCGGCAAGGTGG

TGACGCAAGGTGGCAAAGCCTGGCATGGAGGAGACAGTGGATGTCATCTACTGACAGA

AAGCAGGTCAGGGGAGAGGACTCAAAGGCGCAAGGAAGGAGGTAGCCTGGGGCAATGC

TGGCCTGAAGCCATCGTGGGTACTCAGGACCCCATGAGAAGCCCCCCTTACCTTTGGG

GGAGGAACCAAGGGGGCACCCACACCGGCTCAGCATCTGAGGGACACTGAGATTCCTA

CTAGGCCTGGGTGGTACC

ORF Start: ATG at 45        ORF Stop: TGA at 570
SEQ ID NO:56                175 aa MW at 19416.8 kD NOV8a,        MSPRSCLRSLRLLVFAVFSAAASNWLYLAKLSSVGSISEEETCEKLKGLIQRQVQMCK

TABLE 8A-continued

NOV8 Sequence Analysis

CG133483-01
Protein Sequence  RNLEVMDSVRRGAQLAIEECQYQFRNRRWNCSTLDSLPVFGKVVTQGGKAWHGGDSGC

HLLTESRSGERTQRRKEGGSLGQCWPEAIVGTQDPMRSPPYLWGRNQGGTHTGSASEG

H

Further analysis of the NOV8a protein yielded the following properties shown in Table 8B.

TABLE 8B

Protein Sequence Properties NOV8a

| | |
|---|---|
| PSort analysis: | 0.4753 probability located in outside; 0.1425 probability located in microbody (peroxisome); 0.1000 probability located in endoplasmic reticulum (membrane); 0.1000 probability located in endoplasmic reticulum (lumen) |
| SignalP analysis: | Cleavage site between residues 23 and 24 |

A search of the NOV8a protein against the Geneseq database, a proprietary database that contains sequences published in patents and patent publications, yielded several homologous proteins shown in Table 8C.

TABLE 8C

Geneseq Results for NOV8a

| Geneseq Identifier | Protein/Organism/Length [Patent #, Date] | NOV8a Residues/ Match Residues | Identities/ Similarities for the Matched Region | Expect Value |
|---|---|---|---|---|
| ABB90437 | Human polypeptide SEQ ID NO 2813 - *Homo sapiens*, 185 aa. [WO200190304-A2, Nov. 24, 2001] | 1 . . . 105<br>1 . . . 105 | 105/105 (100%)<br>105/105 (100%) | 8e-55 |
| AAE09707 | Human gene 3 encoding novel protein HE8QR01, SEQ ID NO: 54 - *Homo sapiens*, 365 aa. [WO200155202-A1, Aug. 2, 2001] | 1 . . . 105<br>15 . . . 119 | 105/105 (100%)<br>105/105 (100%) | 8e-55 |
| AAM40675 | Human polypeptide SEQ ID NO 5606 - *Homo sapiens*, 365 aa. [WO200153312-A1, Jul. 26, 2001] | 1 . . . 105<br>15 . . . 119 | 105/105 (100%)<br>105/105 (100%) | 8e-55 |
| AAM38889 | Human polypeptide SEQ ID NO 2034 - *Homo sapiens*, 351 aa. [WO200153312-A1, Jul. 26, 2001] | 1 . . . 105<br>1 . . . 105 | 105/105 (100%)<br>105/105 (100%) | 8e-55 |
| AAU29063 | Human PRO polypeptide sequence #40 - *Homo sapiens*, 351 aa. [WO200168848-A2, Sep. 20, 2001] | 1 . . . 105<br>1 . . . 105 | 105/105 (100%)<br>105/105 (100%) | 8e-55 |

In a BLAST search of public sequence datbases, the NOV8a protein was found to have homology to the proteins shown in the BLASTP data in Table 8D.

TABLE 8D

Public BLASTP Results for NOV8a

| Protein Accession Number | Protein/Organism/Length | NOV8a Residues/ Match Residues | Identities/ Similarities for the Matched Portion | Expect Value |
|---|---|---|---|---|
| P56705 | WNT-4 protein precursor - Homo sapiens (Human), 351 aa. | 1 ... 105<br>1 ... 105 | 105/105 (100%)<br>105/105 (100%) | 2e-54 |
| P22724 | WNT-4 protein precursor - Mus musculus (Mouse), 351 aa. | 1 ... 105<br>1 ... 105 | 105/105 (100%)<br>105/105 (100%) | 2e-54 |
| Q9QXQ5 | WNT-4 protein precursor - Rattus norvegicus (Rat), 351 aa. | 1 ... 105<br>1 ... 105 | 104/105 (99%)<br>104/105 (99%) | 7e-54 |
| JC2451 | Cwnt-4 protein precursor - chicken, 351 aa. | 1 ... 105<br>1 ... 105 | 95/105 (90%)<br>98/105 (92%) | 2e-48 |
| P49337 | WNT-4 protein precursor - Gallus gallus (Chicken), 351 aa. | 1 ... 105<br>1 ... 105 | 95/105 (90%)<br>98/105 (92%) | 2e-48 |

PFam analysis predicts that the NOV8a protein contains the domains shown in the Table 8E.

TABLE 8E

Domain Analysis of NOV8a

| Pfam Domain | NOV8a Match Region | Identities/ Similarities for the Matched Region | Expect Value |
|---|---|---|---|
| wnt | 42 ... 105 | 43/67 (64%)<br>64/67 (96%) | 5.1e-47 |

Example 9

The NOV9 clone was analyzed, and the nucleotide and encoded polypeptide sequences are shown in Table 9A.

TABLE 9A

NOV9 Sequence Analysis

| | | |
|---|---|---|
| NOV9a,<br>CG135316-01<br>DNA Sequence | SEQ ID NO:57 | 1047 bp |

ATGGCCGCGGCCATCGCTAGCGGCTTGATCCGCCAGAAGCGGCAGGCGCGGGAGCAGC

ACTGGGACCGGCCGTCTGCCAGCAGGAGGCGGAGCAGCCCCAGCAAGAACCGCGGGCT

CTGCAACGGCAACCTGGTGGATATCTTCTCCAAAGTGCGCATCTTCGGCCTCAAGAAG

CGCAGGTTGCGGCGCCAAGATCCCCAGCTCAAGGGTATAGTGACCAGGTTATATTGCA

GGCAAGGCTACTACTTGCAAATGCACCCCGATGGAGCTCTCGATGGAACCAAGGATGA

CAGCACTAATTCTACACTCTTCAACCTCATACCAGTGGGACTACGTGTTGTTGCCATC

CAGGGAGTGAAAACAGGGTTGTATATAGCCATGAATGGAGAAGGTTACCTCTACCCAT

CAGAACTTTTTACCCCTGAATGCAAGTTTAAAGAATCTGTTTTTGAAAATTATTATGT

AATCTACTCATCCATGTTGTACAGACAACAGGAATCTGGTAGAGCCTGGTTTTTGGGA

TTAAATAAGGAAGGGCAAGCTATGAAAGGGAACAGAGTAAAGAAAACCAAACCAGCAG

CTCATTTTCTACCCAAGCCATTGGAAGTTGCCATGTACCGAGAACCATCTTTGCATGA

TGTTGGGGAAACGGTCCCGAAGCCTGGGGTGACGCCAAGTAAAAGCACAAGTGCGTCT

AAATCCATTTCAGATATACTCCGTCCTGTTTTTAATGAACCAAACTTAACGCCATCCC

CGTTTCTGGCTGCGTTCCCCTCATACTCAGCAGAGCATGGGCAAGACGGCTGTTGTGT

TCTTTCGTGGTCCGTAAAGTTTAACTTTCTGATCCTTAATAGGAGGATAAGCGCCGTG

ATAGAGAAATCCAAAGGTCATTTGTATTACGATGGCTAG<u>ATAATGTAATGAATTCCAA</u>

<u>TGTCTGTGCATCAGCGAATACGTCATCAAAATTGCTACAAAACAATAATAATAGGTTG</u>

TABLE 9A-continued

NOV9 Sequence Analysis

TTCACAGCTTAAAATGTTTAGGTAGTGAAGAGGAAAGAATATAACCTACATTATTTAT

TGA

NOV9a, CG135316-01 Protein Sequence

ORF Start: ATG at 1
SEQ ID NO:58

ORF Stop: TAG at 907
302 aa MW at 34001.7 kD

MAAAIASGLIRQKRQAREQHWDRPSASRRRSSPSKNRGLCNGNLVDIFSKVRIFGLKK
RRLRRQDPQLKGIVTRLYCRQGYYLQMHPDGALDGTKDDSTNSTLFNLIPVGLRVVAI
QGVKTGLYIAMNGEGYLYPSELFTPECKFKESVFENYYVIYSSMLYRQQESGRAWFLG
LNKEGQAMKGNRVKKTKPAAHFLPKPLEVAMYREPSLHDVGETVPKPGVTPSKSTSAS
KSISDILRPVFNEPNLTPSPFLAAFPSYSAEHGQDGCCVLSWSVKFNFLILNRRISAV
IEKSKGHLYYDG

Further analysis of the NOV9a protein yielded the following properties shown in Table 9B.

TABLE 9B

Protein Sequence Properties NOV9a

| | |
|---|---|
| PSort analysis: | 0.4539 probability located in mitochondrial matrix space; 0.4027 probability located in mitochondrial intermembrane space; 0.3000 probability located in nucleus; 0.1467 probability located in mitochondrial inner membrane |
| SignalP analysis: | No Known Signal Sequence Predicted |

A search of the NOV9a protein against the Geneseq database, a proprietary database that contains sequences published in patents and patent publications, yielded several homologous proteins shown in Table 9C.

TABLE 9C

Geneseq Results for NOV9a

| Geneseq Identifier | Protein/Organism/Length [Patent #, Date] | NOV9a Residues/ Match Residues | Identities/ Similarities for the Matched Region | Expect Value |
|---|---|---|---|---|
| AAE18819 | Human FGF-14 protein - Homo sapiens, 247 aa. [US2002001825-A1, Jan. 3, 2002] | 1 . . . 232<br>1 . . . 232 | 232/232 (100%)<br>232/232 (100%) | e-134 |
| AAB65291 | Human PRO185 protein sequence SEQ ID NO: 499 - Homo sapiens, 247 aa. [WO200073454-A1, Dec. 7, 2000] | 1 . . . 232<br>1 . . . 232 | 232/232 (100%)<br>232/232 (100%) | e-134 |
| AAB31182 | Amino acid sequence of human polypeptide PRO185 - Homo sapiens, 247 aa. [WO200077037-A2, Dec. 21, 2000] | 1 . . . 232<br>1 . . . 232 | 232/232 (100%)<br>232/232 (100%) | e-134 |
| AAB47288 | PRO185 polypeptide - Homo sapiens, 247 aa. [WO200140464-A1, Jun. 7, 2001] | 1 . . . 232<br>1 . . . 232 | 232/232 (100%)<br>232/232 (100%) | e-134 |
| AAE04406 | Human fibroblast growth factor homologous factor 4 (FHF-4) - Homo sapiens, 247 aa. [WO200147957-A2, Jul. 5, 2001] | 1 . . . 232<br>1 . . . 232 | 232/232 (100%)<br>232/232 (100%) | e-134 |

In a BLAST search of public sequence datbases, the NOV9a protein was found to have homology to the proteins shown in the BLASTP data in Table 9D.

TABLE 9D

Public BLASTP Results for NOV9a

| Protein Accession Number | Protein/Organism/Length | NOV9a Residues/ Match Residues | Identities/ Similarities for the Matched Portion | Expect Value |
|---|---|---|---|---|
| Q92915 | Fibroblast growth factor-14 (FGF-14) (Fibroblast growth factor homologous factor 4) (FHF-4) - Homo sapiens (Human), 247 aa. | 1 . . . 232<br>1 . . . 232 | 232/232 (100%)<br>232/232 (100%) | e-133 |
| Q8R5L7 | Fibroblast growth factor14 - Rattus norvegicus (Rat), 247 aa. | 1 . . . 232<br>1 . . . 232 | 230/232 (99%)<br>230/232 (99%) | e-132 |
| P70379 | Fibroblast growth factor-14 (FGF-14) (Fibroblast growth factor homologous factor 4) (FHF-4) - Mus musculus (Mouse), 247 aa. | 1 . . . 232<br>1 . . . 232 | 229/232 (98%)<br>229/232 (98%) | e-130 |
| Q9IAI6 | Fibroblast growth factor homologous factor 4 isoform 1A - Gallus gallus (Chicken), 237 aa (fragment). | 12 . . . 242<br>1 . . . 231 | 213/231 (92%)<br>221/231 (95%) | e-123 |
| Q8R4X0 | Fibroblast growth factor-like factor-4D - Rattus norvegicus (Rat), 211 aa (fragment). | 58 . . . 232<br>22 . . . 196 | 167/175 (95%)<br>168/175 (95%) | 3e-94 |

PFam analysis predicts that the NOV9a protein contains the domains shown in the Table 9E.

TABLE 9E

Domain Analysis of NOV9a

| Pfam Domain | NOV9a Match Region | Identities/ Similarities for the Matched Region | Expect Value |
|---|---|---|---|
| FGF | 71 . . . 200 | 54/147 (37%)<br>100/147 (68%) | 2.7e-43 |

Example 10

The NOV10 clone was analyzed, and the nucleotide and encoded polypeptide sequences are shown in Table 10A.

TABLE 10A

NOV10 Sequence Analysis

| | |
|---|---|
| NOV10a,<br>CG53473-03 DNA Sequence | SEQ ID NO:59    30 bp<br>GGCAAGCTCTGGGCCATCGGTCACTTCATG |
| NOV10a,<br>CG53473-03 Protein Sequence | ORF Start: at 1   ORF Stop: end of sequence<br>SEQ ID NO:60    10 aa MW at 1159.4 kD<br>GKLWAIGHFM |

Further analysis of the NOV10a protein yielded the following properties shown in Table 10B.

TABLE 10B

Protein Sequence Properties NOV10a

| PSort analysis: | |
|---|---|
| SignalP analysis: | No Known Signal Sequence Predicted |

A search of the NOV10a protein against the Geneseq database, a proprietary database that contains sequences published in patents and patent publications, yielded several homologous proteins shown in Table 10C.

TABLE 10C

Geneseq Results for NOV10a

| Geneseq Identifier | Protein/ Organism/ Length [Patent #, Date] | NOV10a Residues/ Match Residues | Identities/ Similarities for the Matched Portion | Expect Value |
|---|---|---|---|---|

In a BLAST search of public sequence datbases, the NOV10a protein was found to have homology to the proteins shown in the BLASTP data in Table 10D.

TABLE 10D

Public BLASTP Results for NOV10a

| Protein Accession Number | Protein/ Organism/ Length | NOV10a Residues/ Match Residues | Identities/ Similarities for the Matched Portion | Expect Value |
|---|---|---|---|---|

PFam analysis predicts that the NOV10a protein contains the domains shown in the Table 10E.

TABLE 10E

Domain Analysis of NOV10a

| Pfam Domain | NOV10a Match Region | Identities/ Similarities for the Matched Region | Expect Value |
|---|---|---|---|
| Bombesin | 1 ... 10 | 7/10 (70%) 10/10 (100%) | 0.41 |

Example 11

The NOV11 clone was analyzed, and the nucleotide and encoded polypeptide sequences are shown in Table 11A.

TABLE 11A

NOV11 Sequence Analysis

```
NOV11a,          SEQ ID NO: 61         126 bp
CG54725-03       GCACACAAACTAGACCTGGAAGAAATTGCCAGCTTGGATAAGGCCAAGCTGAAGGCCA
DNA Sequence
                 CAGAGATGCAGAAGAACACTCTGATGACCAAAGAGACCACAGAGCAGGAGAAGTGGAG

TGAAATTTCC

ORF Start: at 1       ORF Stop: end of sequence
                 SEQ ID NO: 62         42 aa    MW at 4848.5kD
NOV11a,          AHKLDLEEIASLDKAKLKATEMQKNTLMTKETTEQEKWSEIS
CG54725-03
Protein Sequence
```

Further analysis of the NOV11a protein yielded the following properties shown in Table 11B.

TABLE 11B

Protein Sequence Properties NOV11a

| | |
|---|---|
| PSort analysis: | 0.4500 probability located in cytoplasm; 0.3000 probability located in microbody (peroxisome); 0.1000 probability located in mitochondrial matrix space; 0.1000 probability located in lysosome (lumen) |
| SignalP analysis: | No Known Signal Sequence Predicted |

A search of the NOV11a protein against the Geneseq database, a proprietary database that contains sequences published in patents and patent publications, yielded several homologous proteins shown in Table 11C.

TABLE 11C

Geneseq Results for NOV11a

| Geneseq Identifier | Protein/Organism/Length [Patent #, Date] | NOV11a Residues/ Match Residues | Identities/ Similarities for the Matched Region | Expect Value |
|---|---|---|---|---|
| ABB05036 | Human NOV2c protein SEQ ID NO: 8 - Homo sapiens, 43 aa. [WO200190155-A2, Nov. 29, 2001] | 1 ... 42 2 ... 43 | 42/42 (100%) 42/42 (100%) | 5e-17 |
| ABB05035 | Human NOV2b protein SEQ ID NO: 6 - Homo sapiens, 43 aa. [WO200190155-A2, Nov. 29, 2001] | 1 ... 42 2 ... 43 | 42/42 (100%) 42/42 (100%) | 5e-17 |
| ABB05034 | Human NOV2a protein SEQ ID NO: 4 - Homo sapiens, 43 aa. [WO200190155-A2, Nov. 29, 2001] | 1 ... 42 2 ... 43 | 42/42 (100%) 42/42 (100%) | 5e-17 |
| AAY80267 | Thymosin beta 4 peptide isoform Tbeta10 - Unidentified, 43 aa. [WO200006190-A1, Feb. 10, 2000] | 1 ... 42 1 ... 43 | 32/43 (74%) 33/43 (76%) | 9e-08 |
| AAR96932 | Thymosin beta 10 - Synthetic, 43 aa. [WO9611016-A1, Apr. 18, 1996] | 1 ... 42 1 ... 43 | 32/43 (74%) 33/43 (76%) | 9e-08 |

In a BLAST search of public sequence datbases, the NOV11a protein was found to have homology to the proteins shown in the BLASTP data in Table 11D.

TABLE 11D

Public BLASTP Results for NOV11a

| Protein Accession Number | Protein/ Organism/ Length | NOV11a Residues/ Match Residues | Identities/ Similarities for the Matched Portion | Expect Value |
|---|---|---|---|---|
| AAM34215 | Thymosin beta 10 - *Equus caballus* (Horse), 44 aa. | 1 . . . 42<br>2 . . . 44 | 32/43 (74%)<br>33/43 (76%) | 2e-07 |
| P13472 | Thymosin beta-10 - *Homo sapiens* (Human),, 43 aa. | 1 . . . 42<br>1 . . . 43 | 32/43 (74%)<br>33/43 (76%) | 2e-07 |
| CAC38717 | Sequence 1 from Patent WO0129217 - *Homo sapiens* (Human), 58 aa. | 1 . . . 37<br>2 . . . 38 | 26/37 (70%)<br>30/37 (80%) | 1e-06 |
| P21752 | Thymosin beta-9 (Thymosin beta-10) [Contains: Thymosin beta-8] - *Bos taurus* (Bovine), 41 aa. | 1 . . . 37<br>1 . . . 38 | 28/38 (73%)<br>28/38 (73%) | 2e-05 |
| P21753 | Thymosin beta-9 - *Sus scrofa* (Pig), 41 aa. | 1 . . . 37<br>1 . . . 38 | 27/38 (71%)<br>28/38 (73%) | 4e-05 |

PFam analysis predicts that the NOV11a protein contains the domains shown in the Table 11E.

TABLE 11E

Domain Analysis of NOV11a

| Pfam Domain | NOV11a Match Region | Identities/ Similarities for the Matched Region | Expect Value |
|---|---|---|---|
| Thymosin | 1 . . . 40 | 29/41 (71%)<br>32/41 (78%) | 1.8e-11 |

Example 12

The NOV12 clone was analyzed, and the nucleotide and encoded polypeptide sequences are shown in Table 12A.

TABLE 12A

NOV12 Sequence Analysis

| | | |
|---|---|---|
| NOV12a,<br>CG56983-02<br>DNA Sequence | SEQ ID NO: 63 | 108 bp |
| | TGCCCCATCAAACCCGAGGCTCCTGGCGAAGACGAGTCCCTGGAGGAGCTGAGCCACT | |
| | ORF Start: at 1 | ORF Stop: end of sequence |
| | SEQ ID NO: 64 | 36 aa    MW at 4118.6kD |
| NOV12a.<br>CG56983-02<br>Protein Sequence | CPIKPEAPGEDESLEELSHYYASLCHYLNVVTRQLI | |
| NOV12b,<br>CG56983-03<br>DNA Sequence | SEQ ID NO:65 | 45 BP |
| | GCTTCCCTGTGCCACTACCTCAACGTGGTCACCAGACAGTTAATT | |
| | ORF Start: at 1 | ORF Stop: end of sequence |
| | SEQ ID NO: 66 | 15 aa    MW at 1730.0kD |
| NOV12b,<br>CG56983-03<br>Protein Sequence | ASLCHYLNVVTRQLI | |
| NOV12c,<br>CG56983-04<br>DNA Sequence | SEQ ID NO: 67 | 69 bp |
| | CTGGAGGAGCTGAGCCACTATTATGCTTCCCTGTGCCACTACCTCAACGTGGTCACCA<br>GACAGTTAATT | |
| | ORF Start: at 1 | ORF Stop: end of sequence |
| | SEQ ID NO: 68 | 23 aa    MW at 2765.1kD |
| NOV12c,<br>CG56983-04<br>Protein Sequence | LEELSHYYASLCHYLNVVTRQLI | |

Sequence comparison of the above protein sequences yields the following sequence relationships shown in Table 12B.

TABLE 12B

Comparison of NOV12a against NOV12b and NOV12c.

| Protein Sequence | NOV12a Residues/ Match Residues | Identities/ Similarities for the Matched Region |
|---|---|---|
| NOV12b | 22 . . . 36 | 15/15 (100%) |
|  | 1 . . . 15 | 15/15 (100%) |
| NOV12c | 14 . . . 36 | 23/23 (100%) |
|  | 1 . . . 23 | 23/23 (100%) |

Further analysis of the NOV12a protein yielded the following properties shown in Table 12C.

TABLE 12C

| Protein Sequence Properties NOV12a | |
|---|---|
| PSort analysis: | 0.6500 probability located in cytoplasm; 0.1000 probability located in mitochondrial matrix space; 0.1000 probability located in lysosome (lumen); 0.0000 probability located in endoplasmic reticulum (membrane) |
| SignalP analysis: | No Known Signal Sequence Predicted |

A search of the NOV12a protein against the Geneseq database, a proprietary database that contains sequences published in patents and patent publications, yielded several homologous proteins shown in Table 12D.

TABLE 12D

Geneseq Results for NOV12a

| Geneseq Identifier | Protein/Organism/Length [Patent #, Date] | NOV12a Residues/ Match Residues | Identities/ Similarities for the Matched Region | Expect Value |
|---|---|---|---|---|
| AAE09439 | Human sbghPYYa protein - *Homo sapiens*, 70 aa. [WO200160850-A1, Aug. 23, 2001] | 1 . . . 34<br>29 . . . 62 | 34/34 (100%)<br>34/34 (100%) | 1e-14 |
| AAU85987 | Modified human peptide YY - *Homo sapiens*, 36 aa. [WO200210195-A2, Feb. 07, 2002] | 2 . . . 34<br>2 . . . 34 | 27/33 (81%)<br>29/33 (87%) | 6e-09 |
| AAU06188 | Human peptide tyrosine-tyrosine (PYY) - *Homo sapiens*, 36 aa. [WO200158409-A2, Aug. 16, 2001] | 2 . . . 34<br>2 . . . 34 | 27/33 (81%)<br>29/33 (87%) | 6e-09 |
| AAB91223 | Peptide YY SEQ ID NO: 397 - *Homo sapiens*, 36 aa. [WO200069900-A2, Nov. 23, 2000] | 2 . . . 34<br>2 . . . 34 | 27/33 (81%)<br>29/33 (87%) | 6e-09 |
| AAG75364 | Human colon cancer antigen protein SEQ ID NO: 6128 - *Homo sapiens*, 176 aa. [WO200122920-A2, Apr. 05, 2001] | 2 . . . 34<br>54 . . . 86 | 27/33 (81%)<br>29/33 (87%) | 6e-09 |

In a BLAST search of public sequence datbases, the NOV12a protein was found to have homology to the proteins shown in the BLASTP data in Table 12E.

TABLE 12E

Public BLASTP Results for NOV12a

| Protein Accession Number | Protein/Organism/Length | NOV12a Residues/ Match Residues | Identities/ Similarities for the Matched Portion | Expect Value |
|---|---|---|---|---|
| S34568 | peptide YY precursor (clone L1) - human, 90 aa (fragment). | 2 ... 34<br>30 ... 62 | 27/33 (81%)<br>29/33 (87%) | 1e-08 |
| S34569 | peptide YY precursor (clone L2) - human, 90 aa (fragment). | 2 ... 34<br>30 ... 62 | 27/33 (81%)<br>29/33 (87%) | 1e-08 |
| A31358 | peptide YY - human, 36 aa. | 2 ... 34<br>2 ... 34 | 27/33 (81%)<br>29/33 (87%) | 1e-08 |
| P10082 | Peptide YY precursor (PYY) (Peptide tyrosine tyrosine) - *Homo sapiens* (Human), 97 aa. | 2 ... 34<br>30 ... 62 | 27/33 (81%)<br>29/33 (87%) | 1e-08 |
| Q91XD0 | Unknown (protein for MGC:19143) - *Mus musculus* (Mouse), 98 aa. | 2 ... 34<br>30 ... 62 | 27/33 (81%)<br>28/33 (84%) | 2e-08 |

PFam analysis predicts that the NOV12a protein contains the domains shown in the Table 12F.

TABLE 12F

Domain Analysis of NOV12a

| Pfam Domain | NOV12a Match Region | Identities/ Similarities for the Matched Region | Expect Value |
|---|---|---|---|
| hormone3 | 1 ... 34 | 17/37 (46%)<br>25/37 (68%) | 3.1e-11 |

Example 13

The NOV13 clone was analyzed, and the nucleotide and encoded polypeptide sequences are shown in Table 13A.

TABLE 13A

NOV13 Sequence Analysis

| | | |
|---|---|---|
| NOV13a,<br>CG57666-02<br>DNA Sequence | SEQ ID NO: 69 | 72 BP |
| | CGGAGCACACCGAACATCAGGCCCGCGCACAGACTGACAAGAGTGAACCTGCCCATGC<br>CGCGCCGCTACTAC | |
| | ORF Start: at 1 | ORF Stop: end of sequence |
| NOV13a,<br>CG57666-02<br>Protein Sequence | SEQ ID NO: 70<br>RSTPNIRPAHRLTRVNLPMPRRYY | 24 aa    MW at 2965.4kD |

Further analysis of the NOV13a protein yielded the following properties shown in Table 13B.

TABLE 13B

Protein Sequence Properties NOV13a

| | |
|---|---|
| PSort analysis: | 0.8500 probability located in lysosome (lumen); 0.7500 probability located in mitochondrial intermembrane space; 0.6850 probability located in nucleus; 0.3600 probability located in mitochondrial matrix space |
| SignalP analysis: | No Known Signal Sequence Predicted |

A search of the NOV13a protein against the Geneseq database, a proprietary database that contains sequences published in patents and patent publications, yielded several homologous proteins shown in Table 13C.

TABLE 13C

Geneseq Results for NOV13a

| Geneseq Identifier | Protein/Organism/Length [Patent #, Date] | NOV13a Residues/ Match Residues | Identities/ Similarities for the Matched Region | Expect Value |
|---|---|---|---|---|
| ABG07914 | Novel human diagnostic protein #7905 - *Homo sapiens*, 286 aa. [WO200175067-A2, Oct. 11, 2001] | 1 . . . 24 80 . . . 103 | 23/24 (95%) 23/24 (95%) | 7e-07 |
| ABG07914 | Novel human diagnostic protein #7905 - *Homo sapiens*, 286 aa. [WO200175067-A2, Oct. 11, 2001] | 1 . . . 24 80 . . . 103 | 23/24 (95%) 23/24 (95%) | 7e-07 |

In a BLAST search of public sequence datbases, the NOV13a protein was found to have homology to the proteins shown in the BLASTP data in Table 13D.

TABLE 13D

Public BLASTP Results for NOV13a

| Protein Accession Number | Protein/ Organism/ Length | NOV13a Residues/ Match Residues | Identities/ Similarities for the Matched Portion | Expect Value |
|---|---|---|---|---|

PFam analysis predicts that the NOV13a protein contains the domains shown in the Table 13E.

TABLE 13E

Domain Analysis of NOV13a

| Pfam Domain | NOV13a Match Region | Identities/ Similarities for the Matched Region | Expect Value |
|---|---|---|---|

Example 14

The NOV14 clone was analyzed, and the nucleotide and encoded polypeptide sequences are shown in Table 14A.

TABLE 14A

NOV14 Sequence Analysis

NOV14a, CG59651-03 DNA Sequence

SEQ ID NO: 71    934 bp

```
CATGCCCGGGCAAGAACTCAGGACGCTGAATGGCTCTCAGATGCTCCTGGTGTTGCTG
GTGCTCTCGTGGCTGCCGCATGGGGGCGCCCTGTCTCTGGCCGAGGCGAGCCGCGCAA
GTTTCCCGGGACCCTCAGAGTTGCACACCGAAGACTCCAGATTCCGAGAGTTGCGGAA
ACGCTACGAGGACCTGCTAACCAGGCTGCGGGCCAACCAGAGCTGGGAAGATTCGAAC
ACCGACCTCGTCCCGGCCCCTGCAGTCCGGATACTCACGCCAGAAGTGCGGCTGGGAT
CCGGCGGCCACCTGCACCTGCGTATCTCTCGGGCCGCCCTTCCCGAGGGGCTCCCCGA
GGCCTCCCGCCTTCACCGGGCTCTGTTCCGGCTGTCCCCGACGGCGTCAAGGTCGTGG
GACGTGACACGACCTCTGCGGCGTCAGCTCAGCCTTGCAAGACCCCAGGCGCCCGCGC
TGCACCTGCGACTGTCGCCGCCGCCGTCGCAGTCGGACCAACTGCTGGCAGAATCTTC
GTCCGCACGGCCCCAGCTGGAGTTGCACTTGCGGCCGCAAGCCGCCAGGGGGCGCCGC
AGAGCGCGTGCGCGCAACGGGGACCACTGTCCGCTCGGGCCCGGGCGTTGCTGCCGTC
TGCACACGGTCCGCGCGTCGCTGGAAGACCTGGGCTGGGCCGATTGGGTGTTGTCGCC
ACGGGAGGTGCAAGTGACCATGTGCATCGGCGCGTGCCCGAGCCAGTTCCGGGCGGCA
AACATGCACGCGCAGATCAAGACGAGCCTGCACCGCCTGAAGCCCGACACGGTGCCAG
```

TABLE 14A-continued

NOV14 Sequence Analysis

```
                    CGTCCTGCTGCGTGCCCGCCAGCTACAATCCCATGGTGCTCATTCAAAAGACCGACAC

CGGGGTGTCGCTCCAGACCTATGATGACTTGTTAGCCAAAGACTGCCACTGCATATGA

ACTAGT

ORF Start: ATG at 2      ORF Stop: TGA at 926
                    SEQ ID NO: 72            308aa    MW at 34157.7kD
NOV14a,             MPGQELRTLNGSQMLLVLLVLSWLPHGGALSLAEASRASFPGPSELHTEDSRFRELRK
CG59651-03
Protein Sequence    RYEDLLTRLRANQSWEDSNTDLVPAPAVRILTPEVRLGSGGHLHLRISRAALPEGLPE

ASRLHRALFRLSPTASRSWDVTRPLRRQLSLARPQAPALHLRLSPPPSQSDQLLAESS

SARPQLELHLRPQAARGRRRARARNGDHCPLGPGRCCRLHTVRASLEDLGWADWVLSP

REVQVTMCIGACPSQFRAANMHAQIKTSLHRLKPDTVPASCCVPASYNPMVLIQKTDT

GVSLQTYDDLLAKDCHCI

SEQ ID NO: 73            306 bp
NOV14b,             AGATCTTGCCGTCTGCACACGGTCCGCGCGTCGCTGGAAGACCTGGGCTGGGCCGATT
207775400 DNA
Sequence            GGGTGCTGTCGCCACGGGAGGTGCAAGTGACCATGTGCATCGGCGCGTGCCCCGAGCCA

GTTCCGGGCGGCAAACATGCACGCGCAGATCAAGACGAGCCTGCACCGCCTGAAGCCC

GACACGGTGCCAGCGCCCTGCTGCGTGCCCGCCAGCTACAATCCCATGGTGCTCATTC

AAAAGACCGACACCGGGGTGTCGCTCCAGACCTATGATGACTTGTTAGCCAAAGACTG

CCACTGCATACTCGAG

ORF Start: at 1          ORF Stop: end of sequence
                    SEQ ID NO: 74            102 aa   MW at 11338.0kD
NOV14b,             RSCRLHTVRASLEDLGWADWVLSPREVQVTMCIGACPSQFRAANMHAQIKTSLHRLKP
207775400
Protein Sequence    DTVPAPCCVPASYNPMVLIQKTDTGVSLQTYDDLLAKDCHCILE SEQ ID NO: 75            849 bp
NOV14c,             AGATCTCTGTCTCTGGCCGAGGCGAGCCGCGCAAGTTTCCCGGGACCCTCAGAGTTGC
207775387 DNA
Sequence            ACTCCGAAGACTCCAGATTCCGAGAGTTGCGGAAACGCTACGAGGACCTGCTAACCAG

GCTGCGGGCCAACCAGAGCTGGGAAGATTCGAACACCGACCTCGTCCCGGCCCCTGCA

GTCCGGATACTCACGCCAGAAGTGCGGCTGGGATCCGGCGGCCACCTGCACCTGCGTA

TCTCTCGGGCCGCCCTTCCCGAGGGGCTCCCCGAGGCCTCCCGCCTTCACCGGGCTCT

GTTCCGGCTGTCCCCGACGGCGTCAAGGTCGTGGGACGTGACACGACCGCTGCGGCGT

CAGCTCAGCCTTGCAAGACCCCAGGCGCCCGCGCTGCACCTGCGACTGTCGCCGCCGC

CGTCGCAGTCGGACCAACTGCTGGCAGAATCTTCGTCCGCACGGCCCCAGCTGGAGTT

GCACTTGCGGCCGCAAGCCGCCAGGGGGCGCCGCAGAGCGCGTGCGCGCAACGGGGAC

CACTGTCCGCTCGGGCCCGGCGTTGCTGCCGTCTGCACACGGTCCGCGCGTCGCTGG

AAGACCTGGGCTGGGCCGATTGGGTGCTGTCGCCACGGGAGGTGCAAGTGACCATGTG

CATCGGCGCGTGCCCGAGCCAGTTCCGGGCGGCAAACATGCACGCGCAGATCAAGACG

AGCCTGCACCGCCTGAAGCCCGACACGGTGCCAGCGCCCTGCTGCGTGCCCGCCAGCT

ACAATCCCATGGTGCTCATTCAAAAGACCGACACCGGGGTGTCGCTCCAGACCTATGA

TGACTTGTTAGCCAAAGACTGCCACTGCATACTCGAG
                    ORF Start: at 1          ORF Stop: end of sequence
                    SEQ ID NO: 76            283 aa   MW at 31525.5kD
NOV14c              RSLSLAEASRASFPGPSELHSEDSRFRELRKRYEDLLTRLRANQSWEDSNTDLVPAPA
207775387
Protein Sequence    VRILTPEVRLGSGGHLHLRISRAALPEGLPEASRLHRALFRLSPTASRSWDVTRPLRR

QLSLARPQAPALHLRLSPPPSQSDQLLAESSSARPQLELHLRPQAARGRRRARARNGD
```

TABLE 14A-continued

NOV14 Sequence Analysis

HCPLGPGRCCRLHTVRASLEDLGWADWVLSPREVQVTMCIGACPSQFRAANMHAQIKT

SLHRLKPDTVPAPCCVPASYNPMVLIQKTDTGVSLQTYDDLLAKDCHCILE

Sequence comparison of the above protein sequences yields the following sequence relationships shown in Table 14B.

TABLE 14B

Comparison of NOV14a against NOV14b and NOV14c.

| Protein Sequence | NOV14a Residues/ Match Residues | Identities/ Similarities for the Matched Region |
|---|---|---|
| NOV14b | 209 ... 308 | 98/100 (98%) |
|  | 1 ... 100 | 98/100 (98%) |
| NOV14c | 40 ... 308 | 256/269 (95%) |
|  | 13 ... 281 | 257/269 (95%) |

Further analysis of the NOV14a protein yielded the following properties shown in Table 14C.

TABLE 14C

Protein Sequence Properties NOV14a

| PSort analysis: | 0.5851 probability located in outside; 0.1000 probability located in endoplasmic reticulum (membrane); 0.1000 probability located in endoplasmic reticulum (lumen); 0.1000 probability located in microbody (peroxisome) |
| SignalP analysis: | Cleavage site between residues 30 and 31 |

A search of the NOV14a protein against the Geneseq database, a proprietary database that contains sequences published in patents and patent publications, yielded several homologous proteins shown in Table 14D.

TABLE 14D

Geneseq Results for NOV14a

| Geneseq Identifier | Protein/Organism/Length [Patent #, Date] | NOV14a Residues/ Match Residues | Identities/ Similarities for the Matched Region | Expect Value |
|---|---|---|---|---|
| ABB09174 | Human NAG-1 protein SEQ ID NO: 2 - *Homo sapiens*, 308 aa. [WO200220759-A2, Mar. 14, 2002] | 1 ... 308<br>1 ... 308 | 307/308 (99%)<br>307/308 (99%) | e-180 |
| AAE13538 | Human macrophage inhibitory cytokine 1 (MIC-1) wild-type protein - *Homo sapiens*, 308 aa. [WO200181928-A1, Nov. 1, 2001] | 1 ... 308<br>1 ... 308 | 307/308 (99%)<br>307/308 (99%) | e-180 |
| AAB26122 | Human TGF-beta superfamily protein PCIGF - *Homo sapiens*, 308 aa. [WO200056352-A2, Sep. 28, 2000] | 1 ... 308<br>1 ... 308 | 307/308 (99%)<br>307/308 (99%) | e-180 |
| AAW10662 | Human TGF-beta-like cytokine pCL13 - *Homo sapiens*, 308 aa. [WO9700958-A1, Jan. 9, 1997] | 1 ... 308<br>1 ... 308 | 307/308 (99%)<br>307/308 (99%) | e-180 |
| AAR77097 | Human TGF-beta superfamily protein - *Homo sapiens*, 308 aa. [JP07250688-A, Oct. 3, 1995] | 1 ... 308<br>1 ... 308 | 307/308 (99%)<br>307/308 (99%) | e-180 |

In a BLAST search of public sequence datbases, the NOV14a protein was found to have homology to the proteins shown in the BLASTP data in Table 14E.

TABLE 14E

Public BLASTP Results for NOV14a

| Protein Accession Number | Protein/Organism/Length | NOV14a Residues/ Match Residues | Identities/ Similarities for the Matched Portion | Expect Value |
| --- | --- | --- | --- | --- |
| Q99988 | Growth/differentiation factor 15 precursor (GDF-15) (Placental bone morphogenic protein) (Placental TGF-beta) (Macrophage inhibitory cytokine-1) (MIC-1) (Prostate differentiation factor) (NSAID-regulated protein 1) (NRG-1) - *Homo sapiens* (Human), 308 aa. | 1 . . . 308<br>1 . . . 308 | 307/308 (99%)<br>307/308 (99%) | e-180 |
| Q9BWA0 | Prostate differentiation factor (Unknown) (Protein for MGC: 4145) - *Homo sapiens* (Human), 308 aa. | 1 . . . 308<br>1 . . . 308 | 305/308 (99%)<br>307/308 (99%) | e-179 |
| JC5697 | placental transforming growth factor-beta homolog - human, 309 aa. | 1 . . . 308<br>1 . . . 309 | 305/309 (98%)<br>305/309 (98%) | e-176 |
| Q9Z0J7 | Growth/differentiation factor 15 precursor (GDF-15) - *Mus musculus* (Mouse), 303 aa. | 3 . . . 307<br>13 . . . 302 | 182/305 (59%)<br>224/305 (72%) | 7e-96 |
| Q9Z0J6 | Growth/differentiation factor 15 precursor (GDF-15) - *Rattus norvegicus* (Rat), 303 aa. | 14 . . . 307<br>22 . . . 302 | 174/294 (59%)<br>218/294 (73%) | 3e-93 |

PFam analysis predicts that the NOV14a protein contains the domains shown in the Table 14F.

TABLE 14F

Domain Analysis of NOV14a

| Pfam Domain | NOV14a Match Region | Identities/ Similarities for the Matched Region | Expect Value |
| --- | --- | --- | --- |
| TGF-beta | 208 . . . 308 | 32/112 (29%)<br>63/112 (56%) | 2.9e-15 |

Example 15

The NOV15 clone was analyzed, and the nucleotide and encoded polypeptide sequences are shown in Table 15A.

Further analysis of the NOV15a protein yielded the following properties shown in Table 15B.

TABLE 15B

Protein Sequence Properties NOV15a

| PSort analysis: | |
| --- | --- |
| SignalP analysis: | No Known Signal Sequence Predicted |

A search of the NOV15a protein against the Geneseq database, a proprietary database that contains sequences published in patents and patent publications, yielded several homologous proteins shown in Table 15C.

TABLE 15A

NOV15 Sequence Analysis

| NOV15a, CG89614-04 DNA Sequence | SEQ ID NO: 77<br>TGCTACTTCCAGAACTGCCCGAGGGGC | 27 bp |
| --- | --- | --- |
| NOV15a, CG89614-04 Protein Sequence | ORF Start: at 1<br>SEQ ID NO; 78<br>CYFQNCPRG | ORF Stop: end of sequence<br>9    MW at 1087.2kD<br>aa |

TABLE 15C

Geneseq Results for NOV15a

| Geneseq Identifier | Protein/ Organism/ Length [Patent #, Date] | NOV15a Residues/ Match Residues | Identities/ Similarities for the Matched Region | Expect Value |
|---|---|---|---|---|

In a BLAST search of public sequence datbases, the NOV15a protein was found to have homology to the proteins shown in the BLASTP data in Table 15D.

TABLE 15D

Public BLASTP Results for NOV15a

| Protein Accession Number | Protein/ Organism/ Length | NOV15a Residues/ Match Residues | Identities/ Similarities for the Matched Portion | Expect Value |
|---|---|---|---|---|

PFam analysis predicts that the NOV15a protein contains the domains shown in the Table 15E.

TABLE 15E

Domain Analysis of NOV15a

| Pfam Domain | NOV15a Match Region | Identities/ Similarities for the Matched Region | Expect Value |
|---|---|---|---|
| hormone4 | 1 ... 9 | 7/9 (78%) 9/9 (100%) | 0.34 |

Example B

Sequencing Methodology and Identification of NOVX Clones

1. GENECALLING (analysis of DNA to determine its identity) Technology: This is a proprietary method of performing differential gene expression profiling between two or more samples developed at CuraGen and described by Shimkets, et al., "Gene expression analysis by transcript profiling coupled to a gene database query" Nature Biotechnology 17:198–803 (1999). cDNA was derived from various human samples representing multiple tissue types, normal and diseased states, physiological states, and developmental states from different donors. Samples were obtained as whole tissue, primary cells or tissue cultured primary cells or cell lines. Cells and cell lines may have been treated with biological or chemical agents that regulate gene expression, for example, growth factors, chemokines or steroids. The cDNA thus derived was then digested with up to as many as 120 pairs of restriction enzymes and pairs of linker-adaptors specific for each pair of restriction enzymes were ligated to the appropriate end. The restriction digestion generates a mixture of unique cDNA gene fragments. Limited PCR amplification is performed with primers homologous to the linker adapter sequence where one primer is biotinylated and the other is fluorescently labeled. The doubly labeled material is isolated and the fluorescently labeled single strand is resolved by capillary gel electrophoresis. A computer algorithm compares the electropherograms from an experimental and control group for each of the restriction digestions. This and additional sequence-derived information is used to predict the identity of each differentially expressed gene fragment using a variety of genetic databases. The identity of the gene fragment is confirmed by additional, gene-specific competitive PCR or by isolation and sequencing of the gene fragment.

2. SEQCALLING (application service provider featuring software that generates customized sequence databases: identifies human genetic variations and enables scientists to predict an individual's genetic susceptibility or predisposition to disease or response to medication) Technology: cDNA was derived from various human samples representing multiple tissue types, normal and diseased states, physiological states, and developmental states from different donors. Samples were obtained as whole tissue, primary cells or tissue cultured primary cells or cell lines. Cells and cell lines may have been treated with biological or chemical agents that regulate gene expression, for example, growth factors, chemokines or steroids. The cDNA thus derived was then sequenced using CuraGen's proprietary seqCALLING (application service provider featuring software that generates customized sequence databases; identifies human genetic variations and enables scientists to predict an individual's genetic susceptibility or predisposition to disease or response to medication) technology. Sequence traces were evaluated manually and edited for corrections if appropriate. cDNA sequences from all samples were assembled together, sometimes including public human sequences, using bioinformatic programs to produce a consensus sequence for each assembly. Each assembly is included in CuraGen Corporation's database. Sequences were included as components for assembly when the extent of identity with another component was at least 95% over 50 bp. Each assembly represents a gene or portion thereof and includes information on variants, such as splice forms single nucleotide polymorphisms (SNPs), insertions, deletions and other sequence variations.

3. PATHCALLING (processing, accumulating and analyzing data on interactions between proteins, and providing computer databases in the field of biotechnology) Technology:

The NOVX nucleic acid sequences are derived by laboratory screening of cDNA library by the two-hybrid approach. cDNA fragments covering either the full length of the DNA sequence, or part of the sequence, or both, are sequenced. In silico prediction was based on sequences available in CuraGen Corporation's proprietary sequence databases or in the public human sequence databases, and provided either the full length DNA sequence, or some portion thereof.

The laboratory screening was performed using the methods summarized below:

cDNA libraries were derived from various human samples representing multiple tissue types, normal and diseased states, physiological states, and developmental states from different donors. Samples were obtained as whole tissue, primary cells or tissue cultured primary cells or cell lines. Cells and cell lines may have been treated with biological or chemical agents that regulate gene expression, for example, growth factors, chemokines or steroids. The cDNA thus derived was then directionally cloned into the appropriate two-hybrid vector (Gal4-activation domain (Gal4-AD) fusion). Such cDNA libraries as well as commercially available cDNA libraries from Clontech (Palo Alto, Calif.) were then transferred from *E. coli* into a CuraGen Corporation proprietary yeast strain (disclosed in U.S. Pat. Nos. 6,057, 101 and 6,083,693, incorporated herein by reference in their entireties).

Gal4-binding domain (Gal4-BD) fusions of a CuraGen Corportion proprietary library of human sequences was used to screen multiple Gal4-AD fusion cDNA libraries resulting in the selection of yeast hybrid diploids in each of which the Gal4-AD fusion contains an individual cDNA. Each sample was amplified using the polymerase chain reaction (PCR) using non-specific primers at the cDNA insert boundaries. Such PCR product was sequenced; sequence traces were evaluated manually and edited for corrections if appropriate. cDNA sequences from all samples were assembled together, sometimes including public human sequences, using bioinformatic programs to produce a consensus sequence for each assembly. Each assembly is included in CuraGen Corporation's database. Sequences were included as components for assembly when the extent of identity with another component was at least 95% over 50 bp. Each assembly represents a gene or portion thereof and includes information on variants, such as splice forms single nucleotide polymorphisms (SNPs), insertions, deletions and other sequence variations.

Physical clone: the cDNA fragment derived by the screening procedure, covering the entire open reading frame is, as a recombinant DNA, cloned into pACT2 plasmid (Clontech) used to make the cDNA library. The recombinant plasmid is inserted into the host and selected by the yeast hybrid diploid generated during the screening procedure by the mating of both CuraGen Corporation proprietary yeast strains N106' and YULH (U.S. Pat. Nos. 6,057,101 and 6,083,693).

4. RACE: Techniques based on the polymerase chain reaction such as rapid amplification of cDNA ends (RACE), were used to isolate or complete the predicted sequence of the cDNA of the invention. Usually multiple clones were sequenced from one or more human samples to derive the sequences for fragments. Various human tissue samples from different donors were used for the RACE reaction. The sequences derived from these procedures were included in the SeqCalling Assembly process described in preceding paragraphs.

5. Exon Linking: The NOVX target sequences identified in the present invention were subjected to the exon linking process to confirm the sequence. PCR primers were designed by starting at the most upstream sequence available, for the forward primer, and at the most downstream sequence available for the reverse primer. In each case, the sequence was examined, walking inward from the respective termini toward the coding sequence, until a suitable sequence that is either unique or highly selective was encountered, or, in the case of the reverse primer, until the stop codon was reached. Such primers were designed based on in silico predictions for the full length cDNA, part (one or more exons) of the DNA or protein sequence of the target sequence, or by translated homology of the predicted exons to closely related human sequences from other species. These primers were then employed in PCR amplification based on the following pool of human cDNAs: adrenal gland, bone marrow, brain—amygdala, brain—cerebellum, brain—hippocampus, brain—substantia nigra, brain—thalamus, brain—whole, fetal brain, fetal kidney, fetal liver, fetal lung, heart, kidney, lymphoma—Raji, mammary gland, pancreas, pituitary gland, placenta, prostate, salivary gland, skeletal muscle, small intestine, spinal cord, spleen, stomach, testis, thyroid, trachea, uterus. Usually the resulting amplicons were gel purified, cloned and sequenced to high redundancy. The PCR product derived from exon linking was cloned into the pCR2.1 vector from Invitrogen. The resulting bacterial clone has an insert covering the entire open reading frame cloned into the pCR2.1 vector. The resulting sequences from all clones were assembled with themselves, with other fragments in CuraGen Corporation's database and with public ESTs. Fragments and ESTs were included as components for an assembly when the extent of their identity with another component of the assembly was at least 95% over 50 bp. In addition, sequence traces were evaluated manually and edited for corrections if appropriate. These procedures provide the sequence reported herein.

6. Physical Clone: Exons were predicted by homology and the intron/exon boundaries were determined using standard genetic rules. Exons were further selected and refined by means of similarity determination using multiple BLAST (for example, tBlastN, BlastX, and BlastN) searches, and, in some instances, GeneScan and Grail. Expressed sequences from both public and proprietary databases were also added when available to further define and complete the gene sequence. The DNA sequence was then manually corrected for apparent inconsistencies thereby obtaining the sequences encoding the full-length protein.

The PCR product derived by exon linking, covering the entire open reading frame, was cloned into the pCR2.1 vector from Invitrogen to provide clones used for expression and screening purposes.

Example C

Quantitative Expression Analysis of Clones in Various Cells and Tissues

The quantitative expression of various clones was assessed using microtiter plates containing RNA samples from a variety of normal and pathology-derived cells, cell lines and tissues using real time quantitative PCR (RTQ PCR). RTQ PCR was performed on an Applied Biosystems ABI PRISM® 7700 or an ABI PRISM® 7900 HT Sequence Detection System. Various collections of samples are assembled on the plates, and referred to as Panel 1 (containing normal tissues and cancer cell lines), Panel 2 (containing samples derived from tissues from normal and cancer sources), Panel 3 (containing cancer cell lines), Panel 4 (containing cells and cell lines from normal tissues and cells related to inflammatory conditions), Panel 5D/5I (containing human tissues and cell lines with an emphasis on metabolic diseases), AI_comprehensive_panel (containing normal tissue and samples from autoimmune diseases), Panel CNSD.01 (containing central nervous system samples from normal and diseased brains) and CNS_neurodegeneration_panel (containing samples from normal and Alzheimer's diseased brains).

RNA integrity from all samples is controlled for quality by visual assessment of agarose gel electropherograms using 28S and 18S ribosomal RNA staining intensity ratio as a guide (2:1 to 2.5:1 28s:18s) and the absence of low molecular weight RNAs that would be indicative of degradation products. Samples are controlled against genomic DNA contamination by RTQ PCR reactions run in the absence of reverse transcriptase using probe and primer sets designed to amplify across the span of a single exon.

First, the RNA samples were normalized to reference nucleic acids such as constitutively expressed genes (for example, β-actin and GAPDH). Normalized RNA (5 ul) was converted to cDNA and analyzed by RTQ-PCR using One Step RT-PCR Master Mix Reagents (Applied Biosystems; Catalog No. 4309169) and gene-specific primers according to the manufacturer's instructions.

In other cases, non-normalized RNA samples were converted to single strand cDNA (sscDNA) using Superscript II (Invitrogen Corporation; Catalog No. 18064-147) and random hexamers according to the manufacturer's instructions.

Reactions containing up to 10 μg of total RNA were performed in a volume of 20 μl and incubated for 60 minutes at 42° C. This reaction can be scaled up to 50 μg of total RNA in a final volume of 100 μl. sscDNA samples are then normalized to reference nucleic acids as described previously, using 1×TaqMan® Universal Master mix (Applied Biosystems; catalog No. 4324020), following the manufacturer's instructions.

Probes and primers were designed for each assay according to Applied Biosystems Primer Express Software package (version I for Apple Computer's Macintosh Power PC) or a similar algorithm using the target sequence as input. Default settings were used for reaction conditions and the following parameters were set before selecting primers: primer concentration=250 nM, primer melting temperature (Tm) range=58°–60° C., primer optimal Tm=59° C., maximum primer difference=2° C., probe does not have 5'G, probe Tm must be 10° C. greater than primer Tm, amplicon size 75 bp to 100 bp. The probes and primers selected (see below) were synthesized by Synthegen (Houston, Tex., USA). Probes were double purified by HPLC to remove uncoupled dye and evaluated by mass spectroscopy to verify coupling of reporter and quencher dyes to the 5' and 3' ends of the probe, respectively. Their final concentrations were: forward and reverse primers, 900 nM each, and probe, 200 nM.

PCR conditions: When working with RNA samples, normalized RNA from each tissue and each cell line was spotted in each well of either a 96 well or a 384-well PCR plate (Applied Biosystems). PCR cocktails included either a single gene specific probe and primers set, or two multiplexed probe and primers sets (a set specific for the target clone and another gene-specific set multiplexed with the target probe). PCR reactions were set up using TaqMan® One-Step RT-PCR Master Mix (Applied Biosystems, Catalog No. 4313803) following manufacturer's instructions. Reverse transcription was performed at 48° C. for 30 minutes followed by amplification/PCR cycles as follows: 95° C. 10 min, then 40 cycles of 95° C. for 15 seconds, 60° C. for 1 minute. Results were recorded as CT values (cycle at which a given sample crosses a threshold level of fluorescence) using a log scale, with the difference in RNA concentration between a given sample and the sample with the lowest CT value being represented as 2 to the power of delta CT. The percent relative expression is then obtained by taking the reciprocal of this RNA difference and multiplying by 100.

When working with sscDNA samples, normalized sscDNA was used as described previously for RNA samples. PCR reactions containing one or two sets of probe and primers were set up as described previously, using 1×TaqMan® Universal Master mix (Applied Biosystems; catalog No. 4324020), following the manufacturer's instructions. PCR amplification was performed as follows: 95° C. 10 min, then 40 cycles of 95° C. for 15 seconds, 60° C. for 1 minute. Results were analyzed and processed as described previously.

Panels 1, 1.1, 1.2, and 1.3D

The plates for Panels 1, 1.1, 1.2 and 1.3D include 2 control wells (genomic DNA control and chemistry control) and 94 wells containing cDNA from various samples. The samples in these panels are broken into 2 classes: samples derived from cultured cell lines and samples derived from primary normal tissues. The cell lines are derived from cancers of the following types: lung cancer, breast cancer, melanoma, colon cancer, prostate cancer, CNS cancer, squamous cell carcinoma, ovarian cancer, liver cancer, renal cancer, gastric cancer and pancreatic cancer. Cell lines used in these panels are widely available through the American Type Culture Collection (ATCC), a repository for cultured cell lines, and were cultured using the conditions recommended by the ATCC. The normal tissues found on these panels are comprised of samples derived from all major organ systems from single adult individuals or fetuses. These samples are derived from the following organs: adult skeletal muscle, fetal skeletal muscle, adult heart, fetal heart, adult kidney, fetal kidney, adult liver, fetal liver, adult lung, fetal lung, various regions of the brain, the spleen, bone marrow, lymph node, pancreas, salivary gland, pituitary gland, adrenal gland, spinal cord, thymus, stomach, small intestine, colon, bladder, trachea, breast, ovary, uterus, placenta, prostate, testis and adipose.

In the results for Panels 1, 1.1, 1.2 and 1.3D, the following abbreviations are used:

ca.=carcinoma,

*=established from metastasis, met=metastasis, s cell var=small cell variant, non-s=non-sm=non-small, squam=squamous, pl. eff=pl effusion=pleural effusion, glio=glioma, astro=astrocytoma, and neuro=neuroblastoma.

General_Screening_Panel_v1.4 and General_Screening_Panel_v1.5

The plates for Panels 1.4 and 1.5 include 2 control wells (genomic DNA control and chemistry control) and 94 wells containing cDNA from various samples. The samples in Panels 1.4 and 1.5 are broken into 2 classes: samples derived from cultured cell lines and samples derived from primary normal tissues. The cell lines are derived from cancers of the following types: lung cancer, breast cancer, melanoma, colon cancer, prostate cancer, CNS cancer, squamous cell carcinoma, ovarian cancer, liver cancer, renal cancer, gastric cancer and pancreatic cancer. Cell lines used in Panel 1.4 are widely available through the American Type Culture Collection (ATCC), a repository for cultured cell lines, and were cultured using the conditions recommended by the ATCC. The normal tissues found on Panels 1.4 and 1.5 are comprised of pools of samples derived from all major organ systems from 2 to 5 different adult individuals or fetuses. These samples are derived from the following organs: adult skeletal muscle, fetal skeletal muscle, adult heart, fetal heart, adult kidney, fetal kidney, adult liver, fetal liver, adult lung, fetal lung, various regions of the brain, the spleen, bone marrow, lymph node, pancreas, salivary gland, pituitary gland, adrenal gland, spinal cord, thymus, stomach, small intestine, colon, bladder, trachea, breast, ovary, uterus, placenta, prostate, testis and adipose. Abbreviations are as described for Panels 1, 1.1, 1.2, and 1.3D.

Panels 2D and 2.2

The plates for Panels 2D and 2.2 generally include 2 control wells and 94 test samples composed of RNA or cDNA isolated from human tissue procured by surgeons working in close cooperation with the National Cancer Institute's Cooperative Human Tissue Network (CHTN) or the National Disease Research Initiative (NDRI). The tissues are derived from human malignancies and in cases where indicated many malignant tissues have "matched margins" obtained from noncancerous tissue just adjacent to the tumor. These are termed normal adjacent tissues and are denoted "NAT" in the results below. The tumor tissue and the "matched margins" are evaluated by two independent pathologists (the surgical pathologists and again by a pathologist at NDRI or CHTN). This analysis provides a gross histopathological assessment of tumor differentiation grade. Moreover, most samples include the original surgical pathology report that provides information regarding the clinical stage of the patient. These matched margins are taken from the tissue surrounding (i.e. immediately proximal) to the zone of surgery (designated "NAT", for normal adjacent tissue, in Table RR). In addition, RNA and cDNA samples were obtained from various human tissues derived from autopsies performed on elderly people or sudden death victims (accidents, etc.). These tissues were ascertained to be free of disease and were purchased from various commercial sources such as Clontech (Palo Alto, Calif.), Research Genetics, and Invitrogen.

Panel 3D

The plates of Panel 3D are comprised of 94 cDNA samples and two control samples. Specifically, 92 of these samples are derived from cultured human cancer cell lines, 2 samples of human primary cerebellar tissue and 2 controls. The human cell lines are generally obtained from ATCC (American Type Culture Collection), NCI or the German tumor cell bank and fall into the following tissue groups: Squamous cell carcinoma of the tongue, breast cancer, prostate cancer, melanoma, epidermoid carcinoma, sarcomas, bladder carcinomas, pancreatic cancers, kidney cancers, leukemias/lymphomas, ovarian/uterine/cervical, gastric, colon, lung and CNS cancer cell lines. In addition, there are two independent samples of cerebellum. These cells are all cultured under standard recommended conditions and RNA extracted using the standard procedures. The cell lines in panel 3D and 1.3D are of the most common cell lines used in the scientific literature.

Panels 4D, 4R, and 4.1D

Panel 4 includes samples on a 96 well plate (2 control wells, 94 test samples) composed of RNA (Panel 4R) or cDNA (Panels 4D/4.1D) isolated from various human cell lines or tissues related to inflammatory conditions. Total RNA from control normal tissues such as colon and lung (Stratagene, La Jolla, Calif.) and thymus and kidney (Clontech) was employed. Total RNA from liver tissue from cirrhosis patients and kidney from lupus patients was obtained from BioChain (Biochain Institute, Inc., Hayward, Calif.). Intestinal tissue for RNA preparation from patients diagnosed as having Crohn's disease and ulcerative colitis was obtained from the National Disease Research Interchange (NDRI) (Philadelphia, Pa.).

Astrocytes, lung fibroblasts, dermal fibroblasts, coronary artery smooth muscle cells, small airway epithelium, bronchial epithelium, microvascular dermal endothelial cells, microvascular lung endothelial cells, human pulmonary aortic endothelial cells, human umbilical vein endothelial cells were all purchased from Clonetics (Walkersville, Md.) and grown in the media supplied for these cell types by Clonetics. These primary cell types were activated with various cytokines or combinations of cytokines for 6 and/or 12–14 hours, as indicated. The following cytokines were used; IL-1 beta at approximately 1–5 ng/ml, TNF alpha at approximately 5–10 ng/ml, IFN gamma at approximately 20–50 ng/ml, IL-4 at approximately 5–10 ng/ml, IL-9 at approximately 5–10 ng/ml, IL-13 at approximately 5–10 ng/ml. Endothelial cells were sometimes starved for various times by culture in the basal media from Clonetics with 0.1% serum.

Mononuclear cells were prepared from blood of employees at CuraGen Corporation, using Ficoll. LAK cells were prepared from these cells by culture in DMEM 5% FCS (Hyclone), 100 µM non essential amino acids (Gibco/Life Technologies, Rockville, Md.), 1 mM sodium pyruvate (Gibco), mercaptoethanol $5.5 \times 10^{-5}$M (Gibco), and 10 mM Hepes (Gibco) and Interleukin 2 for 4–6 days. Cells were then either activated with 10–20 ng/ml PMA and 1–2 µg/ml ionomycin, IL-12 at 5–10 ng/ml, IFN gamma at 20–50 ng/ml and IL-18 at 5–10 ng/ml for 6 hours. In some cases, mononuclear cells were cultured for 4–5 days in DMEM 5% FCS (Hyclone), 100 µM non essential amino acids (Gibco), 1 mM sodium pyruvate (Gibco), mercaptoethanol $5.5 \times 10^{-5}$M (Gibco), and 10 mM Hepes (Gibco) with PHA (phytohemagglutinin) or PWM (pokeweed mitogen) at approximately 5 µg/ml. Samples were taken at 24, 48 and 72 hours for RNA preparation. MLR (mixed lymphocyte reaction) samples were obtained by taking blood from two donors, isolating the mononuclear cells using Ficoll and mixing the isolated mononuclear cells 1:1 at a final concentration of approximately $2 \times 10^6$ cells/ml in DMEM 5% FCS (Hyclone), 100 µM non essential amino acids (Gibco), 1 mM sodium pyruvate (Gibco), mercaptoethanol ($5.5 \times 10^{-5}$M) (Gibco), and 10 mM Hepes (Gibco). The MLR was cultured and samples taken at various time points ranging from 1–7 days for RNA preparation.

Monocytes were isolated from mononuclear cells using CD14 Miltenyi Beads, +ve VS selection columns and a Vario Magnet according to the manufacturer's instructions. Monocytes were differentiated into dendritic cells by culture in DMEM 5% fetal calf serum (FCS) (Hyclone, Logan, Utah), 100 µM non essential amino acids (Gibco), 1 mM sodium pyruvate (Gibco), mercaptoethanol $5.5 \times 10^{-5}$M (Gibco), and 10 mM Hepes (Gibco), 50 ng/ml GMCSF and 5 ng/ml IL-4 for 5–7 days. Macrophages were prepared by culture of monocytes for 5–7 days in DMEM 5% FCS (Hyclone), 100 µM non essential amino acids (Gibco), 1 mM sodium pyruvate (Gibco), mercaptoethanol $5.5 \times 10^{-5}$M (Gibco), 10 mM Hepes (Gibco) and 10% AB Human Serum or MCSF at approximately 50 ng/ml. Monocytes, macrophages and dendritic cells were stimulated for 6 and 12–14 hours with lipopolysaccharide (LPS) at 100 ng/ml. Dendritic cells were also stimulated with anti-CD40 monoclonal antibody (Pharmingen) at 10 µg/ml for 6 and 12–14 hours.

CD4 lymphocytes, CD8 lymphocytes and NK cells were also isolated from mononuclear cells using CD4, CD8 and CD56 Miltenyi beads, positive VS selection columns and a Vario Magnet according to the manufacturer's instructions. CD45RA and CD45RO CD4 lymphocytes were isolated by depleting mononuclear cells of CD8, CD56, CD14 and CD19 cells using CD8, CD56, CD14 and CD19 Miltenyi beads and positive selection. CD45RO beads were then used to isolate the CD45RO CD4 lymphocytes with the remaining cells being CD45RA CD4 lymphocytes. CD45RA CD4, CD45RO CD4 and CD8 lymphocytes were placed in DMEM 5% FCS (Hyclone), 100 µM non essential amino acids (Gibco), 1 mM sodium pyruvate (Gibco), mercaptoethanol $5.5 \times 10^{-5}$M (Gibco), and 10 mM Hepes (Gibco) and plated at $10^6$ cells/ml onto Falcon 6 well tissue culture plates that had been coated overnight with 0.5 µg/ml anti-CD28 (Pharmingen) and 3 ug/ml anti-CD3 (OKT3, ATCC) in PBS. After 6 and 24 hours, the cells were harvested for RNA preparation. To prepare chronically activated CD8 lymphocytes, we activated the isolated CD8 lymphocytes for 4 days on anti-CD28 and anti-CD3 coated plates and then harvested the cells and expanded them in DMEM 5% FCS (Hyclone), 100 µM non essential amino acids (Gibco), 1 mM sodium pyruvate (Gibco), mercaptoethanol $5.5 \times 10^{-5}$M (Gibco), and 10 mM Hepes (Gibco) and IL-2. The expanded CD8 cells were then activated again with plate bound anti-CD3 and anti-CD28 for 4 days and expanded as before. RNA was isolated 6 and 24 hours after the second activation and after 4 days of the second expansion culture. The isolated NK cells were cultured in DMEM 5% FCS (Hyclone), 100 μM non essential amino acids (Gibco), 1 mM sodium pyruvate (Gibco), mercaptoethanol $5.5 \times 10^{-5}$M (Gibco), and 10 mM Hepes (Gibco) and IL-2 for 4–6 days before RNA was prepared.

To obtain B cells, tonsils were procured from NDRI. The tonsil was cut up with sterile dissecting scissors and then passed through a sieve. Tonsil cells were then spun down and resupended at $10^6$ cells/ml in DMEM 5% FCS (Hyclone), 100 μM non essential amino acids (Gibco), 1 mM sodium pyruvate (Gibco), mercaptoethanol $5.5 \times 10^{-5}$M (Gibco), and 10 mM Hepes (Gibco). To activate the cells, we used PWM at 5 μg/ml or anti-CD40 (Pharmingen) at approximately 10 μg/ml and IL-4 at 5–10 ng/ml. Cells were harvested for RNA preparation at 24,48 and 72 hours.

To prepare the primary and secondary Th1/Th2 and Tr1 cells, six-well Falcon plates were coated overnight with 10 μg/ml anti-CD28 (Pharmingen) and 2 μg/ml OKT3 (ATCC), and then washed twice with PBS. Umbilical cord blood CD4 lymphocytes (Poietic Systems, German Town, Md.) were cultured at $10^5$–$10^6$ cells/ml in DMEM 5% FCS (Hyclone), 100 μM non essential amino acids (Gibco), 1 mM sodium pyruvate (Gibco), mercaptoethanol $5.5 \times 10^{-5}$M (Gibco), 10 mM Hepes (Gibco) and IL-2 (4 ng/ml). IL-12 (5 ng/ml) and anti-IL4 (1 μg/ml) were used to direct to Th1, while IL-4 (5 ng/ml) and anti-IFN gamma (1 μg/ml) were used to direct to Th2 and IL-10 at 5 ng/ml was used to direct to Tr1. After 4–5 days, the activated Th1, Th2 and Tr1 lymphocytes were washed once in DMEM and expanded for 4–7 days in DMEM 5% FCS (Hyclone), 100 μM non essential amino acids (Gibco), 1 mM sodium pyruvate (Gibco), mercaptoethanol $5.5 \times 10^{-5}$M (Gibco), 10 mM Hepes (Gibco) and IL-2 (1 ng/ml). Following this, the activated Th1, Th2 and Tr1 lymphocytes were re-stimulated for 5 days with anti-CD28/OKT3 and cytokines as described above, but with the addition of anti-CD95L (1 μg/ml) to prevent apoptosis. After 4–5 days, the Th1, Th2 and Tr1 lymphocytes were washed and then expanded again with IL-2 for 4–7 days. Activated Th1 and Th2 lymphocytes were maintained in this way for a maximum of three cycles. RNA was prepared from primary and secondary Th1, Th2 and Tr1 after 6 and 24 hours following the second and third activations with plate bound anti-CD3 and anti-CD28 mAbs and 4 days into the second and third expansion cultures in Interleukin 2.

The following leukocyte cells lines were obtained from the ATCC: Ramos, EOL-1, KU-812. EOL cells were further differentiated by culture in 0.1 mM dbcAMP at $5 \times 10^5$ cells/ml for 8 days, changing the media every 3 days and adjusting the cell concentration to $5 \times 10^5$ cells/ml. For the culture of these cells, we used DMEM or RPMI (as recommended by the ATCC), with the addition of 5% FCS (Hyclone), 100 μM non essential amino acids (Gibco), 1 mM sodium pyruvate (Gibco), mercaptoethanol $5.5 \times 10^{-5}$M (Gibco), 10 mM Hepes (Gibco). RNA was either prepared from resting cells or cells activated with PMA at 10 ng/ml and ionomycin at 1 μg/ml for 6 and 14 hours. Keratinocyte line CCD106 and an airway epithelial tumor line NCI-H292 were also obtained from the ATCC. Both were cultured in DMEM 5% FCS (Hyclone), 100 μM non essential amino acids (Gibco), 1 mM sodium pyruvate (Gibco), mercaptoethanol $5.5 \times 10^{-5}$M (Gibco), and 10 mM Hepes (Gibco). CCD1106 cells were activated for 6 and 14 hours with approximately 5 ng/ml TNF alpha and 1 ng/ml IL-1 beta, while NCI-H292 cells were activated for 6 and 14 hours with the following cytokines: 5 ng/ml IL-4, 5 ng/ml IL-9, 5 ng/ml IL-13 and 25 ng/ml IFN gamma.

For these cell lines and blood cells, RNA was prepared by lysing approximately $10^7$ cells/ml using Trizol (Gibco BRL). Briefly, $\frac{1}{10}$ volume of bromochloropropane (Molecular Research Corporation) was added to the RNA sample, vortexed and after 10 minutes at room temperature, the tubes were spun at 14,000 rpm in a Sorvall SS34 rotor. The aqueous phase was removed and placed in a 15 ml Falcon Tube. An equal volume of isopropanol was added and left at −20° C. overnight. The precipitated RNA was spun down at 9,000 rpm for 15 min in a Sorvall SS34 rotor and washed in 70% ethanol. The pellet was redissolved in 300 μl of RNAse-free water and 35 μl buffer (Promega) 5 μl DTT, 7 μl RNAsin and 8 μl DNAse were added. The tube was incubated at 37° C. for 30 minutes to remove contaminating genomic DNA, extracted once with phenol chloroform and re-precipitated with $\frac{1}{10}$ volume of 3M sodium acetate and 2 volumes of 100% ethanol. The RNA was spun down and placed in RNAse free water. RNA was stored at −80° C.

AI_comprehensive Panel_v1.0

The plates for AI_comprehensive panel_v1.0 include two control wells and 89 test samples comprised of cDNA isolated from surgical and postmortem human tissues obtained from the Backus Hospital and Clinomics (Frederick, Md.). Total RNA was extracted from tissue samples from the Backus Hospital in the Facility at CuraGen. Total RNA from other tissues was obtained from Clinomics.

Joint tissues including synovial fluid, synovium, bone and cartilage were obtained from patients undergoing total knee or hip replacement surgery at the Backus Hospital. Tissue samples were immediately snap frozen in liquid nitrogen to ensure that isolated RNA was of optimal quality and not degraded. Additional samples of osteoarthritis and rheumatoid arthritis joint tissues were obtained from Clinomics. Normal control tissues were supplied by Clinomics and were obtained during autopsy of trauma victims.

Surgical specimens of psoriatic tissues and adjacent matched tissues were provided as total RNA by Clinomics. Two male and two female patients were selected between the ages of 25 and 47. None of the patients were taking prescription drugs at the time samples were isolated.

Surgical specimens of diseased colon from patients with ulcerative colitis and Crohns disease and adjacent matched tissues were obtained from Clinomics. Bowel tissue from three female and three male Crohn's patients between the ages of 41–69 were used. Two patients were not on prescription medication while the others were taking dexamethasone, phenobarbital, or tylenol. Ulcerative colitis tissue was from three male and four female patients. Four of the patients were taking lebvid and two were on phenobarbital.

Total RNA from post mortem lung tissue from trauma victims with no disease or with emphysema, asthma or COPD was purchased from Clinomics. Emphysema patients ranged in age from 40–70 and all were smokers, this age range was chosen to focus on patients with cigarette-linked emphysema and to avoid those patients with alpha-1antitrypsin deficiencies. Asthma patients ranged in age from 36–75, and excluded smokers to prevent those patients that could also have COPD. COPD patients ranged in age from 35–80 and included both smokers and non-smokers. Most patients were taking corticosteroids, and bronchodilators.

In the labels employed to identify tissues in the AI_comprehensive panel_v1.0 panel, the following abbreviations are used:

AI=Autoimmunity
Syn=Synovial
Normal=No apparent disease
Rep22/Rep20=individual patients
RA=Rheumatoid arthritis
Backus=From Backus Hospital
OA=Osteoarthritis
(SS) (BA) (MF)=Individual patients
Adj=Adjacent tissue
Match control=adjacent tissues
-M=Male
-F=Female
COPD=Chronic obstructive pulmonary disease
Panels 5D and 5I The plates for Panel 5D and 5I include two control wells and a variety of cDNAs isolated from human tissues and cell lines with an emphasis on metabolic diseases. Metabolic tissues were obtained from patients enrolled in the Gestational Diabetes study. Cells were obtained during different stages in the differentiation of adipocytes from human mesenchymal stem cells. Human pancreatic islets were also obtained.

In the Gestational Diabetes study subjects are young (18–40 years), otherwise healthy women with and without gestational diabetes undergoing routine (elective) Caesarean section. After delivery of the infant, when the surgical incisions were being repaired/closed, the obstetrician removed a small sample (<1 cc) of the exposed metabolic tissues during the closure of each surgical level. The biopsy material was rinsed in sterile saline, blotted and fast frozen within 5 minutes from the time of removal. The tissue was then flash frozen in liquid nitrogen and stored, individually, in sterile screw-top tubes and kept on dry ice for shipment to or to be picked up by CuraGen. The metabolic tissues of interest include uterine wall (smooth muscle), visceral adipose, skeletal muscle (rectus) and subcutaneous adipose. Patient descriptions are as follows:

Patient 2: Diabetic Hispanic, overweight, not on insulin
Patient 7–9: Nondiabetic Caucasian and obese (BMI>30)
Patient 10: Diabetic Hispanic, overweight, on insulin
Patient 11: Nondiabetic African American and overweight
Patient 12: Diabetic Hispanic on insulin Adipocyte differentiation was induced in donor progenitor cells obtained from Osirus (a division of Clonetics/Bio Whittaker) in triplicate, except for Donor 3U which had only two replicates. Scientists at Clonetics isolated, grew and differentiated human mesenchymal stem cells (HuMSCs) for CuraGen based on the published protocol found in Mark F. Pittenger, et al., Multilineage Potential of Adult Human Mesenchymal Stem Cells Science Apr. 2, 1999: 143–147. Clonetics provided Trizol lysates or frozen pellets suitable for mRNA isolation and ds cDNA production. A general description of each donor is as follows:

Donor 2 and 3 U: Mesenchymal Stem cells, Undifferentiated Adipose
Donor 2 and 3 AM: Adipose, AdiposeMidway Differentiated
Donor 2 and 3 AD: Adipose, Adipose Differentiated Human cell lines were generally obtained from ATCC (American Type Culture Collection), NCI or the German tumor cell bank and fall into the following tissue groups: kidney proximal convoluted tubule, uterine smooth muscle cells, small intestine, liver HepG2 cancer cells, heart primary stromal cells, and adrenal cortical adenoma cells. These cells are all cultured under standard recommended conditions and RNA extracted using the standard procedures. All samples were processed at CuraGen to produce single stranded cDNA.

Panel 5I contains all samples previously described with the addition of pancreatic islets from a 58 year old female patient obtained from the Diabetes Research Institute at the University of Miami School of Medicine. Islet tissue was processed to total RNA at an outside source and delivered to CuraGen for addition to panel 5I.

In the labels employed to identify tissues in the 5D and 5I panels, the following abbreviations are used:

GO Adipose=Greater Omentum Adipose
SK=Skeletal Muscle
UT=Uterus
PL=Placenta
AD=Adipose Differentiated
AM=Adipose Midway Differentiated
U=Undifferentiated Stem Cells
Panel CNSD.01

The plates for Panel CNSD.01 include two control wells and 94 test samples comprised of cDNA isolated from postmortem human brain tissue obtained from the Harvard Brain Tissue Resource Center. Brains are removed from calvaria of donors between 4 and 24 hours after death, sectioned by neuroanatomists, and frozen at −80° C. in liquid nitrogen vapor. All brains are sectioned and examined by neuropathologists to confirm diagnoses with clear associated neuropathology.

Disease diagnoses are taken from patient records. The panel contains two brains from each of the following diagnoses: Alzheimer's disease, Parkinson's disease, Huntington's disease, Progressive Supernuclear Palsy, Depression, and "Normal controls". Within each of these brains, the following regions are represented: cingulate gyrus, temporal pole, globus palladus, substantia nigra, Brodman Area 4 (primary motor strip), Brodman Area 7 (parietal cortex), Brodman Area 9 (prefrontal cortex), and Brodman area 17 (occipital cortex). Not all brain regions are represented in all cases; e.g., Huntington's disease is characterized in part by neurodegeneration in the globus palladus, thus this region is impossible to obtain from confirmed Huntington's cases. Likewise Parkinson's disease is characterized by degeneration of the substantia nigra making this region more difficult to obtain. Normal control brains were examined for neuropathology and found to be free of any pathology consistent with neurodegeneration.

In the labels employed to identify tissues in the CNS panel, the following abbreviations are used:

PSP=Progressive supranuclear palsy
Sub Nigra=Substantia nigra
Glob Palladus=Globus palladus
Temp Pole=Temporal pole
Cing Gyr=Cingulate gyrus
BA 4=Brodman Area 4
Panel CNS_Neurodegeneration_V1.0

The plates for Panel CNS_Neurodegeneration_V1.0 include two control wells and 47 test samples comprised of cDNA isolated from postmortem human brain tissue obtained from the Harvard Brain Tissue Resource Center (McLean Hospital) and the Human Brain and Spinal Fluid Resource Center (VA Greater Los Angeles Healthcare System). Brains are removed from calvaria of donors between 4 and 24 hours after death, sectioned by neuroanatomists, and frozen at −80° C. in liquid nitrogen vapor. All brains are sectioned and examined by neuropathologists to confirm diagnoses with clear associated neuropathology.

Disease diagnoses are taken from patient records. The panel contains six brains from Alzheimer's disease (AD) patients, and eight brains from "Normal controls" who showed no evidence of dementia prior to death. The eight normal control brains are divided into two categories: Controls with no dementia and no Alzheimer's like pathology (Controls) and controls with no dementia but evidence of severe Alzheimer's like pathology, (specifically senile plaque load rated as level 3 on a scale of 0–3; 0=no evidence of plaques, 3=severe AD senile plaque load). Within each of these brains, the following regions are represented: hippocampus, temporal cortex (Brodman Area 21), parietal cortex (Brodman area 7), and occipital cortex (Brodman area 17). These regions were chosen to encompass all levels of neurodegeneration in AD. The hippocampus is a region of early and severe neuronal loss in AD; the temporal cortex is known to show neurodegeneration in AD after the hippocampus; the parietal cortex shows moderate neuronal death in the late stages of the disease; the occipital cortex is spared in AD and therefore acts as a "control" region within AD patients. Not all brain regions are represented in all cases.

In the labels employed to identify tissues in the CNS_Neurodegeneration_V1.0 panel, the following abbreviations are used:

AD=Alzheimer's disease brain; patient was demented and showed AD-like pathology upon autopsy Control=Control brains; patient not demented, showing no neuropathology Control (Path)=Control brains; patient not demented but showing sever AD-like pathology SupTemporal Ctx=Superior Temporal Cortex Inf Temporal Ctx=Inferior Temporal Cortex A. CG124728-02 and CG124728-03: Complement-C1Q Expression of gene CG124728-02 and CG124728-03 was assessed using the primer-probe sets Ag918, Ag6167 and Ag6492, described in Tables AA, AB and AC. Results of the RTQ-PCR runs are shown in Tables AD, AE, AF, AG and AH. CG124728-02 and CG124728-03 represent full-length physical clones.

TABLE AA

Probe Name Ag918

| Primers | Sequences | Length | Start Position | SEQ ID No |
|---|---|---|---|---|
| Forward | 5'-gtgaacgagcagggacattac-3' | 21 | 294 | 79 |
| Probe | TET-5'-caagttcacctgccaggtgcctg-3'-TAMRA | 23 | 329 | 80 |
| Reverse | 5'-atggacggcgaagtagtagac-3' | 21 | 354 | 81 |

TABLE AB

Probe Name Ag6 167

| Primers | Sequences | Length | Start Position | SEQ ID No |
|---|---|---|---|---|
| Forward | 5'-ctcgtcctgctgctcct-3' | 17 | 27 | 82 |
| Probe | TET-5'-acaacaagatccccagcctctgc-3'-TAMRA | 23 | 76 | 83 |
| Reverse | 5'-ccggcagtcctggaag-3' | 16 | 114 | 84 |

TABLE AC

Probe Name Ag6492

| Primers | Sequences | Length | Start Position | SEQ ID No |
|---|---|---|---|---|
| Forward | 5'-ttccaggactgccgg-3' | 15 | 115 | 85 |
| Probe | TET-5'-ctcggtgcctccgcgatc-3'-TAMRA | 18 | 200 | 86 |
| Reverse | 5'-cgcttggcgctgaag-3' | 15 | 221 | 87 |

TABLE AD

CNS_neurodegeneration_v1.0

| Tissue Name | Rel. Exp. (%) Ag918, Run 206989724 | Tissue Name | Rel. Exp. (%) Ag918, Run 206989724 |
|---|---|---|---|
| AD 1 Hippo | 23.3 | Control (Path) 3 Temporal Ctx | 5.0 |
| AD 2 Hippo | 28.9 | Control (Path) 4 Temporal Ctx | 13.0 |
| AD 3 Hippo | 10.7 | AD 1 Occipital Ctx | 12.4 |
| AD 4 Hippo | 18.9 | AD 2 Occipital Ctx (Missing) | 0.0 |
| AD 5 hippo | 18.7 | AD 3 Occipital Ctx | 8.8 |
| AD 6 Hippo | 39.0 | AD 4 Occipital Ctx | 17.4 |
| Control 2 Hippo | 17.6 | AD 5 Occipital Ctx | 4.3 |
| Control 4 Hippo | 82.9 | AD 6 Occipital Ctx | 12.1 |
| Control (Path) 3 Hippo | 76.8 | Control 1 Occipital Ctx | 9.5 |
| AD 1 Temporal Ctx | 13.3 | Control 2 Occipital Ctx | 24.7 |
| AD 2 Temporal Ctx | 21.2 | Control 3 Occipital Ctx | 10.4 |
| AD 3 Temporal Ctx | 6.4 | Control 4 Occipital Ctx | 17.7 |
| AD 4 Temporal Ctx | 23.0 | Control (Path) 1 Occipital Ctx | 36.6 |
| AD 5 Inf Temporal Ctx | 24.0 | Control (Path) 2 Occipital Ctx | 9.1 |
| AD 5 SupTemporal Ctx | 100.0 | Control (Path) 3 Occipital Ctx | 4.3 |
| AD 6 Inf Temporal Ctx | 26.2 | Control (Path) 4 Occipital Ctx | 8.8 |
| AD 6 Sup Temporal Ctx | 20.7 | Control 1 Parietal Ctx | 11.4 |
| Control 1 Temporal Ctx | 11.4 | Control 2 Parietal Ctx | 23.0 |
| Control 2 Temporal Ctx | 12.2 | Control 3 Parietal Ctx | 3.5 |
| Control 3 Temporal Ctx | 8.1 | Control (Path) 1 Parietal Ctx | 17.4 |
| Control 4 Temporal Ctx | 13.2 | Control (Path) 2 Parietal Ctx | 7.2 |
| Control (Path) 1 Temporal Ctx | 11.5 | Control (Path) 3 Parietal Ctx | 6.5 |
| Control (Path) 2 Temporal Ctx | 12.5 | Control (Path) 4 Parietal Ctx | 16.8 |

TABLE AE

General_screening_panel_v1.5

| Tissue Name | Rel. Exp. (%) Ag6167, Run 254397160 | Tissue Name | Rel. Exp. (%) Ag6167, Run 254397160 |
|---|---|---|---|
| Adipose | 0.0 | Renal ca. TK-10 | 0.0 |
| Melanoma* Hs688(A).T | 5.6 | Bladder | 0.0 |
| Melanoma* Hs688(B).T | 37.4 | Gastric ca. (liver met.) NCI-N87 | 0.0 |
| Melanoma* M14 | 0.0 | Gastric ca. KATO III | 0.0 |
| Melanoma* LOXIMVI | 0.0 | Colon ca. SW-948 | 0.0 |
| Melanoma* SK-MEL-5 | 0.0 | Colon ca. SW480 | 0.0 |
| Squamous cell carcinoma SCC-4 | 0.0 | Colon ca.* (SW480 met) SW620 | 0.0 |
| Testis Pool | 0.0 | Colon ca. HT29 | 0.0 |

TABLE AE-continued

General_screening_panel_v1.5

| Tissue Name | Rel. Exp. (%) Ag6167, Run 254397160 | Tissue Name | Rel. Exp. (%) Ag6167, Run 254397160 |
|---|---|---|---|
| Prostate ca.* (bone met) PC-3 | 0.0 | Colon ca. HCT-116 | 0.0 |
| Prostate Pool | 0.0 | Colon ca. CaCo-2 | 0.0 |
| Placenta | 0.0 | Colon cancer tissue | 100.0 |
| Uterus Pool | 0.0 | Colon ca. SW1116 | 0.0 |
| Ovarian ca. OVCAR-3 | 0.0 | Colon ca. Colo-205 | 0.0 |
| Ovarian ca. SK-OV-3 | 0.0 | Colon ca. SW-48 | 0.0 |
| Ovarian ca. OVCAR-4 | 0.0 | Colon Pool | 0.0 |
| Ovarian ca. OVCAR-5 | 4.4 | Small Intestine Pool | 0.0 |
| Ovarian ca. IGROV-1 | 0.0 | Stomach Pool | 19.9 |
| Ovarian ca. OVCAR-8 | 4.6 | Bone Marrow Pool | 0.0 |
| Ovary | 9.0 | Fetal Heart | 0.0 |
| Breast ca. MCF-7 | 0.0 | Heart Pool | 0.0 |
| Breast ca. MDA-MB-231 | 0.0 | Lymph Node Pool | 0.0 |
| Breast ca. BT 549 | 0.0 | Fetal Skeletal Muscle | 0.0 |
| Breast ca. T47D | 0.0 | Skeletal Muscle Pool | 0.0 |
| Breast ca. MDA-N | 0.0 | Spleen Pool | 0.0 |
| Breast Pool | 0.0 | Thymus Pool | 0.0 |
| Trachea | 0.0 | CNS cancer (glio/astro) U87-MG | 0.0 |
| Lung | 0.0 | CNS cancer (glio/astro) U-118-MG | 0.0 |
| Fetal Lung | 0.0 | CNS cancer (neuro; met) SK-N-AS | 0.0 |
| Lung ca. NCI-N417 | 0.0 | CNS cancer (astro) SF-539 | 0.0 |
| Lung ca. LX-1 | 0.0 | CNS cancer (astro) SNB-75 | 0.0 |
| Lung ca. NCI-H146 | 0.0 | CNS cancer (glio) SNB-19 | 0.0 |
| Lung ca. SHP-77 | 0.0 | CNS cancer (glio) SF-295 | 0.0 |
| Lung ca. A549 | 0.0 | Brain (Amygdala) Pool | 0.0 |
| Lung ca. NCI-H526 | 0.0 | Brain (cerebellum) | 0.0 |
| Lung ca. NCI-H23 | 0.0 | Brain (fetal) | 0.0 |
| Lung ca. NCI-H460 | 0.0 | Brain (Hippocampus) Pool | 5.0 |
| Lung ca. HOP-62 | 0.0 | Cerebral Cortex Pool | 4.2 |
| Lung ca. NCI-H522 | 0.0 | Brain (Substantia nigra) Pool | 0.0 |
| Liver | 0.0 | Brain (Thalamus) Pool | 34.9 |
| Fetal Liver | 0.0 | Brain (whole) | 0.0 |
| Liver ca. HepG2 | 0.0 | Spinal Cord Pool | 10.1 |
| Kidney Pool | 0.0 | Adrenal Gland | 9.0 |
| Fetal Kidney | 0.0 | Pituitary gland Pool | 0.0 |
| Renal ca. 786-0 | 0.0 | Salivary Gland | 0.0 |
| Renal ca. A498 | 0.0 | Thyroid (female) | 0.0 |
| Renal ca. ACHN | 0.0 | Pancreatic ca. CAPAN2 | 0.0 |
| Renal ca. UO-31 | 6.5 | Pancreas Pool | 0.0 |

TABLE AF

General_screening_panel_v1.6

| Tissue Name | Rel. Exp. (%) Ag6492, Run 277251131 | Tissue Name | Rel. Exp. (%) Ag6492, Run 277251131 |
|---|---|---|---|
| Adipose | 14.8 | Renal ca. TK-10 | 5.3 |
| Melanoma* Hs688(A).T | 69.7 | Bladder | 29.7 |
| Melanoma* Hs688(B).T | 27.7 | Gastric ca. (liver met.) NCI-N87 | 0.0 |

TABLE AF-continued

General_screening_panel_v1.6

| Tissue Name | Rel. Exp. (%) Ag6492, Run 277251131 | Tissue Name | Rel. Exp. (%) Ag6492, Run 277251131 |
|---|---|---|---|
| Melanoma* M14 | 0.0 | Gastric ca. KATO III | 0.0 |
| Melanoma* LOXIMVI | 0.0 | Colon ca. SW-948 | 0.0 |
| Melanoma* SK-MEL-5 | 0.0 | Colon ca. SW480 | 0.0 |
| Squamous cell carcinoma SCC-4 | 0.0 | Colon ca.* (SW480 met) SW620 | 0.0 |
| Testis Pool | 1.3 | Colon ca. HT29 | 0.0 |
| Prostate ca.* (bone met) PC-3 | 0.0 | Colon ca. HCT-116 | 0.0 |
| Prostate Pool | 1.7 | Colon ca. CaCo-2 | 0.0 |
| Placenta | 7.2 | Colon cancer tissue | 100.0 |
| Uterus Pool | 9.3 | Colon ca. SW1116 | 0.0 |
| Ovarian ca. OVCAR-3 | 0.0 | Colon ca. Colo-205 | 0.0 |
| Ovarian ca. SK-OV-3 | 0.0 | Colon ca. SW-48 | 0.0 |
| Ovarian ca. OVCAR-4 | 0.0 | Colon Pool | 25.2 |
| Ovarian ca. OVCAR-5 | 3.9 | Small Intestine Pool | 10.0 |
| Ovarian ca. IGROV-1 | 0.0 | Stomach Pool | 18.3 |
| Ovarian ca. OVCAR-8 | 20.3 | Bone Marrow Pool | 6.7 |
| Ovary | 12.1 | Fetal Heart | 19.9 |
| Breast ca. MCF-7 | 0.0 | Heart Pool | 12.2 |
| Breast ca. MDA-MB-231 | 0.0 | Lymph Node Pool | 60.3 |
| Breast ca. BT 549 | 0.0 | Fetal Skeletal Muscle | 3.8 |
| Breast ca. T47D | 0.0 | Skeletal Muscle Pool | 0.0 |
| Breast ca. MDA-N | 0.0 | Spleen Pool | 24.0 |
| Breast Pool | 23.5 | Thymus Pool | 17.1 |
| Trachea | 2.8 | CNS cancer (glio/astro) U87-MG | 0.0 |
| Lung | 2.0 | CNS cancer (glio/astro) U-118-MG | 0.0 |
| Fetal Lung | 41.2 | CNS cancer (neuro; met) SK-N-AS | 0.0 |
| Lung ca. NCI-N417 | 0.0 | CNS cancer (astro) SF-539 | 0.0 |
| Lung ca. LX-1 | 0.0 | CNS cancer (astro) SNB-75 | 2.7 |
| Lung ca. NCI-H146 | 0.0 | CNS cancer (glio) SNB-19 | 0.0 |
| Lung ca. SHP-77 | 0.0 | CNS cancer (glio) SF-295 | 0.0 |
| Lung ca. A549 | 0.0 | Brain (Amygdala) Pool | 9.7 |
| Lung ca. NCI-H526 | 0.0 | Brain (cerebellum) | 3.8 |
| Lung ca. NCI-H23 | 0.0 | Brain (fetal) | 0.0 |
| Lung ca. NCI-H460 | 0.0 | Brain (Hippocampus) Pool | 16.6 |
| Lung ca. HOP-62 | 0.9 | Cerebral Cortex Pool | 1.2 |
| Lung ca. NCI-H522 | 0.0 | Brain (Substantia nigra) Pool | 39.2 |
| Liver | 1.6 | Brain (Thalamus) Pool | 1.7 |
| Fetal Liver | 2.4 | Brain (whole) | 6.9 |
| Liver ca. HepG2 | 0.0 | Spinal Cord Pool | 28.7 |
| Kidney Pool | 47.0 | Adrenal Gland | 4.7 |
| Fetal Kidney | 11.8 | Pituitary gland Pool | 4.6 |
| Renal ca. 786-0 | 0.0 | Salivary Gland | 2.9 |
| Renal ca. A498 | 0.0 | Thyroid (female) | 7.1 |
| Renal ca. ACHN | 1.6 | Pancreatic ca. CAPAN2 | 0.0 |
| Renal ca. UO-31 | 10.8 | Pancreas Pool | 0.0 |

TABLE AG

Panel 1.3D

| Tissue Name | Rel. Exp. (%) Ag918, Run 152842616 | Tissue Name | Rel. Exp. (%) Ag918, Run 152842616 |
|---|---|---|---|
| Liver adenocarcinoma | 0.0 | Kidney (fetal) | 16.4 |
| Pancreas | 12.2 | Renal ca. 786-0 | 0.0 |
| Pancreatic ca. CAPAN 2 | 0.0 | Renal ca. A498 | 1.3 |
| Adrenal gland | 9.7 | Renal ca. RXF 393 | 0.8 |
| Thyroid | 28.3 | Renal ca. ACHN | 1.4 |
| Salivary gland | 3.5 | Renal ca. UO-31 | 2.7 |
| Pituitary gland | 8.7 | Renal ca. TK-10 | 1.2 |
| Brain (fetal) | 1.2 | Liver | 4.5 |
| Brain (whole) | 19.1 | Liver (fetal) | 9.0 |
| Brain (amygdala) | 18.0 | Liver ca. (hepatoblast) HepG2 | 0.0 |
| Brain (cerebellum) | 3.1 | Lung | 72.2 |
| Brain (hippocampus) | 100.0 | Lung (fetal) | 72.7 |
| Brain (substantia nigra) | 9.9 | Lung ca. (small cell) LX-1 | 0.0 |
| Brain (thalamus) | 32.3 | Lung ca. (small cell) NCI-H69 | 0.4 |
| Cerebral Cortex | 5.1 | Lung ca. (s. cell var.) SHP-77 | 0.2 |
| Spinal cord | 16.2 | Lung ca. (large cell)NCI-H460 | 0.0 |
| glio/astro U87-MG | 0.0 | Lung ca. (non-sm. cell) A549 | 0.0 |
| glio/astro U-118-MG | 0.3 | Lung ca. (non-s. cell) NCI-H23 | 0.8 |
| astrocytoma SW1783 | 0.3 | Lung ca. (non-s. cell) HOP-62 | 2.6 |
| neuro*; met SK-N-AS | 0.0 | Lung ca. (non-s. cl) NCI-H522 | 0.5 |
| astrocytoma SF-539 | 0.0 | Lung ca. (squam.) SW 900 | 0.5 |
| astrocytoma SNB-75 | 3.0 | Lung ca. (squam.) NCI-H596 | 0.0 |
| glioma SNB-19 | 0.0 | Mammary gland | 33.4 |
| glioma U251 | 0.5 | Breast ca.* (pl. ef) MCF-7 | 0.0 |
| glioma SF-295 | 0.0 | Breast ca.* (pl. ef) MDA-MB-231 | 0.0 |
| Heart (fetal) | 51.1 | Breast ca.* (pl. ef) T47D | 0.0 |
| Heart | 11.1 | Breast ca. BT-549 | 0.3 |
| Skeletal muscle (fetal) | 82.9 | Breast ca. MDA-N | 0.0 |
| Skeletal muscle | 3.1 | Ovary | 21.3 |
| Bone marrow | 3.3 | Ovarian ca. OVCAR-3 | 0.0 |
| Thymus | 3.6 | Ovarian ca. OVCAR-4 | 0.0 |
| Spleen | 45.7 | Ovarian ca. OVCAR-5 | 3.8 |
| Lymph node | 22.1 | Ovarian ca. OVCAR-8 | 6.2 |
| Colorectal | 5.0 | Ovarian ca. IGROV-1 | 0.4 |
| Stomach | 33.2 | Ovarian ca.* (ascites) SK-OV-3 | 0.0 |
| Small intestine | 43.8 | Uterus | 31.2 |
| Colon ca. SW480 | 0.0 | Placenta | 8.0 |
| Colon ca.* SW620 (SW480 met) | 0.0 | Prostate | 13.8 |
| Colon ca. HT29 | 0.0 | Prostate ca.* (bone met) PC-3 | 0.5 |
| Colon ca. HCT-116 | 0.0 | Testis | 6.3 |
| Colon ca. CaCo-2 | 0.2 | Melanoma Hs688(A).T | 49.0 |
| Colon ca. tissue (ODO3866) | 52.5 | Melanoma* (met) Hs688(B).T | 25.3 |
| Colon ca. HCC-2998 | 2.6 | Melanoma UACC-62 | 0.0 |
| Gastric ca.* (liver met) NCI-N87 | 0.0 | Melanoma M14 | 0.0 |

TABLE AG-continued

Panel 1.3D

| Tissue Name | Rel. Exp. (%) Ag918, Run 152842616 | Tissue Name | Rel. Exp. (%) Ag918, Run 152842616 |
|---|---|---|---|
| Bladder | 9.9 | Melanoma LOX IMVI | 0.0 |
| Trachea | 18.0 | Melanoma* (met) SK-MEL-5 | 0.0 |
| Kidney | 7.7 | Adipose | 34.2 |

TABLE AH

Panel 4D

| Tissue Name | Rel. Exp. (%) Ag918, Run 152842729 | Tissue Name | Rel. Exp. (%) Ag918, Run 152842729 |
|---|---|---|---|
| Secondary Th1 act | 0.0 | HUVEC IL-1beta | 24.5 |
| Secondary Th2 act | 0.0 | HUVEC IFN gamma | 58.2 |
| Secondary Tr1 act | 0.0 | HUVEC TNF alpha + IFN gamma | 10.2 |
| Secondary Th1 rest | 0.0 | HUVEC TNF alpha + IL4 | 19.2 |
| Secondary Th2 rest | 0.0 | HUVEC IL-11 | 44.8 |
| Secondary Tr1 rest | 0.0 | Lung Microvascular EC none | 55.1 |
| Primary Th1 act | 0.0 | Lung Microvascular EC TNFalpha + IL-1beta | 43.5 |
| Primary Th2 act | 0.2 | Microvascular Dermal EC none | 37.1 |
| Primary Tr1 act | 0.0 | Microsvasular Dermal EC TNFalpha + IL-1beta | 26.6 |
| Primary Th1 rest | 0.0 | Bronchial epithelium TNFalpha + IL1beta | 0.0 |
| Primary Th2 rest | 0.0 | Small airway epithelium none | 0.3 |
| Primary Tr1 rest | 0.0 | Small airway epithelium TNFalpha + IL-1beta | 0.0 |
| CD45RA CD4 lymphocyte act | 2.5 | Coronery artery SMC rest | 7.7 |
| CD45RO CD4 lymphocyte act | 0.0 | Coronery artery SMC TNFalpha + IL-1beta | 7.7 |
| CD8 lymphocyte act | 0.0 | Astrocytes rest | 2.8 |
| Secondary CD8 lymphocyte rest | 0.0 | Astrocytes TNFalpha + IL-1beta | 5.3 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.0 | CCD1106 (Keratinocytes) none | 0.0 |
| LAK cells rest | 0.0 | CCD1106 (Keratinocytes) TNFalpha + IL-1beta | 0.0 |
| LAK cells IL-2 | 0.0 | Liver cirrhosis | 6.7 |
| LAK cells IL-2 + IL-12 | 0.0 | Lupus kidney | 2.6 |
| LAK cells IL-2 + IFN gamma | 0.0 | NCI-H292 none | 0.0 |
| LAK cells IL-2 + IL-18 | 0.0 | NCI-H292 IL-4 | 0.2 |
| LAK cells PMA/ionomycin | 0.0 | NCI-H292 IL-9 | 0.4 |
| NK Cells IL-2 rest | 0.0 | NCI-H292 IL-13 | 0.0 |
| Two Way MLR 3 day | 0.0 | NCI-H292 IFN gamma | 0.5 |
| Two Way MLR 5 day | 0.0 | HPAEC none | 85.9 |
| Two Way MLR 7 day | 0.0 | HPAEC TNF alpha + IL-1 beta | 66.0 |
| PBMC rest | 0.0 | Lung fibroblast none | 15.0 |
| PBMC PWM | 0.0 | Lung fibroblast TNF alpha + IL-1 beta | 3.1 |
| PBMC PHA-L | 0.0 | Lung fibroblast IL-4 | 20.9 |
| Ramos (B cell) none | 0.0 | Lung fibroblast IL-9 | 21.3 |
| Ramos (B cell) ionomycin | 0.0 | Lung fibroblast IL-13 | 15.4 |
| B lymphocytes PWM | 0.9 | Lung fibroblast IFN gamma | 26.6 |

TABLE AH-continued

Panel 4D

| Tissue Name | Rel. Exp. (%) Ag918, Run 152842729 | Tissue Name | Rel. Exp. (%) Ag918, Run 152842729 |
|---|---|---|---|
| B lymphocytes CD40L and IL-4 | 0.0 | Dermal fibroblast CCD1070 rest | 8.4 |
| EOL-1 dbcAMP | 0.0 | Dermal fibroblast CCD1070 TNF alpha | 8.1 |
| EOL-1 dbcAMP PMA/ionomycin | 0.0 | Dermal fibroblast CCD1070 IL-1 beta | 5.6 |
| Dendritic cells none | 0.0 | Dermal fibroblast IFN gamma | 4.0 |
| Dendritic cells LPS | 0.0 | Dermal fibroblast IL-4 | 13.9 |
| Dendritic cells anti-CD40 | 0.0 | IBD Colitis 2 | 0.8 |
| Monocytes rest | 0.0 | IBD Crohn's | 5.7 |
| Monocytes LPS | 0.0 | Colon | 18.2 |
| Macrophages rest | 0.0 | Lung | 97.3 |
| Macrophages LPS | 0.0 | Thymus | 11.5 |
| HUVEC none | 47.6 | Kidney | 2.7 |
| HUVEC starved | 100.0 | | |

CNS_neurodegeneration_v1.0 Summary: Ag918 This panel confirms the expression of the CG124728-02 gene at low levels in the brains of an independent group of individuals. No differential expression of this gene was detected between Alzheimer's diseased postmortem brains and those of non-demented controls in this experiment. See Panel 1.3D for a discussion of this gene in treatment of central nervous system disorders.

Ag6492 Expression of this gene is low/undetectable (CTs>35) across all of the samples on this panel.

General_screening_panel_v1.5 Summary: Ag6167 Low levels of expression of the CG124728-02 gene is restricted to colon cancer tissue (CT=34.9). Therefore, expression of this gene may be used to distinguish this sample from other samples used in this panel and also as marker to detect the presence of colon cancer. In addition, therapeutic modulation of this gene may be useful in the treatment of colon cancer.

General_screening_panel_v1.6 Summary: Ag6492 Highest expression of the CG124728-02 gene is detected in colon cancer tissue (CT=32.8). In addition, low levels of expression of this gene is also detected in two melanoma cell lines. Therefore, expression of this gene may be used to distinguish these samples from other samples used in this panel and also as marker to detect the presence of colon cancer and melanoma. Furthermore, therapeutic modulation of this gene may be useful in the treatment of colon cancer and melanoma.

In addition, low levels of expression of this gene is also found in brain (substantia nigra) and spinal cord. Therefore, therapeutic modulation of this gene may be useful in the treatment of neurological disorders.

Significant expression of this gene is also seen in some of the normal tissue samples derived from spleen, lymph node, bladder, kidney and fetal lung. Therefore, therapeutic modulation of this gene may be useful in the treatment of diseases that affect these tissues.

Interestingly, expression of this gene is higher in fetal (CT=34) as compared to adult lung (CT=38). Therefore, expression of this gene may be useful in distinguishing between fetal and adult lung. In addition, the relative overexpression of this gene in fetal lung suggests that the protein product may enhance lung growth or development in the fetus and thus may also act in a regenerative capacity in the adult. Therefore, therapeutic modulation of the protein encoded by this gene could be useful in treatment of lung related diseases.

Panel 1.3D Summary: Ag918 Highest expression of the CG124728-02 gene is seen in brain (hippocampus) (CT=29.8). In addition, this gene is expressed at moderate levels in all regions of the central nervous system examined, including amygdala, hippocampus, substantia nigra, thalamus, cerebellum, cerebral cortex, and spinal cord. Therefore, therapeutic modulation of this gene product may be useful in the treatment of central nervous system disorders such as Alzheimer's disease, Parkinson's disease, epilepsy, multiple sclerosis, schizophrenia and depression.

Among tissues with metabolic or endocrine function, this gene is expressed at moderate levels in pancreas, adipose, adrenal gland, thyroid, pituitary gland, skeletal muscle, heart, liver and the gastrointestinal tract. This gene encodes a splice variant of the complement C1q tumor necrosis factor-related protein 5 precursor, a member of the C1q family. This family includes proteins such as complement subunit C1q, adiponectin, gliacolin, C1q-related protein, cerebellin, CORS26 etc., all of which are secreted. These proteins have been implicated in tissue differentiation, immune regulation, energy homeostasis, synaptic function and in diseases such as obesity, diabetes and neurodegeneration. Adiponectin, a member of C1q family and protein closely related to complement C1q tumor necrosis factor-related protein 5 precursor, is induced over 100-fold in adipocyte differentiation (Scherer et al., 1995, J Biol Chem 270(45):26746–9 PMID: 7592907) and is involved in adipocyte signaling (Hu et al., 1996, J Biol Chem 271(18):10697–703 PMID: 8631877). Recently, adiponectin has been shown to reverse insulin resistance in mouse models of lipoatrophy and obesity (Yamauchi et al., 2001, Nat Med 7(8):941–6 PMID: 11479627). Therefore this protein, and proteins related to it, are potential antigens for development protein therapeutics for use in the treatment of obesity and type II diabetes.

Low to moderate levels of expression of this gene is also seen in ovarian cancer and melanoma cell lines, as well as in samples derived from colon cancer (ODO3866). Therefore, therapeutic modulation of this gene may be used for the treatment of these cancers.

Panel 4.1D Summary: Ag6167/Ag6492 Expression of this gene is low/undetectable (CTs>35) across all of the samples on this panel.

Panel 4D Summary: Ag918 Highest expression of the CG124728-02 gene is detected in starved HUVEC cells and lung (CT=29.2). In addition, moderate levels of expression of this gene is also detected stimulated and resting HUVEC, lung microvascular EC, microscascular dermal EC, HPAEC, lung and dermal fibroblasts, coronery artery SMC, astrocytes and in normal tissues including colon, thymus and kidney. Therefore, therapeutic modulation of the activity of this gene or its protein product, through the use of small molecule drugs, protein therapeutics or antibodies, might be beneficial in the treatment of autoimmune and inflammatory diseases that involve these cell and tissue types, such as lupus erythematosus, asthma, emphysema, Crohn's disease, ulcerative colitis, rheumatoid arthritis, osteoarthritis, and psoriasis.

Low levels of expression of this gene is also seen in samples derived from liver cirrhosis and lupus erythematosus. Therefore, therapeutic modulation of this gene may be useful in the treatment of liver cirrhosis and lupus erythematosus.

Panel CNS_1.1 Summary: Ag6167 Expression of this gene is low/undetectable (CTs>35) across all of the samples on this panel.

B. CG127616-01 and CG127616-02: Erythropoietin Precursor

Expression of gene CG127616-01 and CG127616-02 was assessed using the primer-probe sets Ag4746 and Ag6361, described in Tables BA and BB. Results of the RTQ-PCR runs are shown in Tables BC, BD and BE. CG127616-01 represents full-length physical clones.

TABLE BA

Probe Name Ag4746

| Primers | Sequences | Length | Start Position | SEQ ID No |
|---|---|---|---|---|
| Forward | 5'-gaatatcacgaaggaagcca-3' | 20 | 155 | 88 |
| Probe | TET-5'-cctcagctgctccactccgaaca-3'-TAMRA | 23 | 193 | 89 |
| Reverse | 5'-cggaaagtgtcagcagtgat-3' | 20 | 216 | 90 |

TABLE BB

Probe Name Ag6361

| Primers | Sequences | Length | Start Position | SEQ ID No |
|---|---|---|---|---|
| Forward | 5'-acaatcactgctgacactttcc-3' | 22 | 213 | 91 |
| Probe | TET-5'-ttccgagtctactccaatttcctccg-3'-TAMRA | 26 | 243 | 92 |
| Reverse | 5'-cctgtgtacagcttcagctttc-3' | 22 | 271 | 93 |

TABLE BC

General_screening_panel_v1.4

| Tissue Name | Rel. Exp. (%) Ag4746, Run 214145483 | Tissue Name | Rel. Exp. (%) Ag4746, Run 214145483 |
|---|---|---|---|
| Adipose | 0.0 | Renal ca. TK-10 | 27.4 |
| Melanoma* Hs688(A).T | 0.0 | Bladder | 29.1 |
| Melanoma* Hs688(B).T | 0.0 | Gastric ca. (liver met.) NCI-N87 | 1.2 |
| Melanoma* M14 | 0.0 | Gastric ca. KATO III | 0.0 |
| Melanoma* LOXIMVI | 0.0 | Colon ca. SW-948 | 0.5 |
| Melanoma* SK-MEL-5 | 0.0 | Colon ca. SW480 | 0.2 |
| Squamous cell carcinoma SCC-4 | 0.6 | Colon ca.* (SW480 met) SW620 | 0.0 |
| Testis Pool | 0.8 | Colon ca. HT29 | 0.0 |
| Prostate ca.* (bone met) PC-3 | 0.6 | Colon ca. HCT-116 | 2.4 |
| Prostate Pool | 1.0 | Colon ca. CaCo-2 | 33.2 |
| Placenta | 1.4 | Colon cancer tissue | 0.0 |
| Uterus Pool | 2.8 | Colon ca. SW1116 | 0.0 |
| Ovarian ca. OVCAR-3 | 1.3 | Colon ca. Colo-205 | 0.0 |
| Ovarian ca. SK-OV-3 | 0.2 | Colon ca. SW-48 | 0.4 |

TABLE BC-continued

General_screening_panel_v1.4

| Tissue Name | Rel. Exp. (%) Ag4746, Run 214145483 | Tissue Name | Rel. Exp. (%) Ag4746, Run 214145483 |
|---|---|---|---|
| Ovarian ca. OVCAR-4 | 0.0 | Colon Pool | 12.3 |
| Ovarian ca. OVCAR-5 | 0.3 | Small Intestine Pool | 0.2 |
| Ovarian ca. IGROV-1 | 0.0 | Stomach Pool | 5.8 |
| Ovarian ca. OVCAR-8 | 1.5 | Bone Marrow Pool | 1.9 |
| Ovary | 0.0 | Fetal Heart | 0.0 |
| Breast ca. MCF-7 | 0.0 | Heart Pool | 0.7 |
| Breast ca. MDA-MB-231 | 3.7 | Lymph Node Pool | 14.5 |
| Breast ca. BT 549 | 3.1 | Fetal Skeletal Muscle | 0.0 |
| Breast ca. T47D | 0.4 | Skeletal Muscle Pool | 0.0 |
| Breast ca. MDA-N | 0.0 | Spleen Pool | 0.2 |
| Breast Pool | 4.9 | Thymus Pool | 1.3 |
| Trachea | 0.0 | CNS cancer (glio/astro) U87-MG | 1.6 |
| Lung | 1.0 | CNS cancer (glio/astro) U-118-MG | 0.0 |
| Fetal Lung | 0.2 | CNS cancer (neuro; met) SK-N-AS | 0.2 |
| Lung ca. NCI-N417 | 0.0 | CNS cancer (astro) SF-539 | 0.0 |
| Lung ca. LX-1 | 1.1 | CNS cancer (astro) SNB-75 | 0.2 |
| Lung ca. NCI-H146 | 1.1 | CNS cancer (glio) SNB-19 | 0.0 |
| Lung ca. SHP-77 | 0.3 | CNS cancer (glio) SF-295 | 1.4 |
| Lung ca. A549 | 0.0 | Brain (Amygdala) Pool | 0.0 |
| Lung ca. NCI-H526 | 0.0 | Brain (cerebellum) | 0.1 |
| Lung ca. NCI-H23 | 18.0 | Brain (fetal) | 1.1 |
| Lung ca. NCI-H460 | 0.2 | Brain (Hippocampus) Pool | 0.4 |
| Lung ca. HOP-62 | 0.0 | Cerebral Cortex Pool | 0.0 |
| Lung ca. NCI-H522 | 0.0 | Brain (Substantia nigra) Pool | 6.1 |
| Liver | 0.0 | Brain (Thalamus) Pool | 0.0 |
| Fetal Liver | 18.8 | Brain (whole) | 4.8 |
| Liver ca. HepG2 | 100.0 | Spinal Cord Pool | 0.0 |
| Kidney Pool | 4.9 | Adrenal Gland | 0.0 |
| Fetal Kidney | 1.0 | Pituitary gland Pool | 0.0 |
| Renal ca. 786-0 | 1.3 | Salivary Gland | 0.0 |
| Renal ca. A498 | 0.5 | Thyroid (female) | 0.0 |
| Renal ca. ACHN | 0.4 | Pancreatic ca. CAPAN2 | 0.0 |
| Renal ca. UO-31 | 0.0 | Pancreas Pool | 7.7 |

TABLE BD

General_screening_panel_v1.6

| Tissue Name | Rel. Exp. (%) Ag6361, Run 277221717 | Tissue Name | Rel. Exp. (%) Ag6361, Run 277221717 |
|---|---|---|---|
| Adipose | 0.4 | Renal ca. TK-10 | 44.8 |
| Melanoma* Hs688(A).T | 0.0 | Bladder | 38.4 |
| Melanoma* Hs688(B).T | 0.0 | Gastric ca. (liver met.) NCI-N87 | 0.1 |
| Melanoma* M14 | 0.6 | Gastric ca. KATO III | 0.4 |
| Melanoma* LOXIMVI | 0.2 | Colon ca. SW-948 | 0.0 |
| Melanoma* SK-MEL-5 | 0.5 | Colon ca. SW480 | 0.0 |
| Squamous cell carcinoma SCC-4 | 0.6 | Colon ca.* (SW480 met) SW620 | 0.0 |
| Testis Pool | 0.8 | Colon ca. HT29 | 0.0 |

TABLE BD-continued

General_screening_panel_v1.6

| Tissue Name | Rel. Exp. (%) Ag6361, Run 277221717 | Tissue Name | Rel. Exp. (%) Ag6361, Run 277221717 |
|---|---|---|---|
| Prostate ca.* (bone met) PC-3 | 1.0 | Colon ca. HCT-116 | 2.2 |
| Prostate Pool | 1.5 | Colon ca. CaCo-2 | 32.5 |
| Placenta | 2.8 | Colon cancer tissue | 0.4 |
| Uterus Pool | 1.1 | Colon ca. SW1116 | 0.0 |
| Ovarian ca. OVCAR-3 | 0.4 | Colon ca. Colo-205 | 0.0 |
| Ovarian ca. SK-OV-3 | 0.0 | Colon ca. SW-48 | 0.0 |
| Ovarian ca. OVCAR-4 | 0.0 | Colon Pool | 8.5 |
| Ovarian ca. OVCAR-5 | 0.0 | Small Intestine Pool | 2.5 |
| Ovarian ca. IGROV-1 | 0.2 | Stomach Pool | 1.0 |
| Ovarian ca. OVCAR-8 | 0.0 | Bone Marrow Pool | 3.6 |
| Ovary | 0.0 | Fetal Heart | 0.0 |
| Breast ca. MCF-7 | 0.3 | Heart Pool | 2.2 |
| Breast ca. MDA-MB-231 | 0.0 | Lymph Node Pool | 8.6 |
| Breast ca. BT 549 | 0.4 | Fetal Skeletal Muscle | 0.3 |
| Breast ca. T47D | 0.0 | Skeletal Muscle Pool | 0.0 |
| Breast ca. MDA-N | 0.0 | Spleen Pool | 0.0 |
| Breast Pool | 9.1 | Thymus Pool | 1.3 |
| Trachea | 0.4 | CNS cancer (glio/astro) U87-MG | 0.0 |
| Lung | 0.2 | CNS cancer (glio/astro) U-118-MG | 0.5 |
| Fetal Lung | 0.6 | CNS cancer (neuro; met) SK-N-AS | 0.1 |
| Lung ca. NCI-N417 | 0.2 | CNS cancer (astro) SF-539 | 0.0 |
| Lung ca. LX-1 | 1.0 | CNS cancer (astro) SNB-75 | 1.1 |
| Lung ca. NCI-H146 | 0.0 | CNS cancer (glio) SNB-19 | 0.0 |
| Lung ca. SHP-77 | 0.0 | CNS cancer (glio) SF-295 | 0.8 |
| Lung ca. A549 | 0.0 | Brain (Amygdala) Pool | 0.2 |
| Lung ca. NCI-H526 | 0.0 | Brain (cerebellum) | 1.1 |
| Lung ca. NCI-H23 | 0.0 | Brain (fetal) | 0.9 |
| Lung ca. NCI-H460 | 0.0 | Brain (Hippocampus) Pool | 0.2 |
| Lung ca. HOP-62 | 0.2 | Cerebral Cortex Pool | 0.1 |
| Lung ca. NCI-H522 | 0.5 | Brain (Substantia nigra) Pool | 0.2 |
| Liver | 0.6 | Brain (Thalamus) Pool | 0.0 |
| Fetal Liver | 24.3 | Brain (whole) | 3.1 |
| Liver ca. HepG2 | 100.0 | Spinal Cord Pool | 0.1 |
| Kidney Pool | 4.8 | Adrenal Gland | 0.0 |
| Fetal Kidney | 0.6 | Pituitary gland Pool | 0.2 |
| Renal ca. 786-0 | 0.0 | Salivary Gland | 0.5 |
| Renal ca. A498 | 0.2 | Thyroid (female) | 0.0 |
| Renal ca. ACHN | 0.6 | Pancreatic ca. CAPAN2 | 0.3 |
| Renal ca. UO-31 | 0.2 | Pancreas Pool | 9.9 |

TABLE BE

Panel 4.1D

| Tissue Name | Rel. Exp. (%) Ag4746, Run 204171268 | Rel. Exp. (%) Ag6361, Run 262456361 | Tissue Name | Rel. Exp. (%) Ag4746, Run 204171268 | Rel. Exp. (%) Ag6361, Run 262456361 |
|---|---|---|---|---|---|
| Secondary Th1 act | 0.0 | 2.1 | HUVEC IL-1beta | 0.0 | 0.0 |
| Secondary Th2 act | 0.0 | 2.5 | HUVEC IFN gamma | 0.0 | 0.0 |
| Secondary Tr1 act | 3.8 | 0.0 | HUVEC TNF alpha + IFN gamma | 0.0 | 0.0 |

TABLE BE-continued

Panel 4.1D

| Tissue Name | Rel. Exp. (%) Ag4746, Run 204171268 | Rel. Exp. (%) Ag6361, Run 262456361 | Tissue Name | Rel. Exp. (%) Ag4746, Run 204171268 | Rel. Exp. (%) Ag6361, Run 262456361 |
|---|---|---|---|---|---|
| Secondary Th1 rest | 0.0 | 0.0 | HUVEC TNF alpha + IL4 | 0.0 | 0.0 |
| Secondary Th2 rest | 0.0 | 0.0 | HUVEC IL-11 | 0.0 | 0.0 |
| Secondary Tr1 rest | 0.0 | 0.0 | Lung Microvascular EC none | 0.0 | 1.2 |
| Primary Th1 act | 0.0 | 0.0 | Lung Microvascular EC TNFalpha + IL-1beta | 0.0 | 1.4 |
| Primary Th2 act | 0.0 | 0.0 | Microvascular Dermal EC none | 0.0 | 0.0 |
| Primary Tr1 act | 0.0 | 0.0 | Microsvascular Dermal EC TNFalpha + IL-1beta | 0.0 | 0.0 |
| Primary Th1 rest | 2.1 | 0.0 | Bronchial epithelium TNFalpha + IL1beta | 0.0 | 0.0 |
| Primary Th2 rest | 0.0 | 0.0 | Small airway epithelium none | 0.0 | 0.0 |
| Primary Tr1 rest | 0.0 | 0.0 | Small airway epithelium TNFalpha + IL-1beta | 0.0 | 0.0 |
| CD45RA CD4 lymphocyte act | 0.0 | 0.0 | Coronery artery SMC rest | 0.0 | 0.0 |
| CD45RO CD4 lymphocyte act | 13.5 | 1.7 | Coronery artery SMC TNFalpha + IL-1beta | 0.0 | 0.0 |
| CD8 lymphocyte act | 0.0 | 0.0 | Astrocytes rest | 13.7 | 0.0 |
| Secondary CD8 lymphocyte rest | 1.0 | 1.3 | Astrocytes TNFalpha + IL-1beta | 3.5 | 7.8 |
| Secondary CD8 lymphocyte act | 0.0 | 0.0 | KU-812 (Basophil) rest | 0.0 | 1.8 |
| CD4 lymphocyte none | 0.0 | 0.0 | KU-812 (Basophil) PMA/ionomycin | 0.0 | 2.0 |
| 2ry Th1/Th2/Tr1_anti-CD95 CH11 | 0.0 | 0.0 | CCD1106 (Keratinocytes) none | 0.0 | 0.0 |
| LAK cells rest | 0.0 | 0.0 | CCD1106 (Keratinocytes) TNFalpha + IL-1beta | 0.0 | 3.2 |
| LAK cells IL-2 | 0.0 | 0.0 | Liver cirrhosis | 100.0 | 100.0 |
| LAK cells IL-2 + IL-12 | 0.0 | 0.0 | NCI-H292 none | 0.0 | 0.0 |
| LAK cells IL-2 + IFN gamma | 0.0 | 1.3 | NCI-H292 IL-4 | 0.0 | 0.0 |
| LAK cells IL-2 + IL-18 | 0.0 | 1.5 | NCI-H292 IL-9 | 6.9 | 0.0 |
| LAK cells PMA/ionomycin | 0.0 | 0.0 | NCI-H292 IL-13 | 0.0 | 0.0 |
| NK Cells IL-2 rest | 0.0 | 0.7 | NCI-H292 IFN gamma | 0.0 | 0.0 |
| Two Way MLR 3 day | 0.0 | 0.0 | HPAEC none | 0.0 | 0.0 |
| Two Way MLR 5 day | 0.0 | 0.0 | HPAEC TNF alpha + IL-1 beta | 0.0 | 0.0 |
| Two Way MLR 7 day | 0.0 | 0.0 | Lung fibroblast none | 0.0 | 0.0 |
| PBMC rest | 0.0 | 0.0 | Lung fibroblast TNF alpha + IL-1 beta | 0.0 | 0.0 |
| PBMC PWM | 0.0 | 0.0 | Lung fibroblast IL-4 | 0.0 | 0.0 |
| PBMC PHA-L | 0.0 | 0.0 | Lung fibroblast IL-9 | 0.0 | 0.0 |
| Ramos (B cell) none | 0.0 | 0.0 | Lung fibroblast IL-13 | 0.0 | 0.0 |
| Ramos (B cell) ionomycin | 0.0 | 1.0 | Lung fibroblast IFN gamma | 0.0 | 0.0 |
| B lymphocytes PWM | 0.0 | 0.0 | Dermal fibroblast CCD1070 rest | 0.0 | 0.0 |
| B lymphocytes CD40L and IL-4 | 3.0 | 0.0 | Dermal fibroblast CCD1070 TNF alpha | 1.0 | 0.0 |
| EOL-1 dbcAMP | 0.0 | 1.9 | Dermal fibroblast CCD1070 IL-1 beta | 0.0 | 1.8 |
| EOL-1 dbcAMP PMA/ionomycin | 0.0 | 0.0 | Dermal fibroblast IFN gamma | 0.0 | 2.7 |
| Dendritic cells none | 0.0 | 0.0 | Dermal fibroblast IL-4 | 11.1 | 4.4 |
| Dendritic cells LPS | 0.0 | 0.0 | Dermal Fibroblasts rest | 0.0 | 0.0 |
| Dendritic cells anti-CD40 | 0.0 | 0.0 | Neutrophils TNFa + LPS | 0.0 | 0.0 |
| Monocytes rest | 3.2 | 0.0 | Neutrophils rest | 0.0 | 0.0 |
| Monocytes LPS | 0.0 | 0.0 | Colon | 0.0 | 0.0 |
| Macrophages rest | 0.0 | 0.0 | Lung | 0.0 | 0.0 |
| Macrophages LPS | 0.0 | 0.0 | Thymus | 3.4 | 1.3 |
| HUVEC none | 0.0 | 0.0 | Kidney | 5.6 | 9.2 |
| HUVEC starved | 0.0 | 0.0 | | | |

CNS_neurodegeneration_v1.0 Summary: Ag4746/Ag6361 Expression of this gene is low/undetectable in all samples on this panel (CTs>35).

General_screening_panel_v1.4 Summary: Ag4746 Highest expression of this gene is seen in a liver cancer cell line (CT=30.3). Moderate levels of expression are also seen in colon, renal and lung cancer cell lines, with low but significant expression detectable in lymph node and fetal liver. The transcript for this gene encodes a putative variant of erythropoietin (Epo), which is produced in the kidney and liver of normal adults. Human erythropoietin (Epo) is an acidic glycoprotein hormone that mediates the production of red blood cells, promotes erythroid differentiation, initiates hemoglobin synthesis. In addition, Epo has been shown to be a potent growth factor for the development of red blood cells from hematopoetic stem cells. Thus, the expression in hematopoietic tissues in this panel is consistent with the characterization of this novel protein as a novel variant of Epo. Therefore, modulation of the expression or function of this gene product may will be useful in the treatment of hematopoietic disorders.

General_screening_panel_v1.6 Summary: Ag6361 Expression on this panel is consistent with expression on Panel 1.4. Highest expression is seen in a liver cancer cell line (CT=30), with moderate levels of expression seen in colon and renal cancer cell lines, with low but significant levels of expression of this gene in kidney, fetal liver, and lymph node. See Panel 1.4 for discussion of this gene in inflammation.

Panel 4.1D Summary: Ag4746/Ag6361 Two experiments with two probe and primer sets produce results that are in excellent agreement. Significant expression is limited to the cirrhotic liver (CTs=32-33), consistent with expression in hematopoietic tissues seen in Panels 1.4 and 1.6.

C. CG128348-01: Apolipoprotein E Precursor-like.

Expression of gene CG128348-01 was assessed using the primer-probe set Ag6834, described in Table CA. Results of the RTQ-PCR runs are shown in Tables CB, CC and CD.

TABLE CA

Probe Name Ag6834

| Primers | Sequences | Length | Start Position | SEQ ID No |
|---|---|---|---|---|
| Forward | 5'-cgcggacgaggtgaa-3' | 15 | 386 | 94 |
| Probe | TET-5'-cgcgcacctccgccacct-3'-TAMRA | 18 | 406 | 95 |
| Reverse | 5'-gtatctgctgggcctgct-3' | 18 | 436 | 96 |

TABLE CB

CNS_neurodegeneration_v1.0

| Tissue Name | Rel. Exp. (%) Ag6834, Run 278022745 | Tissue Name | Rel. Exp. (%) Ag6834, Run 278022745 |
|---|---|---|---|
| AD 1 Hippo | 59.0 | Control (Path) 3 Temporal Ctx | 15.0 |
| AD 2 Hippo | 100.0 | Control (Path) 4 Temporal Ctx | 20.2 |
| AD 3 Hippo | 13.0 | AD 1 Occipital Ctx | 16.2 |
| AD 4 Hippo | 25.7 | AD 2 Occipital Ctx (Missing) | 0.0 |
| AD 5 Hippo | 40.1 | AD 3 Occipital Ctx | 7.6 |
| AD 6 Hippo | 51.1 | AD 4 Occipital Ctx | 25.5 |
| Control 2 Hippo | 40.9 | AD 5 Occipital Ctx | 21.8 |
| Control 4 Hippo | 58.2 | AD 6 Occipital Ctx | 19.3 |
| Control (Path) 3 Hippo | 12.2 | Control 1 Occipital Ctx | 5.4 |
| AD 1 Temporal Ctx | 15.4 | Control 2 Occipital Ctx | 33.2 |
| AD 2 Temporal Ctx | 51.4 | Control 3 Occipital Ctx | 16.3 |
| AD 3 Temporal Ctx | 8.3 | Control 4 Occipital Ctx | 20.6 |
| AD 4 Temporal Ctx | 25.2 | Control (Path) 1 Occipital Ctx | 41.2 |
| AD 5 Inf Temporal Ctx | 35.1 | Control (Path) 2 Occipital Ctx | 8.1 |
| AD 5 Sup Temporal Ctx | 48.6 | Control (Path) 3 Occipital Ctx | 7.0 |
| AD 6 Inf Temporal Ctx | 47.6 | Control (Path) 4 Occipital Ctx | 9.7 |
| AD 6 Sup Temporal Ctx | 31.6 | Control 1 Parietal Ctx | 15.2 |
| Control 1 Temporal Ctx | 17.4 | Control 2 Parietal Ctx | 42.9 |
| Control 2 Temporal Ctx | 45.4 | Control 3 Parietal Ctx | 33.0 |
| Control 3 | 25.7 | Control (Path) 1 | 22.4 |

TABLE CB-continued

CNS_neurodegeneration_v1.0

| Tissue Name | Rel. Exp. (%) Ag6834, Run 278022745 | Tissue Name | Rel. Exp. (%) Ag6834, Run 278022745 |
|---|---|---|---|
| Temporal Ctx Control 3 | 33.9 | Parietal Ctx Control (Path) 2 | 20.3 |
| Temporal Ctx Control (Path) 1 | 29.5 | Parietal Ctx Control (Path) 3 | 10.4 |
| Temporal Ctx Control (Path) 2 | 26.6 | Parietal Ctx Control (Path) 4 | 17.6 |

TABLE CC

General_screening_panel_v1.6

| Tissue Name | Rel. Exp. (%) Ag6834, Run 278019622 | Tissue Name | Rel. Exp. (%) Ag6834, Run 278019622 |
|---|---|---|---|
| Adipose | 0.8 | Renal ca. TK-10 | 15.2 |
| Melanoma* Hs688(A).T | 0.0 | Bladder | 5.9 |
| Melanoma* Hs688(B).T | 0.0 | Gastric ca. (liver met.) NCI-N87 | 0.1 |
| Melanoma* M14 | 4.0 | Gastric ca. KATO III | 0.0 |
| Melanoma* LOXIMVI | 0.1 | Colon ca. SW-948 | 0.0 |
| Melanoma* SK-MEL-5 | 0.2 | Colon ca. SW480 | 3.4 |
| Squamous cell carcinoma SCC-4 | 0.2 | Colon ca.* (SW480 met) SW620 | 0.3 |
| Testis Pool | 1.5 | Colon ca. HT29 | 0.0 |
| Prostate ca.* (bone met) PC-3 | 0.1 | Colon ca. HCT-116 | 0.1 |
| Prostate Pool | 0.0 | Colon ca. CaCo-2 | 44.8 |
| Placenta | 1.1 | Colon cancer tissue | 39.0 |
| Uterus Pool | 0.5 | Colon ca. SW1116 | 0.1 |
| Ovarian ca. OVCAR-3 | 7.2 | Colon ca. Colo-205 | 0.0 |
| Ovarian ca. SK-OV-3 | 0.1 | Colon ca. SW-48 | 0.0 |
| Ovarian ca. OVCAR-4 | 0.5 | Colon Pool | 1.2 |
| Ovarian ca. OVCAR-5 | 100.0 | Small Intestine Pool | 0.3 |
| Ovarian ca. IGROV-1 | 0.7 | Stomach Pool | 0.9 |
| Ovarian ca. OVCAR-8 | 64.6 | Bone Marrow Pool | 0.7 |
| Ovary | 11.3 | Fetal Heart | 0.3 |
| Breast ca. MCF-7 | 0.3 | Heart Pool | 0.4 |
| Breast ca. MDA-MB-231 | 0.0 | Lymph Node Pool | 0.7 |
| Breast ca. BT 549 | 0.5 | Fetal Skeletal Muscle | 0.5 |
| Breast ca. T47D | 3.0 | Skeletal Muscle Pool | 0.1 |
| Breast ca. MDA-N | 0.0 | Spleen Pool | 5.3 |
| Breast Pool | 2.4 | Thymus Pool | 3.1 |
| Trachea | 0.7 | CNS cancer (glio/astro) U87-MG | 0.0 |
| Lung | 0.9 | CNS cancer (glio/astro) U-118-MG | 0.2 |
| Fetal Lung | 0.2 | CNS cancer (neuro; met) SK-N-AS | 1.1 |
| Lung ca. NCI-N417 | 0.2 | CNS cancer (astro) SF-539 | 0.2 |
| Lung ca. LX-1 | 0.1 | CNS cancer (astro) SNB-75 | 0.7 |
| Lung ca. NCI-H146 | 0.1 | CNS cancer (glio) SNB-19 | 0.1 |
| Lung ca. SHP-77 | 0.2 | CNS cancer (glio) SF-295 | 0.1 |
| Lung ca. A549 | 0.3 | Brain (Amygdala) Pool | 20.9 |
| Lung ca. NCI-H526 | 1.4 | Brain (cerebellum) | 11.5 |
| Lung ca. NCI-H23 | 0.7 | Brain (fetal) | 3.5 |

TABLE CC-continued

General_screening_panel_v1.6

| Tissue Name | Rel. Exp. (%) Ag6834, Run 278019622 | Tissue Name | Rel. Exp. (%) Ag6834, Run 278019622 |
|---|---|---|---|
| Lung ca. NCI-H460 | 0.0 | Brain (Hippocampus) Pool | 17.6 |
| Lung ca. HOP-62 | 3.4 | Cerebral Cortex Pool | 9.0 |
| Lung ca. NCI-H522 | 9.9 | Brain (Substantia nigra) Pool | 26.4 |
| Liver | 31.2 | Brain (Thalamus) Pool | 12.6 |
| Fetal Liver | 26.1 | Brain (whole) | 7.7 |
| Liver ca. HepG2 | 52.9 | Spinal Cord Pool | 28.1 |
| Kidney Pool | 0.9 | Adrenal Gland | 52.5 |
| Fetal Kidney | 2.9 | Pituitary gland Pool | 0.6 |
| Renal ca. 786-0 | 0.0 | Salivary Gland | 0.4 |
| Renal ca. A498 | 0.0 | Thyroid (female) | 8.1 |
| Renal ca. ACHN | 0.0 | Pancreatic ca. CAPAN2 | 0.1 |
| Renal ca. UO-31 | 0.7 | Pancreas Pool | 1.6 |

TABLE CD

Panel 4.1D

| Tissue Name | Rel. Exp. (%) Ag6834, Run 278022645 | Tissue Name | Rel. Exp. (%) Ag6834, Run 278022645 |
|---|---|---|---|
| Secondary Th1 act | 0.0 | HUVEC IL-1beta | 0.0 |
| Secondary Th2 act | 0.0 | HUVEC IFN gamma | 0.7 |
| Secondary Tr1 act | 0.0 | HUVEC TNF alpha + IFN gamma | 0.0 |
| Secondary Th1 rest | 0.0 | HUVEC TNF alpha + IL4 | 0.1 |
| Secondary Th2 rest | 0.0 | HUVEC IL-11 | 0.3 |
| Secondary Tr1 rest | 0.0 | Lung Microvascular EC none | 0.0 |
| Primary Th1 act | 0.1 | Lung Microvascular EC TNFalpha + IL-1beta | 0.0 |
| Primary Th2 act | 0.2 | Microvascular Dermal EC none | 0.0 |
| Primary Tr1 act | 0.0 | Microvasular Dermal EC TNFalpha + IL-1beta | 0.0 |
| Primary Th1 rest | 0.0 | Bronchial epithelium TNFalpha + IL1beta | 3.9 |
| Primary Th2 rest | 0.0 | Small airway epithelium none | 1.4 |
| Primary Tr1 rest | 0.0 | Small airway epithelium TNFalpha + IL-1beta | 0.1 |
| CD45RA CD4 lymphocyte act | 0.0 | Coronery artery SMC rest | 0.3 |
| CD45RO CD4 lymphocyte act | 0.1 | Coronery artery SMC TNFalpha + IL-1beta | 0.0 |
| CD8 lymphocyte act | 0.0 | Astrocytes rest | 0.0 |
| Secondary CD8 lymphocyte rest | 0.0 | Astrocytes TNFalpha + IL-1beta | 0.3 |
| Secondary CD8 lymphocyte act | 0.0 | KU-812 (Basophil) rest | 1.9 |
| CD4 lymphocyte none | 0.0 | KU-812 (Basophil) PMA/ionomycin | 5.4 |
| 2ry Th1/Th2/Tr1_anti-CD95 CH11 | 0.0 | CCD1106 (Keratinocytes) none | 3.5 |
| LAK cells rest | 30.8 | CCD1106 (Keratinocytes) TNFalpha + IL-1beta | 1.7 |
| LAK cells IL-2 | 0.7 | Liver cirrhosis | 16.8 |
| LAK cells IL-2 + IL-12 | 1.0 | NCI-H292 none | 0.6 |
| LAK cells IL-2 + IFN gamma | 1.2 | NCI-H292 IL-4 | 0.0 |
| LAK cells IL-2 + IL-18 | 0.3 | NCI-H292 IL-9 | 1.1 |
| LAK cells PMA/ionomycin | 35.1 | NCI-H292 IL-13 | 0.6 |
| NK Cells IL-2 rest | 0.0 | NCI-H292 IFN gamma | 0.0 |
| Two Way MLR 3 day | 1.4 | HPAEC none | 0.0 |
| Two Way MLR 5 day | 2.1 | HPAEC TNF alpha + IL-1 beta | 0.0 |

TABLE CD-continued

Panel 4.1D

| Tissue Name | Rel. Exp. (%) Ag6834, Run 278022645 | Tissue Name | Rel. Exp. (%) Ag6834, Run 278022645 |
|---|---|---|---|
| Two Way MLR 7 day | 1.6 | Lung fibroblast none | 1.0 |
| PBMC rest | 0.0 | Lung fibroblast TNF alpha + IL-1 beta | 0.5 |
| PBMC PWM | 0.0 | Lung fibroblast IL-4 | 0.7 |
| PBMC PHA-L | 0.3 | Lung fibroblast IL-9 | 0.6 |
| Ramos (B cell) none | 0.0 | Lung fibroblast IL-13 | 1.4 |
| Ramos (B cell) ionomycin | 0.0 | Lung fibroblast IFN gamma | 1.4 |
| B lymphocytes PWM | 0.0 | Dermal fibroblast CCD1070 rest | 1.1 |
| B lymphocytes CD40L and IL-4 | 0.4 | Dermal fibroblast CCD1070 TNF alpha | 0.6 |
| EOL-1 dbcAMP | 0.0 | Dermal fibroblast CCD1070 IL-1 beta | 0.2 |
| EOL-1 dbcAMP PMA/ionomycin | 0.0 | Dermal fibroblast IFN gamma | 0.0 |
| Dendritic cells none | 22.7 | Dermal fibroblast IL-4 | 0.8 |
| Dendritic cells LPS | 30.6 | Dermal Fibroblasts rest | 0.0 |
| Dendritic cells anti-CD40 | 31.0 | Neutrophils TNFa + LPS | 0.0 |
| Monocytes rest | 0.0 | Neutrophils rest | 0.0 |
| Monocytes LPS | 6.0 | Colon | 1.8 |
| Macrophages rest | 92.7 | Lung | 11.4 |
| Macrophages LPS | 100.0 | Thymus | 1.4 |
| HUVEC none | 0.4 | Kidney | 94.6 |
| HUVEC starved | 0.0 | | |

CNS_neurodegeneration_v1.0 Summary: Ag6834 This profile confirms the expression of this gene at moderate levels in the brain. See Panel 1.4 for discussion of this gene in the central nervous system.

General_screening_panel_v1.6 Summary: Ag6834 Highest expression of this gene is seen in an ovarian cancer cell line (CT=28.3). Moderate levels of expression are also seen in the brain, adrenal, liver, ovary, and spleen. This expression is consistent with the characterization of the protein encoded by this gene as a putative apolipoprotein E molecule. Apolipoprotein E, a plasma protein, is a protein component of very-low-density lipoprotein (VLDL) and chylomicrons that is involved in the transport of cholesterol and other hydrophobic molecules.

Certain forms of apolipoprotein E have been linked to disorders of cholesterol metabolism and coronary heart disease. Interestingly, ApoE4 is a major risk factor for Alzheimer's disease and may play a similar role in other types of dementia. Masliah suggested that apoE may play a role in maintaining the stability of the synapto-dendritic apparatus (Cedazo-Minguez A, J Cell Mol Med July-September 2001 ;5(3):254–66; Masliah E, Prog Neurobiol December 1996; 50(5–6):493–503). Thus, based on the homology of this protein to apolipoprotein E, and its localization to the brain and vascular tissues, modulation of the expression or function of this gene may be useful in the treatment of neurological and/or cardiovascular disorders.

Panel 4.1D Summary: Ag6834 Highest expression of this gene is seen in macrophages (CT=29), with moderate levels of expression also detected in dendritic cells, LAK cells, and normal kidney. Since macrophages are one of the cell types that synthesize apolipoprotein E, prominent expression in macrophages on this panel is in agreement with the identification of the protein encoded by this gene as a novel apolipoprotein E. Boisvert et al. demonstrated the contribution of macrophage-derived apoE to hepatic clearance of serum cholesterol by performing bone marrow transplantation on hypercholesterolemic apoE-deficient 'knockout' mice and showing dramatic reduction in serum cholesterol levels the extent of atherosclerosis in the bone marrow-treated mice. (J Clin Invest August 1995; 96(2):1118–24). Thus, expression in this panel is consistent with expression in Panel 1.6 and suggests that therapeutic modulation of the expression or function of this gene product may be useful in the treatment of cardiovascular disease.

D. CG128348-02: Apolipoprotein E Precursor.

Expression of gene CG128348-02 was assessed using the primer-probe set Ag6835, described in Table DA. Results of the RTQ-PCR runs are shown in Tables DB, DC and DD.

TABLE DA

Probe Name Ag6835

| Primers | Sequences | Length | Start Position | SEQ ID No |
|---|---|---|---|---|
| Forward | 5'-cctggacgaggtgaagga-3' | 18 | 503 | 97 |
| Probe | TET-5'-cagcttggcgcgcacctcc3'-TAMRA | 19 | 530 | 98 |
| Reverse | 5'-cctgcaggcgtatctgct-3' | 18 | 562 | 99 |

TABLE DB

CNS_neurodegeneration_v1.0

| Tissue Name | Rel. Exp. (%) Ag6835, Run 278022746 | Tissue Name | Rel. Exp. (%) Ag6835, Run 278022746 |
|---|---|---|---|
| AD 1 Hippo | 51.4 | Control (Path) 3 Temporal Ctx | 11.9 |
| AD 2 Hippo | 100.0 | Control (Path) 4 Temporal Ctx | 17.6 |
| AD 3 Hippo | 11.0 | AD 1 Occipital Ctx | 14.2 |
| AD 4 Hippo | 31.2 | AD 2 Occipital Ctx (Missing) | 0.0 |
| AD 5 hippo | 33.2 | AD 3 Occipital Ctx | 10.7 |
| AD 6 Hippo | 54.0 | AD 4 Occipital Ctx | 24.8 |
| Control 2 Hippo | 42.3 | AD 5 Occipital Ctx | 14.3 |
| Control 4 Hippo | 55.5 | AD 6 Occipital Ctx | 18.6 |
| Control (Path) 3 Hippo | 9.0 | Control 1 Occipital Ctx | 5.0 |
| AD 1 Temporal Ctx | 16.7 | Control 2 Occipital Ctx | 28.5 |
| AD 2 Temporal Ctx | 49.0 | Control 3 Occipital Ctx | 14.3 |
| AD 3 Temporal Ctx | 11.4 | Control 4 Occipital Ctx | 20.0 |
| AD 4 Temporal Ctx | 25.7 | Control (Path) 1 Occipital Ctx | 41.8 |
| AD 5 Inf Temporal Ctx | 27.2 | Control (Path) 2 Occipital Ctx | 6.7 |
| AD 5 SupTemporal Ctx | 38.7 | Control (Path) 3 Occipital Ctx | 5.3 |
| AD 6 Inf Temporal Ctx | 35.4 | Control (Path) 4 Occipital Ctx | 6.5 |
| AD 6 Sup Temporal Ctx | 28.5 | Control 1 Parietal Ctx | 12.6 |
| Control 1 Temporal Ctx | 19.9 | Control 2 Parietal Ctx | 39.0 |
| Control 2 Temporal Ctx | 46.3 | Control 3 Parietal Ctx | 24.5 |
| Control 3 Temporal Ctx | 21.6 | Control (Path) 1 Parietal Ctx | 27.4 |
| Control 4 Temporal Ctx | 34.9 | Control (Path) 2 Parietal Ctx | 17.9 |
| Control (Path) 1 Temporal Ctx | 24.1 | Control (Path) 3 Parietal Ctx | 8.7 |
| Control (Path) 2 Temporal Ctx | 21.3 | Control (Path) 4 Parietal Ctx | 15.6 |

TABLE DC

General_screening_panel_v1.6

| Tissue Name | Rel. Exp. (%) Ag6835, Run 278019624 | Tissue Name | Rel. Exp. (%) Ag6835, Run 278019624 |
|---|---|---|---|
| Adipose | 1.4 | Renal ca. TK-10 | 17.1 |
| Melanoma* Hs688(A).T | 0.0 | Bladder | 5.8 |
| Melanoma* Hs688(B).T | 0.1 | Gastric ca. (liver met.) NCI-N87 | 0.2 |
| Melanoma* M14 | 1.8 | Gastric ca. KATO III | 0.0 |
| Melanoma* LOXIMVI | 0.0 | Colon ca. SW-948 | 0.1 |
| Melanoma* SK-MEL-5 | 0.3 | Colon ca. SW480 | 2.9 |
| Squamous cell carcinoma SCC-4 | 0.1 | Colon ca.* (SW480 met) SW620 | 0.2 |
| Testis Pool | 1.5 | Colon ca. HT29 | 0.0 |
| Prostate ca.* (bone met) PC-3 | 0.2 | Colon ca. HCT-116 | 0.0 |
| Prostate Pool | 0.0 | Colon ca. CaCo-2 | 45.7 |
| Placenta | 1.6 | Colon cancer tissue | 49.0 |

TABLE DC-continued

General_screening_panel_v1.6

| Tissue Name | Rel. Exp. (%) Ag6835, Run 278019624 | Tissue Name | Rel. Exp. (%) Ag6835, Run 278019624 |
|---|---|---|---|
| Uterus Pool | 0.4 | Colon ca. SW1116 | 0.0 |
| Ovarian ca. OVCAR-3 | 6.8 | Colon ca. Colo-205 | 0.0 |
| Ovarian ca. SK-OV-3 | 0.1 | Colon ca. SW-48 | 0.0 |
| Ovarian ca. OVCAR-4 | 0.6 | Colon Pool | 1.3 |
| Ovarian ca. OVCAR-5 | 100.0 | Small Intestine Pool | 0.7 |
| Ovarian ca. IGROV-1 | 0.3 | Stomach Pool | 0.5 |
| Ovarian ca. OVCAR-8 | 73.2 | Bone Marrow Pool | 0.7 |
| Ovary | 14.6 | Fetal Heart | 0.2 |
| Breast ca. MCF-7 | 0.3 | Heart Pool | 0.4 |
| Breast ca. MDA-MB-231 | 0.0 | Lymph Node Pool | 0.8 |
| Breast ca. BT 549 | 0.8 | Fetal Skeletal Muscle | 0.6 |
| Breast ca. T47D | 4.1 | Skeletal Muscle Pool | 0.3 |
| Breast ca. MDA-N | 0.0 | Spleen Pool | 4.8 |
| Breast Pool | 1.8 | Thymus Pool | 3.0 |
| Trachea | 0.4 | CNS cancer (glio/astro) U87-MG | 0.1 |
| Lung | 2.0 | CNS cancer (glio/astro) U-118-MG | 0.0 |
| Fetal Lung | 0.2 | CNS cancer (neuro; met) SK-N-AS | 0.5 |
| Lung ca. NCI-N417 | 0.1 | CNS cancer (astro) SF-539 | 0.2 |
| Lung ca. LX-1 | 0.0 | CNS cancer (astro) SNB-75 | 0.5 |
| Lung ca. NCI-H146 | 0.2 | CNS cancer (glio) SNB-19 | 0.4 |
| Lung ca. SHP-77 | 0.0 | CNS cancer (glio) SF-295 | 0.0 |
| Lung ca. A549 | 1.1 | Brain (Amygdala) Pool | 20.7 |
| Lung ca. NCI-H526 | 0.6 | Brain (cerebellum) | 15.8 |
| Lung ca. NCI-H23 | 0.8 | Brain (fetal) | 4.5 |
| Lung ca. NCI-H460 | 0.0 | Brain (Hippocampus) Pool | 23.8 |
| Lung ca. HOP-62 | 3.3 | Cerebral Cortex Pool | 10.5 |
| Lung ca. NCI-H522 | 13.2 | Brain (Substantia nigra) Pool | 34.6 |
| Liver | 27.7 | Brain (Thalamus) Pool | 13.7 |
| Fetal Liver | 43.2 | Brain (whole) | 15.4 |
| Liver ca. HepG2 | 59.0 | Spinal Cord Pool | 26.2 |
| Kidney Pool | 1.1 | Adrenal Gland | 51.8 |
| Fetal Kidney | 1.1 | Pituitary gland Pool | 0.8 |
| Renal ca. 786-0 | 0.0 | Salivary Gland | 0.6 |
| Renal ca. A498 | 0.1 | Thyroid (female) | 7.7 |
| Renal ca. ACHN | 0.2 | Pancreatic ca. CAPAN2 | 0.2 |
| Renal ca. UO-31 | 0.6 | Pancreas Pool | 1.6 |

TABLE DD

Panel 4.1D

| Tissue Name | Rel. Exp. (%) Ag6835, Run 278022647 | Tissue Name | Rel. Exp. (%) Ag6835, Run 278022647 |
|---|---|---|---|
| Secondary Th1 act | 0.1 | HUVEC IL-1beta | 0.2 |
| Secondary Th2 act | 0.0 | HUVEC IFN gamma | 0.0 |
| Secondary Tr1 act | 0.0 | HUVEC TNF alpha + IFN gamma | 0.0 |
| Secondary Th1 rest | 0.0 | HUVEC TNF alpha + IL4 | 0.0 |
| Secondary Th2 rest | 0.0 | HUVEC IL-11 | 0.0 |
| Secondary Tr1 rest | 0.0 | Lung Microvascular EC none | 0.0 |

TABLE DD-continued

Panel 4.1D

| Tissue Name | Rel. Exp. (%) Ag6835, Run 278022647 | Tissue Name | Rel. Exp. (%) Ag6835, Run 278022647 |
|---|---|---|---|
| Primary Th1 act | 0.0 | Lung Microvascular EC TNFalpha + IL-1beta | 0.0 |
| Primary Th2 act | 0.0 | Microvascular Dermal EC none | 0.0 |
| Primary Tr1 act | 0.0 | Microvasular Dermal EC TNFalpha + IL-1beta | 0.0 |
| Primary Th1 rest | 0.0 | Bronchial epithelium TNFalpha + IL1beta | 1.8 |
| Primary Th2 rest | 0.0 | Small airway epithelium none | 1.5 |
| Primary Tr1 rest | 0.0 | Small airway epithelium TNFalpha + IL-1beta | 0.0 |
| CD45RA CD4 lymphocyte act | 0.0 | Coronery artery SMC rest | 0.0 |
| CD45RO CD4 lymphocyte act | 0.0 | Coronery artery SMC TNFalpha + IL-1beta | 0.0 |
| CD8 lymphocyte act | 0.0 | Astrocytes rest | 0.3 |
| Secondary CD8 lymphocyte rest | 0.0 | Astrocytes TNFalpha + IL-1beta | 0.1 |
| Secondary CD8 lymphocyte act | 0.0 | KU-812 (Basophil) rest | 1.8 |
| CD4 lymphocyte none | 0.0 | KU-812 (Basophil) PMA/ionomycin | 3.2 |
| 2ry Th1/Th2/Tr1_anti-CD95 CH11 | 0.0 | CCD1106 (Keratinocytes) none | 1.2 |
| LAK cells rest | 17.7 | CCD1106 (Keratinocytes) TNFalpha + IL-1beta | 1.3 |
| LAK cells IL-2 | 0.1 | Liver cirrhosis | 13.6 |
| LAK cells IL-2 + IL-12 | 0.0 | NCI-H292 none | 0.3 |
| LAK cells IL-2 + IFN gamma | 0.2 | NCI-H292 IL-4 | 0.4 |
| LAK cells IL-2 + IL-18 | 0.1 | NCI-H292 IL-9 | 0.5 |
| LAK cells PMA/ionomycin | 32.8 | NCI-H292 IL-13 | 0.2 |
| NK Cells IL-2 rest | 0.0 | NCI-H292 IFN gamma | 0.5 |
| Two Way MLR 3 day | 0.7 | HPAEC none | 0.0 |
| Two Way MLR 5 day | 1.2 | HPAEC TNF alpha + IL-1 beta | 0.0 |
| Two Way MLR 7 day | 0.9 | Lung fibroblast none | 0.1 |
| PBMC rest | 0.0 | Lung fibroblast TNF alpha + IL-1 beta | 0.3 |
| PBMC PWM | 0.0 | Lung fibroblast IL-4 | 0.7 |
| PBMC PHA-L | 0.0 | Lung fibroblast IL-9 | 0.9 |
| Ramos (B cell) none | 0.0 | Lung fibroblast IL-13 | 0.6 |
| Ramos (B cell) ionomycin | 0.0 | Lung fibroblast IFN gamma | 1.8 |
| B lymphocytes PWM | 0.0 | Dermal fibroblast CCD1070 rest | 0.4 |
| B lymphocytes CD40L and IL-4 | 0.3 | Dermal fibroblast CCD1070 TNF alpha | 0.3 |
| EOL-1 dbcAMP | 0.1 | Dermal fibroblast CCD1070 IL-1 beta | 0.0 |
| EOL-1 dbcAMP PMA/ionomycin | 0.0 | Dermal fibroblast IFN gamma | 0.0 |
| Dendritic cells none | 13.9 | Dermal fibroblast IL-4 | 0.1 |
| Dendritic cells LPS | 16.6 | Dermal Fibroblasts rest | 0.1 |
| Dendritic cells anti-CD40 | 19.3 | Neutrophils TNFa + LPS | 0.0 |
| Monocytes rest | 0.0 | Neutrophils rest | 0.0 |
| Monocytes LPS | 5.6 | Colon | 0.2 |
| Macrophages rest | 46.7 | Lung | 5.6 |
| Macrophages LPS | 100.0 | Thymus | 0.2 |
| HUVEC none | 0.0 | Kidney | 65.5 |
| HUVEC starved | 0.0 | | |

CNS_neurodegeneration_v1.0 Summary: Ag6835 This profile confirms the expression of this gene at moderate levels in the brain. This expression is consistent with expression seen in CG128348-01. See that gene for discussion of this gene in CNS disorders.

General_screening_panel_v1.6 Summary: Ag6835 Highest expression of this gene is seen in an ovarian cancer cell line (CT=26). Moderate levels of expression are also seen in two colon cancer cell lines, brain, adrenal, liver, ovary, and spleen. This expression is consistent with expression seen in CG128348-01. See that gene for discussion of this gene in disease.

Panel 4.1D Summary: Ag6835 Highest expression of this gene is seen in macrophages (CT=27), with prominent levels of expression also detected in dendritic cells, LAK cells, and normal kidney. This expression is consistent with expression seen in CG128348-01. See that gene for discussion of this gene in disease.

E. CG128348-03: Apolipoprotein E Precursor

Expression of gene CG128348-03 was assessed using the primer-probe set Ag6836, described in Table EA.

TABLE EA

Probe Name Ag6836

| Primers | Sequences | Length | Start Positition | SEQ ID No |
|---|---|---|---|---|
| Forward | 5'-gccgatgacctggagga-3' | 17 | 525 | 100 |
| Probe | TET-5'-cccagcagatacgcctgcaggc-3'-TAMRA | 22 | 547 | 101 |
| Reverse | 5'-aggcgggcctggaag-3' | 15 | 575 | 102 |

CNS_neurodegeneration_v1.0 Summary: Ag6836 Expression of this gene is low/undetectable in all samples on this panel (CTs>35).

General_screening_panel_v1.6 Summary: Ag6836 Expression of this gene is low/undetectable in all samples on this panel (CTs>35).

Panel 4.1D Summary: Ag6836 Expression of this gene is low/undetectable in all samples on this panel (CTs>35).

F. CG129136-01: 4-1BB Ligand.

Expression of gene CG129136-01 was assessed using the primer-probe set Ag4938, described in Table FA. Results of the RTQ-PCR runs are shown in Tables FB and FC.

TABLE FA

Probe Name Ag4938

| Primers | Sequences | Length | Start Position | SEQ ID No |
|---|---|---|---|---|
| Forward | 5'-gccaaggctggagtctactatg-3' | 22 | 437 | 103 |
| Probe | TET-5'-tcacttgcgctgcacctgca3'-TAMRA | 20 | 361 | 104 |
| Reverse | 5'-cctggcctcagtgtgaagat-3' | 20 | 201 | 105 |

TABLE FB

General_screening_panel_v1.5

| Tissue Name | Rel. Exp. (%) Ag4938, Run 228850853 | Tissue Name | Rel. Exp. (%) Ag4938, Run 228850853 |
|---|---|---|---|
| Adipose | 0.0 | Renal ca. TK-10 | 5.7 |
| Melanoma* Hs688(A).T | 2.0 | Bladder | 0.0 |
| Melanoma* Hs688(B).T | 0.0 | Gastric ca. (liver met.) NCI-N87 | 0.6 |
| Melanoma* M14 | 4.0 | Gastric ca. KATO III | 1.8 |
| Melanoma* LOXIMVI | 1.4 | Colon ca. SW-948 | 58.2 |
| Melanoma* SK-MEL-5 | 0.9 | Colon ca. SW480 | 2.3 |
| Squamous cell carcinoma SCC-4 | 0.8 | Colon ca.* (SW480 met) SW620 | 0.0 |
| Testis Pool | 0.0 | Colon ca. HT29 | 0.0 |
| Prostate ca.* (bone met) PC-3 | 0.0 | Colon ca. HCT-116 | 12.3 |
| Prostate Pool | 0.0 | Colon ca. CaCo-2 | 0.0 |
| Placenta | 0.0 | Colon cancer tissue | 8.8 |
| Uterus Pool | 0.0 | Colon ca. SW1116 | 3.8 |
| Ovarian ca. OVCAR-3 | 3.5 | Colon ca. Colo-205 | 4.5 |
| Ovarian ca. SK-OV-3 | 27.0 | Colon ca. SW-48 | 0.5 |
| Ovarian ca. OVCAR-4 | 2.9 | Colon Pool | 0.0 |
| Ovarian ca. OVCAR-5 | 12.0 | Small Intestine Pool | 0.0 |
| Ovarian ca. IGROV-1 | 73.7 | Stomach Pool | 0.0 |
| Ovarian ca. OVCAR-8 | 38.7 | Bone Marrow Pool | 0.0 |
| Ovary | 0.0 | Fetal Heart | 0.0 |
| Breast ca. MCF-7 | 0.0 | Heart Pool | 0.0 |
| Breast ca. MDA-MB-231 | 2.2 | Lymph Node Pool | 0.0 |
| Breast ca. BT 549 | 5.9 | Fetal Skeletal Muscle | 0.0 |
| Breast ca. T47D | 0.0 | Skeletal Muscle Pool | 0.0 |
| Breast ca. MDA-N | 7.9 | Spleen Pool | 0.0 |
| Breast Pool | 0.0 | Thymus Pool | 0.0 |
| Trachea | 0.7 | CNS cancer (glio/astro) U87-MG | 27.5 |
| Lung | 0.0 | CNS cancer (glio/astro) U-118-MG | 0.5 |
| Fetal Lung | 0.9 | CNS cancer (neuro; met) SK-N-AS | 0.0 |
| Lung ca. NCI-N417 | 0.0 | CNS cancer (astro) SF-539 | 0.4 |
| Lung ca. LX-1 | 0.6 | CNS cancer (astro) SNB-75 | 9.9 |
| Lung ca. NCI-H146 | 0.0 | CNS cancer (glio) SNB-19 | 100.0 |
| Lung ca. SHP-77 | 0.0 | CNS cancer (glio) SF-295 | 1.3 |
| Lung ca. A549 | 5.5 | Brain (Amygdala) Pool | 0.0 |
| Lung ca. NCI-H526 | 2.1 | Brain (cerebellum) | 0.6 |
| Lung ca. NCI-H23 | 0.4 | Brain (fetal) | 0.8 |
| Lung ca. NCI-H460 | 13.7 | Brain (Hippocampus) Pool | 0.9 |
| Lung ca. HOP-62 | 0.0 | Cerebral Cortex Pool | 0.0 |
| Lung ca. NCI-H522 | 0.0 | Brain (Substantia nigra) Pool | 4.7 |
| Liver | 0.0 | Brain (Thalamus) Pool | 0.0 |
| Fetal Liver | 0.0 | Brain (whole) | 0.0 |
| Liver ca. HepG2 | 0.0 | Spinal Cord Pool | 0.0 |
| Kidney Pool | 0.0 | Adrenal Gland | 0.0 |
| Fetal Kidney | 0.0 | Pituitary gland Pool | 0.0 |
| Renal ca. 786-0 | 17.6 | Salivary Gland | 0.0 |
| Renal ca. A498 | 3.4 | Thyroid (female) | 0.0 |
| Renal ca. ACHN | 2.4 | Pancreatic ca. CAPAN2 | 1.4 |
| Renal ca. UO-31 | 9.1 | Pancreas Pool | 0.0 |

TABLE FC

Panel 4.1D

| Tissue Name | Rel. Exp. (%) Ag4938, Run 225245203 | Tissue Name | Rel. Exp. (%) Ag4938, Run 225245203 |
|---|---|---|---|
| Secondary Th1 act | 0.0 | HUVEC IL-1beta | 0.0 |
| Secondary Th2 act | 2.0 | HUVEC IFN gamma | 0.0 |
| Secondary Tr1 act | 3.8 | HUVEC TNF alpha + IFN gamma | 0.0 |
| Secondary Th1 rest | 0.0 | HUVEC TNF alpha + IL4 | 0.0 |
| Secondary Th2 rest | 0.0 | HUVEC IL-11 | 0.0 |
| Secondary Tr1 rest | 1.8 | Lung Microvascular EC none | 0.0 |
| Primary Th1 act | 1.0 | Lung Microvascular EC TNFalpha + IL-1beta | 0.0 |
| Primary Th2 act | 1.3 | Microvascular Dermal EC none | 0.0 |
| Primary Tr1 act | 3.0 | Microsvasular Dermal EC TNFalpha + IL-1 beta | 0.0 |
| Primary Th1 rest | 0.0 | Bronchial epithelium TNFalpha + IL1beta | 4.7 |
| Primary Th2 rest | 0.0 | Small airway epithelium none | 0.0 |
| Primary Tr1 rest | 0.0 | Small airway epithelium TNFalpha + IL-1beta | 1.2 |
| CD45RA CD4 lymphocyte act | 0.0 | Coronery artery SMC rest | 0.0 |
| CD45RO CD4 lymphocyte act | 0.0 | Coronery artery SMC TNFalpha + IL-1beta | 0.0 |
| CD8 lymphocyte act | 0.0 | Astrocytes rest | 1.7 |
| Secondary CD8 lymphocyte rest | 0.7 | Astrocytes TNFalpha + IL-1beta | 4.9 |
| Secondary CD8 lymphocyte act | 0.9 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.0 | CCD1106 (Keratinocytes) none | 0.0 |
| LAK cells rest | 0.0 | CCD1106 (Keratinocytes) TNFalpha + IL-1beta | 0.0 |
| LAK cells IL-2 | 0.0 | Liver cirrhosis | 0.0 |
| LAK cells IL-2 + IL-12 | 0.0 | NCI-H292 none | 0.0 |
| LAK cells IL-2 + IFN gamma | 0.0 | NCI-H292 IL-4 | 0.0 |
| LAK cells IL-2 + IL-18 | 0.0 | NCI-H292 IL-9 | 1.4 |
| LAK cells PMA/ionomycin | 2.0 | NCI-H292 IL-13 | 0.0 |
| NK Cells IL-2 rest | 0.0 | NCI-H292 IFN gamma | 0.0 |
| Two Way MLR 3 day | 0.0 | HPAEC none | 0.0 |
| Two Way MLR 5 day | 0.0 | HPAEC TNF alpha + IL-1 beta | 0.0 |
| Two Way MLR 7 day | 0.0 | Lung fibroblast none | 0.6 |
| PBMC rest | 0.0 | Lung fibroblast TNF alpha + IL-1 beta | 0.0 |
| PBMC PWM | 0.0 | Lung fibroblast IL-4 | 0.0 |
| PBMC PHA-L | 0.0 | Lung fibroblast IL-9 | 0.0 |
| Ramos (B cell) none | 0.0 | Lung fibroblast IL-13 | 0.0 |
| Ramos (B cell) ionomycin | 0.0 | Lung fibroblast IFN gamma | 0.0 |
| B lymphocytes PWM | 0.6 | Dermal fibroblast CCD1070 rest | 0.0 |
| B lymphocytes CD40L and IL-4 | 0.0 | Dermal fibroblast CCD1070 TNF alpha | 0.0 |
| EOL-1 dbcAMP | 4.0 | Dermal fibroblast CCD1070 IL-1 beta | 0.0 |
| EOL-1 dbcAMP PMA/ionomycin | 2.9 | Dermal fibroblast IFN gamma | 0.0 |
| Dendritic cells none | 0.0 | Dermal fibroblast IL-4 | 1.1 |
| Dendritic cells LPS | 1.2 | Dermal Fibroblasts rest | 1.4 |
| Dendritic cells anti-CD40 | 0.0 | Neutrophils TNFa + LPS | 0.0 |
| Monocytes rest | 0.0 | Neutrophils rest | 0.7 |
| Monocytes LPS | 4.1 | Colon | 1.1 |
| Macrophages rest | 0.0 | Lung | 3.0 |

TABLE FC-continued

Panel 4.1D

| Tissue Name | Rel. Exp. (%) Ag4938, Run 225245203 | Tissue Name | Rel. Exp. (%) Ag4938, Run 225245203 |
|---|---|---|---|
| Macrophages LPS | 3.9 | Thymus | 6.0 |
| HUVEC none | 0.0 | Kidney | 100.0 |
| HUVEC starved | 0.0 | | |

General_screening_panel_v1.5 Summary: Ag4938 Highest expression of this gene is seen in a brain cancer cell line (CT=31.7). Overall, expression of this gene appears to be associated exclusively with cancer cell lines, with moderate levels of expression also seen in cell lines from colon, ovarian, lung, and renal cancers. Thus, expression of this gene could be used to differentiate between thiese samples and other samples on this panel and as a marker to detect the presence of these cancers. Furthermore, therapeutic modulation of the expression or function of this gene may be effective in the treatment of colon, ovarian, lung, and renal cancers. This gene is a variant of CG129136-02. See the discussion of expression for that gene for further discussion of this gene in the treatment of immunological disease and cancer.

Panel 4.1D Summary: Ag4938 This gene is only expressed at detectable levels in the kidney (CT=32.7). Thus, expression of this gene could be used to differentiate the kidney derived sample from other samples on this panel and as a marker of kidney tissue. In addition, therapeutic targeting of the expression or function of this gene may modulate kidney function and be important in the treatment of inflammatory or autoimmune diseases that affect the kidney, including lupus and glomerulonephritis.

G. CG129136-03: 4-1BB Ligand.

Expression of gene CG129136-03 was assessed using the primer-probe sets Ag6625 and Ag6950, described in Tables GA and GB. Results of the RTQ-PCR runs are shown in Tables GC and GD.

TABLE GA

Probe Name Ag6625

| Primers | Sequences | Length | Start Position | SEQ ID No |
|---|---|---|---|---|
| Forward | 5'-gaagcgtcagaggcgtattc-3' | 20 | 78 | 106 |
| Probe | TET-5'-atggaatacgcctctgacgctgtcat-3'-TAMRA | 26 | 51 | 107 |
| Reverse | 5'-ctgacgctgtcaggaatacg-3' | 20 | 17 | 108 |

TABLE GB

Probe Name Ag6950

| Primers | Sequences | Length | Start Position | SEQ ID No |
|---|---|---|---|---|
| Forward | 5'-gccggcagcgagca-3' | 14 | 193 | 109 |
| Probe | TET-5'-agcagcagcccgcgaccagggcc-3'-TAMRA | 24 | 161 | 110 |
| Reverse | 5'-tcgcgcctgccgcgta-3' | 16 | 137 | 111 |

TABLE GC

General_screening_panel_v1.6

| Tissue Name | Rel. Exp. (%) Ag6950, Run 278388889 | Tissue Name | Rel. Exp. (%) Ag6950, Run 278388889 |
|---|---|---|---|
| Adipose | 0.0 | Renal ca. TK-10 | 15.8 |
| Melanoma* Hs688(A).T | 1.7 | Bladder | 1.1 |
| Melanoma* Hs688(B).T | 3.2 | Gastric ca. (liver met.) NCI-N87 | 3.2 |
| Melanoma* M14 | 4.4 | Gastric ca. KATO III | 6.0 |

TABLE GC-continued

General_screening_panel_v1.6

| Tissue Name | Rel. Exp. (%) Ag6950, Run 278388889 | Tissue Name | Rel. Exp. (%) Ag6950, Run 278388889 |
|---|---|---|---|
| Melanoma* LOXIMVI | 7.1 | Colon ca. SW-948 | 100.0 |
| Melanoma* SK-MEL-5 | 8.1 | Colon ca. SW480 | 4.2 |
| Squamous cell carcinoma SCC-4 | 5.0 | Colon ca.* (SW480 met) SW620 | 0.9 |
| Testis Pool | 0.4 | Colon ca. HT29 | 0.3 |
| Prostate ca.* (bone met) PC-3 | 0.9 | Colon ca. HCT-116 | 13.9 |
| Prostate Pool | 0.0 | Colon ca. CaCo-2 | 0.6 |
| Placenta | 0.0 | Colon cancer tissue | 23.7 |
| Uterus Pool | 0.3 | Colon ca. SW1116 | 6.7 |
| Ovarian ca. OVCAR-3 | 0.4 | Colon ca. Colo-205 | 12.2 |
| Ovarian ca. SK-OV-3 | 44.1 | Colon ca. SW-48 | 2.3 |
| Ovarian ca. OVCAR-4 | 7.5 | Colon Pool | 0.8 |
| Ovarian ca. OVCAR-5 | 32.3 | Small Intestine Pool | 0.6 |
| Ovarian ca. IGROV-1 | 54.0 | Stomach Pool | 2.9 |
| Ovarian ca. OVCAR-8 | 41.5 | Bone Marrow Pool | 0.5 |
| Ovary | 0.0 | Fetal Heart | 0.3 |
| Breast ca. MCF-7 | 0.5 | Heart Pool | 0.3 |
| Breast ca. MDA-MB-231 | 2.6 | Lymph Node Pool | 0.3 |
| Breast ca. BT 549 | 17.2 | Fetal Skeletal Muscle | 0.0 |
| Breast ca. T47D | 0.7 | Skeletal Muscle Pool | 0.2 |
| Breast ca. MDA-N | 6.1 | Spleen Pool | 0.3 |
| Breast Pool | 0.6 | Thymus Pool | 0.4 |
| Trachea | 1.7 | CNS cancer (glio/astro) U87-MG | 23.2 |
| Lung | 0.4 | CNS cancer (glio/astro) U-118-MG | 0.7 |
| Fetal Lung | 10.9 | CNS cancer (neuro; met) SK-N-AS | 0.0 |
| Lung ca. NCI-N417 | 0.2 | CNS cancer (astro) SF-539 | 1.9 |
| Lung ca. LX-1 | 3.9 | CNS cancer (astro) SNB-75 | 9.0 |
| Lung ca. NCI-H146 | 0.0 | CNS cancer (glio) SNB-19 | 55.1 |
| Lung ca. SHP-77 | 3.1 | CNS cancer (glio) SF-295 | 8.7 |
| Lung ca. A549 | 5.2 | Brain (Amygdala) Pool | 1.3 |
| Lung ca. NCI-H526 | 2.2 | Brain (cerebellum) | 1.0 |
| Lung ca. NCI-H23 | 1.5 | Brain (fetal) | 1.1 |
| Lung ca. NCI-H460 | 14.6 | Brain (Hippocampus) Pool | 1.1 |
| Lung ca. HOP-62 | 3.0 | Cerebral Cortex Pool | 1.4 |
| Lung ca. NCI-H522 | 1.7 | Brain (Substantia nigra) Pool | 2.8 |
| Liver | 0.2 | Brain (Thalamus) Pool | 1.4 |
| Fetal Liver | 0.0 | Brain (whole) | 0.0 |
| Liver ca. HepG2 | 1.0 | Spinal Cord Pool | 0.8 |
| Kidney Pool | 0.1 | Adrenal Gland | 0.3 |
| Fetal Kidney | 0.2 | Pituitary gland Pool | 0.2 |
| Renal ca. 786-0 | 28.3 | Salivary Gland | 0.2 |
| Renal ca. A498 | 12.8 | Thyroid (female) | 0.1 |
| Renal ca. ACHN | 9.7 | Pancreatic ca. CAPAN2 | 9.0 |
| Renal ca. UO-31 | 12.9 | Pancreas Pool | 1.8 |

TABLE GD

Panel 4.1D

| Tissue Name | Rel. Exp. (%) Ag6950, Run 283838220 | Tissue Name | Rel. Exp. (%) Ag6950, Run 283838220 |
|---|---|---|---|
| Secondary Th1 act | 3.1 | HUVEC IL-1beta | 0.0 |
| Secondary Th2 act | 7.2 | HUVEC IFN gamma | 0.0 |
| Secondary Tr1 act | 3.3 | HUVEC TNF alpha + IFN gamma | 0.0 |
| Secondary Th1 rest | 1.8 | HUVEC TNF alpha + IL4 | 0.0 |
| Secondary Th2 rest | 2.7 | HUVEC IL-11 | 0.0 |
| Secondary Tr1 rest | 7.6 | Lung Microvascular EC none | 0.0 |
| Primary Th1 act | 5.7 | Lung Microvascular EC TNFalpha + IL-1beta | 0.0 |
| Primary Th2 act | 11.8 | Microvascular Dermal EC none | 0.0 |
| Primary Tr1 act | 20.0 | Microvsasular Dermal EC TNFalpha + IL-1beta | 0.0 |
| Primary Th1 rest | 0.7 | Bronchial epithelium TNFalpha + IL1beta | 6.4 |
| Primary Th2 rest | 0.0 | Small airway epithelium none | 3.8 |
| Primary Tr1 rest | 0.0 | Small airway epithelium TNFalpha + IL-1beta | 3.6 |
| CD45RA CD4 lymphocyte act | 0.0 | Coronery artery SMC rest | 1.9 |
| CD45RO CD4 lymphocyte act | 5.1 | Coronery artery SMC TNFalpha + IL-1beta | 3.8 |
| CD8 lymphocyte act | 1.7 | Astrocytes rest | 0.0 |
| Secondary CD8 lymphocyte rest | 0.0 | Astrocytes TNFalpha + IL-1beta | 14.4 |
| Secondary CD8 lymphocyte act | 10.1 | KU-812 (Basophil) rest | 0.0 |
| CD4 lymphocyte none | 0.0 | KU-812 (Basophil) PMA/ionomycin | 2.4 |
| 2ry Th1/Th2/Tr1_anti-CD95 CH11 | 6.8 | CCD1106 (Keratinocytes) none | 1.5 |
| LAK cells rest | 1.4 | CCD1106 (Keratinocytes) TNFalpha + IL-1beta | 0.0 |
| LAK cells IL-2 | 0.0 | Liver cirrhosis | 0.0 |
| LAK cells IL-2 + IL-12 | 0.5 | NCI-H292 none | 0.6 |
| LAK cells IL-2 + IFN gamma | 2.4 | NCI-H292 IL-4 | 1.0 |
| LAK cells IL-2 + IL-18 | 2.1 | NCI-H292 IL-9 | 0.0 |
| LAK cells PMA/ionomycin | 15.6 | NCI-H292 IL-13 | 0.0 |
| NK Cells IL-2 rest | 1.5 | NCI-H292 IFN gamma | 0.0 |
| Two Way MLR 3 day | 1.6 | HPAEC none | 3.2 |
| Two Way MLR 5 day | 0.8 | HPAEC TNF alpha + IL-1 beta | 2.2 |
| Two Way MLR 7 day | 4.8 | Lung fibroblast none | 0.0 |
| PBMC rest | 0.0 | Lung fibroblast TNF alpha + IL-1 beta | 0.0 |
| PBMC PWM | 3.6 | Lung fibroblast IL-4 | 0.0 |
| PBMC PHA-L | 3.4 | Lung fibroblast IL-9 | 0.0 |
| Ramos (B cell) none | 1.0 | Lung fibroblast IL-13 | 0.0 |
| Ramos (B cell) ionomycin | 0.7 | Lung fibroblast IFN gamma | 0.0 |
| B lymphocytes PWM | 0.6 | Dermal fibroblast CCD1070 rest | 0.0 |
| B lymphocytes CD40L and IL-4 | 6.3 | Dermal fibroblast CCD1070 TNF alpha | 1.9 |
| EOL-1 dbcAMP | 15.1 | Dermal fibroblast CCD1070 IL-1beta | 0.0 |
| EOL-1 dbcAMP PMA/ionomycin | 3.5 | Dermal fibroblast IFN gamma | 5.9 |
| Dendritic cells none | 0.0 | Dermal fibroblast IL-4 | 6.7 |
| Dendritic cells LPS | 1.6 | Dermal Fibroblasts rest | 2.4 |
| Dendritic cells anti-CD40 | 0.0 | Neutrophils TNFa + LPS | 0.0 |
| Monocytes rest | 0.0 | Neutrophils rest | 0.0 |
| Monocytes LPS | 100.0 | Colon | 0.0 |
| Macrophages rest | 0.0 | Lung | 0.0 |

TABLE GD-continued

Panel 4.1D

| Tissue Name | Rel. Exp. (%) Ag6950, Run 283838220 | Tissue Name | Rel. Exp. (%) Ag6950, Run 283838220 |
|---|---|---|---|
| Macrophages LPS | 10.5 | Thymus | 1.9 |
| HUVEC none | 2.8 | Kidney | 0.0 |
| HUVEC starved | 0.0 | | |

General_screening_panel_v1.6 Summary: Ag6625 Highest expression of this gene is seen in a colon cancer cell line (CT=28). Overall, expression of this gene appears to be more highly associated with cancer cell lines, with moderate levels of expression also seen in cell lines from brain, breast, ovarian, lung, melanoma and renal cancers. Thus, expression of this gene could be used to differentiate between thiese samples and other samples on this panel and as a marker to detect the presence of these cancers. This gene has homology to 4-1BBL, a cytokine that binds to TNFRSF9 and induces the proliferation of activated peripheral blood T cells and may also play a role in activation-induced cell death (AICD). Therefore, therapeutic modulation of the expression or function of this gene may be effective in the treatment of colon, ovarian, lung, and renal cancers.

Panel 4.1D Summary: Ag6950 Highest expression of this gene is seen in LPS treated monocytes. (CT=31.7). Low but significant levels of expression are also seen in TNF-a and IL-1 beta treated astrocytes, PMA/ionomycin treated LAK cells, eosinophils and LPS activated macrophates. This gene encodes a protein wiht homology to 4-1BB-L, a member of a family of receptors found on the surfaces of cells of the immune system that have been shown to enhance primary T-cell proliferation (Alderson, Eur J Immunol September 1994; 24(9):2219–27). Therefore, modulation of the expression of the putative cytokine encoded by this transcript may prevent the recruitment of monocytes and the initiation of the inflammatory process, and reduce the symptoms of patients suffering from autoimmune and inflammatory diseases such as asthma, allergies, inflammatory bowel disease, lupus erythematosus, or rheumatoid arthritis.

H. CG133483-01: Win4 Like Protein

Expression of gene CG133483-01 was assessed using the primer-probe set Ag4836, described in Table HA.

TABLE HA

Probe Name Aq4836

| Primers | Sequences | Length | Start Position | SEQ ID No |
|---|---|---|---|---|
| Forward | 5'-gctggaactgctccacact-3' | 19 | 301 | 112 |
| Probe | TET-5'-actccttgcccgtcttcggcaag-3'-TAMRA | 23 | 322 | 113 |
| Reverse | 5'-gacatccactgtctcctccat-3' | 21 | 373 | 114 |

General_screening_panel_v1.5 Summary: Ag4836 Expression of this gene is low/undetectable in all samples on this panel (CTs>35).

Panel 4.1D Summary: Ag4836 Expression of this gene is low/undetectable in all samples on this panel (CTs>35).

I. CG135316-01: FGF14 Splice Variant.

Expression of gene CG135316-01 was assessed using the primer-probe sets Ag4899 and Ag5109, described in Tables IA and IB. Results of the RTQ-PCR runs are shown in Tables IC, ID and IE.

TABLE IA

Probe Name Ag4899

| Primers | Sequences | Length | Start Position | SEQ ID No |
|---|---|---|---|---|
| Forward | 5'-gacgccaagtaaaagcacaag-3' | 21 | 669 | 115 |
| Probe | TET-5'-tgcgtctaaatccatttcagatatactccg-3'-TAMRA | 30 | 690 | 116 |
| Reverse | 5'-tggcgttaagtttggttcatta-3' | 22 | 729 | 117 |

TABLE IB

Probe Name Ag5109

| Primers | Sequences | Length | Start Position | SEQ ID No |
|---|---|---|---|---|
| Forward | 5'-atttcagatatactccgtcctgtt-3' | 24 | 703 | 118 |
| Probe | TET-5'-aatgaaccaaacttaacgccatcccc-3'-TAMRA | 26 | 730 | 119 |
| Reverse | 5'-gggaacgcagccaga-3' | 15 | 759 | 120 |

TABLE IC

CNS_neurodegeneration_v1.0

| Tissue Name | Rel. Exp. (%) Ag5109, Run 233609875 | Tissue Name | Rel. Exp. (%) Ag5109, Run 233609875 |
|---|---|---|---|
| AD 1 Hippo | 7.4 | Control (Path) 3 Temporal Ctx | 1.7 |
| AD 2 Hippo | 12.2 | Control (Path) 4 Temporal Ctx | 24.5 |
| AD 3 Hippo | 3.6 | AD 1 Occipital Ctx | 8.9 |
| AD 4 Hippo | 2.9 | AD 2 Occipital Ctx (Missing) | 0.0 |
| AD 5 Hippo | 92.0 | AD 3 Occipital Ctx | 3.5 |
| AD 6 Hippo | 30.8 | AD 4 Occipital Ctx | 7.2 |
| Control 2 Hippo | 14.6 | AD 5 Occipital Ctx | 28.7 |
| Control 4 Hippo | 3.6 | AD 6 Occipital Ctx | 14.5 |
| Control (Path) 3 Hippo | 2.0 | Control 1 Occipital Ctx | 1.3 |
| AD 1 Temporal Ctx | 7.9 | Control 2 Occipital Ctx | 52.5 |
| AD 2 Temporal Ctx | 13.2 | Control 3 Occipital Ctx | 12.2 |
| AD 3 Temporal Ctx | 2.7 | Control 4 Occipital Ctx | 1.3 |
| AD 4 Temporal Ctx | 13.8 | Control (Path) 1 Occipital Ctx | 64.2 |
| AD 5 Inf Temporal Ctx | 100.0 | Control (Path) 2 Occipital Ctx | 8.0 |
| AD 5 Sup Temporal Ctx | 21.5 | Control (Path) 3 Occipital Ctx | 1.6 |
| AD 6 Inf Temporal Ctx | 29.9 | Control (Path) 4 Occipital Ctx | 14.5 |
| AD 6 Sup Temporal Ctx | 25.3 | Control 1 Parietal Ctx | 1.7 |
| Control 1 Temporal Ctx | 1.2 | Control 2 Parietal Ctx | 24.3 |

TABLE IC-continued

CNS_neurodegeneration_v1.0

| Tissue Name | Rel. Exp. (%) Ag5109, Run 233609875 | Tissue Name | Rel. Exp. (%) Ag5109, Run 233609875 |
|---|---|---|---|
| Control 2 Temporal Ctx | 30.8 | Control 3 Parietal Ctx | 13.1 |
| Control 3 Temporal Ctx | 10.2 | Control (Path) 1 Parietal Ctx | 70.2 |
| Control 3 Temporal Ctx | 3.0 | Control (Path) 2 Parietal Ctx | 13.6 |
| Control (Path) 1 Temporal Ctx | 35.8 | Control (Path) 3 Parietal Ctx | 1.1 |
| Control (Path) 2 Temporal Ctx | 25.2 | Control (Path) 4 Parietal Ctx | 32.3 |

TABLE ID

General_screening_panel_v1.5

| Tissue Name | Rel. Exp. (%) Ag5109, Run 228969350 | Tissue Name | Rel. Exp. (%) Ag5109, Run 228969350 |
|---|---|---|---|
| Adipose | 0.4 | Renal ca. TK-10 | 0.0 |
| Melanoma* Hs688(A).T | 42.9 | Bladder | 2.1 |
| Melanoma* Hs688(B).T | 17.1 | Gastric ca. (liver met.) NCI-N87 | 0.0 |
| Melanoma* M14 | 0.3 | Gastric ca. KATO III | 0.0 |
| Melanoma* LOXIMVI | 0.0 | Colon ca. SW-948 | 0.0 |
| Melanoma* SK-MEL-5 | 37.9 | Colon ca. SW480 | 0.0 |
| Squamous cell carcinoma SCC-4 | 4.7 | Colon ca.* (SW480 met) SW620 | 1.3 |
| Testis Pool | 1.3 | Colon ca. HT29 | 0.0 |
| Prostate ca.* (bone met) PC-3 | 5.6 | Colon ca. HCT-116 | 0.0 |
| Prostate Pool | 0.6 | Colon ca. CaCo-2 | 0.0 |
| Placenta | 0.0 | Colon cancer tissue | 1.1 |
| Uterus Pool | 0.6 | Colon ca. SW1116 | 0.0 |
| Ovarian ca. OVCAR-3 | 0.0 | Colon ca. Colo-205 | 0.0 |
| Ovarian ca. SK-OV-3 | 0.1 | Colon ca. SW-48 | 0.0 |
| Ovarian ca. OVCAR-4 | 0.0 | Colon Pool | 1.2 |
| Ovarian ca. OVCAR-5 | 2.3 | Small Intestine Pool | 0.7 |
| Ovarian ca. IGROV-1 | 0.7 | Stomach Pool | 1.0 |
| Ovarian ca. OVCAR-8 | 0.4 | Bone Marrow Pool | 2.6 |
| Ovary | 0.6 | Fetal Heart | 1.4 |
| Breast ca. MCF-7 | 0.0 | Heart Pool | 1.7 |
| Breast ca. MDA-MB-231 | 0.7 | Lymph Node Pool | 1.6 |
| Breast ca. BT 549 | 0.3 | Fetal Skeletal Muscle | 0.0 |
| Breast ca. T47D | 0.0 | Skeletal Muscle Pool | 0.7 |
| Breast ca. MDA-N | 6.7 | Spleen Pool | 0.2 |
| Breast Pool | 1.4 | Thymus Pool | 0.4 |
| Trachea | 5.3 | CNS cancer (glio/astro) U87-MG | 10.4 |
| Lung | 0.3 | CNS cancer (glio/astro) U-118-MG | 10.4 |
| Fetal Lung | 2.5 | CNS cancer (neuro; met) SK-N-AS | 39.2 |
| Lung ca. NCI-N417 | 2.9 | CNS cancer (astro) SF-539 | 0.8 |
| Lung ca. LX-1 | 0.1 | CNS cancer (astro) SNB-75 | 1.7 |
| Lung ca. NCI-H146 | 25.9 | CNS cancer (glio) SNB-19 | 0.4 |
| Lung ca. SHP-77 | 47.3 | CNS cancer (glio) SF-295 | 12.2 |

TABLE ID-continued

General_screening_panel_v1.5

| Tissue Name | Rel. Exp. (%) Ag5109, Run 228969350 | Tissue Name | Rel. Exp. (%) Ag5109, Run 228969350 |
|---|---|---|---|
| Lung ca. A549 | 0.0 | Brain (Amygdala) Pool | 11.1 |
| Lung ca. NCI-H526 | 0.0 | Brain (cerebellum) | 100.0 |
| Lung ca. NCI-H23 | 0.1 | Brain (fetal) | 20.3 |
| Lung ca. NCI-H460 | 11.2 | Brain (Hippocampus) Pool | 18.4 |
| Lung ca. HOP-62 | 1.0 | Cerebral Cortex Pool | 20.2 |
| Lung ca. NCI-H522 | 0.0 | Brain (Substantia nigra) Pool | 10.5 |
| Liver | 0.0 | Brain (Thalamus) Pool | 24.8 |
| Fetal Liver | 0.2 | Brain (whole) | 18.8 |
| Liver ca. HepG2 | 0.0 | Spinal Cord Pool | 3.8 |
| Kidney Pool | 1.7 | Adrenal Gland | 1.2 |
| Fetal Kidney | 1.0 | Pituitary gland Pool | 4.7 |
| Renal ca. 786-0 | 0.1 | Salivary Gland | 0.1 |
| Renal ca. A498 | 0.1 | Thyroid (female) | 0.1 |
| Renal ca. ACHN | 0.1 | Pancreatic ca. CAPAN2 | 0.7 |
| Renal ca. UO-31 | 0.3 | Pancreas Pool | 0.9 |

TABLE IE

Panel 4.1D

| Tissue Name | Rel. Exp. (%) Ag5109, Run 229739339 | Tissue Name | Rel. Exp. (%) Ag5109, Run 229739339 |
|---|---|---|---|
| Secondary Th1 act | 0.0 | HUVEC IL-1beta | 21.0 |
| Secondary Th2 act | 3.5 | HUVEC IFN gamma | 15.2 |
| Secondary Tr1 act | 0.0 | HUVEC TNF alpha + IFN gamma | 5.7 |
| Secondary Th1 rest | 0.0 | HUVEC TNF alpha + IL4 | 6.4 |
| Secondary Th2 rest | 0.0 | HUVEC IL-11 | 10.7 |
| Secondary Tr1 rest | 0.0 | Lung Microvascular EC none | 100.0 |
| Primary Th1 act | 0.0 | Lung Microvascular EC TNFalpha + IL-1beta | 15.6 |
| Primary Th2 act | 3.5 | Microvascular Dermal EC none | 74.7 |
| Primary Tr1 act | 0.0 | Microsvasular Dermal EC TNFalpha + IL-1beta | 18.3 |
| Primary Th1 rest | 0.0 | Bronchial epithelium TNFalpha + IL1beta | 0.0 |
| Primary Th2 rest | 0.0 | Small airway epithelium none | 2.7 |
| Primary Tr1 rest | 0.0 | Small airway epithelium TNFalpha + IL-1 beta | 3.1 |
| CD45RA CD4 lymphocyte act | 4.7 | Coronery artery SMC rest | 31.9 |
| CD45RO CD4 lymphocyte act | 0.0 | Coronery artery SMC TNFalpha + IL-1beta | 9.2 |
| CD8 lymphocyte act | 0.0 | Astrocytes rest | 0.0 |
| Secondary CD8 lymphocyte rest | 0.0 | Astrocytes TNFalpha + IL-1beta | 0.0 |
| Secondary CD8 lymphocyte act | 2.8 | KU-812 (Basophil) rest | 29.9 |
| CD4 lymphocyte none | 0.0 | KU-812 (Basophil) PMA/ionomycin | 68.3 |
| 2ry Th1/Th2/Tr1_anti-CD95 CH11 | 0.0 | CCD1106 (Keratinocytes) none | 0.0 |
| LAK cells rest | 0.0 | CCD1106 (Keratinocytes) TNFalpha + IL-1beta | 0.0 |
| LAK cells IL-2 | 0.0 | Liver cirrhosis | 10.6 |
| LAK cells IL-2 + IL-12 | 0.0 | NCI-H292 none | 0.0 |
| LAK cells IL-2 + IFN gamma | 0.0 | NCI-H292 IL-4 | 0.0 |
| LAK cells IL-2 + IL-18 | 0.0 | NCI-H292 IL-9 | 2.5 |
| LAK cells PMA/ionomycin | 9.2 | NCI-H292 IL-13 | 0.0 |

TABLE IE-continued

Panel 4.1D

| Tissue Name | Rel. Exp. (%) Ag5109, Run 229739339 | Tissue Name | Rel. Exp. (%) Ag5109, Run 229739339 |
|---|---|---|---|
| NK Cells IL-2 rest | 0.0 | NCI-H292 IFN gamma | 3.2 |
| Two Way MLR 3 day | 0.0 | HPAEC none | 37.1 |
| Two Way MLR 5 day | 0.0 | HPAEC TNF alpha + IL-1 beta | 0.0 |
| Two Way MLR 7 day | 0.0 | Lung fibroblast none | 77.9 |
| PBMC rest | 0.0 | Lung fibroblast TNF alpha + IL-1 beta | 10.9 |
| PBMC PWM | 0.0 | Lung fibroblast IL-4 | 30.8 |
| PBMC PHA-L | 0.0 | Lung fibroblast IL-9 | 92.7 |
| Ramos (B cell) none | 0.0 | Lung fibroblast IL-13 | 28.3 |
| Ramos (B cell) ionomycin | 6.2 | Lung fibroblast IFN gamma | 82.9 |
| B lymphocytes PWM | 0.0 | Dermal fibroblast CCD1070 rest | 39.2 |
| B lymphocytes CD40L and IL-4 | 0.0 | Dermal fibroblast CCD1070 TNF alpha | 10.8 |
| EOL-1 dbcAMP | 0.0 | Dermal fibroblast CCD1070 IL-1 beta | 3.3 |
| EOL-1 dbcAMP PMA/ionomycin | 3.8 | Dermal fibroblast IFN gamma | 12.5 |
| Dendritic cells none | 0.0 | Dermal fibroblast IL-4 | 38.2 |
| Dendritic cells LPS | 0.0 | Dermal Fibroblasts rest | 75.8 |
| Dendritic cells anti-CD40 | 0.0 | Neutrophils TNFa + LPS | 0.0 |
| Monocytes rest | 0.0 | Neutrophils rest | 0.0 |
| Monocytes LPS | 0.0 | Colon | 0.0 |
| Macrophages rest | 7.6 | Lung | 3.1 |
| Macrophages LPS | 0.0 | Thymus | 0.0 |
| HUVEC none | 17.7 | Kidney | 10.8 |
| HUVEC starved | 25.0 | | |

CNS_neurodegeneration_v1.0 Summary: Ag5109 This panel confirms the expression of the CG135316-01 gene at low levels in the brains of an independent group of individuals. See Panel 1.5 for a discussion of this gene in treatment of central nervous system disorders.

Ag4899 Expression of this gene is low/undetectable (CTs>35) across all of the samples on this panel.

General_screening_panel_v1.5 Summary: Ag5109 Highest expression of the CG135316-01 gene is detected in brain (cerebellum) (CT=24.9). this gene is expressed at high levels in all regions of the central nervous system examined, including amygdala, hippocampus, substantia nigra, thalamus, cerebellum, cerebral cortex, and spinal cord. Therefore, therapeutic modulation of this gene product may be useful in the treatment of central nervous system disorders such as Alzheimer's disease, Parkinson's disease, epilepsy, multiple sclerosis, schizophrenia and depression.

High to moderate levels of expression of this gene is also seen in number of cancer cell lines derived from melanoma, pancreatic, brain, lung, breast, ovarian, and prostate cancers. Therefore, therapeutic modulation of the protein encoded by this gene may be useful in the treatment of these cancers.

Among tissues with metabolic or endocrine function, this gene is expressed at moderate levels in pancreas, adipose, adrenal gland, pituitary gland, skeletal muscle, heart, fetal liver and the gastrointestinal tract. Therefore, therapeutic modulation of the activity of this gene may prove useful in the treatment of endocrine/metabolically related diseases, such as obesity and diabetes.

Expression of this gene is higher in adult (CT=32) as compared to fetal skeletal muscle (CT=40). Therefore, expression of this gene may be used to distinguish between fetal and adult skeletal muscle.

In addition, this gene is expressed at much higher levels in fetal (CT=30–33) when compared to adult lung and liver respectively (CT=33–38). This observation suggests that expression of this gene can be used to distinguish fetal from adult lung and liver. In addition, the relative overexpression of this gene in fetal tissue suggests that the protein product may enhance growth or development of lung and liver in the fetus and thus may also act in a regenerative capacity in the adult. Therefore, therapeutic modulation of the protein encoded by this gene could be useful in treatment of lung and liver related diseases.

Ag4899 Expression of this gene is low/undetectable (CTs>35) across all of the samples on this panel Panel 4.1D Summary: Ag5109 Highest expression of the CG135316-01 gene is detected in lung microvascular EC cells (CT=33.4). Low levels of expression of this gene is also seen in microvascular dermal EC, and HPAEC. Interestingly, expression of this gene is downregulated in cytokine stimulated endothelial cells. In addition, low levels of expression of this gene is also seen in basophils, lung fibroblasts and dermal fibroblast cells. Therefore, therapeutic modulation of the FGF encoded by this gene or use of this gene as protein therapeutic may be useful in the treatment of autoimmune and inflammatory diseases that involve endothelial cells, such as lupus erythematosus, asthma, emphysema, Crohn's disease, ulcerative colitis, rheumatoid arthritis, osteoarthritis, and psoriasis.

Ag4899 Expression of this gene is low/undetectable (CTs>35) across all of the samples on this panel.

Example D

Identification of Single Nucleotide Polymorphisms in NOVX Nucleic Acid Sequences Variant sequences are also included in this application. A variant sequence can include a single nucleotide polymorphism (SNP). A SNP can, in some instances, be referred to as a "cSNP" to denote that the nucleotide sequence containing the SNP originates as a cDNA. A SNP can arise in several ways. For example, a SNP may be due to a substitution of one nucleotide for another at the polymorphic site. Such a substitution can be either a transition or a transversion. A SNP can also arise from a deletion of a nucleotide or an insertion of a nucleotide, relative to a reference allele. In this case, the polymorphic site is a site at which one allele bears a gap with respect to a particular nucleotide in another allele. SNPs occurring within genes may result in an alteration of the amino acid encoded by the gene at the position of the SNP. Intragenic SNPs may also be silent, when a codon including a SNP encodes the same amino acid as a result of the redundancy of the genetic code. SNPs occurring outside the region of a gene, or in an intron within a gene, do not result in changes in any amino acid sequence of a protein but may result in altered regulation of the expression pattern. Examples include alteration in temporal expression, physiological response regulation, cell type expression regulation, intensity of expression, and stability of transcribed message.

SEQCALLING (application service provider featuring software that generates customized sequence databases: identifies human genetic variations and enables scientists to predict an individual's genetic susceptibility or predisposition to disease or response to medication) assemblies produced by the exon linking process were selected and extended using the following criteria. Genomic clones having regions with 98% identity to all or part of the initial or extended sequence were identified by BLASTN searches using the relevant sequence to query human genomic databases. The genomic clones that resulted were selected for further analysis because this identity indicates that these clones contain the genomic locus for these SEQCALLING (application service provider featuring software that generates customized sequence databases: identifies human genetic variations and enables scientists to predict an individual's genetic susceptibility or predisposition to disease or response to medication) assemblies. These sequences were analyzed for putative coding regions as well as for similarity to the known DNA and protein sequences. Programs used for these analyses include Grail, Genscan, BLAST, HMMER, FASTA, Hybrid and other relevant programs.

Some additional genomic regions may have also been identified because selected SEQCALLING (application service provider featuring software that generates customized sequence databases: identifies human genetic variations and enables scientists to predict an individual's genetic susceptibility or predisposition to disease or response to medication) assemblies map to those regions. Such SEQCALLING (application service provider featuring software that generates customized sequence databases: identifies human genetic variations and enables scientists to predict an individual's genetic susceptibility or predisposition to disease or response to medication) sequences may have overlapped with regions defined by homology or exon prediction. They may also be included because the location of the fragment was in the vicinity of genomic regions identified by similarity or exon prediction that had been included in the original predicted sequence. The sequence so identified was manually assembled and then may have been extended using one or more additional sequences taken from CuraGen Corporation's human SEQCALLING (application service provider featuring software that generates customized sequence databases: identifies human genetic variations and enables scientists to predict an individual's genetic susceptibility or predisposition to disease or response to medication) database. SeqCalling fragments suitable for inclusion were identified by the CURATOOLS (computer software program which analyzes sequences of genes and proteins, 3D molecules and performs literature searches) program SeqExtend or by identifying fragments to the appropriate regions of the genomic clones analyzed.

The regions defined by the procedures described above were then manually integrated and corrected for apparent inconsistencies that may have arisen, for example, from miscalled bases in the original fragments or from discrepancies between predicted exon junctions, EST locations and regions of sequence similarity, to derive the final sequence disclosed herein. When necessary, the process to identify and analyze SeqCalling assemblies and genomic clones was reiterated to derive the full length sequence (Alderborn et al., Determination of Single Nucleotide Polymorphisms by Real-time Pyrophosphate DNA Sequencing. Genome Research. 10 (8) 1249–1265, 2000).

Variants are reported individually but any combination of all or a select subset of variants are also included as contemplated NOVX embodiments of the invention.

NOV4a SNP Data

Three polymorphic variants of NOV4a have been identified and are shown in Table 16A.

| Variant | Nucleotides | | | Amino Acids | | |
| --- | --- | --- | --- | --- | --- | --- |
| | Position | Initial | Modified | Position | Initial | Modified |
| 13379729 | 192 | G | A | 60 | Gly | Arg |
| 13379730 | 269 | A | G | 85 | Ala | Ala |
| 13379731 | 564 | A | C | 184 | Ser | Arg |

NOV5a SNP Data

One polymorphic variant of NOV5a has been identified and is shown in Table 16B.

| Variant | Nucleotides | | | Amino Acids | | |
| --- | --- | --- | --- | --- | --- | --- |
| | Position | Initial | Modified | Position | Initial | Modified |
| 13378449 | 351 | T | C | 57 | Ile | Thr |

NOV6a SNP Data

Four polymorphic variants of NOV6a have been identified and are shown in Table 16C.

| Variant | Nucleotides | | | Amino Acids | | |
| --- | --- | --- | --- | --- | --- | --- |
| | Position | Initial | Modified | Position | Initial | Modified |
| 13379732 | 139 | G | A | 41 | Gly | Asp |
| 13379733 | 167 | C | T | 50 | Arg | Arg |
| 13379736 | 550 | T | G | 178 | Val | Gly |
| 13379737 | 556 | C | T | 180 | Ala | Val |

NOV7a SNP Data

Two polymorphic variants of NOV7a have been identified and are shown in Table 16D.

| Variant | Nucleotides | | | Amino Acids | | |
| --- | --- | --- | --- | --- | --- | --- |
| | Position | Initial | Modified | Position | Initial | Modified |
| 13374892 | 50 | C | G | 17 | Pro | Ala |
| 13379683 | 591 | G | A | 197 | Gly | Glu |

NOV14a SNP Data
Eight polymorphic variants of NOV14a have been identified and is shown in Table 16E.

|  | Nucleotides | | | Amino Acids | | |
| --- | --- | --- | --- | --- | --- | --- |
| Variant | Position | Initial | Modified | Position | Initial | Modified |
| 13374704 | 26 | C | G | 9 | Leu | Val |
| 13379710 | 139 | G | A | 46 | Leu | Leu |
| 13374705 | 143 | A | T | 48 | Thr | Ser |
| 13379725 | 334 | C | T | 111 | Pro | Pro |
| 13379724 | 421 | T | G | 140 | Pro | Pro |
| 13379723 | 605 | C | G | 202 | His | Asp |
| 13379704 | 616 | C | T | 205 | Leu | Leu |
| 13379703 | 688 | G | C | 229 | Val | Val |

Example E

Each of the clones listed below is related to a clone or family of clones listed in Example A. The relationship is identifiable as the clone listed below will have the same NOVX number as the clones to which it is related. For example, NOV2B below is related to NOV2a of Example A.

NOV2B

The NOV2b clone was analyzed, and the nucleotide and encoded polypeptide are shown in Table 17A.

TABLE 17A

NOV2b Sequence Analysis

| | | |
| --- | --- | --- |
| NOV2b, CG109754-01 DNA Sequence | SEQ ID NO:121 | 173 bp |
| | aaatcctccgggctcttaggaaatttcactccgcttctgcccagtggtctctttggtcgg cagggtgttcttctcctgcgtctccgttttcttcagcttggccctattgaagctggcgat tcccccacgtctggtttgtctgccattttcttaaaacaatcggtaccatccg | |
| NOV2b, CG109754-01 Protein Sequence | SEQ ID NO:122 | 43 aa |
| | MADKPDVGGIASFNRAKLKKTETQEKNTLPTKETTGQKRSEIS | |

NOV3B

The NOV3b clone was analyzed, and the nucleotide and encoded polypeptide sequences are shown in Table 18A.

TABLE 18A

NOV3b Sequence Analysis

| | | |
| --- | --- | --- |
| NOV3b, CG114834-01 DNA Sequence | SEQ ID NO: 123 | 330 bp |
| | atgtcagatgcagctgtagacaccagctctgaaatcattgccaaggacttaaaggagaag aaggaagttgtgaaagaggcggaaaatggaagagacgcccctgctaacgggaatgctaat gaggaaaatggggagcaggaggctgacaaggaggtagatgaagaagggaagaaagtggg gaggaagaggaggaggaaaaagaaggtgatggtgaggaagaggatggagatgaagaggaa gctgagtctgctacaggcaagcgggcagctgaagatgatgaggatgatgatgtcgatacc aagaagcagaagaccgacaaggatgactaa | |
| NOV3b, CG114834-01 Protein Sequence | SEQ ID NO: 124 | 109 aa |
| | MSDAAVDTSSEIIAKDLKEKKEVVKEAENGRDAPANGNANEENGEQEADKEVDEEGEESG EEEEEEKEGDCEEEDGDEEEAESATGKRAAEDDEDDDVDTKKQKTDKDD | |

NOV10B

The NOV10b clone was analyzed, and the nucleotide and encoded polypeptide sequences are shown in Table 19A.

TABLE 19A

NOV10b Sequence Analysis

| | | |
|---|---|---|
| NOV10b, CG53473-01 DNA Sequence | SEQ ID NO: 125 | 646 bp |
| | agcgcgcccgaacgaagccgcggcccgggcacagcatggcccgcggcgggagggcgctcg | |
| | gatgttcggcagcctcctgcacttcgccctgctcgctgccggcgtcgtcccgctcagctg | |
| | ggatctcccggagccccgcagccgagccagcaagatccgagtgcactcgcgaggcaagct | |
| | ctgggccatcggtcacttcatgggcaagaagagtctggagccttccagcccatccccatt | |
| | ggggacagctccccacacctccctgagggaccagcgactgcagctgagtcatgatctgct | |
| | cggaatcctcctgctaaagaaggctctgggcgtgagcctcagccgcccgcaccccaaat | |
| | ccagtacaggaggctgctggtacaaatactgcagaaatgacaccaataatggggcagaca | |
| | caacagcgtggcttagattgtgcccacccagggaaggtgctgaatgggaccctgttgatg | |
| | gccccatctggatgtaaatcctgagctcaaatctctgttactccattactgtgatttctg | |
| | gctgggtcaccagaaatatcgctgatgcagacacagattatgttcctgctgtatttcctg | |
| | cttccctgttgaattggtgaataaaaccttgctctatacatacaaa | |
| NOV10b, CG53473-01 Protein Sequence | SEQ ID NO: 126 | 112 aa |
| | MFGSLLHFALLAAGVVPLSWDLPEPRSRASKIRVHSRGKLWAIGHFMGKKSLEPSSPSPL GTAPHTSLRDQRLQLSHDLLGILLLKKALGVSLSRPAPQIQYRRLLVQILQK | |

NOV11B

The NOV11b clone was analyzed, and the nucleotide and encoded polypeptide sequences are shown in Table 20A.

TABLE 20A

NOV11b Sequence Analysis

| | | |
|---|---|---|
| NOV11b, CG54725-01 DNA Sequence | SEQ ID NO: 127 | 147 bp |
| | agaaaatggcacacaaactagacctggaagaaattgccagcttggataaggccaagctga | |
| | aggccacagagatgcagaagaacactctgatgaccaaagagaccacagagcaggagaagt | |
| | ggagtgaaatttcctgagagcctcgag | |
| NOV 11b, CG54725-01 Protein Sequence | SEQ ID NO: 128 | 43 aa |
| | MAHKLDLEEIASLDKAKLKATEMQKNTLMTKETTEQEKWSEIS | |

NOV12D

The NOV12d clone was analyzed, and the nucleotide and encoded polypeptide sequences are shown in Table 21A.

TABLE 21A

NOV12d Sequence Analysis

| | | |
|---|---|---|
| NOV12d, CG56983-01 DNA Sequence | SEQ ID NO: 129 | 348 bp |
| | ctatccctatggtgtcggtgtgcaggccgtggcctgctgtggccatagcacttctggctc | |
| | tgctggtctgcctgggggcgctggtcgacacctgccccatcaaacccgaggctcctggcg | |
| | aagacgagtccctggaggagctgagccactattatgcttccctgtgccactacctcaacg | |
| | tggtcaccagacagttaatttcagagagaaacctaccagacaccattgtgtccaaggaag | |

TABLE 21A-continued

NOV12d Sequence Analysis tatttttcacaagcacaaaggaaagacctgtgaggacacagaaggaaggttgccatctgc aagccaaggagagaagcctctgaaaaaaccaaacctgctggcaccttg

| | SEQ ID NO: 130 | 104 aa |
|---|---|---|
| NOV 12d,<br>CG56983-01<br>Protein<br>Sequence | MVSVCRPWPAVAIALLALLVCLGALVDTCPIKPEAPGEDESLEELSHYYASLCHYLNVVT<br>RQLISERNLPDTIVSKEVFFTSTKERPVRTQKEGCHLQAKERSL | |

NOV15B

The NOV15b clone was analyzed, and the nucleotide and encoded polypeptide sequences are shown in Table 22A.

TABLE 22A

NOV15b Sequence Analysis

| | SEQ ID NO: 131 | 515 bp |
|---|---|---|
| NOV15b,<br>CG89614-01<br>DNA<br>Sequence | gcctgacaccatgctgcccgcctgcttcctcggcctactggccttctcctccgcgtgcta<br><br>cttccagaactgcccgaggggcggcaagagggccatgtccgacctggagctgagacagtg<br><br>cctcccctgcggccccgggggcaaaggccgctgcttcgggcccagcatttgctgcgcgga<br><br>cgagctgggctgcttcgtgggcacggctgaggcgctgcgctgccaggaggagaactacct<br><br>gccgtcgccctgccagtccggccagaaggcgtgcgggagcgggggccgctgcgccgcctt<br><br>cggcgtttgctgcaacgacgagagctgcgtgaccgagtccgagtgccgcgagggctttca<br><br>ccgccgcgcccgcgccagcgaccggagcaacgccacgcaactggacaggccggccggggc<br><br>cttgctgctgcggctggtgcagctggccggggcgcccgagccctttgagcccgcccagcc<br><br>cgacgcctactgagccccgcgctcgccccaccggc | |
| | SEQ ID NO: 132 | 160 aa |
| NOV15b,<br>CG89614-01<br>Protein<br>Sequence | MLPACFLGLLAFSSACYFQNCPRGGKRAMSDLELRQCLPCGPGGKGRCFGPSICCADELG<br>CFVGTAEALRCQEENYLPSPCQSGQKACGSGGRCAAFGVCCNDESCVTESECREGFHRRA<br>RASDRSNATQLDRPAGALLLRLVQLAGAPEPFEPAQPDAY | |

Other Embodiments

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. The choice of nucleic acid starting material, clone of interest, or library type is believed to be a matter of routine for a person of ordinary skill in the art with knowledge of the embodiments described herein. Other aspects, advantages, and modifications considered to be within the scope of the following claims. The claims presented are representative of the inventions disclosed herein. Other, unclaimed inventions are also contemplated. Applicants reserve the right to pursue such inventions in later claims.

We claim:

1. An isolated nucleic acid molecule comprising an open reading frame encoding an amino acid sequence of SEQ ID NO:10.

2. The nucleic acid molecule of claim 1, wherein the nucleic acid molecule is naturally occurring.

3. The isolated nucleic acid molecule of claim 1, comprising nucleotides 15–636 of SEQ ID NO:9 or nucleotides 14–634 of SEQ ID NO:11.

4. An isolated nucleic acid molecule, wherein said nucleic acid molecule hybridizes under stringent conditions to the nucleotide sequence of claim 3, or a complement of said nucleotide sequence, and wherein said stringent conditions comprise 6×SSC, 50 mM Tris HCl (pH 7.5), 1 mM EDTA, 0.02% PVP, 0.02% Ficoll, 0.02% BSA, and 500 mg/ml denatured salmon sperm DNA at 65° C. followed by one or more washes in 0.2×SSC, 0.0 1% BSA at 50° C.

5. A vector comprising the nucleic acid molecule of claim 1.

6. The vector of claim 5, further comprising a promoter operably linked to said nucleic acid molecule.

7. A cell comprising the vector of claim 5.

8. A method of producing a polypeptide comprising an amino acid sequence of SEQ ID NO:10 comprising culturing a cell under conditions that lead to expression of the polypeptide, wherein said cell comprises the vector of claim 5 or 6.

9. The method of claim 8 wherein the cell is a bacterial cell.

10. The method of claim 8 wherein the cell is an insect cell.

11. The method of claim 8 wherein the cell is a yeast cell.

12. The method of claim 8 wherein the cell is a mammalian cell.

13. An isolated nucleic acid molecule comprising an open reading frame encoding amino acids 16–207 of SEQ ID NO:10.

14. The isolated nucleic acid molecule of claim 13 comprising nucleotides 59–635 of SEQ ID NO:9 or nucleotides 58–634 of SEQ ID NO:11.

15. A vector comprising the nucleic acid molecule of claim 13.

16. A cell comprising the vector of claim 15.

17. A method of producing a polypeptide comprising amino acids 16–207 of SEQ ID NO:10, said method comprising culturing a cell under conditions that lead to expression of the polypeptide, wherein said cell comprises a vector of claim 15.

* * * * *